(12) United States Patent
Ruoslahti et al.

(10) Patent No.: US 12,290,569 B2
(45) Date of Patent: *May 6, 2025

(54) METHODS AND COMPOSITIONS USING PEPTIDES AND PROTEINS WITH C-TERMINAL ELEMENTS

(71) Applicant: Sanford Burnham Prebys Medical Discovery Institute, La Jolla, CA (US)

(72) Inventors: Erkki Ruoslahti, La Jolla, CA (US); Tambet Teesalu, La Jolla, CA (US); Kazuki Sugahara, La Jolla, CA (US)

(73) Assignee: Sanford Burnham Prebys Medical Discovery Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/373,496

(22) Filed: Jul. 12, 2021

(65) Prior Publication Data

US 2022/0175941 A1 Jun. 9, 2022

Related U.S. Application Data

(63) Continuation of application No. 16/524,869, filed on Jul. 29, 2019, now Pat. No. 11,059,718, which is a continuation of application No. 12/821,050, filed on Jun. 22, 2010, now Pat. No. 10,370,245.

(60) Provisional application No. 61/249,140, filed on Oct. 6, 2009, provisional application No. 61/219,086, filed on Jun. 22, 2009.

(51) Int. Cl.
*A61K 47/66* (2017.01)
*B82Y 5/00* (2011.01)

(52) U.S. Cl.
CPC .............. *A61K 47/66* (2017.08); *B82Y 5/00* (2013.01)

(58) Field of Classification Search
CPC ........ A61K 47/66; A61K 9/127; A61K 47/50; B82Y 5/00; A61P 19/02; A61P 29/00; A61P 35/00; C12Q 1/02; G01N 33/15
See application file for complete search history.

(56) References Cited

U.S. PATENT DOCUMENTS

| | | | |
|---|---|---|---|
| 5,262,176 | A | 11/1993 | Palmacci |
| 5,662,885 | A | 9/1997 | Pollak |
| 6,177,542 | B1 | 1/2001 | Ruoslahti |
| 6,530,944 | B2 | 3/2003 | West |
| 6,576,239 | B1 | 6/2003 | Ruoslahti |
| 6,967,238 | B2 | 11/2005 | Blaschuk |
| 7,034,109 | B2 | 4/2006 | Bonny |
| 7,063,847 | B1 | 6/2006 | Sanderson |
| 7,544,767 | B2 | 6/2009 | Ruoslahti |
| 2001/0002150 | A1 | 5/2001 | Frigo |
| 2002/0055174 | A1 | 5/2002 | Rittner |
| 2002/0068272 | A1 | 6/2002 | Larocca |
| 2002/0132990 | A1 | 9/2002 | Huston |
| 2002/0193295 | A1 | 12/2002 | Calenoff |
| 2003/0003100 | A1 | 1/2003 | Levy |
| 2003/0077289 | A1 | 4/2003 | Wang |
| 2003/0082143 | A1 | 5/2003 | Larocca |
| 2003/0082176 | A1 | 5/2003 | Lebowitz |
| 2003/0083261 | A1 | 5/2003 | Yu |
| 2003/0125283 | A1 | 7/2003 | Gatenby |
| 2003/0148263 | A1 | 8/2003 | Larocca |
| 2003/0166601 | A1 | 9/2003 | Woodle |
| 2004/0005309 | A1 | 1/2004 | Lebowitz |
| 2004/0219169 | A1 | 11/2004 | Bermudes |
| 2005/0038239 | A1 | 2/2005 | Catchpole |
| 2005/0054563 | A1 | 3/2005 | Desnoyer |
| 2005/0071088 | A1 | 3/2005 | Landfield |
| 2005/0085417 | A1 | 4/2005 | Wickstrom |
| 2005/0147993 | A1 | 7/2005 | Khan |
| 2005/0233356 | A1 | 10/2005 | Jones |
| 2005/0260756 | A1 | 11/2005 | Troy |
| 2005/0281805 | A1 | 12/2005 | Lebowitz |
| 2006/0014712 | A1 | 1/2006 | Neuman |
| 2006/0051315 | A1 | 3/2006 | Scaria |
| 2006/0070133 | A1 | 3/2006 | Dean |
| 2006/0100134 | A1 | 5/2006 | Guo |
| 2006/0147922 | A1 | 7/2006 | Watts |
| 2006/0147997 | A1 | 7/2006 | Ramakrishnan |
| 2006/0153775 | A1 | 7/2006 | Von Wronski |
| 2006/0154340 | A1 | 7/2006 | Louie |
| 2006/0160743 | A1 | 7/2006 | Zhang |
| 2006/0172941 | A1 | 8/2006 | Rastelli |

(Continued)

FOREIGN PATENT DOCUMENTS

| | | |
|---|---|---|
| EP | 0045665 | 2/1982 |
| JP | 2006257074 | 9/2006 |

(Continued)

OTHER PUBLICATIONS

Abi-Habib, et al., "A urokinase-activated recombinant diphtheria toxin targeting the granulocyte-macrophage colony-stimulating factor receptor is selectively cytotoxic to human acute myeloid leukemia blasts", Blood, 104: 2143-8(2004).

(Continued)

*Primary Examiner* — Jessica Worsham
(74) *Attorney, Agent, or Firm* — PABST PATENT GROUP LLP

(57) ABSTRACT

Disclosed are compositions and methods useful for targeting and internalizing molecules into cells of interest and for penetration by molecules of tissues of interest. The compositions and methods are based on peptide sequences that are selectively internalized by a cell, penetrate tissue, or both. The disclosed internalization and tissue penetration is useful for delivering therapeutic and detectable agents to cells and tissues of interest.

19 Claims, 23 Drawing Sheets

Specification includes a Sequence Listing.

(56) References Cited

U.S. PATENT DOCUMENTS

| | | | |
|---|---|---|---|
| 2006/0233807 A1 | 10/2006 | Svanborg |
| 2006/0239968 A1 | 10/2006 | Arap |
| 2006/0242725 A1 | 10/2006 | Strong |
| 2006/0257942 A1 | 11/2006 | Waldo |
| 2007/0041904 A1 | 2/2007 | Jiang |
| 2007/0111251 A1 | 5/2007 | Rosania |
| 2007/0111270 A1 | 5/2007 | Zhang |
| 2007/0157328 A1 | 7/2007 | Ramrakha |
| 2007/0212332 A1 | 9/2007 | Baylink |
| 2007/0231862 A1 | 10/2007 | Diamond |
| 2007/0287680 A1 | 12/2007 | Cuchelkar |
| 2007/0292920 A1 | 12/2007 | Lin |
| 2007/0299043 A1 | 12/2007 | Hunter |
| 2008/0014143 A1 | 1/2008 | Ruoslahti |
| 2008/0234183 A1 | 9/2008 | Hallbrink |
| 2008/0305119 A1 | 12/2008 | Dewhurst |
| 2008/0311136 A1 | 12/2008 | Beusker |
| 2009/0031733 A1 | 2/2009 | Weaver |
| 2009/0087899 A1 | 4/2009 | McKnight |
| 2009/0092548 A1 | 4/2009 | Ferrara |
| 2009/0176660 A1 | 7/2009 | Yla-Herttuala |
| 2009/0176710 A1 | 7/2009 | Hadwiger |
| 2009/0186802 A1 | 7/2009 | Alluis |
| 2009/0226372 A1 | 9/2009 | Ruoslahti |
| 2009/0246133 A1 | 10/2009 | Ruoslahti |
| 2009/0257951 A1 | 10/2009 | Ruoslahti |
| 2009/0258926 A1 | 10/2009 | Divita |
| 2009/0280058 A1 | 11/2009 | Troy |
| 2009/0305329 A1 | 12/2009 | Szilak |
| 2009/0317802 A1 | 12/2009 | Bhatia |
| 2009/0325866 A1 | 12/2009 | Kim |
| 2010/0016215 A1 | 1/2010 | Moulton |
| 2010/0022466 A1 | 1/2010 | Raucher |
| 2010/0048487 A1 | 2/2010 | Uno |
| 2010/0061932 A1 | 3/2010 | Brock |
| 2010/0061942 A1 | 3/2010 | Ma |
| 2010/0099627 A1 | 4/2010 | Seger |
| 2010/0143454 A1 | 6/2010 | McLinden |
| 2010/0172835 A1 | 7/2010 | Ruoslahti |
| 2010/0279918 A1 | 11/2010 | Langel |

FOREIGN PATENT DOCUMENTS

| | | |
|---|---|---|
| WO | 1995022996 | 8/1995 |
| WO | 2002018572 | 3/2002 |
| WO | 0231109 | 4/2002 |
| WO | 03106491 | 12/2003 |
| WO | 2004074432 | 9/2004 |
| WO | 2005042034 | 5/2005 |
| WO | 2006096207 | 9/2006 |
| WO | 2007014391 | 1/2007 |
| WO | 2007090194 | 8/2007 |
| WO | 2007108749 | 9/2007 |
| WO | 2009036092 | 3/2009 |
| WO | 2009105671 | 8/2009 |
| WO | 2009126349 | 10/2009 |
| WO | 2010075540 | 7/2010 |

OTHER PUBLICATIONS

Acevedo, et al, "Semaphorin 3A suppresses VEGF-mediated angiogenesis yet acts as a vascular permeability factor", Blood, 111:2674-80 (2008).

Allam, et al., "Cholera toxin triggers apoptosis in human lung cancer cell lines", Cancer Res., 57:2615-2618 (1997).

Almquist, et al., "Synthesis and biological activity of a ketomethylene analogue of a tripeptide inhibitor of angiotensin converting enzyme", J. Med. Chem., 23:1392-8 (1980).

Altin and Pagler, "A one-step procedure for biotinylation and chemical cross-linking of lymphocyte surface and intracellular membrane-associated molecules", Anal Biochem., 224:382-9(1995).

Andreasen, "The plasminogen activation system in tumor growth, invasion, and metastasis", Cell. Mol. Life Sci., 57:25-40 (2000).

Arap, et al., "Cancer treatment by targeted drug delivery to tumor vasculature in a mouse model", Science 279:377-380 (1998).

Arap, et al., "Targeting the prostate for destruction through a vascular address", PNAS, 99:1527-1531 (2002).

Arbeit, et al., "Progressive squamous epithelial neoplasia in K14-human papillomavirus type 16 transgenic mice", J Virol., 68:4358-68 (1994).

Arleth, et al., "Detailed structure of hairy mixed micelles formed by phosphatidylcholine and PEGylated phospholipids in aqueous media", Langmuir, 21:3279-90 (2005).

Assa-Munt, et al., "Solution structures and integrin binding activities of an RGD peptide with two isomers", Biochemistry, 40:2373-8 (2001).

Bardeesy, et al., "Pancreatic cancer biology and genetics", Nature Rev Cancer, 2:897-909, 2002).

Bartlett, et al., "Impact of tumor-specific targeting on the biodistribution and efficacy of siRNA nanoparticles measured by multimodality in vivo imaging", PNAS, 104:15549-54 (2007).

Benner, "Expanding the genetic lexicon: incorporating nonstandard amino acids into proteins by ribosome-based synthesis", TIB Tech, 12:158-63 (1994).

Berg, et al., "Physiological functions of endosomal proteolysis", Biochem. J., 307: 313-26 (1995).

Biacchesi, et al., "Modification of the trypsin-dependent cleavage activation site of the human metapneumovirus fusion protein to be trypsin independent does not increase replication or spread in rodents or nonhuman primates", J. Virol., 80:5798-5806 (2006).

Biology Online, accessed Dec. 23, 2016.

Blasi and Carmeliet, "uPAR: a versatile signalling orchestrator", Nat Rev Mol Cell Biol., 3:932-43 (2002).

Brewis, et al., "Particle assembly incorporating a VP22-BH3 fusion protein, facilitating intracellular delivery, regulated release, and apoptosis", Mol. Ther., 7:262-70 (2003).

Brooks, et al., "Integrin alpha v beta 3 antagonists promote tumor regression by inducing apoptosis of angiogenic blood vessels", Cell, 79:1157-64 (1994).

Brown and Ruoslahti, "Metadherin, a cell-surface protein in breast tumors that mediates lung metastasis", Cancer Cell, 5:365-374 (2004).

Cahill, et al., "Site specific mutagenesis with unnatural amino acids", TIBS, 14(10):400-3 (1989).

Caveliers, et al., "Evaluation of 99mTc-RP128 as a potential inflammation imaging agent: human dosimetry and first clinical results", J. Nucl. Med., 42:154-61 (2001).

Chambers, et al., "Flavivirus genome organization, expression, and replication", Annu. Rev. Microbiol., 44:649-88 (1990).

Cheresh, et al., "Biosynthetic and functional properties of an Arg-Gly-Asp-directed receptor involved in human melanoma cell attachment to vitronectin, fibrinogen, and von Willebrand factor", J Biol Chem., 262:17703-17710 (1987).

Christian, et al., "Nucleolin expressed at the cell surface is a marker of endothelial cells in tumor blood vessels", J Cell Biol. 163:871-8 (2003).

Conese, et al., "alpha-2 Macroglobulin receptor/Ldl receptor-related protein(Lrp)-dependent internalization of the urokinase receptor", J Cell Biol., 131:1609-22 (1995).

Curnis, et al., "Coupling tumor necrosis factor-a with av integrin ligands improves its antineoplastic activity", Cancer Res. 64:565-571 (2004).

Debele, et al., "Specificity profiling of seven human tissue kallikreins reveals individual subsite preferences", J Biol Chem., 281: 25678-88 (2006).

Derfus, et al., "Targeted Quantum Dot Conjugates for siRNA Delivery", Bioconjug Chem, 18:1391-6 (2007).

Derossi, et al., "Trojan peptides: the penetratin system for intracellular delivery", Trends Cell Biol., 8:84-7 (1998).

Dharap, et al., "Targeted proapoptotic LHRH-BH3 peptide", Pharm Res., 20:889-96 (2003).

Drake, et al., "Assessing tumor growth and distribution in a model of prostate cancer metastasis using bioluminescence imaging", Clin Exp Metastasis, 22:674-684 (2005).

(56) References Cited

OTHER PUBLICATIONS

Duckert, et al., "Prediction of proprotein convertase cleavage sites", Protein Eng. Design & Selection, 17(1):107-12 (2004).
Dykxhoorn, et al., "The silent treatment: siRNAs as small molecule drugs", Gene Ther. 13:541-52 (2006).
Elango, et al., "The mumps virus fusion protein mRNA sequence and homology among the paramyxoviridae proteins", J. Gen. Virol. 70:801-807 (1989).
Eliceiri and Cheresh, "Adhesion events in angiogenesis", Curr Opin Cell Biol 13:563-68 (2001).
Elliott and O'Hare, "Intercellular trafficking and protein delivery by a herpesvirus structural protein", Cell, 88:223-33 (1997).
Esmon, et al., "Cell mediated events that control blood coagulation and vascular injury", Annu. Rev. Cell. Biol., 9:1-26 (1993).
Falanga, et al. "Wound bed score and its correlation with healing of chronic wounds", Dermatol Ther 19:383-90 (2006).
Fenart and Cecchelli, "Protein transport in cerebral endothelium. In vitro transcytosis of transferring", Meth. Mol. Med., 89:277-90 (2003).
Fogal, et al., "Mitochondrial/ Cell surface protein p32/gC1qR as a molecular target in tumor cells and tumor stroma", Cancer Res., 68:7210-18 (2008).
Folkman, "Angiogenesis", Annu Rev Med. 57:1-18, (2006).
Fujikawa, et al., "Activation of bovine factor X (Stuart factor): conversion of factor Xa alpha to factor Xa beta", PNAS, 72:3359-63 (1975).
Gammon, et al., "Quantitative Analysis of Permeation Peptide Complexes Labeled with Technetium-99m: Chiral and Sequence-Specific Effects on Net Cell Uptake", Bioconjugate Chem., 14:368-76 (2003).
GenBank Accession No. Q1YF93 "CueR-like heavy metal response, transcription regulator", 1 page, Submitted Mar. 2006, first published May 2, 2006, accessed Aug. 24, 2011.
Geretti, et al., "Neuropilin structure governs VEGF and semaphorin binding and regulates angiogenesis", Angiogenesis, 11:31-39 (2008).
Gonzalez-Reyes, et al., "Cleavage of the human respiratory syncytial virus fusion protein at two distinct sites is required for activation of membrane fusion", PNAS, 98:9859-64 (2001).
Goodman and Ro, "Peptidomimetics for Drug Design", Buerger's Medicinal Chemistry Drug Discovery vol. 1 (ed M.E. Wolff; John Wiley & Sons, pp. 803-861 (1995).
Gordon, et al., "Proteolytic activation of bacterial toxins by eukaryotic cells is performed by furin and by additional cellular proteases", Infec. Immun. 63:82-7(1995).
Grabitz, et al., "Science with no fiction: measuring the veracity of scientific reports by citation analysis", 1-9, bioRxiv.org., Preprint Article (2017).
Grebrehiwet, et al., "gC1q-R/p33: structure-function predictions from the crystal structure", Immunobiology, 205:421-32 (2002).
Green, et al., "Autonomous functional domains of chemically synthesized human immunodeficiency virus tat trans-activator protein", Cell, 55:1179-88 (1988).
Hagedorn and Bikfalvi, "Target molecules for anti-angiogenic therapy: from basic research to clinical trials", Crit. Rev. Oncol. Hematol. 34:89-110 (2000).
Hambley and Hait,"Is Anticancer Drug Development Heading in the Right Direction?" Cancer Res., 69:1259-62 (2009).
Hamzah, et al., "Vascular Targeting of Anti-CD40/IL2 into Autochthonous Tumors Enhances Immunotherapy", J. Clin. Invest., 118:1691-99 (2008).
Hanahan, "Heritable formation of pancreatic-cell tumors in transgenic mice expressing recombinant insulin/simian virus 40 oncogenes", Nature, 315:115-22 (1985).
Hann, "On the double bond isostere of the peptide bond: preparation of an enkephalin analogue", J. Chem. Soc Perkin Trans., 1: 307-14 (1982).
Hansen, et al., "A urokinase-type plasminogen activator-inhibiting cyclic peptide with an unusuall P2 residue and an extended protease binding surface demonstrates new modalities for enzyme inhibition", J Biol Chem., 280:38242-37 (2005).

Heldin, et al., "High interstitial fluid pressure—an obstacle in cancer therapy", Nat Rev Cancer 4:806-13 (2004).
Hezel, et al., "Genetics and biology of pancreatic ductal adenocarcinoma", Genes Dev, 20:1218-49 (2006).
Hoffman, et al., "In vivo and ex vivo selections using phage-displayed libraries", Phage Display: A Practical Approach, T. Clarkson and H. Lowman, eds. (Oxford, U.K.: Oxford University Press), Chap 10:171(2004).
Hoffman, et al., "Progressive vascular changes in a transgenic mouse model of squamous cell carcinoma", Cancer Cell, 4:383-91 (2003).
Holladay, et al., "Synthesis of hydroxyethylene and ketomethylene dipeptide isosteres", Tetrahedron Lett, 24:4401-4 (1983).
Hong, et al., "Targeting neuropilin 1 as an antitumor strategy in lung cancer", Clinical. Cancer Res., 13(6): 4759-68 (2007).
Hooper, et al., "Membrane protein secretases", Biochem. J. 321:265-279 (1997).
Horswill, et al., "Cyclic Peptides, a Chemical Genetics Tool for Biologists", Cell Cycle, 4(4):552-555 (2005).
Hruby, "Conformational restrictions of biologically active peptides via amino acid side chain groups", Life Sci., 31:189-99 (1982).
Hudson, et al., "Methionine enkephalin and isosteric analogues. I. Synthesis on a phenolic resin support". Int J Pept Prot Res., 14:177-85 (1979).
Ibba and Hennecke, "Towards engineering proteins by site-directed incorporation in vivo of non-natural amino acids", Biotechnology, 12:678-82 (1994).
Ibba, "Strategies for in vitro and in vivo translation with non-natural amino acids", Biotechnology and & Genetic Engineering Reviews, 13:197-216 (1995).
International Preliminary Report on Patentability and Written Opinion for PCT/US2009/031305 dated (Jul. 20, 2010).
International Search Report and Written Opinion for application PCT/US09/34713 (24520.35.9001) dated Aug. 4, 2009.
International Search Report PCT application PCT/US2009/34713 dated Aug. 4, 2009.
International Search Report PCT application PCT/US2010/039539 dated Oct. 25, 2010.
International Search Report PCT/US2009/031305, mailed Mar. 10, 2010.
Jain, "Normalization of tumor vasculature: An emerging concept in antiangiogenic therapy", Science, 307:58-62 (2005).
Jain, "Vascular and interstitial barriers to delivery of therapeutic agents in tumors", Cancer Metastasis Rev, 9:253-266 (1990).
Jain, et al., "Effect of vascular normalization by antiangiogenic therapy on interstitial hypertension, peritumor edema, and lymphatic metastasis: insights from a mathematical model", Cancer Res., 67:2729-35 (2007).
Jarvinen and Ruoslahti, "Molecular changes in the vasculature of injured tissues", Am. J. Path., 171:702-711 (2007).
Jennings-White, et al., "Synthesis of ketomethylene analogs of dipeptides", Tetrahedron Lett., 23:2533 (1982).
Jia, et al., "Characterization of a bicyclic peptide neuropilin-1 (NP-1) antagonist (EG3287) reveals importance of vascular endothelial growth factor exon 8 for NP-1 binding and role of NP-1 in KDR signaling", J. Biol. Chem., 281:13493-502 (2006).
Jia, et al., "Cysteine-rich and basic domain HIV-1 Tat peptides inhibit angiogenesis and induce endothelial cell apoptosis", Biochem. Biophys. Res. Commun., 283:469-79 (2001).
Jiang, et al., Tumor imagining by means of proteolytic activation of cell-openetrating peptides, PNAS, 101:17867-72 (2004).
Johannsen, et al., "Proteins of purified Epstein-Barr virus", PNAS, 101:16286-91 (2004).
Joliot, et al., "Antenapedia homeobox peptide regulates neural morphogenesis", PNAS, 88:1864-68 (1991).
Joyce, et al., "Stage-specific vascular markers revealed by phage display in a mouse model of pancreatic islet tumorigenesis", Cancer Cell, 4:393-403 (2003).
Kamei, et al., "Importance of intermolecular interaction on the improvement of intestinal therapeutic peptide/protein absorption using cell-penetrating peptides", J Contr. Rel., 136:179-86 (2009).
Kamei, et al., "Usefulness of cell-penetrating peptides to improve intestinal insulin absorption.", J Contr. Rel., 132:21-5 (2008).

(56) References Cited

OTHER PUBLICATIONS

Kandela, et al., "Registered report: Coadministration of a tumor-penetrating peptide enhances the efficacy of cancer drugs", eLife. 10.7554/eLife.06959, includes opublished correction (2015).
Karmali, et al., "Targeting of albumin-embedded paclitaxel nanoparticles to tumors", Nanomedicine, 5:73-82 (2009).
Ke, et al., "Optimal subsite occupancy and design of selective inhibitor of urokinase", J. Biol. Chem., 272:20456-62 (1997).
Kerbel, et al., "The anti-angiogenic basis of metronomic chemotherapy", Nat Rev Cancer, 4:423-36 (2004).
Kirsch, et al., "Anti-angiogenic treatment strategies for malignant brain tumors", J. Neurooncol., 50:149-63 (2000).
Klenk, et al., "Host cell proteases controlling virus pathogenicity", Trends Microbiol, 2:39-43 (1994).
Koga, et al., "Nucleotide Sequence and Expression of the Feline Vascular Endothelial Growth Factor", J. Vet. Med. Sci., 64(5):453-456 (2002).
Koivunen, et al., "Phage libraries displaying cyclic peptides with different ring sizes: ligand specificities of the RGD-directed integrins", Biotechnology, 13:265-70 (1995).
Koivunen, et al., "Selection of peptides binding to the alpha 5 beta 1 integrin from phage display library", J Biol Chem, 268:20205-10 (1993).
Kolonin, et al., "Synchronous selection of homing peptides for multiple tissues by in vivo phage display", FASEB, 20:979-81 (2006).
Koya, et a., "Nucleotide sequence and expression of the feline vascular endothelial growth factor", J Vet Med Sci., 64(5):453-6 (2002).
Kreitman and Pastan, "Recombinant toxins containing human granulocyte-macrophage colony-stimulating factor and either pseudomonas exotoxin or diphtheria toxin kill gastrointestinal cancer and leukemia cells", Blood, 90:252-9 (1997).
Kumar, et al., "Transvascular delivery of small interfering RNA to the central nervous system", Nature, 448:39-43 (2007).
Laakkonen, et al., "A tumor-homing peptide with a targeting specificity related to lymphatic vessels", Nature Med., 8:751-55 (2002b).
Laakkonen, et al., "Antitumor activity of a homing peptide that targets tumor lymphatics and tumor cells", PNAS, 101:9381-86 (2004).
Laakkonen, et al., "Peptide targeting of tumor lymph vessels", Ann NY Ac Sci., 1131:37-43 (2008).
Li and Huang "Surface-modified LPD nanoparticles for tumor targeting", Ann N.Y. Acad. Sci. 1082, 1-8 (2006).
Li, et al., "The role of the transferrin-transferrin-receptor system in drug delivery and targeting", Trends Pharmacol. Sci. 23, 206-209 (2002).
Liu, et al. "Targeting of tumor cells by cell surface urokinase plasminogen activator-dependent anthrax toxim", J Biol Chem. 276:17976-84 (2001).
Liu, et al., "In vivo biodistribution and highly efficient tumour targeting of carbon nanotubes in mice", Nat. Nanotech., 2:47-52 (2007).
Liu, et al., "In vivo interrogation of the molecular display of atherosclerotic lesion surfaces", American Journal of Pathology, 163:1859-71 (2003).
Liu, et al., "Prostate-specific Membrane Antigen Directed Selective Thrombotic Infarction of Tumors", Cancer Res., 62:5470-5 (2002).
Maeda, et al., "Vascular permeability enhancement in solid tumor: various factors, mechanisms involved and its implications", Int Immunopharmacol, 3:319-28 (2003).
Mantis, et al., "Replication Study: Coadministration of a tumor-penetrating peptide enhances the efficacy of cancer drugs", eLife, 10.7554/eLife.17584 (2017).
Marin, et al., "Role of vascular nitric oxide physiological and pathological conditions", Pharmacol Ther, 75:111-34 (1997).
Martin, et al., "Cancer gene therapy by thyroid hormone-mediated expression of toxin genes", Cancer Res., 60:3218-24 (2000).

Mayer, et al., "The role of tumor-associated macrophages in the delivery of liposomal doxorubicin to solid murine fibrosarcoma tumors", J Pharm. Exp Ther, 280:1406-14 (1997).
Meade and Dowdy, "Exogenous siRNA delivery using peptide transduction domains/cell penetrating peptides", Adv. Drug Delivery Reviews. 59(2-3):134-40 (2007).
Medarova, et al., "In vivo imaging of siRNA delivery and silencing in tumors",. Nat Med, 13: 372-7 (2007).
Miles and Miles, "Vascular reactions to histamine, histamine-liberator and leukotaxine in the skin of guinea-pigs", J Physiol, 118:228-57 (1952).
Minchinton and Tannock, "Drug penetration in solid tumours", Nat Rev Cancer 6:583-92 (2006).
Moghimi, et al., "Long-circulating and target-specific nanoparticles: Theory to practice", Pharm. Rev. 53:283-318 (2001).
Monsky, et al., "Augmentation of transvascular transport of macromolecules and nanoparticles in tumors using vascular endothelial growth factor", Cancer Res 59:4129-35 (1999).
Morishiita, et al., "A novel approach using functional peptides for efficient intestinal absorption of insulin", J Contr. Rel, 118:177-84 (2007).
Morley, "Modulation of the action of regulatory peptides by structural modification", Trends, Pharm Sci,. 463-468 (1980).
Moulard. and Decroly, "Maturation of HIV envelope glycoprotein precursors by cellular endoproteases", Biochim. Biophys. Acta, 1469:121-132 (2000).
Murakami and Etlinger, "Degradation of proteins with blocked amino groups by cytoplasmic proteases", Biochem. Biophys. Res. Comm., 146:1249-59 (1987).
Murohara, et al., "Vascular endothelial growth factor/vascular permeability factor enhances vascular permeability via nitric oxide and prostacyclin", Circ., 97:99-107 (1998).
Murphy, et al., "Nanoparticle-mediated drug delivery to tumor vasculature suppresses metastasis", PNAS, 105:9343-48 (2008).
Myrberg, et al., "Design of a Tumor-Homing Cell-Penetrating Peptide", Bioconjugate Chem., 19:70-75 (2008).
Nyberg, et al., "Trypsins and their role in carcinoma growth", Exp Cell Res., 312:1219-28 (2006).
Osborne and Coronado-Heinsohn, "Targeting the epidermal growth factor receptor in breast cancer cell lines with a recombinant ligand fusion toxin (DAB389EGF)", Cancer J. Sci. Am. 2:175 (1996).
Park, et al., "Magnetic iron oxide nanoworms for tumor targeting and imaging",. Adv. Mater., 20:1630-5 (2008).
Park, et al., "Systematic surface engineering of magnetic nanoworms for in vivo tumor targeting", Small, 5:694-700 (2009).
Pasqualini, et al., "Alpha v integrins as receptors for tumor targeting by circulating ligands", Nature Biotechnol., 15:542-6 (1997).
Pellet-Many, et al., "Neuropilins: structure, function and role in disease", Biochem J, 411:211-26 (2008).
Pellinen, et al., "Integrin traffic", J Cell Sci 119:3723-31 (2006).
Pero, et al., "Combination treatment with Grb7 peptide and Doxorubicin or Trastuzumab (Herceptin) results in cooperative cell growth inhibition in breast cancer cells", British Journal of Cancer, 96(10):1520-1525 (2007).
Pierschbacher And Ruoslahtii, "Cell attachment activity of fibronectin can be duplicated by small synthetic fragments of the molecule", Nature, 309:30-33 (1984).
Pilch, et al., "Peptides selected for binding to clotted plasma accumulate in tumor stroma and wonds", PNAS, 103:2800-4 (2006).
Pipkorn, et al. , "Delivery of substances and their target-specific topical activation", Biochim Biophys Acta, 1758(5):606-10 (2006).
Pirollo, et al., "Materializing the potential of small interfering RNA via a tumor-targeting nanodelivery system", Cancer Res.,67:2938-43 (2007).
Polyakov, et al., "Novel Tat-Peptide Chelates for Direct Transduction of Technetium-99m and Rhenium into Human Cells for Imaging and Radiotherapy". Bioconjugate Chem., 11:762-71 (2000).
Porkka, et al.,"A fragment of the HMGN2 protein homes to the nuclei of tumor cells and tumor endothelial cells in vivo", PNAS, 99:7444-9 (2002).
Puente, et al., "Human and mouse proteases: a comparative genomic approach", Nat Rev Genet, 4:544-8 (2003).

(56) References Cited

OTHER PUBLICATIONS

Rajotte and Ruoslahti, "Membrane dipeptidase is the receptor for a lung-targeting peptide identified by in vivo phage display", J. Biol. Chem., 274:11593-11598 (1999).
Rajotte, et al., "Molecular heterogeneity of the vascular endothelium revealed by in vivo phage display", J Clin Invest., 102:430-7 (1998).
Rijken, "Plasminogen activators and plasminogen activator inhibitors: biochemical aspects", Baillieres Clin Haematol., 8:291-312 (1995).
Rizo and Gierasch, "Constrained peptides: models of bioactive peptides and protein substructures", Ann. Rev. Biochem., 61:387 (1992).
Rubinstein, et al., "Receptor for the globular heads of C1q (gC1q-R, p33, hyaluronan-binding protein) is preferentially expressed by adenocarcinoma cells", Int J Cancer 100:741-50 (2004).
Ruiz-Linares, et al., "Processing of yellow fever virus polyprotein: role of cellular proteases in maturation of the structural proteins", J. Virol., 63:4199-4209 (1989).
Ruoslahti and Rajotte, "An address system in the vasculature of normal tissues and tumors", Annu. Rev. Immunol., 18:813-827 (2000).
Ruoslahti, "RGD story: a personal account. A Landmark Essay", Matrix Biology 2:459-65 (2003).
Ruoslahti, "Specialization of tumour vasculature", Nat. Rev. Cancer, 2:83-90 (2002).
Ruoslahti, et al. , "Vascular homing peptides with cell-penetrating properties",. Curr. Pharm. Des., 11(28):3655-60 (2005).
Ruoslahti, et al., "Targeting of drugs and nanoparticles to tumors", The Journal of Cell Biology, 188(6):759-768 (2010).
Ruoslahti,. "Drug targeting to specific vascular sites", Drug Discovery Today. 7:1138-43 (2002).
Ruoslahti,"Vascular zip codes in angiogenesis and metastasis", Biochem. Soc. Transact., 32:397-402 (2004).
Rusnak, et al., "The effects of the novel, reversible epidermal growth factor receptor/ErbB-2 tyrosine kinase inhibitor, GW2016, on the growth of human normal and tumor-derived cell lines in vitro and in vivo", Mol Cancer Ther., 1:85-94 (2001).
Sanchez, et al., "Crimean-congo hemorrhagic fever virus glycoprotein precursor is cleaved by Furin-like and SKI-1 proteases to generate a novel 38-kilodalton glycoprotein", J. Virol., 80:514-25 (2006).
Sandgren, et al., "Nuclear targeting of macromolecular polyanious by an HIV—Tate derived peptide. Role for cell-surface proteoglycans", J. Biol. Chem., 277:38877-83 (2002).
Sehgal, et al., "Photoinduced cytotoxicity and biodistribution of prostate cancer cell-targeted porphyrins", J. Med. Chem, 51:6014-20 (2008).
Simberg, et al., "Biomimetic amplification of nanoparticle homing to tumors", PNAS, 104:932-936 (2007).
Singer, et al., "Cutaneous wound healing", NEJM, 341:738-46 (1999).
Sipkins, et al., "Detection of tumor angiogenesis in vivo by alphaVbeta3-targeted magnetic resonance imaging", Nat. Med., 4:623-26 (1998).
Sjoberg, et al., "Furin cleavage potentiates the membrane fusion-controlling intersubunit disulfide bond isomerization activity of leukemia virus", Env. J. Virol., 80:5540-51 (2006).
Smyth and Trapani, "Granzymes: exogenous proteinases that induce target cell apoptosis", Immunology Today, 16:202-206 (1995).
Soker, et al., "Neuropilin-1 is expressed by endothelial and tumor cells as an isoform-specific receptor for vascular endothelial growth factor", Cell, 92:735-45 (1998).
Sokoloff, et al., "A new peptide ligand that targets particles and heterologous proteins to hepatocytes in vivo", Mol. Ther. 8:867-72 (2003).
Sokoloff, et al., "The interactions of peptides with the innate immune system studied with use of T7 phage peptide display", Mol. Ther., 2:131-39 (2000).
Spatola, et al., "Structure-activity relationships of enkephalins containing serially replaced thiomethylene amide bond surrogates", Life Sci 38:1243-9 (1986).
Spatola, "Peptide Backbone Modifications", Chemistry and Biochemistry of Amino Acids, Pepides, and Proteins, B. Weinstein, eds., Marcel Dekker, New York, p. 267 (1983).
Spiridon, et al., "Targeting multiple Her-2 epitopes with monoclonal antibodies results in improved antigrowth activity of a human breast cancer cell line in vitro and in vivo", Clin Cancer Res, 8:1720-30 (2002).
Starzec, et al., "Antiangiogenic and antitumor activities of peptide inhibiting the vascular endothelial growth factor binding to neuropilin-1", Life Sci, 79:2370-81 (2006).
Steinhauer, "Role of hemagglutinin cleavage for the pathogenicity of influenza virus", Virology, 258:1-20 (1999).
Sternlicht, et al., "How matrix metalloproteinases regulate cell behavior", Annu. Rev. Cell. Dev. Biol., 17:463-513 (2001).
Sugahara, et al. "Coadministration of a tumor-penetrating peptide enhances the efficacy of cancer drugs", Am. Assoc. Adv of Sci., 328(5981):1031-35 (2010).
Sugahara, et al., "Chondroitin sulfate E fragments enhance CD44 cleavage and CD44 dependent motility in tumor cells", Cancer Res., 68:7191-9 (2008).
Sugahara, et al., "Hyaluronan oligosaccharides induce CD44 cleavage and promote cell migration in CD44-expressing tumor cells", J Biol Chem., 278:32259-65 (2003).
Sugahara, et al., "Tissue penetrating delivery of compounds and nanoparticles into tumors", Cancer Cell 16(6):510-20 (2009).
Talanian, et al., "Substrate specificities of caspase family proteases", J. Biol. Chem., 272: 9677-82 (1997).
Teesalu, et al., "Tumor-Penetrating Peptides", Frontiers in Oncology, 3 (2013).
Teesalu, et al., "C-end rule peptides mediate neuropilin-1-dependent cell, vascular and tissue penetration", PNAS, 106(38):16157-62 (2009).
Thomas, "Furin at the cutting edge: from protein traffic to embryogenesis and disease", Nature Rev. Mol. Cell. Biol. 3:753-66 (2002).
Thomas, et al., "Tissue distribution and pharmacokinetics of an ATWLPPR-conjugated chlorin-type photosensitizer targeting neuropilin-1 in glioma-bearing nude mice", Photochemical & photobiological Sciences, 7(4):433 (2008).
Thornberry, et al., "A combinatorial approach defines specificities of members of the caspase family and granzyme B. Functional relationships established for key mediators of apoptosis", J. Biol. Chem. 272: 17907-11 (1997).
Thorson, et al., "A biosynthetic approach for the incorporation of unnatural amino acids into proteins", Methods in Molec. Biol., 77:43-73 (1991).
Thurber, et al., "Antibody tumor penetration: transport opposed by systemic and antigen-mediated clearance", Adv Drug Deliv Rev, 60:1421-34 (2008).
Tian, et al., "A 20 residues Motif Delineates the Furin Cleavage Site and its Physical Properties May Influence Viral Fusion", BioChemistry Insights, 2:9-20 (2009).
Tirand, et al., "A peptide competing with VEGF165 binding on neuropilin-1 mediates targeting of a chlorin-type photosensitizer and potentiates its photodynamic activity in human endothelial cells", J Contr. Rel., 111:153-64 (2006).
Tkachenko, et al., "Multifunctional gold nanoparticle-peptide complexes for nuclear targeting", J Am Chem Soc. 125:4700-1 (2003).
Torgersen, et al., "Internalization of cholera toxin by diffeent endocytic mechanisms", J. Cell. Sci., 114:3737-47 (2001).
Tucker, "Alpha v integrin inhibitors and cancer therapy", Curr Opin Investig Drugs 4:722-31 (2003).
Tyagi, et al., "Internalization of HIV—1 tat requires cell surface heparan sulfate proteoglycans", J. Biol. Chem., 276:3254-61 (2001).
Uhland, "Matriptase and its putative role in cancer", Cell. Mol. Life Sci., 63:2968-78 (2006).
Uprichard, "The therapeutic potential of RNA interference", FEBS Lett., 579:5996-6007 (2005).
Vander Kooi, et al., "Structural basis for ligand and heparin binding to neuropilin B domains", PNAS, 104(15):6152-57 (2007).
Varsanyi, et al., "Isolation and characterization of the measles virus F1 polypeptide: comparison with other paramyxovirus fusion proteins", Virology 147:110-17 (1985).

(56) References Cited

OTHER PUBLICATIONS

Vey, et al., "Proteolytic processing of human cytomegalovirus glycoprotein B (gpUL55) is mediated by the human endoprotease furin", Virology 206:746-49 (1995).

von Maltzahn, et al., "In vivo tumor cell targeting with "click" nanoparticles", Bioconjug Chem, 19:1570-8 (2008).

Von Wronski, et al., "Tuftsin binds neuropilin-1 through a sequence similar to that encoded by exon 8 of vascular endothelial growth factor", JBC, 281:5702-10 (2006).

Weissleder, et al., "Cell-specific targeting of nanoparticles by multivalent attachment of small molecules", Nat. Biotechnol., 23:1418-23 (2005).

Weissleder, et al., "Long-circulating iron oxide for MR imaging", Adv. Drug Deliv. Rev., 16: 321-34 (1995).

Werb, "ECM and cell surface proteolysis: regulating cellular ecology", Cell, 91:439-42 (1997).

White, et al. Antibody-targeted immunotherapy for treatment of malignancy, Annu Rev Med., 52:125-41 (2001).

Wolfsberg, et al., "ADAM, a novel family of membrane proteins containing A Disintegrin And Metalloprotease domain: multipotential functions in cell-cell and cell-matrix interactions", J. Cell Biol., 131:275-8 (1995).

Wool-Lewis and Bates, "Endoproteolytic processing of the ebola virus envelope glycoprotein: cleavage is not required for function", J. Virol. 73:1419-26 (1999).

Yang, et al., "A fluorescent orthotopic bone metasis model of human prostate cancer", Cancer Res, 59:781-6, 1999).

Yuan, et al., "Microvascular permeability and interstitial penetration of sterically stabilized (stealth) liposomes in a human tumor xenograft", Cancer Res, 54:3352-56 (1994).

Zhang, et al., "Dynamic imaging of arginine-rich heart-targeted vehicles in a mouse model", Biomaterials, 29:1976-88 (2008).

Zhang, et al., Lymphatic zip codes in premalignant lesions and tumors. Cancer Res. 66, 5696-5706 (2006).

Zhang, et al., "Molecular profiling of heart endothelial cells", Circulation. 112:1601-11 (2005).

Zorko and Langel, "Cell-penetrating peptides: mechanism and kinetics of cargo delivery", Adv Drug Deliv Rev. 57:529-45 (2005).

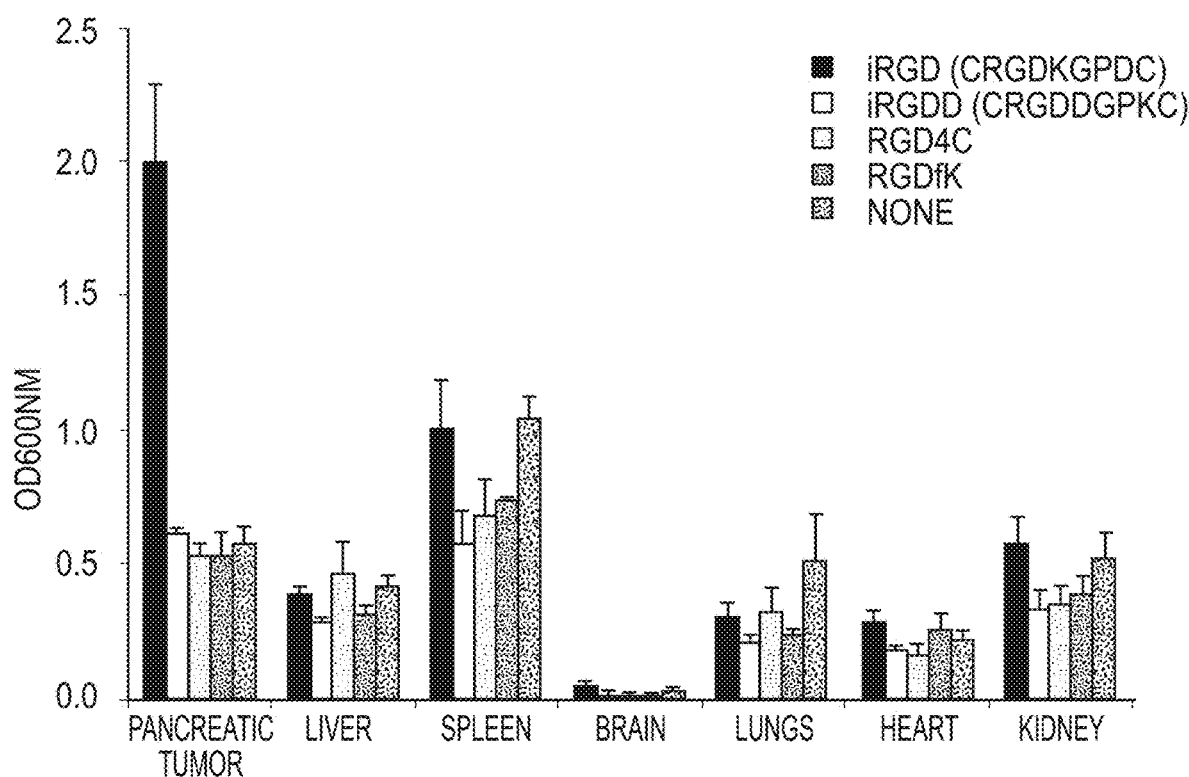
*FIG. 5B*
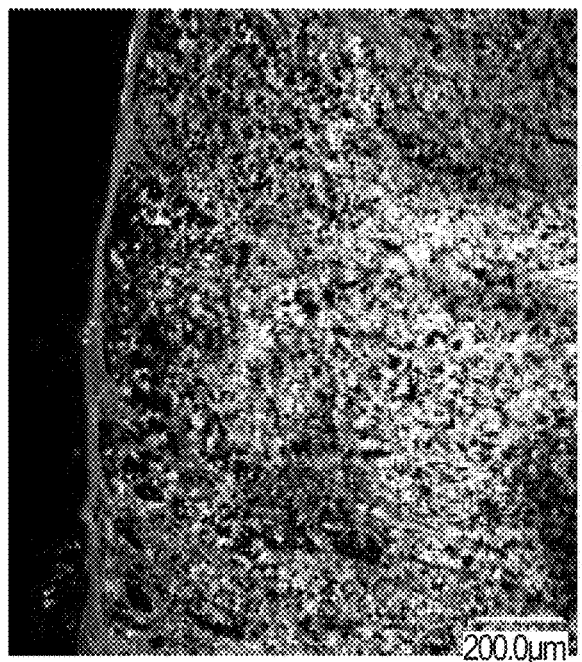 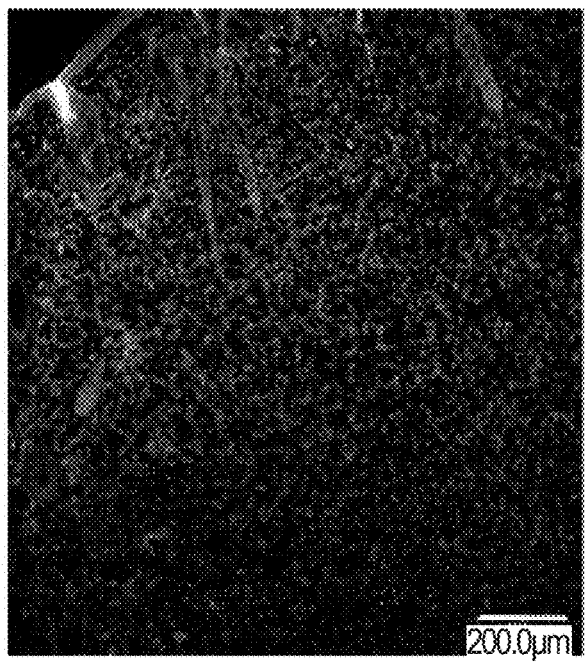
*FIG. 6A*  *FIG. 6B*

METHODS AND COMPOSITIONS USING PEPTIDES AND PROTEINS WITH C-TERMINAL ELEMENTS

CROSS-REFERENCE TO RELATED APPLICATIONS

This application is a continuation of U.S. application Ser. No. 16/524,869, filed Jul. 29, 2019, which is a continuation of U.S. application Ser. No. 12/821,050, filed Jun. 22, 2010, which claims benefit of U.S. Provisional Application No. 61/219,086, filed Jun. 22, 2009, and U.S. Provisional Application No. 61/249,140, filed Oct. 6, 2009. Application Ser. No. 16/524,869, filed Jul. 29, 2019, Application Ser. No. 12/821,050, filed Jun. 22, 2010, Application No. 61/219,086, filed Jun. 22, 2009, and Application No. 61/249,140, filed Oct. 6, 2009, are hereby incorporated herein by reference in their entirety.

STATEMENT REGARDING FEDERALLY SPONSORED RESEARCH

This invention was made with government support under W81XWH-08-1-0727 awarded by the Medical Research and Development Command, and P01 CA104898, R01 CA115410, R01 CA119414, U54 CA119335. P30 CA030199, and R01 CA124427 awarded by the National Institutes of Health. The government has certain rights in the invention.

REFERENCE TO SEQUENCE LISTING

The Sequence Listing submitted Jul. 29, 2019, as a text file named "SBMRI_46.8404_ST25.txt," created on Aug. 7, 2017, and having a size of 63,527 bytes is hereby incorporated by reference pursuant to 37 C.F.R. § 1.52(e)(5).

FIELD OF THE INVENTION

The present invention relates generally to the fields of molecular medicine, more specifically, to cell and tissue-penetrating peptides.

BACKGROUND OF THE INVENTION

Peptides that are internalized into cells are commonly referred to as cell-penetrating peptides. There are two main classes of such peptides: hydrophobic and cationic (Zorko and Langel, 2005). The cationic peptides, which are commonly used to introduce nucleic acids, proteins into cells, include the prototypic cell-penetrating peptides (CPP), Tat, and penetratin (Derossi et al., 1998; Meade and Dowdy, 2007). A herpes virus protein, VP22, is capable of both entering and exiting cells and carrying a payload with it (Elliott and O'Hare, 1997; Brewis et al., 2003). A major limitation of these peptides as delivery vehicles is that they are not selective; they enter into all cells. An activatable delivery system can be used which is more specific for one cell type or tissue.

Tissue penetration is a serious limitation in the delivery of compositions to cells. Comparison of the distribution of fluorescein-labeled peptides to that of iron oxide particles coated with the same peptide shows that the particles remain close to the tumor blood vessels, whereas the fluorescent peptide reaches all areas of the tumor. The frequently cited "leakiness" of tumor vessels does not appear to substantially mitigate this problem. Moreover, anti-angiogenic treatments that cause "normalization" of tumor vasculature (Jain, 2005), creating a need to target tumors whose vasculature is not leaky. Thus, it is important to find new ways of improving the passage of diverse compositions into the extravascular space. A number of proteins are known to translocate through the endothelium of blood vessels, including the blood-brain barrier. A prime example is transferrin, which is carried across the blood-brain barrier by the transferrin receptor. This system has been used to bring other payloads into the brain (Li et al., 2002; Fenart and Cecchelli, 2003). Peptide signals for endothelial transcytosis that can mediate translocation of compositions from the circulation into tissues is useful.

Thus, there is a need for new therapeutic strategies for selectively targeting various types of cells, and for internalizing proteins and peptides into those cells and penetration of tissue by proteins and peptides. There is also a need for increasing the delivery of compounds and compositions to and into cells and tissues. The present invention satisfies these needs by providing peptides that can be selectively targeted, and selectively internalized, by various types of cells and/or can penetrate tissue. Related advantages also are provided.

BRIEF SUMMARY OF THE INVENTION

Disclosed are methods of enhancing internalization, penetration, or both of a co-composition into or through a cell, tissue, or both, the method comprising: exposing the cell, tissue, or both to a CendR element and the co-composition, thereby enhancing internalization, penetration, or both of the co-composition into or through the cell, tissue, or both, wherein, prior to exposing the cell, tissue, or both, the CendR element and the co-composition are not covalently coupled or non-covalently associated with each other.

Also disclosed are methods of enhancing internalization of a co-composition into a cell, the method comprising: exposing the cell to a CendR element and the co-composition, thereby enhancing internalization of the co-composition into the cell, wherein, prior to exposing the cell, the CendR element and the co-composition are not covalently coupled or non-covalently associated with each other.

Disclosed are methods of enhancing penetration of a co-composition into and through a tissue, the method comprising: exposing the tissue to a CendR element and the co-composition, thereby enhancing penetration of the co-composition into and through the tissue, wherein, prior to exposing the tissue, the CendR element and the co-composition are not covalently coupled or non-covalently associated with each other.

Also disclosed are compositions comprising a CendR element and a co-composition, wherein the CendR element and the co-composition are not covalently coupled or non-covalently associated with each other. Also disclosed are compositions comprising a protein or peptide and a co-composition, wherein the protein or peptide comprises a CendR element and an accessory peptide, wherein the CendR element and the co-composition are not covalently coupled or non-covalently associated with each other. Also disclosed are compositions comprising a protein or peptide and a co-composition, wherein the protein or peptide comprises an amino acid sequence, wherein the amino acid sequence comprises a CendR element and an accessory peptide, wherein the CendR element and the co-composition are not covalently coupled or non-covalently associated with each other. Also disclosed are compositions comprising a CendR element, an accessory molecule, and a co-composition, wherein the CendR element and the co-composition are not covalently coupled or non-covalently associated with each other, wherein the CendR element and the accessory molecule are covalently coupled or non-covalently associate with each other. In these compositions, the accessory peptide can overlap with the CendR element or be separate from the CendR element.

Examples of useful accessory molecules include homing molecules, targeting molecules, affinity ligands, cell penetrating molecules, endosomal escape molecules, subcellular targeting molecules, nuclear targeting molecules. Different accessory molecules can have similar or different functions from each other. Accessory molecules having similar functions, different functions, or both, can be associated a CendR element, CendR composition, CendR conjugate, CendR molecule, CendR compound, CendR protein, and/or CendR peptide.

Also disclosed are compositions comprising a protein or peptide and a co-composition, wherein the protein or peptide comprises a CendR element and a homing peptide, wherein the CendR element and the co-composition are not covalently coupled or non-covalently associated with each other. Also disclosed are compositions comprising a protein or peptide and a co-composition, wherein the protein or peptide comprises an amino acid sequence, wherein the amino acid sequence comprises a CendR element and a homing peptide, wherein the CendR element and the co-composition are not covalently coupled or non-covalently associated with each other. Also disclosed are compositions comprising a CendR element, a homing molecule, and a co-composition, wherein the CendR element and the co-composition are not covalently coupled or non-covalently associated with each other, wherein the CendR element and the homing molecule are covalently coupled or non-covalently associate with each other. In these compositions, the homing peptide can overlap with the CendR element or be separate from the CendR element.

Also disclosed are methods of enhancing internalization, penetration, or both of a cargo composition into or through a cell, tissue, or both, the method comprising: exposing the cell, tissue, or both to a CendR element and the cargo composition, thereby enhancing internalization, penetration, or both of the cargo composition into or through the cell, tissue, or both, wherein the CendR element and the cargo composition are covalently coupled or non-covalently associated with each other.

Also disclosed are methods of enhancing internalization of a cargo composition into a cell, the method comprising: exposing the cell to a CendR element and the cargo composition, thereby enhancing internalization of the cargo composition into the cell, wherein the CendR element and the cargo composition are covalently coupled or non-covalently associated with each other.

Disclosed are methods of enhancing penetration of a cargo composition into and through a tissue, the method comprising: exposing the tissue to a CendR element and the cargo composition, thereby enhancing penetration of the cargo composition into and through the tissue, wherein the CendR element and the cargo composition are covalently coupled or non-covalently associated with each other.

Also disclosed are compositions comprising a CendR element and a cargo composition, wherein the CendR element and the cargo composition are covalently coupled or non-covalently associated with each other. Also disclosed are compositions comprising a protein or peptide and a cargo composition, wherein the protein or peptide comprises a CendR element and an accessory peptide, wherein the CendR element and the cargo composition are covalently coupled or non-covalently associated with each other. Also disclosed are compositions comprising a protein or peptide and a cargo composition, wherein the protein or peptide comprises an amino acid sequence, wherein the amino acid sequence comprises a CendR element and an accessory peptide, wherein the CendR element and the cargo composition are covalently coupled or non-covalently associated with each other. Also disclosed are compositions comprising a CendR element, an accessory molecule, and a cargo composition, wherein the CendR element and the cargo composition are covalently coupled or non-covalently associated with each other, wherein the CendR element and the accessory molecule are covalently coupled or non-covalently associate with each other. In these compositions, the accessory peptide can overlap with the CendR element or be separate from the CendR element.

Also disclosed are compositions comprising a protein or peptide and a cargo composition, wherein the protein or peptide comprises a CendR element and a homing peptide, wherein the CendR element and the cargo composition are covalently coupled or non-covalently associated with each other. Also disclosed are compositions comprising a protein or peptide and a cargo composition, wherein the protein or peptide comprises an amino acid sequence, wherein the amino acid sequence comprises a CendR element and a homing peptide, wherein the CendR element and the cargo composition are covalently coupled or non-covalently associated with each other. Also disclosed are compositions comprising a CendR element, a homing molecule, and a cargo composition, wherein the CendR element and the cargo composition are covalently coupled or non-covalently associated with each other, wherein the CendR element and the homing molecule are covalently coupled or non-covalently associate with each other. In these compositions, the homing peptide can overlap with the CendR element or be separate from the CendR element.

In some forms, the CendR element is a type 1 CendR element. In some forms, the CendR element is a type 2 CendR element. In some forms, the CendR element is not a type 1 CendR element. In some forms, the CendR element is not a type 2 CendR element. In some forms, the CendR element is a type 1 CendR element and not a type 2 CendR element. In some forms, the CendR element is a type 2 CendR element and not a type 1 CendR element. In some forms, the CendR element is a type 1 CendR element or a type 2 CendR element.

The CendR element can permeabilize the cell, tissue, or both. The cell, tissue, or both can be in a subject. The cell, tissue, or both can be exposed to the CendR element and the co-composition by administering the CendR element and the co-composition to the subject. The CendR element and the co-composition can be administered to the subject simultaneously. The CendR element and the co-composition can be administered to the subject in a single composition comprising the CendR element and the co-composition. The CendR element and the co-composition can be administered to the subject in separate compositions. The CendR element and the co-composition can be administered to the subject at different times. The CendR element and the co-composition can be administered to the subject in separate compositions. The CendR element and the co-composition can be administered to the subject by separate routes. In some forms, the CendR element and the co-composition are not bound to each other. The cell, tissue, or both can be exposed to the CendR element and the cargo composition by administering the CendR element and the cargo composition to the subject.

The CendR element and the cargo composition can be administered to the subject simultaneously. The CendR element and the cargo composition can be administered to the subject in a single composition comprising the CendR element and the cargo composition.

Multiple different CendR elements, CendR peptides, CendR proteins, CendR compounds, CendR conjugates, CendR compositions, or a combination can be used together. Similarly, multiple different co-compositions, multiple different cargo compositions, or a combination can be used together. Where such multiple different CendR elements, CendR peptides, CendR proteins, CendR compounds, CendR conjugates, CendR compositions, or a combination are used together, they can be used with a single type of co-composition, a single type of cargo composition, multiple different co-compositions, multiple different cargo compositions, or a combination. Similarly, when multiple different co-compositions, multiple different cargo compositions, or a combination can be used together, they can be used with a single type of CendR element, CendR peptide, CendR protein, CendR compound, CendR conjugate, or CendR composition, or with multiple different CendR elements, CendR peptides, CendR proteins, CendR compounds, CendR conjugates, CendR compositions, or a combination.

For example, an iRGD (which combines a CendR element and an RGD element in a single peptide) can be used together with one or multiple different CendR elements, CendR peptides, CendR proteins, CendR compounds, CendR conjugates, CendR compositions, or a combination, one or multiple different co-compositions, multiple different cargo compositions, or a combination, or any combination of these. In such combinations, the iRGD itself can be combined in the same conjugate or composition with one or more cargo compositions, one or more accessory molecules, one or more homing molecules, etc.

The cell, tissue, or both can be exposed to combinations of different CendR components and combinations of different co-compositions by administering the CendR components and the co-compositions to the subject. One or more of the CendR components and one or more of the co-compositions can be administered to the subject simultaneously. One or more of the CendR components and one or more of the co-compositions can be administered to the subject in one or more single compositions comprising the CendR component(s) and the co-composition(s). One or more of the CendR components and one or more of the co-compositions can be administered to the subject in one or more separate compositions. One or more of the CendR components and one or more of the co-compositions can be administered to the subject at different times. The CendR element and the co-composition can be administered to the subject in one or more separate compositions. One or more of the CendR components and one or more of the co-compositions can be administered to the subject by one or more separate routes. In some forms, the CendR element and the co-composition are not bound to each other.

The cell, tissue, or both can be exposed to combinations of different CendR components and combinations of different cargo compositions by administering the CendR components and the cargo compositions to the subject. One or more of the CendR components and one or more of the cargo compositions can be administered to the subject simultaneously. One or more of the CendR components and one or more of the cargo compositions can be administered to the subject in one or more single compositions comprising the CendR component(s) and the cargo composition(s). One or more of the CendR components and one or more of the cargo compositions can be administered to the subject in one or more separate compositions. One or more of the CendR components and one or more of the cargo compositions can be administered to the subject at different times. The CendR element and the cargo composition can be administered to the subject in one or more separate compositions. One or more of the CendR components and one or more of the cargo compositions can be administered to the subject by one or more separate routes.

The cell, tissue, or both can be exposed to an iRGD and the co-composition by administering the iRGD and the co-composition to the subject. The iRGD and the co-composition can be administered to the subject simultaneously. The iRGD and the co-composition can be administered to the subject in a single composition comprising the iRGD and the co-composition. The iRGD and the co-composition can be administered to the subject in separate compositions. The iRGD and the co-composition can be administered to the subject at different times. The iRGD and the co-composition can be administered to the subject in separate compositions. The iRGD and the co-composition can be administered to the subject by separate routes. In some forms, the iRGD and the co-composition are not bound to each other. The cell, tissue, or both can be exposed to the iRGD and the cargo composition by administering the iRGD and the cargo composition to the subject. The iRGD and the cargo composition can be administered to the subject simultaneously. The iRGD and the cargo composition can be administered to the subject in a single composition comprising the iRGD and the cargo composition.

The CendR element can be comprised in an amino acid sequence in a protein or peptide. In some forms, the protein or peptide can be internalized into a cell, penetrate tissue, or both when the amino acid sequence is present in the protein or peptide but not when the amino acid sequence is not present in the protein or peptide. In some forms, the protein or peptide can penetrate tissue when the amino acid sequence is present in the protein or peptide but not when the amino acid sequence is not present in the protein or peptide. In some forms, the protein or peptide can be internalized into a cell and penetrate tissue when the amino acid sequence is present in the protein or peptide but not when the amino acid sequence is not present in the protein or peptide. In some forms, the amino acid sequence can be internalized into a cell, penetrate tissue, or both without being associated with the co-composition. In some forms, the amino acid sequence can penetrate tissue without being associated with the co-composition. In some forms, the amino acid sequence can be internalized into a cell and penetrate tissue without being associated with the co-composition. In some forms, the amino acid sequence is the only functional internalization element in the protein or peptide.

In some forms, the internalization, penetration, or both of the co-composition into or through a cell, tissue, or both is enhanced when the cell, tissue, or both is exposed to the CendR element but not when the cell, tissue, or both is not exposed to the CendR element. In some forms, the penetration of the co-composition into or through tissue is enhanced when the tissue is exposed to the CendR element but not when the tissue is not exposed to the CendR element. In some forms, the internalization and penetration of the co-composition into or through a cell and tissue is enhanced when the cell and tissue are exposed to the CendR element but not when the cell and tissue is not exposed to the CendR element. In some forms, the internalization, penetration, or both of the co-composition into or through a cell, tissue, or both is enhanced when the amino acid sequence is present in the protein or peptide but not when the amino acid sequence is not present in the protein or peptide. In some forms, the penetration of the co-composition into or through tissue is enhanced when the amino acid sequence is present in the protein or peptide but not when the amino acid sequence is not present in the protein or peptide. In some forms, the internalization and penetration of the co-composition into or through a cell and tissue is enhanced when the amino acid sequence is present in the protein or peptide but not when the amino acid sequence is not present in the protein or peptide.

In some forms, the internalization, penetration, or both of the cargo composition into or through a cell, tissue, or both is enhanced when the cell, tissue, or both is exposed to the CendR element but not when the cell, tissue, or both is not exposed to the CendR element. In some forms, the penetration of the cargo composition into or through tissue is enhanced when the tissue is exposed to the CendR element but not when the tissue is not exposed to the CendR element. In some forms, the internalization and penetration of the cargo composition into or through a cell and tissue is enhanced when the cell and tissue are exposed to the CendR element but not when the cell and tissue is not exposed to the CendR element. In some forms, the internalization, penetration, or both of the cargo composition into or through a cell, tissue, or both is enhanced when the amino acid sequence is present in the protein or peptide but not when the amino acid sequence is not present in the protein or peptide. In some forms, the penetration of the cargo composition into or through tissue is enhanced when the amino acid sequence is present in the protein or peptide but not when the amino acid sequence is not present in the protein or peptide. In some forms, the internalization and penetration of the cargo composition into or through a cell and tissue is enhanced when the amino acid sequence is present in the protein or peptide but not when the amino acid sequence is not present in the protein or peptide.

The CendR element can be associated with one or more accessory molecules. For example, an accessory molecule can be a part of an amino acid sequence, a protein, or a peptide that comprises the CendR element. As another example, the accessory molecule can be covalently coupled or non-covalently associated with the CendR element or an amino acid sequence, a protein, or a peptide that comprises the CendR element. The accessory molecule can be separate from or overlapping with the CendR element. For example, some accessory molecules are amino acid sequences. This can allow the amino acid sequence consisting of the CendR element to overlap the amino acid sequence that consists of the accessory amino acid sequence. For example, iRGD, LyP-1, iNGR, and RGR peptides each contain both an accessory sequence and CendR sequence overlapping with one another in the peptide. Alternatively the accessory peptide can be a separate entity that does not overlap with the CendR element. For example, a HER2 binding peptide, CREKA (SEQ ID NO:7) peptide, NGR peptide, or an RGD peptide that is not a CendR element can consist of amino acid sequence that does not overlap with a CendR element. In some forms, the accessory molecule can comprise a sequence in, for example, a CendR peptide that binds to a specific receptor distinct from the receptor for the CendR element.

The CendR element can be associated with one or more accessory molecules. For example, an accessory molecule can be a part of an amino acid sequence, a protein, or a peptide that comprises the CendR element. As another example, the accessory molecule can be covalently coupled or non-covalently associated with the CendR element or an amino acid sequence, a protein, or a peptide that comprises the CendR element. The accessory molecule can be separate from or overlapping with the CendR element. For example, some accessory molecules are amino acid sequences. This can allow the amino acid sequence consisting of the CendR element to overlap the amino acid sequence that consists of the accessory amino acid sequence. For example, iRGD, LyP-1, iNGR, and RGR peptides each contain both an accessory sequence and CendR sequence overlapping with one another in the peptide. Alternatively the accessory peptide can be a separate entity that does not overlap with the CendR element. For example, a HER2 binding peptide, CREKA peptide, NGR peptide, or an RGD peptide that is not a CendR element can consist of amino acid sequence that does not overlap with a CendR element. In some forms, the accessory molecule can comprise a sequence in, for example, a CendR peptide that binds to a specific receptor distinct from the receptor for the CendR element.

The amino acid sequence can comprise one or more accessory peptides. For example, the amino acid sequences can comprise a iRGD peptide, a LyP-1 peptide, a RGR peptide, a HER2 binding peptide, a CREKA (SEQ ID NO:7) peptide, a NGR peptide, iNGR, a RGD peptide that is not a CendR element, or a combination. The protein or peptide can comprise one or more accessory peptides. For example, the amino acid sequences can comprise a iRGD peptide, a LyP-1 peptide, a RGR peptide, a HER2 binding peptide, a CREKA (SEQ ID NO:7) peptide, a NGR peptide, iNGR, a RGD peptide that is not a CendR element, or a combination.

In some forms, the co-composition does not comprise an accessory molecule. The co-composition can comprise one or more accessory molecules. In some forms, the co-composition does not comprise an accessory peptide. The co-composition can comprise one or more accessory peptides. The co-composition can selectively home to a tumor. In some forms, the co-composition does not selectively home to tumor vasculature. The co-composition can selectively home to tumor vasculature. In some forms, the cargo composition does not comprise an accessory molecule. The cargo composition can comprise one or more accessory molecules. In some forms, the cargo composition does not comprise an accessory peptide. The cargo composition can comprise one or more accessory peptides. The cargo composition can selectively home to a tumor. In some forms, the cargo composition does not selectively home to tumor vasculature. The cargo composition can selectively home to tumor vasculature.

The CendR element can be associated with one or more homing molecules. For example, a homing molecule can be a part of an amino acid sequence, a protein, or a peptide that comprises the CendR element. As another example, the homing molecule can be covalently coupled or non-covalently associated with the CendR element or an amino acid sequence, a protein, or a peptide that comprises the CendR element. The homing molecule can be separate from or overlapping with the CendR element. For example, some homing molecules are amino acid sequences. This can allow the amino acid sequence consisting of the CendR element to overlap the amino acid sequence that consists of the homing amino acid sequence. For example, iRGD, LyP-1, iNGR, and RGR peptides each contain both a homing sequence and CendR sequence overlapping with one another in the peptide. Alternatively the homing peptide can be a separate entity that does not overlap with the CendR element. For example, a HER2 binding peptide, CREKA peptide, NGR peptide, or an RGD peptide that is not a CendR element can consist of amino acid sequence that does not overlap with a CendR element. In some forms, the homing molecule can comprise a sequence in, for example, a CendR peptide that binds to a specific receptor distinct from the receptor for the CendR element.

Many homing molecules and homing peptides home to the vasculature of the target tissue. However, for the sake of convenience homing is referred to in some places herein as homing to the tissue associated with the vasculature to which the homing molecule or homing peptide may actually home. Thus, for example, a homing peptide that homes to tumor vasculature can be referred to herein as homing to tumor tissue or to tumor cells. By including or associating a homing molecule or homing peptide with, for example, a protein, peptide, amino acid sequence, co-composition, cargo composition, or CendR element the protein, peptide, amino acid sequence, co-composition, cargo composition, or CendR element can be targeted or can home to the target of the homing molecule or homing peptide. In this way, the protein, peptide, amino acid sequence, co-composition, cargo composition, or CendR element can be said to home to the target of the homing molecule or homing peptide. For convenience and unless otherwise indicated, reference to homing of a protein, peptide, amino acid sequence, co-composition, cargo composition, CendR element, etc. is intended to indicate that the protein, peptide, amino acid sequence, co-composition, cargo composition, CendR element, etc. includes or is associated with an appropriate homing molecule or homing peptide.

The protein or peptide can selectively home to a tumor. The protein or peptide can selectively home to tumor vasculature. The protein or peptide can selectively home to one or more particular types of tumor. The protein or peptide can selectively home to the vasculature of one or more particular types of tumor. The protein or peptide can selectively home to one or more particular stages of a tumor or cancer. The protein or peptide can selectively home to the vasculature of one or more particular stages of a tumor or cancer. The protein or peptide can selectively home to one or more particular stages of one or more particular types of tumor. The protein or peptide can selectively home to the vasculature of one or more different stages of one or more particular types of tumor.

The protein or peptide can selectively home to lung tissue. The protein or peptide can selectively home to lung vasculature. The protein or peptide can selectively home to heart tissue. The protein or peptide can selectively home to heart vasculature. The protein or peptide can selectively home to brain cells, brain stem cells, brain tissue, and/or brain vasculature, kidney cells, kidney stem cells, kidney tissue, and/or kidney vasculature, skin cells, skin stem cells, skin tissue, and/or skin vasculature, lung cells, lung tissue, and/or lung vasculature, pancreatic cells, pancreatic tissue, and/or pancreatic vasculature, intestinal cells, intestinal tissue, and/or intestinal vasculature, adrenal gland cells, adrenal tissue, and/or adrenal vasculature, retinal cells, retinal tissue, and/or retinal vasculature, liver cells, liver tissue, and/or liver vasculature, prostate cells, prostate tissue, and/or prostate vasculature, endometriosis cells, endometriosis tissue, and/or endometriosis vasculature, ovary cells, ovary tissue, and/or ovary vasculature, tumor cells, tumors, tumor blood vessels, and/or tumor vasculature, bone cells, bone tissue, and/or bone vasculature, bone marrow cells, bone marrow tissue, and/or bone marrow vasculature, cartilage cells, cartilage tissue, and/or cartilage vasculature, stem cells, embryonic stem cells, pluripotent stem cells, induced pluripotent stem cells, adult stem cells, hematopoietic stem cells, neural stem cells, mesenchymal stem cells, mammary stem cells, endothelial stem cells, olfactory adult stem cells, neural crest stem cells, cancer stem cells, blood cells, erythrocytes, platelets, leukocytes, granulocytes, neutrophils, eosinphils, basophils, lymphoid cells, lymphocytes, monocytes, wound vasculature, vasculature of injured tissue, vasculature of inflamed tissue, atherosclerotic plaques, or a combination.

The amino acid sequence can be selected for internalization into a cell. The amino acid sequence can be selected for tissue penetration. The amino acid sequence can be selected for internalization into a cell and tissue penetration. The amino acid sequence can comprise one or more homing peptides. For example, the amino acid sequences can comprise a iRGD peptide, a LyP-1 peptide, a RGR peptide, a HER2 binding peptide, a CREKA (SEQ ID NO:7) peptide, a NGR peptide, iNGR, a RGD peptide that is not a CendR element, or a combination. The amino acid sequence can comprise a CREKA (SEQ ID NO:7) peptide.

The protein or peptide can comprise one or more homing peptides. For example, the amino acid sequences can comprise a iRGD peptide, a LyP-1 peptide, a RGR peptide, a HER2 binding peptide, a CREKA (SEQ ID NO:7) peptide, a NGR peptide, iNGR, a RGD peptide that is not a CendR element, or a combination. The protein or peptide can comprise iRGD. The protein or peptide can comprise a LyP-1 peptide. The protein or peptide can comprise iNGR. The protein or peptide can comprise RGR peptide. The protein or peptide can comprise a CREKA (SEQ ID NO:7) peptide.

In some forms, the CendR element and the co-composition are not covalently coupled or non-covalently associated with each other. In some forms, the co-composition does not comprise a functional internalization element. The co-composition can comprise a functional internalization element. In some forms, the co-composition does not comprise a homing molecule. The co-composition can comprise one or more homing molecules. In some forms, the co-composition does not comprise a homing peptide. The co-composition can comprise one or more homing peptides. The co-composition can selectively home to a tumor. In some forms, the co-composition does not selectively home to tumor vasculature. The co-composition can selectively home to tumor vasculature.

In some forms, the CendR element and the cargo composition are not covalently coupled or non-covalently associated with each other. In some forms, the cargo composition does not comprise a functional internalization element. The cargo composition can comprise a functional internalization element. In some forms, the cargo composition does not comprise a homing molecule. The cargo composition can comprise one or more homing molecules. In some forms, the cargo composition does not comprise a homing peptide. The cargo composition can comprise one or more homing peptides. The cargo composition can selectively home to a tumor. In some forms, the cargo composition does not selectively home to tumor vasculature. The cargo composition can selectively home to tumor vasculature.

The amino acid sequence can selectively home to a tumor. The amino acid sequence can selectively home to tumor vasculature. The amino acid sequence can selectively home to one or more particular types of tumor. The amino acid sequence can selectively home to the vasculature of one or more particular types of tumor. The amino acid sequence can selectively home to one or more particular stages of a tumor or cancer. The amino acid sequence can selectively home to the vasculature of one or more particular stages of a tumor or cancer. The amino acid sequence can selectively home to one or more particular stages of one or more particular types of tumor. The amino acid sequence can selectively home to the vasculature of one or more different stages of one or more particular types of tumor.

The amino acid sequence can selectively home to lung tissue. The amino acid sequence can selectively home to lung vasculature. The amino acid sequence can selectively home to heart tissue. The amino acid sequence can selectively home to heart vasculature. The amino acid sequence can selectively home to brain cells, brain stem cells, brain tissue, and/or brain vasculature, kidney cells, kidney stem cells, kidney tissue, and/or kidney vasculature, skin cells, skin stem cells, skin tissue, and/or skin vasculature, lung cells, lung tissue, and/or lung vasculature, pancreatic cells, pancreatic tissue, and/or pancreatic vasculature, intestinal cells, intestinal tissue, and/or intestinal vasculature, adrenal gland cells, adrenal tissue, and/or adrenal vasculature, retinal cells, retinal tissue, and/or retinal vasculature, liver cells, liver tissue, and/or liver vasculature, prostate cells, prostate tissue, and/or prostate vasculature, endometriosis cells, endometriosis tissue, and/or endometriosis vasculature, ovary cells, ovary tissue, and/or ovary vasculature, tumor cells, tumors, tumor blood vessels, and/or tumor vasculature, bone cells, bone tissue, and/or bone vasculature, bone marrow cells, bone marrow tissue, and/or bone marrow vasculature, cartilage cells, cartilage tissue, and/or cartilage vasculature, stem cells, embryonic stem cells, pluripotent stem cells, induced pluripotent stem cells, adult stem cells, hematopoietic stem cells, neural stem cells, mesenchymal stem cells, mammary stem cells, endothelial stem cells, olfactory adult stem cells, neural crest stem cells, cancer stem cells, blood cells, erythrocytes, platelets, leukocytes, granulocytes, neutrophils, eosinphils, basophils, lymphoid cells, lymphocytes, monocytes, wound vasculature, vasculature of injured tissue, vasculature of inflamed tissue, atherosclerotic plaques, or a combination.

The CendR element can selectively home to a tumor when it is coupled to or associated with a homing molecule. Such CendR element can selectively home to tumor vasculature. A CendR element coupled to or associated with a homing molecule can selectively home to one or more particular types of tumor. A CendR element coupled to or associated with a homing molecule can selectively home to the vasculature of one or more particular types of tumor. A CendR element coupled to or associated with a homing molecule can selectively home to one or more particular stages of a tumor or cancer. A CendR element coupled to or associated with a homing molecule can selectively home to the vasculature of one or more particular stages of a tumor or cancer. A CendR element coupled to or associated with a homing molecule can selectively home to one or more particular stages of one or more particular types of tumor. A CendR element coupled to or associated with a homing molecule can selectively home to the vasculature of one or more different stages of one or more particular types of tumor.

A CendR element coupled to or associated with a homing molecule can selectively home to lung tissue. A CendR element coupled to or associated with a homing molecule can selectively home to lung vasculature. A CendR element coupled to or associated with a homing molecule can selectively home to heart tissue. A CendR element coupled to or associated with a homing molecule can selectively home to heart vasculature. A CendR element coupled to or associated with a homing molecule can selectively home to brain cells, brain stem cells, brain tissue, and/or brain vasculature, kidney cells, kidney stem cells, kidney tissue, and/or kidney vasculature, skin cells, skin stem cells, skin tissue, and/or skin vasculature, lung cells, lung tissue, and/or lung vasculature, pancreatic cells, pancreatic tissue, and/or pancreatic vasculature, intestinal cells, intestinal tissue, and/or intestinal vasculature, adrenal gland cells, adrenal tissue, and/or adrenal vasculature, retinal cells, retinal tissue, and/or retinal vasculature, liver cells, liver tissue, and/or liver vasculature, prostate cells, prostate tissue, and/or prostate vasculature, endometriosis cells, endometriosis tissue, and/or endometriosis vasculature, ovary cells, ovary tissue, and/or ovary vasculature, tumor cells, tumors, tumor blood vessels, and/or tumor vasculature, bone cells, bone tissue, and/or bone vasculature, bone marrow cells, bone marrow tissue, and/or bone marrow vasculature, cartilage cells, cartilage tissue, and/or cartilage vasculature, stem cells, embryonic stem cells, pluripotent stem cells, induced pluripotent stem cells, adult stem cells, hematopoietic stem cells, neural stem cells, mesenchymal stem cells, mammary stem cells, endothelial stem cells, olfactory adult stem cells, neural crest stem cells, cancer stem cells, blood cells, erythrocytes, platelets, leukocytes, granulocytes, neutrophils, eosinphils, basophils, lymphoid cells, lymphocytes, monocytes, wound vasculature, vasculature of injured tissue, vasculature of inflamed tissue, atherosclerotic plaques, or a combination.

The CendR element can be the only functional internalization element in the CendR composition, conjugate, molecule, protein, peptide, etc., the CendR element can be the only functional tissue penetration element in the CendR composition, conjugate, molecule, protein, peptide, etc., or both. The selected amino acid sequence can be the only functional internalization element in the CendR composition, conjugate, molecule, protein, peptide, etc., the selected amino acid sequence can be the only functional tissue penetration element in the CendR composition, conjugate, molecule, protein, peptide, etc., or both.

The CendR element can be an activatable CendR element. The CendR element can be a protease-activatable CendR element. The protein or peptide can be circular (cyclic) or can contain a loop. The CendR element can be at the C-terminal end of the protein or peptide. The CendR element can comprise a terminal carboxyl group. A blocking group can be coupled to the terminal carboxyl group. The bond coupling the blocking group and the terminal carboxyl group can be selected to be cleavable by a protease, enzyme, cleaving agent, and/or cleaving conditions present in proximity to the cell of interest. The blocking group can be coupled to the C-terminal amino acid of the CendR element. The blocking group can be coupled to an amino acid of the CendR element other than the C-terminal amino acid of the CendR element.

Also disclosed are methods of producing an activatable CendR element that can be activated in proximity to a cell of interest, the method comprising forming an activatable CendR element wherein a blocking group is coupled to a CendR element via a cleavable bond, wherein the cleavable bond is cleavable by an enzyme, cleaving agent, and/or cleaving conditions present in proximity to the cell of interest. The cell can be in a subject. The enzyme, cleaving agent, and/or cleaving conditions that is present in proximity to the cell of interest can be identified. The enzyme, cleaving agent, and/or cleaving conditions present in proximity to the cell of interest can be identified prior to forming the activatable CendR element. The cleavable bond can be selected based on the enzyme that is present in proximity to the cell of interest. The cleavable bond can be selected based on the cleaving agent present at site where the CendR element is delivered, homes, travels or accumulates, such as the cell of interest. The cleavable bond can be selected based on the cleaving conditions present at site where the CendR element is delivered, homes, travels or accumulates, such as the cell of interest. The cleavable bond can be selected prior to forming the activatable CendR element. The CendR element can comprise a terminal carboxyl group, wherein the blocking group is coupled to the terminal carboxyl group. Also disclosed are methods of producing an activatable CendR element, the method comprising forming an activatable CendR element wherein a blocking group is coupled to a CendR element via a cleavable bond. The cleavable bond can be cleaved in any suitable way. For example, the cleavable bond can be cleaved enzymatically or non-enzymatically. For enzymatic cleavage, the cleaving enzyme can be supplied or can be present at a site where the CendR element is delivered, homes, travels or accumulates. For example, the enzyme can be present in proximity to a cell to which the CendR element is delivered, homes, travels, or accumulates. For non-enzymatic cleavage, the CendR element can be brought into contact with a cleaving agent, can be placed in cleaving conditions, or both. A cleaving agent is any substance that can mediate or stimulate cleavage of the cleavable bond. Cleaving conditions can be any solution or environmental conditions that can mediate or stimulate cleavage of the cleavable bond.

Also disclosed are methods of forming an activatable CendR element, the method comprising causing a blocking group to be covalently coupled to a CendR element, wherein a bond coupling the blocking group and the CendR element is cleavable. Also disclosed are methods of forming an activatable CendR element, the method comprising causing a blocking group to be covalently coupled to an amino acid sequence, wherein the amino acid sequence comprises a CendR element the CendR element, wherein a bond coupling the blocking group and the CendR element is cleavable. Also disclosed are methods of forming an activatable CendR element, the method comprising (a) selecting an amino acid sequence for internalization into a cell and/or penetration of tissue, wherein the amino acid sequence comprises a CendR element, and (b) causing a blocking group to be covalently coupled to the CendR element, wherein a bond coupling the blocking group and the CendR element is cleavable. The blocking group covalently coupled to the CendR element reduces or prevents internalization into a cell and/or penetration of tissue. The blocking group covalently coupled to the CendR element can reduce or prevent internalization into a cell and/or penetration of tissue compared to the same CendR element with no blocking group. The activatable CendR element can comprise the selected amino acid sequence and the blocking group. The cell can be in a subject. The enzyme, cleaving agent, and/or cleaving conditions present in proximity to the cell of interest can be identified. The enzyme, cleaving agent, and/or cleaving conditions present in proximity to the cell of interest can be identified prior to forming the activatable CendR element. The cleavable bond can be selected based on the enzyme that is present in proximity to the cell of interest. The cleavable bond can be selected based on the cleaving agent present at site where the CendR element is delivered, homes, travels or accumulates, such as the cell of interest. The cleavable bond can be selected based on the cleaving conditions present at site where the CendR element is delivered, homes, travels or accumulates, such as the cell of interest. The cleavable bond can be selected prior to forming the activatable CendR element. The CendR element can comprise a terminal carboxyl group, wherein the blocking group is coupled to the terminal carboxyl group.

Disclosed herein is a method of forming a homing CendR composition, the method comprising selecting an amino acid sequence for internalization into a cell, wherein the amino acid sequence comprises a C-terminal element, and causing a homing molecule to be covalently coupled to or non-covalently associated with the selected amino acid sequence, wherein the CendR composition comprises the selected amino acid sequence and the coupled or associated homing molecule.

Disclosed is a method of making a homing CendR composition comprising: (a) selecting an amino acid sequence for internalization into a cell, wherein the amino acid sequence comprises a C-terminal element, (b) causing a homing molecule to be covalently coupled to or non-covalently associated with the selected amino acid sequence, wherein the CendR composition comprises the selected amino acid sequence and the coupled or associated homing molecule.

Also disclosed is a method of delivering a co-composition into a cell, the method comprising: exposing the cell to a CendR composition and the co-composition, wherein the CendR composition can then enter the cell, thereby delivering the co-composition into the cell.

Also disclosed is a method of causing a co-composition to penetrate tissue, the method comprising: exposing the tissue to a CendR composition and the co-composition, wherein the CendR composition can then enter and exit cells in the tissue, thereby causing the co-composition to penetrate the tissue.

Further disclosed is a method of delivering a co-composition into a cell, the method comprising: exposing the cell to the co-composition and a CendR composition comprising an activatable CendR element, whereupon a cleaving agent activates the activatable CendR element of the CendR composition, wherein the CendR composition can then enter the cell, thereby delivering the co-composition into the cell.

Further disclosed is a method of causing a co-composition to penetrate tissue, the method comprising: exposing the tissue to the co-composition and a CendR composition comprising an activatable CendR element, whereupon a cleaving agent activates the activatable CendR element of the CendR composition, wherein the CendR composition can then enter and pass cells in the tissue, thereby causing the co-composition to penetrate the tissue.

Also disclosed is a method of delivering a cargo composition into a cell, the method comprising: exposing the cell to a CendR composition and the cargo composition, wherein the CendR composition can then enter the cell, thereby delivering the cargo composition into the cell.

Also disclosed is a method of causing a cargo composition to penetrate tissue, the method comprising: exposing the tissue to a CendR composition and the cargo composition, wherein the CendR composition can then enter and exit cells in the tissue, thereby causing the cargo composition to penetrate the tissue.

Further disclosed is a method of delivering a cargo composition into a cell, the method comprising: exposing the cell to the cargo composition and a CendR composition comprising an activatable CendR element, whereupon a cleaving agent activates the activatable CendR element of the CendR composition, wherein the CendR composition can then enter the cell, thereby delivering the cargo composition into the cell.

Further disclosed is a method of causing a cargo composition to penetrate tissue, the method comprising: exposing the tissue to the cargo composition and a CendR composition comprising an activatable CendR element, whereupon a cleaving agent activates the activatable CendR element of the CendR composition, wherein the CendR composition can then enter and pass cells in the tissue, thereby causing the cargo composition to penetrate the tissue.

Also disclosed is a method of delivering a cargo composition into a cell, the method comprising: exposing the cell to a CendR composition and the cargo composition, wherein the CendR composition comprises the cargo composition, wherein the CendR composition can then enter the cell, thereby delivering the cargo composition into the cell.

Also disclosed is a method of causing a cargo composition to penetrate tissue, the method comprising: exposing the tissue to a CendR composition and the cargo composition, wherein the CendR composition comprises the cargo composition, wherein the CendR composition can then enter and exit cells in the tissue, thereby causing the cargo composition to penetrate the tissue.

Further disclosed is a method of delivering a cargo composition into a cell, the method comprising: exposing the cell to the cargo composition and a CendR composition comprising an activatable CendR element, whereupon a cleaving agent activates the activatable CendR element of the CendR composition, wherein the CendR composition can then enter the cell, thereby delivering the cargo composition into the cell, wherein the CendR composition comprises the cargo composition.

Further disclosed is a method of causing a cargo composition to penetrate tissue, the method comprising: exposing the tissue to the cargo composition and a CendR composition comprising an activatable CendR element, whereupon a cleaving agent activates the activatable CendR element of the CendR composition, wherein the CendR composition can then enter and pass cells in the tissue, thereby causing the cargo composition to penetrate the tissue, wherein the CendR composition comprises the cargo composition.

Cells that can internalize a CendR element can be identified by (a) exposing a cell to a CendR element; and (b) determining if the CendR element was internalized. The cell can be in an assay, for example. The CendR element can be coupled to a homing molecule, thereby forming a CendR composition. Cells that can internalize an activatable CendR element can be identified by (a) exposing a cell to an activatable CendR element; (b) determining if the activatable CendR element was internalized. The activatable CendR element can be unblocked before exposure to the cell, but does not need to be. This can be used to test the blocking ability of the blocker, for example. The activatable CendR element can also be a protease-activated CendR element.

Cancer cells, or subjects harboring cancer cells, can be identified as candidates for CendR-based therapy by (a) exposing the cancer cell to a CendR element; and (b) determining if the CendR element was internalized by the cancer cell, wherein an internalized CendR element identifies the cancer cell or the subject as being a candidate for CendR-based therapy. The cell can be in an assay, or can be in a subject, for example. The CendR element can be coupled to a homing molecule, thereby forming a CendR composition.

Tumors, or subjects harboring a tumor, can be identified as a candidate for CendR-based therapy by (a) exposing tissue from the tumor to a CendR element; and (b) determining if the CendR element passed through the tissue or was internalized by cells in the tissue, wherein a passed-through or internalized CendR element identifies the tumor or the subject as being a candidate for CendR-based therapy.

An activatable CendR element that can be activated in proximity to a cell of interest can be made by forming an activatable CendR element wherein a blocking group is coupled to a CendR element via a cleavable bond, wherein the cleavable bond is cleavable by an enzyme present in proximity to the cell of interest. This can further comprise, prior to forming the activatable CendR element, identifying the enzyme, cleaving agent, and/or cleaving conditions present in proximity to the cell of interest. This can further comprise, prior to forming the activatable CendR element, selecting the cleavable bond based on the enzyme, cleaving agent, and/or cleaving conditions present in proximity to the cell of interest.

An activatable CendR element can be formed by (a) selecting an amino acid sequence for internalization into a cell, wherein the amino acid sequence comprises a C-terminal element, wherein the C-terminal element comprises a terminal carboxyl group, and (b) causing a blocking group to be covalently coupled to the terminal carboxyl group of the selected amino acid sequence, wherein the bond coupling the blocking group and the terminal carboxyl group is cleavable, wherein the activatable CendR element comprises the selected amino acid sequence and the blocking group. This can further comprise, prior to step (b), selecting the bond coupling the blocking group and the terminal carboxyl group to be cleavable by a protease, enzyme, cleaving agent, and/or cleaving conditions present in proximity to the cell of interest.

Activatable CendR element can be made by the method comprising (a) selecting an amino acid sequence for internalization into a cell, wherein the amino acid sequence comprises a C-terminal element, wherein the C-terminal element comprises a terminal carboxyl group, and (b) causing a blocking group to be covalently coupled to the terminal carboxyl group of the selected amino acid sequence, wherein the bond coupling the blocking group and the terminal carboxyl group is cleavable, wherein the activatable CendR element comprises the selected amino acid sequence and the blocking group. The method can further comprise, prior to step (b), selecting the bond coupling the blocking group and the terminal carboxyl group to be cleavable by a protease, enzyme, cleaving agent, and/or cleaving conditions present in proximity to the cell of interest.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 4A, Fluorescein-labeled (FAM) iRGD or control peptide (200 µg in PBS) was intravenously injected into LSL-Kras, p53-fl/+, p48-Cre mice bearing de novo pancreatic ductal adenocarcinoma (PDAC). The peptides were allowed to circulate for 2 hrs. and organs were collected and viewed under UV light. Arrowheads point to the tumors. Dotted lines show where the organs were placed. FIG. 4B, Confocal images of orthotopic 22Rv-1 human prostate cancer xenografts from mice injected with the indicated peptides, phage, and micelles. iRGD was compared to a similar integrin-binding but non-penetrating peptide, CRDGC (SEQ ID NO:36). The circulation time was 2 hrs. for the free peptides, 15 min. for the peptide-displaying phage, and 3 hrs. for the peptide-coupled micelles. Arrows point to FAM-CRGDC peptide or CRGDC phage in or just outside the vessel walls, illustrating its homing to the tumor vasculature. Representative fields from multiple sections of each of these three tumors are shown. Scale bars=50 µm. FIG. 4C, Quantification of tumor homing area of iRGD and CRGDC peptides. Cryo-sections of 22Rv-1 orthotopic tumors from mice injected with FAM-iRGD or FAM-CRGDC peptide were immunohistochemically stained with an anti-FITC antibody. The samples were subjected to image analysis with Scanscope CM-1 scanner for quantification of the FAM-positive areas. Statistical analysis was performed with Student's t-test. n=3; error bars, s.e.m.; triple asterisk, $p<0.001$.

FIGS. 5A and 5B show tumor-specific entry of Evans Blue (albumin) into extravascular tumor tissue in iRGD-injected mice. iRGD is SEQ ID NO:3. iRGDD is SEQ ID NO:4. Mice bearing orthotopically transplanted pancreatic or breast cancer xenografts were injected with 1 µg of Evans Blue, followed 5 min later by 100 µg of iRGD peptide in PBS, PBS alone, or a control peptide. Tumors and tissues were collected 30 min. later and examined for dye content. FIG. 5A shows that the tumors of iRGD-injected mice contain more blue color than the control tumors. FIG. 5B shows quantification of the results from mice with the pancreatic tumors and non-tumor tissues of the same mice. About 4 times more dye accumulated in the iRGD-treated tumors than in control tumors. The control peptides included non-CendR RGD peptides.

FIGS. 6A and 6B show tumor penetration assay ex vivo. PPC1 human prostate cancer subcutaneous xenografts were excised and maintained in short-term culture containing $10^{10}$ phage particles/ml, iRGD in FIG. 6A, and control phage with a CG7C insert in FIG. 6B. After 90 min. at 37° C., the tumors were washed, fixed, and sectioned. Phage was detected with antibodies against the phage coat protein. Note that the iRGD phage has penetrated deep into the tumor. Scale bar 200 µm.

(FIG. 9A) Evans Blue accumulation in tissues of mice injected with iRGD (main panel) and in the tumor of a PBS-injected control mouse (inset). Note the dark blue color in the primary tumor and a tumor that has invaded the left kidney (arrowheads) of the iRGD-injected mouse. T, tumor; P, pancreas; S, spleen. (FIGS. 9B to 9D) Quantification of Evans Blue in the pancreatic tumors and tissues. In (FIG. 9B), different amounts of iRGD were injected. In (FIG. 9C), the effect of iRGD was compared with that of control RGD peptides that lack the RXXK/R CendR sequence (SEQ ID NO:6). In (FIG. 9D), 50 µg of an anti-neuropilin-1 blocking antibody or a control IgG was injected before iRGD. Statistical analyses were done with ANOVA in (FIG. 9B) and (FIG. 9D), and Student's t-test in (FIG. 9C). n=3; error bars, s.e.m.; double asterisk, $p<0.01$; triple asterisk, $p<0.001$.

(FIG. 10A) Macroscopic appearance of tissues and the following tumors are shown; orthotopic xenografts of BT474 human breast and 22Rv1 human prostate cancer, and genetically engineered de novo mouse pancreatic ductal adenocarcinoma (PDAC). (FIG. 10B) Macroscopic appearance of GFP-PC-3 disseminated tumors generated by intracardiac injection of the tumor cells and normal tissues are shown. Note the blue color in the tumors from mice that received both the dye and iRGD, including many of the small nodules in the GFP-PC-3 disseminated tumor model (left upper panel, arrowheads). The green fluorescent signals (white coloring) in the right panels of the GFP-PC-3 disseminated tumors show the location of the tumor nodules. (FIG. 10C) Quantification of Evans Blue in jaw tumors of the GFP-PC-3 disseminated tumor model. Note the tumor-specific accumulation of the dye when iRGD was co-injected with the dye, but not when the co-injection was with control RGD peptides that lack the RXXK/R CendR motif (SEQ ID NO:6) or PBS only. Statistical analysis was performed with Student's t-test; error bars, s.e.m.; double asterisk, $p<0.01$; n=3.

(FIG. 13A) Immunofluorescence of the tumors. For FAM-CRGDC (SEQ ID NO:36), images taken under UV light are also shown (left most panels). The dotted lines show where the tissues were placed. Phage were detected with a T7 phage antibody. Colors are described in the panels. The light colored specs represent FAM-CRGDC (SEQ ID NO:36) positive staining; the light gray areas represent Dextran positive staining; the light colored specs represent Iron-oxide nanoworms or phage staining. Scale bars=100 µm. (FIG. 13B) Quantification of the positive areas for the FAM-CRGDC (SEQ ID NO:36) and dextrans in the tumor sections. Cryosections were stained immunohistochemically with an anti-FITC antibody (FAM-CRGDC) (SEQ ID NO:36) or an anti-dextran antibody (dextrans), and scanned with Scanscope for analysis. (FIG. 13C) Quantification of phage accumulated in the tissues based on phage titer.

(FIGS. 14A and 14B) Nude mice bearing orthotopic 22Rv1 human prostate tumors were intravenously injected with DOX-liposomes (3 mg DOX/kg) followed 5 min later by 100 nmol iRGD or PBS. Tumors and tissues were collected 3 hours later. In (FIG. 14A), the tumors were sectioned and stained with an anti-CD31 antibody. The doxorubicin is represented by the light specs that look like four halos in the left panel. Scale bars=200 µm, n=3. In (FIG. 14B), DOX in the tissues was quantified. (FIG. 14C) Nude mice bearing 2 week-old orthotopic 22Rv1 tumors received daily intravenous injections of DOX-liposomes (1 or 3 mg DOX/kg) or PBS, combined with 2 µmol/kg iRGD, cyclo(-RGDfK-) (SEQ ID NO:40), or PBS. The tumors were harvested and weighed after 17 days of treatment. The number of mice in each group was 5. One of 3 experiments that gave similar results is shown. (FIG. 14D) TUNEL staining was performed immunohistochemically on tissue sections of the tumor and heart samples from the treatment study, and quantified for positivity. Statistical analyses were performed with Student's t-test in (FIG. 14B), and ANOVA in (FIG. 14C) and (FIG. 14D); error bars, s.e.m.; n.s., not significant; single asterisk, $p<0.05$; double asterisk, $p<0.01$; triple asterisk, $p<0.001$.

(FIGS. 18A and 18B) Mice bearing orthotopic BT474 human breast tumors were intravenously injected with Herceptin (3 mg/kg) followed 5 min later by 100 nmol iRGD or PBS. Tissues were collected 3 hours later. In (FIG. 18A), tumor sections were immunohistochemically stained for Herceptin with an anti-human IgG antibody, and the positive areas (darker shadings) were quantified. n=3. In (FIG. 18B), Herceptin in the tissues was quantified with a competitive ELISA. n=3. (FIG. 18C) Tumor treatment study with co-administration of Herceptin and iRGD. BT474 tumor mice were intravenously injected every 4 days for 24 days with Herceptin at 3 or 9 mg/kg on the first day of treatment (day 0 in the graph) and 1.5 or 4.5 mg/kg in subsequent injections, or PBS. The treatment was combined with daily injections of 4 µmol/kg iRGD or PBS on the days of Herceptin injection, and 2 µmol/kg iRGD or PBS on the other days. The number of mice in each group was 10. One of 4 experiments that gave similar results is shown. Statistical analyses were performed with Student's t-test in (FIG. 18A) and (FIG. 18B), and ANOVA in (FIG. 18C); error bars, s.e.m.; n.s., not significant; single asterisk, p<0.05; double asterisk, p<0.01; triple asterisk, p<0.001.

DETAILED DESCRIPTION OF THE INVENTION

Figure 1:
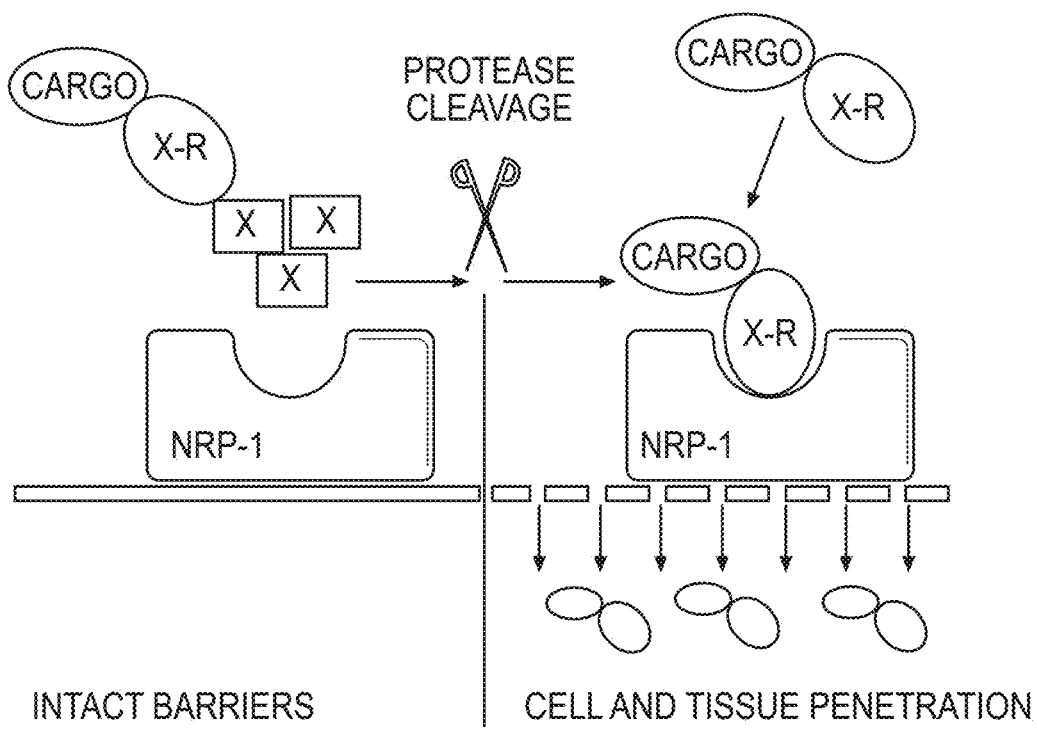
FIG. 1 shows a schematic representation the tissue-targeting/tissue-penetrating CendR system.

The disclosed method and compositions can be understood more readily by reference to the following detailed description of particular embodiments and the Examples included therein and to the Figures and their previous and following description.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

B. General

Disclosed herein is a new technological platform that enables intracellular delivery, exit and tissue penetration of compositions. The delivery can be general and can be targeted to cells or tissues of interest, such as tumors. Internalization of compositions (including nanoparticles, drugs, detectable markers, and other compounds) and their payload into target cells and penetration into target tissue can increase the efficiency of the targeting. Cell type-specific internalization and tissue type-specific penetration of payloads without covalent coupling or non-covalent association of the payload with cell or tissue-specific penetrating peptides has not previously been achievable.

Cell-penetrating delivery vehicles are important in a number of ways. First, cell-penetrating targeting elements can take payloads into the cytoplasm, which is critical, for example, in the delivery of nucleic acid-based therapeutics. Second, internalization can improve targeting because internalization of the peptide and its payload into cells makes the homing more effective (Christian et al., 2003; Jiang et al., 2004; Laakkonen et al., 2004; Weissleder at al., 2005). Third, as described here, cell-penetrating properties, combined with tissue-penetrating properties enhance extravasation and tissue spread. Tat, penetratin and other prototypic cell-penetrating peptides have not been ascribed tissue-penetrating properties.

The disclosed CendR peptides are different from the prototypic cell-penetrating peptides (CPPs) in that the cell-penetrating properties of CendR peptides depend on stereo-specific binding to a specific cell surface receptor, whereas both L-amino acid and D-amino acid CPPs are active (Langel, 2007; Meade and Dowdy, 2007). Moreover, the CendR peptides can be specific for a particular pathological lesion (such as tumors) or an individual tissue.

The ability of compositions to penetrate into the extravascular space is a major factor limiting the targeting efficacy of compositions in vivo. A simple peptide motif, with a C-terminal element as a defining feature, has been identified that signals highly efficient internalization of phage and free peptides into cells. This internalization phenomenon has been named the "C-end rule" or "CendR". Proteolysis that uncovers a C-terminal element can serve as a switch that triggers the internalization signal. Various compositions can be internalized through this mechanism. For example, homing peptide-mediated accumulation can occur at a target site with general or cell type-specific proteolysis that exposes a C-terminal element which allows for highly specific homing systems with target-triggered internalization. The CendR pathway can also be used for exit of compositions of interest from the vasculature and their spread into tissue. The C-terminal element can cause spread of compositions from the vasculature (and thus can be spread into tumor tissue from an intravenous injection, for example). CendR elements can also be used to mediate passage of compositions of interest through other CendR-capable membranes, such as mucous membranes and the blood-brain barrier. As used herein, "tissue penetration" and "penetration of tissue" refer to passage into or through a tissue beyond or through the outer or a first layer of cells or through a tissue membrane. Such passage or penetration through tissue (which can also be referred to as extravasation and tissue penetration) can be a function of, for example, cell internalization and passage between cells in the tissue. Throughout this application, when the term "tissue penetration" is used, it is understood that such penetration can also extend to other barriers and CendR-capable membranes found throughout the body, such as the blood brain barrier.

Unlike the known cell-penetrating peptides, the disclosed internalizing element is position-dependent—it is inactive when present in positions other than the C-terminus of the peptide. Another distinguishing feature is that the CendR element is stereo-specific; that is, CendR elements composed entirely of D-amino acids are inactive. A latent CendR peptide can be activated by cleavage by, for example, the appropriate proteolytic enzyme to expose, for example, a C-terminal arginine, lysine, or lysine-glycine. Throughout the application, when the term "CendR element" or "C-terminal element" is used, it is used to describe a C-terminal arginine, a C-terminal lysine, or a C-terminal lysine-glycine pair, where glycine is at the furthest C-terminal position. In other words, in the case where a lysine is on the C terminus end, the CendR element can remain functional with a glycine on the C terminus side of the lysine. However, it is not necessary to have glycine on the end in order for the lysine residue to be functional as a C-terminal element, so that lysine can be present without glycine and still be functional. The converse is not true, however, in that glycine cannot function as a C-terminal element without the presence of lysine adjacent to it. Arginine does not require either lysine or glycine to function as a C-terminal element, as long as it remains in the furthest C-terminal position. Such CendR elements can be referred to as type 1 CendR elements.

The term "CendR element" or "C-terminal element" can also be used to describe a C-terminal histidine and amino acid sequences having the sequence $X_1X_2X_3X_4$, where $X_1$ can be R, K or H, where $X_4$ can be R, K, H, or KG, and where $X_2$ and $X_3$ can each be, independently, any amino acid. Such CendR elements can be referred to as type 2 CendR elements. The $X_2$ and $X_3$ amino acids can be selected for specific purposes. For example, $X_2$, $X_3$, or both can be chosen to form all or a portion of a protease recognition sequence. This would be useful, for example, to specify or enable cleavage of a peptide having the CendR element as a latent or cryptic CendR element that is activated by cleavage following the $X_4$ amino acid. Examples of such amino acid choices are shown in Tables 1 and 2. The $X_1$, $X_2$ and $X_3$ amino acids can also be selected, for example, to recruit additional proteins to NRP-1 molecules at the cell surface. This can be applied, for example, to modulate the selectivity and internalization and/or tissue penetration potency of CendR elements (and the compositions, conjugates, proteins, and peptides containing CendR elements). The $X_2$ and $X_3$ amino acids can also be selected to prevent protease cleavage within the $X_1$-$X_4$ motif. For example, $X_2$ and/or $X_3$ can be proline, which reduces or eliminates protease cleavage, such as by carboxypeptidase, between the proline and the next downstream amino acid. As another example, one or more of the bonds between $X_1$, $X_2$, $X_3$, and/or $X_4$ can be modified to reduce or eliminate protease cleavage at those bonds. Optionally, certain amino acids can also be excluded from use for $X_2$, $X_3$, or both. For example, if desired, G and D can be excluded from simultaneous use as $X_2$ and $X_3$, respectively. Some type 2 CendR elements can also be described as R/K/HXXR/K/H (SEQ ID NO:20), R/KXXR/K (SEQ ID NO:23), and R/K/HXXKG (SEQ ID NO:21).

Examples of CendR elements include XXR/K/H, XXR/K, XXR/H, XXK/H, XXR, XXK, XXH, XXKG, RXXR/K/H, RXXR/K, RXXR/H, RXXK/H, RXXR, RXXK, RXXH, RXXKG, KXXR/K/H, KXXR/K, KXXR/H, KXXK/H, KXXR, KXXK, KXXH, KXXKG, HXXR/K/H, HXXR/K, HXXR/H, HXXK/H, HXXR, HXXK, HXXH, HXXKG, R/K/HXXR, R/KXXR, R/HXXR, K/HXXR, RXXR, KXXR, HXXR, R/K/HXXK, R/KXXK, R/HXXK, K/HXXK, RXXK, KXXK, HXXK, R/K/HXXH, R/KXXH, R/HXXH, K/HXXH, RXXH, KXXH, HXXH, R/K/HXXKG (SEQ ID NO:21), R/KXXKG, R/HXXKG, K/HXXKG, RXXKG, KXXKG, and HXXKG.

For the sake of convenience, amino acid motifs that would constitute a CendR element if an arginine, lysine, lysine-glycine pair, or histidine were at the C-terminus and where the exposure in the future of the arginine, lysine, lysine-glycine pair, or histidine at the C-terminus is planned or intended, can be referred to as CendR elements or latent CendR elements.

This protease-controllable internalization system can be useful in engineering compositions with functions such as cell type-specific and/or tissue type-specific uptake and the ability to spread the compositions in tissues. In addition, this rule can be relevant for a multitude of biological processes, including viral infection and phagocytosis. As viruses can naturally use the CendR pathway for infecting the cells, the CendR compositions, conjugates, molecules, proteins and/or elements can be useful for interfering with the process of viral infection.

The disclosed tissue/cell penetration system makes it possible to derive peptides that not only home to a specific target tissue, but also penetrate into that tissue. These peptides contain two active sequence motifs, a binding site for a specific receptor as well as a sequence motif that binds to a tissue-penetration receptor. The two sequence motifs can overlap with one another. CendR peptides activate a transport system that takes along materials presented with a CendR peptide. A variety of homing CendR peptides can be used to target drugs and other compounds and compositions to different targets cells and tissues. For example, the receptor for one type of CendR peptide is preferentially expressed in hypoxic areas of tumors, so having a panel of these peptides can allow more thorough coverage of tumor tissue than can be accomplished with a single peptide. Co-compositions and cargos of various sizes can be used with the CendR peptides. Including a tumor-penetrating CendR peptide (or a combination of two) with a drug can result in a higher concentration of the drug in the tumor without affecting its concentration in non-tumor tissues. The disclosed methods and compositions can also result in a broader distribution of the drug within the tumor. As a result, anti-tumor activity can be enhanced. CendR elements can be combined with numerous other elements, such as accessory molecules and homing motifs, as well as components to be delivered and internalized, such as co-compositions and cargo compositions.

Penetration into tumor tissue is an issue with all anticancer drugs because of the high intra-tumor fluid pressure that forces tissue fluid to flow out of the tumor, which works against diffusion of drugs into the extravascular tumor tissue (Jain et al., 2007). The presumed reasons are that the blood vessels tend to be leaky and the lymphatic vessels are poorly functional in tumors. If a drug were completely tumor-specific and innocuous in normal tissues (and if cost were not an issue), it would be possible to administer so much of that drug that it would overwhelm any barriers to the delivery of sufficient doses to all parts of the tumor. This obviously is not the case with anti-cancer agents; drug toxicity limits the dosing, and tumor penetration is a major obstacle. The disclosed methods and compositions can have the highest impact on drugs that either have penetration problems, or that are effective but highly toxic even at the standard therapeutic doses. Essentially all anti-cancer drugs have one or both of these problems.

It has been discovered that certain peptide motifs specifically increase the penetration of drugs into tumors and into other cells and tissues. Disclosed are tumor-homing peptides that specifically increase the penetration of drugs into tumors. These peptides contain both a tumor-specific homing sequence as well as a tissue-penetrating and internalizing motif named CendR. The CendR element is cryptic in these peptides and is activated by a proteolytic cleavage at the target tumor. Drug, fluorophore and nanoparticle payloads attached to these peptides accumulate in tumors and penetrate deep into the extravascular tumor tissue. However, it has also been discovered that the payload does not need to be either coupled to or associated with the CendR peptide. The free CendR peptide specifically induces tissue permeability (termed CendIT effect—CendR-Induced Transendothelium & tissue effect) in the tumor, allowing a co-injected drug or nanoparticle to extravasate and penetrate into tumor tissue. This same effect can be achieved with any cells and tissue with CendR receptors. The increase in tumor concentration of a co-injected compound demonstrated is about 4-fold.

Tumor-penetrating CendR peptides can be used, for example, to augment tumor imaging and tumor treatment with anti-cancer drugs. FDA-approved imaging agents, such as iron oxide nanoparticle MRI contrast agent, can be injected into tumor-bearing mice with a tumor-homing CendR peptide, or with a combination of peptides, followed by imaging. Any known or future drug can be used with CendR peptides to affect and inhibit tumor growth. For example, the co-composition can be any clinically used anti-cancer drugs. Drug accumulation and distribution in tumor tissue, as well as anti-tumor efficacy can be determined using known techniques (examples of such are described herein).

The disclosed enhancement of internalization and tissue penetration has broad application. Using the disclosed CendR elements and peptides, the effective targeting, delivery, and penetration of any drug, compound or composition can be augmented and enhanced. The effect of targeted and homing CendR peptides has several significant implications. First, drugs and other compounds and compositions can be delivered to cells and tissues of interest at higher concentrations than is possible in standard therapy. This is a result of the increased internalization and tissue penetration mediated by the CendR peptide. This is particularly significant because the amount of drug that can be administered is generally limited by side effects. Increasing the drug concentration at the target without increasing the amount of drug administered can thus extend and enhance the effectiveness of any known or future drugs and therapeutics. When using targeting or homing CendR peptides, the increase in drug concentration only occurs in targeted cells and tissues and not in non-targeted tissues. In such cases, the efficacy of the treatment is increased, while side effects remain the same. Second, the dose or amount of drug or other compound or composition can be reduced without compromising the efficacy of the treatment. The CendR peptide would result in the same drug concentration at the target cell or tissue even though the amount of drug administered is less. Third, because the adjuvant CendR peptide and the drug, imaging agent, or other compound or composition need not be coupled to one another, a validated and approved CendR peptide can be used to augment any drug, imaging agent, or other compound or composition.

The disclosed methods and compositions address a major problem in therapy and in vivo diagnosis in general, and in cancer therapy and in vivo diagnosis, in particular: the poor penetration of drugs and other compounds and compositions into tissue. Tumor-homing peptides that effectively and specifically penetrate into tumor tissue have been discovered that can carry an attached payload, such as a fluorophore, drug, or nanoparticle contrast agent deep into extravascular tumor tissue. It has now been discovered that it is not necessary for the payload to be coupled or bound to the tumor-penetrating peptide; the peptide specifically induces tissue permeability in the tumor, allowing a co-injected compound to extravasate and penetrate into tumor tissue.

The tumor-penetrating peptide concept has tremendous utility: (1) It delivers more drug (or diagnostic probe or other compound or composition) into the tumor than would reach the tumor from a standard regimen. This means better efficacy and reduced side effects. (2) The procedure can help solve the tumor penetration problem. Drugs generally do not penetrate farther than 3-5 cell diameters from blood vessels, which leaves more distantly located tumor cells without any drug, or exposes them to low drug concentrations that are likely to facilitate the development of resistance (Hambley and Hait, 2009). The disclosed methods and compositions make it possible to obtain more even drug distribution within tumors. (3) The fact that the drug does not have to be coupled to the peptide means that once a tumor-penetrating peptide has been clinically validated, it can be used to augment the efficacy of any imaging agent or anti-cancer drug.

In another example, the CendR peptides can be used in nanomedicine. One of the main goals of nanomedicine is to design devices that surpass simple drugs by performing multiple functions in diagnosing, monitoring, and treating disease. New technologies can be applied to solve some of the main problems in the medical uses of multifunctional nanoparticles, such as poor penetration into extravascular tissue.

Disclosed are CendR compositions, CendR conjugates, CendR molecules, CendR compounds, CendR proteins, CendR peptides, and CendR elements. CendR elements and CendR compounds are the basic feature of CendR compositions, CendR conjugates, CendR molecules, CendR proteins, CendR peptides, and the like. CendR compositions are any composition, conglomeration, conjugate, molecule, protein, peptide, etc. that comprises a CendR element or a CendR compound. CendR conjugates are associations, whether covalent or non-covalent, of a CendR element or CendR compound and one or more other elements, peptides, proteins, compounds, molecules, agents, compounds, etc. For example, a CendR conjugate can comprise a CendR peptide, CendR protein, CendR compound, CendR molecule, etc. CendR molecules are molecules that comprise a CendR element or a CendR compound. For example, a CendR molecule can comprise a CendR compound, CendR protein, CendR peptide, etc. In general, CendR peptides, CendR proteins, CendR compounds, CendR molecules, and CendR conjugates are all forms of CendR compositions. CendR compounds, CendR peptides and CendR proteins can be forms of CendR molecules. Unless the context indicates otherwise, reference to a CendR composition is intended to refer to CendR compositions, CendR molecules, CendR compounds, CendR proteins, CendR peptides, CendR elements, and the like. A CendR component is any molecule, peptide, protein, compound, conjugate, composition, etc. that comprises a CendR element. Examples of CendR components include, for example, CendR compositions, CendR molecules, CendR compounds, CendR proteins, CendR peptides, and CendR elements.

CendR components can comprise one or more CendR elements. Where a CendR element comprises two or more CendR elements, it is useful for the CendR component to be designed to allow some or all of the CendR elements to be exposed or exposable at the C-terminus of a protein or peptide. This can be accomplished in numerous ways in, for example, conjugates and compositions. This can also be accomplished in, for example, branching peptides and proteins.

Disclosed are methods of enhancing internalization, penetration, or both of a co-composition into or through a cell, tissue, or both, the method comprising: exposing the cell, tissue, or both to a CendR element and the co-composition, thereby enhancing internalization, penetration, or both of the co-composition into or through the cell, tissue, or both, wherein, prior to exposing the cell, tissue, or both, the CendR element and the co-composition are not covalently coupled or non-covalently associated with each other.

Also disclosed are methods of enhancing internalization of a co-composition into a cell, the method comprising: exposing the cell to a CendR element and the co-composition, thereby enhancing internalization of the co-composition into the cell, wherein, prior to exposing the cell, the CendR element and the co-composition are not covalently coupled or non-covalently associated with each other.

Disclosed are methods of enhancing penetration of a co-composition into and through a tissue, the method comprising: exposing the tissue to a CendR element and the co-composition, thereby enhancing penetration of the co-composition into and through the tissue, wherein, prior to exposing the tissue, the CendR element and the co-composition are not covalently coupled or non-covalently associated with each other.

Disclosed are methods of enhancing internalization, penetration, or both of a co-composition into or through a cell, tissue, or both, the method comprising: exposing the cell, tissue, or both to a CendR peptide and the co-composition, thereby enhancing internalization, penetration, or both of the co-composition into or through the cell, tissue, or both, wherein, prior to exposing the cell, tissue, or both, the CendR element and the co-composition are not covalently coupled or non-covalently associated with each other.

Also disclosed are methods of enhancing internalization of a co-composition into a cell, the method comprising: exposing the cell to a CendR peptide and the co-composition, thereby enhancing internalization of the co-composition into the cell, wherein, prior to exposing the cell, the CendR element and the co-composition are not covalently coupled or non-covalently associated with each other. Disclosed are methods of enhancing penetration of a co-composition into and through a tissue, the method comprising: exposing the tissue to a CendR peptide and the co-composition, thereby enhancing penetration of the co-composition into and through the tissue, wherein, prior to exposing the tissue, the CendR element and the co-composition are not covalently coupled or non-covalently associated with each other.

Disclosed are methods of enhancing internalization, penetration, or both of a co-composition into or through a cell, tissue, or both, the method comprising: exposing the cell, tissue, or both to a CendR composition and the co-composition, thereby enhancing internalization, penetration, or both of the co-composition into or through the cell, tissue, or both, wherein, prior to exposing the cell, tissue, or both, the CendR element and the co-composition are not covalently coupled or non-covalently associated with each other.

Also disclosed are methods of enhancing internalization of a co-composition into a cell, the method comprising: exposing the cell to a CendR composition and the co-composition, thereby enhancing internalization of the co-composition into the cell, wherein, prior to exposing the cell, the CendR element and the co-composition are not covalently coupled or non-covalently associated with each other.

Disclosed are methods of enhancing penetration of a co-composition into and through a tissue, the method comprising: exposing the tissue to a CendR composition and the co-composition, thereby enhancing penetration of the co-composition into and through the tissue, wherein, prior to exposing the tissue, the CendR element and the co-composition are not covalently coupled or non-covalently associated with each other.

Disclosed are methods of enhancing internalization, penetration, or both of a co-composition into or through a cell, tissue, or both, the method comprising: exposing the cell, tissue, or both to a CendR conjugate and the co-composition, thereby enhancing internalization, penetration, or both of the co-composition into or through the cell, tissue, or both, wherein, prior to exposing the cell, tissue, or both, the CendR element and the co-composition are not covalently coupled or non-covalently associated with each other.

Also disclosed are methods of enhancing internalization of a co-composition into a cell, the method comprising: exposing the cell to a CendR conjugate and the co-composition, thereby enhancing internalization of the co-composition into the cell, wherein, prior to exposing the cell, the CendR element and the co-composition are not covalently coupled or non-covalently associated with each other.

Disclosed are methods of enhancing penetration of a co-composition into and through a tissue, the method comprising: exposing the tissue to a CendR conjugate and the co-composition, thereby enhancing penetration of the co-composition into and through the tissue, wherein, prior to exposing the tissue, the CendR element and the co-composition are not covalently coupled or non-covalently associated with each other.

In any of the disclosed methods, such as, for example, the disclosed methods using co-compositions, the CendR element(s) or other CendR component(s) used in the method can be a CendR element comprising a cargo composition. Similarly, in any of the disclosed methods, such as, for example, the disclosed methods using cargo compositions, one or more compositions can also be used in the method, where the CendR element(s) and the co-composition(s) are not covalently coupled or non-covalently associated with each other.

Disclosed are methods of enhancing internalization, penetration, or both of a cargo composition into or through a cell, tissue, or both, the method comprising: exposing the cell, tissue, or both to a CendR element and the cargo composition, thereby enhancing internalization, penetration, or both of the cargo composition into or through the cell, tissue, or both, wherein the CendR element and the cargo composition are covalently coupled or non-covalently associated with each other.

Also disclosed are methods of enhancing internalization of a cargo composition into a cell, the method comprising: exposing the cell to a CendR element and the cargo composition, thereby enhancing internalization of the cargo composition into the cell, wherein the CendR element and the cargo composition are covalently coupled or non-covalently associated with each other.

Disclosed are methods of enhancing penetration of a cargo composition into and through a tissue, the method comprising: exposing the tissue to a CendR element and the cargo composition, thereby enhancing penetration of the cargo composition into and through the tissue, wherein the CendR element and the cargo composition are covalently coupled or non-covalently associated with each other.

Disclosed are methods of enhancing internalization, penetration, or both of a cargo composition into or through a cell, tissue, or both, the method comprising: exposing the cell, tissue, or both to a CendR peptide and the cargo composition, thereby enhancing internalization, penetration, or both of the cargo composition into or through the cell, tissue, or both, wherein the CendR element and the cargo composition are covalently coupled or non-covalently associated with each other.

Also disclosed are methods of enhancing internalization of a cargo composition into a cell, the method comprising: exposing the cell to a CendR peptide and the cargo composition, thereby enhancing internalization of the cargo composition into the cell, wherein the CendR element and the cargo composition are covalently coupled or non-covalently associated with each other. Disclosed are methods of enhancing penetration of a cargo composition into and through a tissue, the method comprising: exposing the tissue to a CendR peptide and the cargo composition, thereby enhancing penetration of the cargo composition into and through the tissue, wherein the CendR element and the cargo composition are covalently coupled or non-covalently associated with each other.

Disclosed are methods of enhancing internalization, penetration, or both of a cargo composition into or through a cell, tissue, or both, the method comprising: exposing the cell, tissue, or both to a CendR composition and the cargo composition, thereby enhancing internalization, penetration, or both of the cargo composition into or through the cell, tissue, or both, wherein the CendR element and the cargo composition are covalently coupled or non-covalently associated with each other.

Also disclosed are methods of enhancing internalization of a cargo composition into a cell, the method comprising: exposing the cell to a CendR composition and the cargo composition, thereby enhancing internalization of the cargo composition into the cell, wherein the CendR element and the cargo composition are covalently coupled or non-covalently associated with each other.

Disclosed are methods of enhancing penetration of a cargo composition into and through a tissue, the method comprising: exposing the tissue to a CendR composition and the cargo composition, thereby enhancing penetration of the cargo composition into and through the tissue, wherein the CendR element and the cargo composition are covalently coupled or non-covalently associated with each other.

Disclosed are methods of enhancing internalization, penetration, or both of a cargo composition into or through a cell, tissue, or both, the method comprising: exposing the cell, tissue, or both to a CendR conjugate and the cargo composition, thereby enhancing internalization, penetration, or both of the cargo composition into or through the cell, tissue, or both, wherein the CendR element and the cargo composition are covalently coupled or non-covalently associated with each other.

Also disclosed are methods of enhancing internalization of a cargo composition into a cell, the method comprising: exposing the cell to a CendR conjugate and the cargo composition, thereby enhancing internalization of the cargo composition into the cell, wherein the CendR element and the cargo composition are covalently coupled or non-covalently associated with each other.

Disclosed are methods of enhancing penetration of a cargo composition into and through a tissue, the method comprising: exposing the tissue to a CendR conjugate and the cargo composition, thereby enhancing penetration of the cargo composition into and through the tissue, wherein the CendR element and the cargo composition are covalently coupled or non-covalently associated with each other.

The CendR element can permeabilize the cell, tissue, or both. The cell, tissue, or both can be in a subject. The cell, tissue, or both can be exposed to the CendR element and the co-composition by administering the CendR element and the co-composition to the subject. The CendR element and the co-composition can be administered to the subject simultaneously. The CendR element and the co-composition can be administered to the subject in a single composition comprising the CendR element and the co-composition. The CendR element and the co-composition can be administered to the subject in separate compositions. The CendR element and the co-composition can be administered to the subject at different times. The CendR element and the co-composition can be administered to the subject in separate compositions. The CendR element and the co-composition can be administered to the subject by separate routes. In some forms, the CendR element and the co-composition are not bound to each other. The cell, tissue, or both can be exposed to the CendR element and the cargo composition by administering the CendR element and the cargo composition to the subject. The CendR element and the cargo composition can be administered to the subject simultaneously. The CendR element and the cargo composition can be administered to the subject in a single composition comprising the CendR element and the cargo composition. Such a composition can be administered alone or in combination with any other component, such as those disclosed herein. For example, the CendR/cargo composition can be administered or used together with one or more other CendR components, one or more other cargo compositions, one or more co-compositions, or any combination of these. The CendR element can be in a composition comprising the CendR element and any other component, such as those disclosed herein. For example, the CendR composition can further comprise one or more other CendR components, one or more cargo compositions, or any combination of these.

Multiple different CendR elements, CendR peptides, CendR proteins, CendR compounds, CendR conjugates, CendR compositions, or a combination can be used together. Similarly, multiple different co-compositions, multiple different cargo compositions, or a combination can be used together. Where such multiple different CendR elements, CendR peptides, CendR proteins, CendR compounds, CendR conjugates, CendR compositions, or a combination are used together, they can be used with a single type of co-composition, a single type of cargo composition, multiple different co-compositions, multiple different cargo compositions, or a combination. Similarly, when multiple different co-compositions, multiple different cargo compositions, or a combination can be used together, they can be used with a single type of CendR element, CendR peptide, CendR protein, CendR compound, CendR conjugate, or CendR composition, or with multiple different CendR elements, CendR peptides, CendR proteins, CendR compounds, CendR conjugates, CendR compositions, or a combination. By used together is meant used together in the same composition, at the same time, in the same treatment, in the same treatment regime, in the same course of treatment, etc.

For example, a CendR element can be used together with one or multiple different CendR elements, CendR peptides, CendR proteins, CendR compounds, CendR conjugates, CendR compositions, or a combination, one or multiple different co-compositions, multiple different cargo compositions, or a combination, or any combination of these. In such combinations, the CendR element itself can be combined in the same conjugate or composition with one or more cargo compositions, one or more accessory molecules, one or more homing molecules, etc.

As another example, an iRGD (which combines a CendR element and an RGD element in a single peptide) can be used together with one or multiple different CendR elements, CendR peptides, CendR proteins, CendR compounds, CendR conjugates, CendR compositions, or a combination, one or multiple different co-compositions, multiple different cargo compositions, or a combination, or any combination of these. In such combinations, the iRGD itself can be combined in the same conjugate or composition with one or more cargo compositions, one or more accessory molecules, one or more homing molecules, etc.

The cell, tissue, or both can be exposed to combinations of different CendR components and combinations of different co-compositions by administering the CendR components and the co-compositions to the subject. One or more of the CendR components and one or more of the co-compositions can be administered to the subject simultaneously. One or more of the CendR components and one or more of the co-compositions can be administered to the subject in one or more single compositions comprising the CendR component(s) and the co-composition(s). One or more of the CendR components and one or more of the co-compositions can be administered to the subject in one or more separate compositions. One or more of the CendR components and one or more of the co-compositions can be administered to the subject at different times. The CendR element and the co-composition can be administered to the subject in one or more separate compositions. One or more of the CendR components and one or more of the co-compositions can be administered to the subject by one or more separate routes. In some forms, the CendR element and the co-composition are not bound to each other.

The cell, tissue, or both can be exposed to combinations of different CendR components and combinations of different cargo compositions by administering the CendR components and the cargo compositions to the subject. One or more of the CendR components and one or more of the cargo compositions can be administered to the subject simultaneously. One or more of the CendR components and one or more of the cargo compositions can be administered to the subject in one or more single compositions comprising one or more of the CendR component(s) and one or more of the cargo composition(s). One or more of the CendR components and one or more of the cargo compositions can be administered to the subject in one or more separate compositions. One or more of the CendR components and one or more of the cargo compositions can be administered to the subject at different times. The CendR element and the cargo composition can be administered to the subject in one or more separate compositions. One or more of the CendR components and one or more of the cargo compositions can be administered to the subject by one or more separate routes. Various CendR components in any of the various forms disclosed herein and, optionally, any of various co-compositions, can be administered together or separately at various times, modes, forms, regimes, dosages, etc.

The cell, tissue, or both can be exposed to an iRGD and the co-composition by administering the iRGD and the co-composition to the subject. The iRGD and the co-composition can be administered to the subject simultaneously. The iRGD and the co-composition can be administered to the subject in a single composition comprising the iRGD and the co-composition. The iRGD and the co-composition can be administered to the subject in separate compositions. The iRGD and the co-composition can be administered to the subject at different times. The iRGD and the co-composition can be administered to the subject in separate compositions. The iRGD and the co-composition can be administered to the subject by separate routes. In some forms, the iRGD and the co-composition are not bound to each other. The cell, tissue, or both can be exposed to the iRGD and the cargo composition by administering the iRGD and the cargo composition to the subject. The iRGD and the cargo composition can be administered to the subject simultaneously. The iRGD and the cargo composition can be administered to the subject in a single composition comprising the iRGD and the cargo composition. Such a composition can be administered alone or in combination with any other component, such as those disclosed herein. For example, the iRGD/cargo composition can be administered or used together with one or more other CendR components, one or more other cargo compositions, one or more co-compositions, or any combination of these. The iRGD can be in a composition comprising the iRGD and any other component, such as those disclosed herein. For example, the iRGD composition can further comprise one or more other CendR components, one or more cargo compositions, or any combination of these.

The CendR peptide can permeabilize the cell, tissue, or both. The cell, tissue, or both can be in a subject. The cell, tissue, or both can be exposed to the CendR peptide and the co-composition by administering the CendR peptide and the co-composition to the subject. The CendR peptide and the co-composition can be administered to the subject simultaneously. The CendR peptide and the co-composition can be administered to the subject in a single composition comprising the CendR peptide and the co-composition. The CendR peptide and the co-composition can be administered to the subject in separate compositions. The CendR peptide and the co-composition can be administered to the subject at different times. The CendR peptide and the co-composition can be administered to the subject in separate compositions. The CendR peptide and the co-composition can be administered to the subject by separate routes. In some forms, the CendR peptide and the co-composition are not bound to each other. The cell, tissue, or both can be exposed to the CendR peptide and the cargo composition by administering the CendR peptide and the cargo composition to the subject. The CendR peptide and the cargo composition can be administered to the subject simultaneously. The CendR peptide and the cargo composition can be administered to the subject in a single composition comprising the CendR peptide and the cargo composition.

The CendR composition can permeabilize the cell, tissue, or both. The cell, tissue, or both can be in a subject. The cell, tissue, or both can be exposed to the CendR composition and the co-composition by administering the CendR composition and the co-composition to the subject. The CendR composition and the co-composition can be administered to the subject simultaneously. The CendR composition and the co-composition can be administered to the subject in a single composition comprising the CendR composition and the co-composition. The CendR composition and the co-composition can be administered to the subject in separate compositions. The CendR composition and the co-composition can be administered to the subject at different times. The CendR composition and the co-composition can be administered to the subject in separate compositions. The CendR composition and the co-composition can be administered to the subject by separate routes. In some forms, the CendR composition and the co-composition are not bound to each other. The cell, tissue, or both can be exposed to the CendR composition and the cargo composition by administering the CendR composition and the cargo composition to the subject. The CendR composition and the cargo composition can be administered to the subject simultaneously. The CendR composition and the cargo composition can be administered to the subject in a single composition comprising the CendR composition and the cargo composition. More generally, CendR components can comprise both a CendR element and a cargo composition. For example, CendR peptides, CendR proteins, CendR conjugates, and CendR compositions can comprise both a CendR element and a cargo composition.

The CendR conjugate can permeabilize the cell, tissue, or both. The cell, tissue, or both can be in a subject. The cell, tissue, or both can be exposed to the CendR conjugate and the co-composition by administering the CendR conjugate and the co-composition to the subject. The CendR conjugate and the co-composition can be administered to the subject simultaneously. The CendR conjugate and the co-composition can be administered to the subject in a single composition comprising the CendR conjugate and the co-composition. The CendR conjugate and the co-composition can be administered to the subject in separate compositions. The CendR conjugate and the co-composition can be administered to the subject at different times. The CendR conjugate and the co-composition can be administered to the subject in separate compositions. The CendR conjugate and the co-composition can be administered to the subject by separate routes. In some forms, the CendR conjugate and the co-composition are not bound to each other. The cell, tissue, or both can be exposed to the CendR conjugate and the cargo composition by administering the CendR conjugate and the cargo composition to the subject. The CendR conjugate and the cargo composition can be administered to the subject simultaneously. The CendR conjugate and the cargo composition can be administered to the subject in a single composition comprising the CendR conjugate and the cargo composition.

The CendR element can be all or part of an amino acid sequence. The amino acid sequence can be all or part of a protein or peptide. The CendR peptide can be all or part of a protein or peptide comprising an amino acid sequence. The CendR conjugate can comprise a protein or peptide comprising an amino acid sequence. The CendR composition can comprise a protein or peptide comprising an amino acid sequence. The amino acid sequence can comprise a CendR element. The amino acid sequence can further comprise one or more accessory molecules. The amino acid sequence can further comprise one or more homing molecules. The protein or peptide can further comprise one or more accessory molecules. The protein or peptide can further comprise one or more homing molecules. The CendR conjugate can comprise one or more cargo compositions. The CendR composition can comprise one or more cargo compositions.

In some forms, the protein or peptide can be internalized into a cell, penetrate tissue, or both when the amino acid sequence is present in the protein or peptide but not when the amino acid sequence is not present in the protein or peptide. In some forms, the protein or peptide can penetrate tissue when the amino acid sequence is present in the protein or peptide but not when the amino acid sequence is not present in the protein or peptide. In some forms, the protein or peptide can be internalized into a cell and penetrate tissue when the amino acid sequence is present in the protein or peptide but not when the amino acid sequence is not present in the protein or peptide. In some forms, the amino acid sequence can be internalized into a cell, penetrate tissue, or both without being associated with the co-composition. In some forms, the amino acid sequence can penetrate tissue without being associated with the co-composition. In some forms, the amino acid sequence can be internalized into a cell and penetrate tissue without being associated with the co-composition. In some forms, the amino acid sequence is the only functional internalization element in the protein or peptide. In some forms, the internalization, penetration, or both of the co-composition into or through a cell, tissue, or both is enhanced when the amino acid sequence is present in the protein or peptide but not when the amino acid sequence is not present in the protein or peptide. In some forms, the penetration of the co-composition into or through tissue is enhanced when the amino acid sequence is present in the protein or peptide but not when the amino acid sequence is not present in the protein or peptide. In some forms, the internalization and penetration of the co-composition into or through a cell and tissue is enhanced when the amino acid sequence is present in the protein or peptide but not when the amino acid sequence is not present in the protein or peptide. In some forms, the internalization, penetration, or both of the cargo composition into or through a cell, tissue, or both is enhanced when the amino acid sequence is present in the protein or peptide but not when the amino acid sequence is not present in the protein or peptide. In some forms, the penetration of the cargo composition into or through tissue is enhanced when the amino acid sequence is present in the protein or peptide but not when the amino acid sequence is not present in the protein or peptide. In some forms, the internalization and penetration of the cargo composition into or through a cell and tissue is enhanced when the amino acid sequence is present in the protein or peptide but not when the amino acid sequence is not present in the protein or peptide.

In some forms, the protein or peptide can be internalized into a cell, penetrate tissue, or both when the CendR element is present in the protein or peptide but not when the CendR element is not present in the protein or peptide. In some forms, the protein or peptide can penetrate tissue when the CendR element is present in the protein or peptide but not when the CendR element is not present in the protein or peptide. In some forms, the protein or peptide can be internalized into a cell and penetrate tissue when the CendR element is present in the protein or peptide but not when the CendR element is not present in the protein or peptide. In some forms, the CendR element can be internalized into a cell, penetrate tissue, or both without being associated with the co-composition. In some forms, the CendR element can penetrate tissue without being associated with the co-composition. In some forms, the CendR element can be internalized into a cell and penetrate tissue without being associated with the co-composition. In some forms, the CendR element is the only functional internalization element in the protein or peptide. In some forms, the internalization, penetration, or both of the co-composition into or through a cell, tissue, or both is enhanced when the cell, tissue, or both is exposed to the CendR element but not when the cell, tissue, or both is not exposed to the CendR element. In some forms, the penetration of the co-composition into or through tissue is enhanced when the tissue is exposed to the CendR element but not when the tissue is not exposed to the CendR element. In some forms, the internalization and penetration of the co-composition into or through a cell and tissue is enhanced when the cell and tissue are exposed to the CendR element but not when the cell and tissue is not exposed to the CendR element. In some forms, the internalization, penetration, or both of the cargo composition into or through a cell, tissue, or both is enhanced when the cell, tissue, or both is exposed to the CendR element but not when the cell, tissue, or both is not exposed to the CendR element. In some forms, the penetration of the cargo composition into or through tissue is enhanced when the tissue is exposed to the CendR element but not when the tissue is not exposed to the CendR element. In some forms, the internalization and penetration of the cargo composition into or through a cell and tissue is enhanced when the cell and tissue are exposed to the CendR element but not when the cell and tissue is not exposed to the CendR element.

In some forms, the CendR peptide can be internalized into a cell, penetrate tissue, or both when the CendR element is present in the CendR peptide but not when the CendR element is not present in the CendR peptide. In some forms, the CendR peptide can penetrate tissue when the CendR element is present in the CendR peptide but not when the CendR element is not present in the CendR peptide. In some forms, the CendR peptide can be internalized into a cell and penetrate tissue when the CendR element is present in the CendR peptide but not when the CendR element is not present in the CendR peptide. In some forms, the CendR peptide can be internalized into a cell, penetrate tissue, or both without being associated with the co-composition. In some forms, the CendR peptide can penetrate tissue without being associated with the co-composition. In some forms, the CendR peptide can be internalized into a cell and penetrate tissue without being associated with the co-composition. In some forms, the CendR element is the only functional internalization element in the CendR peptide. In some forms, the internalization, penetration, or both of the co-composition into or through a cell, tissue, or both is enhanced when the cell, tissue, or both is exposed to the CendR peptide but not when the cell, tissue, or both is not exposed to the CendR peptide. In some forms, the penetration of the co-composition into or through tissue is enhanced when the tissue is exposed to the CendR peptide but not when the tissue is not exposed to the CendR peptide. In some forms, the internalization and penetration of the co-composition into or through a cell and tissue is enhanced when the cell and tissue are exposed to the CendR peptide but not when the cell and tissue is not exposed to the CendR peptide. In some forms, the internalization, penetration, or both of the cargo composition into or through a cell, tissue, or both is enhanced when the cell, tissue, or both is exposed to the CendR peptide but not when the cell, tissue, or both is not exposed to the CendR peptide. In some forms, the penetration of the cargo composition into or through tissue is enhanced when the tissue is exposed to the CendR peptide but not when the tissue is not exposed to the CendR peptide. In some forms, the internalization and penetration of the cargo composition into or through a cell and tissue is enhanced when the cell and tissue are exposed to the CendR peptide but not when the cell and tissue is not exposed to the CendR peptide.

In some forms, the CendR conjugate can be internalized into a cell, penetrate tissue, or both when the CendR element is present in the CendR conjugate but not when the CendR element is not present in the CendR conjugate. In some forms, the CendR conjugate can penetrate tissue when the CendR element is present in the CendR conjugate but not when the CendR element is not present in the CendR conjugate. In some forms, the CendR conjugate can be internalized into a cell and penetrate tissue when the CendR element is present in the CendR conjugate but not when the CendR element is not present in the CendR conjugate. In some forms, the CendR conjugate can be internalized into a cell, penetrate tissue, or both without being associated with the co-composition. In some forms, the CendR conjugate can penetrate tissue without being associated with the co-composition. In some forms, the CendR conjugate can be internalized into a cell and penetrate tissue without being associated with the co-composition. In some forms, the CendR element is the only functional internalization element in the CendR conjugate. In some forms, the internalization, penetration, or both of the co-composition into or through a cell, tissue, or both is enhanced when the cell, tissue, or both is exposed to the CendR conjugate but not when the cell, tissue, or both is not exposed to the CendR conjugate. In some forms, the penetration of the co-composition into or through tissue is enhanced when the tissue is exposed to the CendR conjugate but not when the tissue is not exposed to the CendR conjugate. In some forms, the internalization and penetration of the co-composition into or through a cell and tissue is enhanced when the cell and tissue are exposed to the CendR conjugate but not when the cell and tissue is not exposed to the CendR conjugate. In some forms, the internalization, penetration, or both of the cargo composition into or through a cell, tissue, or both is enhanced when the cell, tissue, or both is exposed to the CendR conjugate but not when the cell, tissue, or both is not exposed to the CendR conjugate. In some forms, the penetration of the cargo composition into or through tissue is enhanced when the tissue is exposed to the CendR conjugate but not when the tissue is not exposed to the CendR conjugate. In some forms, the internalization and penetration of the cargo composition into or through a cell and tissue is enhanced when the cell and tissue are exposed to the CendR conjugate but not when the cell and tissue is not exposed to the CendR conjugate.

In some forms, the CendR composition can be internalized into a cell, penetrate tissue, or both when the CendR element is present in the CendR composition but not when the CendR element is not present in the CendR composition. In some forms, the CendR composition can penetrate tissue when the CendR element is present in the CendR composition but not when the CendR element is not present in the CendR composition. In some forms, the CendR composition can be internalized into a cell and penetrate tissue when the CendR element is present in the CendR composition but not when the CendR element is not present in the CendR composition. In some forms, the CendR composition can be internalized into a cell, penetrate tissue, or both without being associated with the co-composition. In some forms, the CendR composition can penetrate tissue without being associated with the co-composition. In some forms, the CendR composition can be internalized into a cell and penetrate tissue without being associated with the co-composition. In some forms, the CendR element is the only functional internalization element in the CendR composition. In some forms, the internalization, penetration, or both of the co-composition into or through a cell, tissue, or both is enhanced when the cell, tissue, or both is exposed to the CendR composition but not when the cell, tissue, or both is not exposed to the CendR composition. In some forms, the penetration of the co-composition into or through tissue is enhanced when the tissue is exposed to the CendR composition but not when the tissue is not exposed to the CendR composition. In some forms, the internalization and penetration of the co-composition into or through a cell and tissue is enhanced when the cell and tissue are exposed to the CendR composition but not when the cell and tissue is not exposed to the CendR composition. In some forms, the internalization, penetration, or both of the cargo composition into or through a cell, tissue, or both is enhanced when the cell, tissue, or both is exposed to the CendR composition but not when the cell, tissue, or both is not exposed to the CendR composition. In some forms, the penetration of the cargo composition into or through tissue is enhanced when the tissue is exposed to the CendR composition but not when the tissue is not exposed to the CendR composition. In some forms, the internalization and penetration of the cargo composition into or through a cell and tissue is enhanced when the cell and tissue are exposed to the CendR composition but not when the cell and tissue is not exposed to the CendR composition.

The CendR element can be an activatable CendR element. The activatable CendR element can be a protease-activatable CendR element. The CendR peptide can be an activatable CendR peptide. The activatable CendR peptide can be a protease-activatable CendR peptide. The CendR peptide can be at the C-terminal end of the protein or peptide. The CendR conjugate can be an activatable CendR conjugate. The activatable CendR conjugate can be a protease-activatable CendR conjugate. The CendR conjugate can be at the C-terminal end of the protein or peptide. The CendR composition can be an activatable CendR composition. The activatable CendR composition can be a protease-activatable CendR composition. The CendR composition can be at the C-terminal end of the protein or peptide.

The protein or peptide can be circular. The protein or peptide can be linear. The CendR element can be at the C-terminal end of the protein or peptide. The co-composition can comprise a therapeutic agent. The co-composition can comprise a detection agent. The co-composition can comprise a carrier, vehicle, or both. The co-composition can comprise, for example, a therapeutic protein, a therapeutic compound, a therapeutic composition, an anti-angiogenic agent, a pro-angiogenic agent, a cancer chemotherapeutic agent, a toxin, a cytotoxic agent, an anti-inflammatory agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination.

The cargo composition can comprise a therapeutic agent. The cargo composition can comprise a detection agent. The cargo composition can comprise a carrier, vehicle, or both. The cargo composition can comprise, for example, a therapeutic protein, a therapeutic compound, a therapeutic composition, an anti-angiogenic agent, a pro-angiogenic agent, a cancer chemotherapeutic agent, a toxin, a cytotoxic agent, an anti-inflammatory agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination.

In some forms, the CendR element and the co-composition are not covalently coupled or non-covalently associated with each other. In some forms, the CendR peptide and the co-composition are not covalently coupled or non-covalently associated with each other. In some forms, the CendR conjugate and the co-composition are not covalently coupled or non-covalently associated with each other. In some forms, the CendR composition and the co-composition are not covalently coupled or non-covalently associated with each other. In some forms, the CendR element and the cargo composition are covalently coupled or non-covalently associated with each other. In some forms, the CendR peptide and the cargo composition are covalently coupled or non-covalently associated with each other. In some forms, the CendR conjugate and the cargo composition are covalently coupled or non-covalently associated with each other. In some forms, the CendR composition and the cargo composition are covalently coupled or non-covalently associated with each other.

Disclosed are compositions comprising a CendR element and a co-composition. Also disclosed are compositions comprising a CendR peptide and a co-composition. Also disclosed are compositions comprising a CendR conjugate and a co-composition. Also disclosed are compositions comprising a CendR composition and a co-composition. Disclosed are compositions comprising a CendR element and a co-composition, wherein the CendR element and the co-composition are not covalently coupled or non-covalently associated with each other. Also disclosed are compositions comprising a CendR peptide and a co-composition, wherein the CendR peptide and the co-composition are not covalently coupled or non-covalently associated with each other. Also disclosed are compositions comprising a CendR conjugate and a co-composition, wherein the CendR conjugate and the co-composition are not covalently coupled or non-covalently associated with each other. Also disclosed are compositions comprising a CendR composition and a co-composition, wherein the CendR composition and the co-composition are not covalently coupled or non-covalently associated with each other.

Disclosed are compositions comprising a CendR element and one or more co-compositions. Also disclosed are compositions comprising a CendR peptide and one or more co-compositions. Also disclosed are compositions comprising a CendR conjugate and one or more co-composition. Also disclosed are compositions comprising a CendR composition and one or more co-compositions. Disclosed are compositions comprising a CendR element and one or more co-compositions, wherein the CendR element and at least one of the co-compositions are not covalently coupled or non-covalently associated with each other. Also disclosed are compositions comprising a CendR peptide and one or more co-compositions, wherein the CendR peptide and at least one of the co-compositions are not covalently coupled or non-covalently associated with each other. Also disclosed are compositions comprising a CendR conjugate and one or more co-compositions, wherein the CendR conjugate and at least one of the co-compositions are not covalently coupled or non-covalently associated with each other. Also disclosed are compositions comprising a CendR composition and one or more co-compositions, wherein the CendR composition and at least one of the co-compositions are not covalently coupled or non-covalently associated with each other.

Disclosed are compositions comprising a CendR element and a cargo composition. Also disclosed are compositions comprising a CendR peptide and a cargo composition. Also disclosed are compositions comprising a CendR conjugate and a cargo composition. Also disclosed are compositions comprising a CendR composition and a cargo composition. Disclosed are compositions comprising a CendR element and a cargo composition, wherein the CendR element and the cargo composition are covalently coupled or non-covalently associated with each other. Also disclosed are compositions comprising a CendR peptide and a cargo composition, wherein the CendR peptide and the cargo composition are covalently coupled or non-covalently associated with each other. Also disclosed are compositions comprising a CendR conjugate and a cargo composition, wherein the CendR conjugate and the cargo composition are covalently coupled or non-covalently associated with each other. Also disclosed are compositions comprising a CendR composition and a cargo composition, wherein the CendR composition and the cargo composition are covalently coupled or non-covalently associated with each other.

Disclosed are compositions comprising a CendR element and one or more cargo compositions. Also disclosed are compositions comprising a CendR peptide and one or more cargo compositions. Also disclosed are compositions comprising a CendR conjugate and one or more cargo composition. Also disclosed are compositions comprising a CendR composition and one or more cargo compositions. Disclosed are compositions comprising a CendR element and one or more cargo compositions, wherein the CendR element and at least one of the cargo compositions are covalently coupled or non-covalently associated with each other. Also disclosed are compositions comprising a CendR peptide and one or more cargo compositions, wherein the CendR peptide and at least one of the cargo compositions are covalently coupled or non-covalently associated with each other. Also disclosed are compositions comprising a CendR conjugate and one or more cargo compositions, wherein the CendR conjugate and at least one of the cargo compositions are covalently coupled or non-covalently associated with each other. Also disclosed are compositions comprising a CendR composition and one or more cargo compositions, wherein the CendR composition and at least one of the cargo compositions are covalently coupled or non-covalently associated with each other.

Also disclosed are compositions comprising a CendR element, an accessory molecule, and a co-composition, wherein the CendR element and the co-composition are not covalently coupled or non-covalently associated with each other, wherein the CendR element and the accessory molecule are covalently coupled or non-covalently associate with each other. Also disclosed are compositions comprising a CendR peptide, an accessory molecule, and a co-composition, wherein the CendR peptide and the co-composition are not covalently coupled or non-covalently associated with each other, wherein the CendR peptide and the accessory molecule are covalently coupled or non-covalently associate with each other. Also disclosed are compositions comprising a CendR conjugate, an accessory molecule, and a co-composition, wherein the CendR conjugate and the co-composition are not covalently coupled or non-covalently associated with each other, wherein the CendR conjugate and the accessory molecule are covalently coupled or non-covalently associate with each other. Also disclosed are compositions comprising a CendR composition, an accessory molecule, and a co-composition, wherein the CendR composition and the co-composition are not covalently coupled or non-covalently associated with each other, wherein the CendR composition and the accessory molecule are covalently coupled or non-covalently associate with each other. Also disclosed are compositions comprising a CendR peptide, an accessory molecule, and a co-composition, wherein the CendR peptide and the co-composition are not covalently coupled or non-covalently associated with each other, wherein the CendR peptide comprises the accessory molecule. Also disclosed are compositions comprising a CendR conjugate, an accessory molecule, and a co-composition, wherein the CendR conjugate and the co-composition are not covalently coupled or non-covalently associated with each other, wherein the CendR conjugate comprises the accessory molecule. Also disclosed are compositions comprising a CendR composition, an accessory molecule, and a co-composition, wherein the CendR composition and the co-composition are not covalently coupled or non-covalently associated with each other, wherein the CendR composition comprises the accessory molecule. In these compositions, the accessory molecule can be or can comprise an accessory peptide. The accessory peptide can overlap with the CendR element or be separate from the CendR element. In these compositions, the composition can comprise one or more co-compositions and/or one or more accessory molecules, wherein the CendR element, CendR peptide, CendR conjugate, or CendR composition and at least one of the co-compositions are not covalently coupled or non-covalently associated with each other, wherein the CendR element, CendR peptide, CendR conjugate, or CendR composition and at least one of the accessory molecules are covalently coupled or non-covalently associated with each other.

Also disclosed are compositions comprising a CendR element, a homing molecule, and a co-composition, wherein the CendR element and the co-composition are not covalently coupled or non-covalently associated with each other, wherein the CendR element and the homing molecule are covalently coupled or non-covalently associate with each other. Also disclosed are compositions comprising a CendR peptide, a homing molecule, and a co-composition, wherein the CendR peptide and the co-composition are not covalently coupled or non-covalently associated with each other, wherein the CendR peptide and the homing molecule are covalently coupled or non-covalently associate with each other. Also disclosed are compositions comprising a CendR conjugate, a homing molecule, and a co-composition, wherein the CendR conjugate and the co-composition are not covalently coupled or non-covalently associated with each other, wherein the CendR conjugate and the homing molecule are covalently coupled or non-covalently associate with each other. Also disclosed are compositions comprising a CendR composition, a homing molecule, and a co-composition, wherein the CendR composition and the co-composition are not covalently coupled or non-covalently associated with each other, wherein the CendR composition and the homing molecule are covalently coupled or non-covalently associate with each other. Also disclosed are compositions comprising a CendR peptide, a homing molecule, and a co-composition, wherein the CendR peptide and the co-composition are not covalently coupled or non-covalently associated with each other, wherein the CendR peptide comprises the homing molecule. Also disclosed are compositions comprising a CendR conjugate, a homing molecule, and a co-composition, wherein the CendR conjugate and the co-composition are not covalently coupled or non-covalently associated with each other, wherein the CendR conjugate comprises the homing molecule. Also disclosed are compositions comprising a CendR composition, a homing molecule, and a co-composition, wherein the CendR composition and the co-composition are not covalently coupled or non-covalently associated with each other, wherein the CendR composition comprises the homing molecule. In these compositions, the homing molecule can be or can comprise a homing peptide. The homing peptide can overlap with the CendR element or be separate from the CendR element. In these compositions, the composition can comprise one or more co-compositions and/or one or more homing molecules, wherein the CendR element, CendR peptide, CendR conjugate, or CendR composition and at least one of the co-compositions are not covalently coupled or non-covalently associated with each other, wherein the CendR element, CendR peptide, CendR conjugate, or CendR composition and at least one of the homing molecules are covalently coupled or non-covalently associated with each other.

Also disclosed are compositions comprising a CendR element, an accessory molecule, and a cargo composition, wherein the CendR element and the cargo composition are covalently coupled or non-covalently associated with each other, wherein the CendR element and the accessory molecule are covalently coupled or non-covalently associate with each other. Also disclosed are compositions comprising a CendR peptide, an accessory molecule, and a cargo composition, wherein the CendR peptide and the cargo composition are covalently coupled or non-covalently associated with each other, wherein the CendR peptide and the accessory molecule are covalently coupled or non-covalently associate with each other. Also disclosed are compositions comprising a CendR conjugate, an accessory molecule, and a cargo composition, wherein the CendR conjugate and the cargo composition are covalently coupled or non-covalently associated with each other, wherein the CendR conjugate and the accessory molecule are covalently coupled or non-covalently associate with each other. Also disclosed are compositions comprising a CendR composition, an accessory molecule, and a cargo composition, wherein the CendR composition and the cargo composition are covalently coupled or non-covalently associated with each other, wherein the CendR composition and the accessory molecule are covalently coupled or non-covalently associate with each other. Also disclosed are compositions comprising a CendR peptide, an accessory molecule, and a cargo composition, wherein the CendR peptide and the cargo composition are covalently coupled or non-covalently associated with each other, wherein the CendR peptide comprises the accessory molecule. Also disclosed are compositions comprising a CendR conjugate, an accessory molecule, and a cargo composition, wherein the CendR conjugate and the cargo composition are covalently coupled or non-covalently associated with each other, wherein the CendR conjugate comprises the accessory molecule. Also disclosed are compositions comprising a CendR composition, an accessory molecule, and a cargo composition, wherein the CendR composition and the cargo composition are covalently coupled or non-covalently associated with each other, wherein the CendR composition comprises the accessory molecule. In these compositions, the accessory molecule can be or can comprise an accessory peptide. The accessory peptide can overlap with the CendR element or be separate from the CendR element. In these compositions, the composition can comprise one or more cargo compositions and/or one or more accessory molecules, wherein the CendR element, CendR peptide, CendR conjugate, or CendR composition and at least one of the cargo compositions are covalently coupled or non-covalently associated with each other, wherein the CendR element, CendR peptide, CendR conjugate, or CendR composition and at least one of the accessory molecules are covalently coupled or non-covalently associated with each other.

Also disclosed are compositions comprising a CendR element, a homing molecule, and a cargo composition, wherein the CendR element and the cargo composition are covalently coupled or non-covalently associated with each other, wherein the CendR element and the homing molecule are covalently coupled or non-covalently associate with each other. Also disclosed are compositions comprising a CendR peptide, a homing molecule, and a cargo composition, wherein the CendR peptide and the cargo composition are covalently coupled or non-covalently associated with each other, wherein the CendR peptide and the homing molecule are covalently coupled or non-covalently associate with each other. Also disclosed are compositions comprising a CendR conjugate, a homing molecule, and a cargo composition, wherein the CendR conjugate and the cargo composition are covalently coupled or non-covalently associated with each other, wherein the CendR conjugate and the homing molecule are covalently coupled or non-covalently associate with each other. Also disclosed are compositions comprising a CendR composition, a homing molecule, and a cargo composition, wherein the CendR composition and the cargo composition are covalently coupled or non-covalently associated with each other, wherein the CendR composition and the homing molecule are covalently coupled or non-covalently associate with each other. Also disclosed are compositions comprising a CendR peptide, a homing molecule, and a cargo composition, wherein the CendR peptide and the cargo composition are covalently coupled or non-covalently associated with each other, wherein the CendR peptide comprises the homing molecule. Also disclosed are compositions comprising a CendR conjugate, a homing molecule, and a cargo composition, wherein the CendR conjugate and the cargo composition are covalently coupled or non-covalently associated with each other, wherein the CendR conjugate comprises the homing molecule. Also disclosed are compositions comprising a CendR composition, a homing molecule, and a cargo composition, wherein the CendR composition and the cargo composition are covalently coupled or non-covalently associated with each other, wherein the CendR composition comprises the homing molecule. In these compositions, the homing molecule can be or can comprise a homing peptide. The homing peptide can overlap with the CendR element or be separate from the CendR element. In these compositions, the composition can comprise one or more cargo compositions and/or one or more homing molecules, wherein the CendR element, CendR peptide, CendR conjugate, or CendR composition and at least one of the cargo compositions are not covalently coupled or non-covalently associated with each other, wherein the CendR element, CendR peptide, CendR conjugate, or CendR composition and at least one of the homing molecules are covalently coupled or non-covalently associated with each other.

Also disclosed are compositions comprising a protein or peptide and a co-composition, wherein the protein or peptide comprises a CendR element and an accessory peptide, wherein the CendR element and the co-composition are not covalently coupled or non-covalently associated with each other. Also disclosed are compositions comprising a protein or peptide and a co-composition, wherein the protein or peptide comprises an amino acid sequence, wherein the amino acid sequence comprises a CendR element and an accessory peptide, wherein the CendR element and the co-composition are not covalently coupled or non-covalently associated with each other. In these compositions, the accessory peptide can overlap with the CendR element or be separate from the CendR element. In these compositions, the composition can comprise one or more co-compositions and/or one or more accessory peptides, wherein the protein or peptide and at least one of the co-compositions are not covalently coupled or non-covalently associated with each other, wherein the protein or peptide and at least one of the accessory peptides are covalently coupled or non-covalently associated with each other.

Also disclosed are compositions comprising a protein or peptide and a co-composition, wherein the protein or peptide comprises a CendR element and a homing peptide, wherein the CendR element and the co-composition are not covalently coupled or non-covalently associated with each other. Also disclosed are compositions comprising a protein or peptide and a co-composition, wherein the protein or peptide comprises an amino acid sequence, wherein the amino acid sequence comprises a CendR element and a homing peptide, wherein the CendR element and the co-composition are not covalently coupled or non-covalently associated with each other. In these compositions, the homing peptide can overlap with the CendR element or be separate from the CendR element. In these compositions, the composition can comprise one or more co-compositions and/or one or more homing peptides, wherein the protein or peptide and at least one of the co-compositions are not covalently coupled or non-covalently associated with each other, wherein the protein or peptide and at least one of the homing peptides are covalently coupled or non-covalently associated with each other.

Also disclosed are compositions comprising a protein or peptide and a cargo composition, wherein the protein or peptide comprises a CendR element and an accessory peptide, wherein the CendR element and the cargo composition are covalently coupled or non-covalently associated with each other. Also disclosed are compositions comprising a protein or peptide and a cargo composition, wherein the protein or peptide comprises an amino acid sequence, wherein the amino acid sequence comprises a CendR element and an accessory peptide, wherein the CendR element and the cargo composition are covalently coupled or non-covalently associated with each other. In these compositions, the accessory peptide can overlap with the CendR element or be separate from the CendR element. In these compositions, the composition can comprise one or more cargo compositions and/or one or more accessory peptides, wherein the protein or peptide and at least one of the cargo compositions are covalently coupled or non-covalently associated with each other, wherein the protein or peptide and at least one of the accessory peptides are covalently coupled or non-covalently associated with each other.

Also disclosed are compositions comprising a protein or peptide and a cargo composition, wherein the protein or peptide comprises a CendR element and a homing peptide, wherein the CendR element and the cargo composition are covalently coupled or non-covalently associated with each other. Also disclosed are compositions comprising a protein or peptide and a cargo composition, wherein the protein or peptide comprises an amino acid sequence, wherein the amino acid sequence comprises a CendR element and a homing peptide, wherein the CendR element and the cargo composition are covalently coupled or non-covalently associated with each other. In these compositions, the homing peptide can overlap with the CendR element or be separate from the CendR element. In these compositions, the composition can comprise one or more cargo compositions and/or one or more homing peptides, wherein the protein or peptide and at least one of the cargo compositions are not covalently coupled or non-covalently associated with each other, wherein the protein or peptide and at least one of the homing peptides are covalently coupled or non-covalently associated with each other.

As used herein, reference to components (such as a CendR element and a co-composition) as being "not covalently coupled" means that the components are not connected via covalent bonds (for example, that the CendR element and the co-composition are not connected via covalent bonds). That is, there is no continuous chain of covalent bonds between, for example, the CendR element and the co-composition. Conversely, reference to components (such as a CendR element and a cargo composition) as being "covalently coupled" means that the components are connected via covalent bonds (for example, that the CendR element and the cargo composition are connected via covalent bonds). That is, there is a continuous chain of covalent bonds between, for example, the CendR element and the cargo composition. Components can be covalently coupled either directly or indirectly. Direct covalent coupling refers to the presence of a covalent bond between atoms of each of the components. Indirect covalent coupling refers to the absence of a covalent bond between atoms of each of the components. That is, some other atom or atoms not belonging to either of the coupled components intervenes between atoms of the components. Both direct and indirect covalent coupling involve a continuous chain of covalent bonds.

Non-covalent association refers to association of components via non-covalent bonds and interactions. A non-covalent association can be either direct or indirect. A direct non-covalent association refers to a non-covalent bond involving atoms that are each respectively connected via a chain of covalent bonds to the components. Thus, in a direct non-covalent association, there is no other molecule intervening between the associated components. An indirect non-covalent association refers to any chain of molecules and bonds linking the components where the components are not covalently coupled (that is, there is a least one separate molecule other than the components intervening between the components via non-covalent bonds).

Reference to components (such as a CendR element and a co-composition) as not being "non-covalently associated" means that there is no direct or indirect non-covalent association between the components. That is, for example, no atom covalently coupled to a CendR element is involved in a non-covalent bond with an atom covalently coupled to a co-composition. Within this meaning, a CendR element and a co-composition can be together in a composition where they are indirectly associated via multiple intervening non-covalent bonds while not being non-covalently associated as that term is defined herein. For example, a CendR element and a co-composition can be mixed together in a carrier where they are not directly non-covalently associated. A CendR element and a co-composition that are referred to as not indirectly non-covalently associated cannot be mixed together in a continuous composition. Reference to components (such as a CendR element and a co-composition) as not being "directly non-covalently associated" means that there is no direct non-covalent association between the components (an indirect non-covalent association may be present). Reference to components (such as a CendR element and a co-composition) as not being "indirectly non-covalently associated" means that there is no direct or indirect non-covalent association between the components.

It is understood that components can be non-covalently associated via multiple chains and paths including both direct and indirect non-covalent associations. For the purposes of these definitions, the presence a single direct non-covalent association makes the association a direct non-covalent association even if there are also indirect non-covalent associations present. Similarly, the presence of a covalent connection between components means the components are covalently coupled even if there are also non-covalent associations present. It is also understood that covalently coupled components that happened to lack any non-covalent association with each other are not considered to fall under the definition of components that are not non-covalently associated.

In some forms, the co-composition does not comprise a functional internalization element. The co-composition can comprise a functional internalization element. In some forms, the co-composition does not comprise a homing molecule. The co-composition can comprise a homing molecule. In some forms, the co-composition does not comprise a homing peptide. The co-composition can comprise a homing peptide. The co-composition can selectively home to a tumor. In some forms, the co-composition does not selectively home to tumor vasculature. The co-composition can selectively home to tumor vasculature. In some forms, the co-composition does not comprise an accessory molecule. The co-composition can comprise an accessory molecule. In some forms, the co-composition does not comprise a accessory peptide. The co-composition can comprise an accessory peptide. The co-composition can selectively home to a tumor.

The CendR element can be associated with one or more accessory molecules. For example, an accessory molecule can be a part of an amino acid sequence, protein, peptide, conjugate, or composition that comprises the CendR element. As another example, the accessory molecule can be covalently coupled or non-covalently associated with the CendR element or an amino acid sequence, protein, peptide, conjugate, or composition that comprises the CendR element. Accessory molecules can be any molecule, compound, component, etc. that has a useful function and that can be used in combination with a CendR element, CendR composition, CendR conjugate, CendR molecule, CendR compound, CendR protein, and/or CendR peptide. Examples of useful accessory molecules include homing molecules, targeting molecules, affinity ligands, cell penetrating molecules, endosomal escape molecules, subcellular targeting molecules, nuclear targeting molecules. Different accessory molecules can have similar or different functions from each other. Accessory molecules having similar functions, different functions, or both, can be associated a CendR element, CendR composition, CendR conjugate, CendR molecule, CendR compound, CendR protein, and/or CendR peptide.

The accessory molecule can be separate from or overlapping with the CendR element. For example, some accessory molecules are amino acid sequences. This can allow the amino acid sequence consisting of the CendR element to overlap the amino acid sequence that consists of the accessory amino acid sequence. For example, iRGD, LyP-1, iNGR, and RGR peptides each contain both an accessory sequence and CendR sequence overlapping with one another in the peptide. Alternatively the accessory molecule can be a separate entity that does not overlap with the CendR element. For example, a HER2 binding peptide, CREKA (SEQ ID NO:7) peptide, NGR peptide, iNGR, or an RGD peptide that is not a CendR element can consist of amino acid sequence that does not overlap with a CendR element. In some forms, the accessory molecule can comprise a sequence in, for example, a CendR peptide that binds to a specific receptor distinct from the receptor for the CendR element.

The CendR peptide can be associated with one or more accessory molecules. For example, an accessory molecule can be a part of an amino acid sequence, protein, peptide, conjugate, or composition that comprises the CendR peptide. As another example, the accessory molecule can be covalently coupled or non-covalently associated with the CendR peptide or an amino acid sequence, protein, peptide, conjugate, or composition that comprises the CendR peptide. The CendR conjugate can be associated with one or more accessory molecules. For example, an accessory molecule can be a part of a conjugate or composition that comprises the CendR conjugate. As another example, the accessory molecule can be covalently coupled or non-covalently associated with the CendR conjugate or a conjugate or composition that comprises the CendR conjugate.

The CendR composition can be associated with one or more accessory molecules. For example, an accessory molecule can be a part of a composition that comprises the CendR composition. As another example, the accessory molecule can be covalently coupled or non-covalently associated with the CendR composition or a composition that comprises the CendR composition.

The amino acid sequence can be associated with one or more accessory molecules. For example, an accessory molecule can be a part of an amino acid sequence, protein, peptide, conjugate, or composition that comprises the amino acid sequence. As another example, the accessory molecule can be covalently coupled or non-covalently associated with the amino acid sequence or an amino acid sequence, protein, peptide, conjugate, or composition that comprises the amino acid sequence. For example, the amino acid sequences can comprise a iRGD peptide, a LyP-1 peptide, a RGR peptide, a HER2 binding peptide, a CREKA (SEQ ID NO:7) peptide, a NGR peptide, iNGR, a RGD peptide that is not a CendR element, or a combination. The amino acid sequence can comprise a CREKA (SEQ ID NO:7) peptide. The protein or peptide can be associated with one or more accessory molecules. For example, an accessory molecule can be a part of a protein, peptide, conjugate, or composition that comprises the peptide. As another example, the accessory molecule can be covalently coupled or non-covalently associated with the peptide or a protein, peptide, conjugate, or composition that comprises the peptide. For example, an accessory molecule can be a part of a protein, conjugate, or composition that comprises the protein. As another example, the accessory molecule can be covalently coupled or non-covalently associated with the protein or a protein, conjugate, or composition that comprises the protein. For example, the protein or peptide can comprise a iRGD peptide, a LyP-1 peptide, a RGR peptide, a HER2 binding peptide, a CREKA (SEQ ID NO:7) peptide, a NGR peptide, iNGR, a RGD peptide that is not a CendR element, or a combination. The conjugate can be associated with one or more accessory molecules. For example, an accessory molecule can be a part of a conjugate or composition that comprises the conjugate. As another example, the accessory molecule can be covalently coupled or non-covalently associated with the conjugate or a conjugate or composition that comprises the conjugate. For example, the conjugate can comprise a iRGD peptide, a LyP-1 peptide, a RGR peptide, a HER2 binding peptide, a CREKA (SEQ ID NO:7) peptide, a NGR peptide, iNGR, a RGD peptide that is not a CendR element, or a combination. The composition can be associated with one or more accessory molecules. For example, an accessory molecule can be a part of a composition that comprises the composition. As another example, the accessory molecule can be covalently coupled or non-covalently associated with the composition or a composition that comprises the composition. For example, the composition can comprise a iRGD peptide, a LyP-1 peptide, a RGR peptide, a HER2 binding peptide, a CREKA (SEQ ID NO:7) peptide, a NGR peptide, iNGR, a RGD peptide that is not a CendR element, or a combination.

The CendR element can be associated with one or more homing molecules. For example, a homing molecule can be a part of an amino acid sequence, protein, peptide, conjugate, or composition that comprises the CendR element. As another example, the homing molecule can be covalently coupled or non-covalently associated with the CendR element or an amino acid sequence, protein, peptide, conjugate, or composition that comprises the CendR element. The homing molecule can be separate from or overlapping with the CendR element. For example, some homing molecules are amino acid sequences. This can allow the amino acid sequence consisting of the CendR element to overlap the amino acid sequence that consists of the homing amino acid sequence. For example, iRGD, LyP-1, iNGR, and RGR peptides each contain both a homing sequence and CendR sequence overlapping with one another in the peptide. Alternatively the homing molecule can be a separate entity that does not overlap with the CendR element. For example, a HER2 binding peptide, CREKA (SEQ ID NO:7) peptide, NGR peptide, iNGR, or an RGD peptide that is not a CendR element can consist of amino acid sequence that does not overlap with a CendR element. In some forms, the homing molecule can comprise a sequence in, for example, a CendR peptide that binds to a specific receptor distinct from the receptor for the CendR element.

The CendR peptide can be associated with one or more homing molecules. For example, a homing molecule can be a part of an amino acid sequence, protein, peptide, conjugate, or composition that comprises the CendR peptide. As another example, the homing molecule can be covalently coupled or non-covalently associated with the CendR peptide or an amino acid sequence, protein, peptide, conjugate, or composition that comprises the CendR peptide. The CendR conjugate can be associated with one or more homing molecules. For example, a homing molecule can be a part of a conjugate or composition that comprises the CendR conjugate. As another example, the homing molecule can be covalently coupled or non-covalently associated with the CendR conjugate or a conjugate or composition that comprises the CendR conjugate. The CendR composition can be associated with one or more homing molecules. For example, a homing molecule can be a part of a composition that comprises the CendR composition. As another example, the homing molecule can be covalently coupled or non-covalently associated with the CendR composition or a composition that comprises the CendR composition.

The amino acid sequence can be associated with one or more homing molecules. For example, a homing molecule can be a part of an amino acid sequence, protein, peptide, conjugate, or composition that comprises the amino acid sequence. As another example, the homing molecule can be covalently coupled or non-covalently associated with the amino acid sequence or an amino acid sequence, protein, peptide, conjugate, or composition that comprises the amino acid sequence. For example, the amino acid sequences can comprise a iRGD peptide, a LyP-1 peptide, a RGR peptide, a HER2 binding peptide, a CREKA (SEQ ID NO:7) peptide, a NGR peptide, iNGR, a RGD peptide that is not a CendR element, or a combination. The amino acid sequence can comprise a CREKA (SEQ ID NO:7) peptide. The protein or peptide can be associated with one or more homing molecules. For example, a homing molecule can be a part of a protein, peptide, conjugate, or composition that comprises the peptide. As another example, the homing molecule can be covalently coupled or non-covalently associated with the peptide or a protein, peptide, conjugate, or composition that comprises the peptide. For example, a homing molecule can be a part of a protein, conjugate, or composition that comprises the protein. As another example, the homing molecule can be covalently coupled or non-covalently associated with the protein or a protein, conjugate, or composition that comprises the protein. For example, the protein or peptide can comprise a iRGD peptide, a LyP-1 peptide, a RGR peptide, a HER2 binding peptide, a CREKA (SEQ ID NO:7) peptide, a NGR peptide, iNGR, a RGD peptide that is not a CendR element, or a combination. The protein or peptide can comprise iRGD. The protein or peptide can comprise a LyP-1 peptide. The protein or peptide can comprise iNGR. The protein or peptide can comprise RGR peptide. The protein or peptide can comprise a CREKA (SEQ ID NO:7) peptide. The conjugate can be associated with one or more homing molecules. For example, a homing molecule can be a part of a conjugate or composition that comprises the conjugate. As another example, the homing molecule can be covalently coupled or non-covalently associated with the conjugate or a conjugate or composition that comprises the conjugate. For example, the conjugate can comprise a iRGD peptide, a LyP-1 peptide, a RGR peptide, a HER2 binding peptide, a CREKA (SEQ ID NO:7) peptide, a NGR peptide, iNGR, a RGD peptide that is not a CendR element, or a combination. The conjugate can comprise iRGD. The conjugate can comprise a LyP-1 peptide. The conjugate can comprise iNGR. The conjugate can comprise RGR peptide. The conjugate can comprise a CREKA (SEQ ID NO:7) peptide. The composition can be associated with one or more homing molecules. For example, a homing molecule can be a part of a composition that comprises the composition. As another example, the homing molecule can be covalently coupled or non-covalently associated with the composition or a composition that comprises the composition. For example, the composition can comprise a iRGD peptide, a LyP-1 peptide, a RGR peptide, a HER2 binding peptide, a CREKA (SEQ ID NO:7) peptide, a NGR peptide, iNGR, a RGD peptide that is not a CendR element, or a combination. The composition can comprise iRGD. The composition can comprise a LyP-1 peptide. The composition can comprise iNGR. The composition can comprise RGR peptide. The composition can comprise a CREKA (SEQ ID NO:7) peptide.

The amino acid sequence can be selected for internalization into a cell. The amino acid sequence can be selected for tissue penetration. The amino acid sequence can be selected for internalization into a cell and tissue penetration. The protein or peptide can be selected for internalization into a cell. The protein or peptide can be selected for tissue penetration. The protein or peptide can be selected for internalization into a cell and tissue penetration. The conjugate can be selected for internalization into a cell. The conjugate can be selected for tissue penetration. The conjugate can be selected for internalization into a cell and tissue penetration. The composition can be selected for internalization into a cell. The composition can be selected for tissue penetration. The composition can be selected for internalization into a cell and tissue penetration.

The CendR element, CendR peptide, CendR conjugate, CendR composition, amino acid sequence, protein or peptide, conjugate, composition, co-composition, cargo composition, or a combination can selectively home to a tumor. The CendR element, CendR peptide, CendR conjugate, CendR composition, amino acid sequence, protein or peptide, conjugate, composition, co-composition, cargo composition, or a combination can selectively home to tumor vasculature. The CendR element, CendR peptide, CendR conjugate, CendR composition, amino acid sequence, protein or peptide, conjugate, composition, co-composition, cargo composition, or a combination can selectively home to one or more particular types of tumor. The CendR element, CendR peptide, CendR conjugate, CendR composition, amino acid sequence, protein or peptide, conjugate, composition, co-composition, cargo composition, or a combination can selectively home to the vasculature of one or more particular types of tumor. The CendR element, CendR peptide, CendR conjugate, CendR composition, amino acid sequence, protein or peptide, conjugate, composition, co-composition, cargo composition, or a combination can selectively home to one or more particular stages of a tumor or cancer. The CendR element, CendR peptide, CendR conjugate, CendR composition, amino acid sequence, protein or peptide, conjugate, composition, co-composition, cargo composition, or a combination can selectively home to the vasculature of one or more particular stages of a tumor or cancer. The CendR element, CendR peptide, CendR conjugate, CendR composition, amino acid sequence, protein or peptide, conjugate, composition, co-composition, cargo composition, or a combination can selectively home to one or more particular stages of one or more particular types of tumor. The CendR element, CendR peptide, CendR conjugate, CendR composition, amino acid sequence, protein or peptide, conjugate, composition, co-composition, cargo composition, or a combination can selectively home to the vasculature of one or more different stages of one or more particular types of tumor.

The CendR element, CendR peptide, CendR conjugate, CendR composition, amino acid sequence, protein or peptide, conjugate, composition, co-composition, cargo composition, or a combination can selectively home to lung tissue. The CendR element, CendR peptide, CendR conjugate, CendR composition, amino acid sequence, protein or peptide, conjugate, composition, co-composition, cargo composition, or a combination can selectively home to lung vasculature. The CendR element, CendR peptide, CendR conjugate, CendR composition, amino acid sequence, protein or peptide, conjugate, composition, co-composition, cargo composition, or a combination can selectively home to heart tissue. The CendR element, CendR peptide, CendR conjugate, CendR composition, amino acid sequence, protein or peptide, conjugate, composition, co-composition, cargo composition, or a combination can selectively home to heart vasculature. The CendR element, CendR peptide, CendR conjugate, CendR composition, amino acid sequence, protein or peptide, conjugate, composition, co-composition, cargo composition, or a combination can selectively home to brain cells, brain stem cells, brain tissue, and/or brain vasculature, kidney cells, kidney stem cells, kidney tissue, and/or kidney vasculature, skin cells, skin stem cells, skin tissue, and/or skin vasculature, lung cells, lung tissue, and/or lung vasculature, pancreatic cells, pancreatic tissue, and/or pancreatic vasculature, intestinal cells, intestinal tissue, and/or intestinal vasculature, adrenal gland cells, adrenal tissue, and/or adrenal vasculature, retinal cells, retinal tissue, and/or retinal vasculature, liver cells, liver tissue, and/or liver vasculature, prostate cells, prostate tissue, and/or prostate vasculature, endometriosis cells, endometriosis tissue, and/or endometriosis vasculature, ovary cells, ovary tissue, and/or ovary vasculature, tumor cells, tumors, tumor blood vessels, and/or tumor vasculature, bone cells, bone tissue, and/or bone vasculature, bone marrow cells, bone marrow tissue, and/or bone marrow vasculature, cartilage cells, cartilage tissue, and/or cartilage vasculature, stem cells, embryonic stem cells, pluripotent stem cells, induced pluripotent stem cells, adult stem cells, hematopoietic stem cells, neural stem cells, mesenchymal stem cells, mammary stem cells, endothelial stem cells, olfactory adult stem cells, neural crest stem cells, cancer stem cells, blood cells, erythrocytes, platelets, leukocytes, granulocytes, neutrophils, eosinphils, basophils, lymphoid cells, lymphocytes, monocytes, wound vasculature, vasculature of injured tissue, vasculature of inflamed tissue, atherosclerotic plaques, or a combination.

CendR compositions, CendR conjugates, CendR molecules, CendR compounds, CendR proteins, CendR peptides, and CendR elements can be designed and produced in any suitable manner. For example, the CendR element in the disclosed CendR compositions, CendR conjugates, CendR molecules, CendR compounds, CendR proteins, and CendR peptides can be designed or produced by selecting an amino acid sequence for internalization into a cell and/or penetration of tissue, wherein the amino acid sequence comprises a C-terminal element, wherein a protein or peptide comprises the selected amino acid sequence, wherein the selected amino acid sequence is at the C-terminal end of the protein or peptide.

Disclosed are compositions comprising a CendR element and a co-composition, wherein the CendR element and the co-composition are not covalently coupled or non-covalently associated with each other. Also disclosed are compositions comprising a CendR element and a cargo composition, wherein the CendR element and the cargo composition are covalently coupled or non-covalently associated with each other, wherein the CendR element is a type 2 CendR element.

Also disclosed are methods of enhancing internalization, penetration, or both of a co-composition into or through a cell, tissue, or both, the method comprising exposing the cell, tissue, or both to a CendR element and the co-composition, thereby enhancing internalization, penetration, or both of the co-composition into or through the cell, tissue, or both. In some forms, prior to exposing the cell, tissue, or both, the CendR element and the co-composition are not covalently coupled or non-covalently associated with each other.

Also disclosed are methods of enhancing internalization, penetration, or both of a cargo composition into or through a cell, tissue, or both, the method comprising exposing the cell, tissue, or both to a CendR element and the cargo composition, thereby enhancing internalization, penetration, or both of the cargo composition into or through the cell, tissue, or both. The CendR element and the cargo composition can be covalently coupled or non-covalently associated with each other. The CendR element can be a type 2 CendR element. The methods can further comprise, prior to exposing the cell, tissue, or both to the CendR element, coupling the CendR element to the cargo composition.

The CendR element can permeabilize the cell, tissue, or both. The cell, tissue, or both can be in a subject. The cell, tissue, or both can be exposed to the CendR element and the co-composition by administering the CendR element and the co-composition to the subject. The cell, tissue, or both can be exposed to the CendR element and the cargo composition by administering the CendR element and the cargo composition to the subject.

The CendR element can be associated with one or more accessory molecules. The CendR element can be associated with a plurality of accessory molecules. In some forms, at least one of the accessory molecules overlaps with the CendR element. In some forms, at least one of the accessory molecules does not overlap with the CendR element. In some forms, at least one of the accessory molecules can comprise an RGD peptide, iRGD, a Lyp-1 peptide, a NGR peptide, iNGR, an RGR peptide, a HER2 binding peptide, or a combination. One or more of the accessory molecules can be independently a homing molecule, a targeting molecules, an affinity ligand, a cell penetrating peptide, an endosomal escape molecule, a subcellular targeting molecule, a nuclear targeting molecule, or a combination. One or more of the accessory molecules can be homing molecules. One or more of the accessory molecules can be accessory peptides. One or more of the accessory molecules can comprise iRGD. One or more of the accessory molecules can comprise a Lyp-1 peptide. One or more of the accessory molecules can comprise iNGR. One or more of the accessory molecules can comprise RGR peptide.

The CendR element can selectively home to brain cells, tissue, or both, kidney cells, tissue, or both, skin and tendon cells, tissue, or both, lung cells, tissue, or both, pancreatic cells, tissue, or both, intestinal cells, tissue, or both, adrenal gland cells, tissue, or both, retinal cells, tissue, or both, liver cells, tissue, or both, prostate cells, tissue, or both, endometriosis cells, tissue, or both, ovary cells, tissue, or both, heart cells, tissue, or both, tumor cells, tumors, tumor blood vessels, or a combination. The CendR element can selectively home to a tumor. The CendR element can selectively home to tumor vasculature. The CendR element can selectively home to lung tissue. The CendR element can selectively home to heart tissue.

The CendR element can be an activatable CendR element. The activatable CendR element can be a protease-activatable CendR element. The protease-activatable CendR element can be activatable by a serine protease, plasmin, a plasminogen activator, urokinase, a proprotein convertase, a furin, a carboxypeptidase, carboxypeptidase A, a glutamate-specific carboxypeptidase, a proline-specific carboxypeptidase, PSMA, or a combination.

The CendR element and the co-composition can be administered to the subject simultaneously. The CendR element and the co-composition can be administered to the subject in a single composition comprising the CendR element and the co-composition. The CendR element and the co-composition can be administered to the subject in separate compositions. The CendR element and the co-composition can be administered to the subject at different times. The CendR element and the co-composition can be administered to the subject in separate compositions. The CendR element and the co-composition can be administered to the subject by separate routes.

In some forms, the CendR element and the co-composition are not bound to each other. The co-composition or cargo composition can comprise a therapeutic agent. The co-composition or cargo composition can comprise a detection agent. The co-composition or cargo composition can comprise a carrier, vehicle, or both. The co-composition or cargo composition can comprise a therapeutic protein, a therapeutic compound, a therapeutic composition, a cancer chemotherapeutic agent, a toxin, a cytotoxic agent, an anti-inflammatory agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, an anti-angiogenic agent, a pro-angiogenic agent, or a combination.

The CendR element can be comprised in an amino acid sequence. The amino acid sequence can be comprised in a protein or peptide. The CendR element can be comprised in a protein or peptide. In some forms, the protein or peptide can be internalized into a cell, penetrate tissue, or both when the amino acid sequence is present in the protein or peptide but not when the amino acid sequence is not present in the protein or peptide. In some forms, the protein or peptide can penetrate tissue when the amino acid sequence is present in the protein or peptide but not when the amino acid sequence is not present in the protein or peptide. In some forms, the protein or peptide can be internalized into a cell and penetrate tissue when the amino acid sequence is present in the protein or peptide but not when the amino acid sequence is not present in the protein or peptide.

In some forms, the amino acid sequence can be internalized into a cell, penetrate tissue, or both without being associated with the co-composition. In some forms, the amino acid sequence can be internalized into a cell, penetrate tissue, or both without being associated with the cargo composition. In some forms, the amino acid sequence can penetrate tissue without being associated with the co-composition. In some forms, the amino acid sequence can penetrate tissue without being associated with the cargo composition. In some forms, the amino acid sequence can be internalized into a cell and penetrate tissue without being associated with the co-composition. In some forms, the amino acid sequence can be internalized into a cell and penetrate tissue without being associated with the cargo composition. In some forms, the amino acid sequence can be the only functional internalization element in the protein or peptide.

The protein or peptide can be circular. The CendR element can be at the C-terminal end of the protein or peptide. In some forms, the internalization, penetration, or both of the co-composition or cargo composition into or through a cell, tissue, or both can be enhanced when the amino acid sequence is present in the protein or peptide but not when the amino acid sequence is not present in the protein or peptide. In some forms, the penetration of the co-composition or cargo composition into or through tissue can be enhanced when the amino acid sequence is present in the protein or peptide but not when the amino acid sequence is not present in the protein or peptide. In some forms, the internalization and penetration of the co-composition or cargo composition into or through a cell and tissue can be enhanced when the amino acid sequence is present in the protein or peptide but not when the amino acid sequence is not present in the protein or peptide. In some forms, the internalization, penetration, or both of the co-composition or cargo composition into or through a cell, tissue, or both can be enhanced when the CendR element is present in the protein or peptide but not when the amino acid sequence is not present in the protein or peptide. In some forms, the penetration of the co-composition or cargo composition into or through tissue can be enhanced when the CendR element is present in the protein or peptide but not when the amino acid sequence is not present in the protein or peptide. In some forms, the internalization and penetration of the co-composition or cargo composition into or through a cell and tissue can be enhanced when the CendR element is present in the protein or peptide but not when the amino acid sequence is not present in the protein or peptide.

The amino acid sequence can be associated with one or more accessory molecules. The protein or peptide can be associated with one or more accessory molecules. One or more of the accessory molecules can be independently a homing molecule, a targeting molecule, an affinity ligand, a cell penetrating peptide, an endosomal escape molecule, a subcellular targeting molecule, a nuclear targeting molecule, or a combination. One or more of the accessory molecules can be homing molecules. One or more of the homing molecules can be independently an RGD peptide, iRGD, Lyp-1 peptide, NGR peptide, iNGR, RGR peptide, HER2 binding peptide, or a combination.

The protein or peptide can comprise one or more accessory peptides. The amino acid sequence can comprise one or more accessory peptides. One or more of the accessory peptides can be independently a homing peptide, a targeting molecule, an affinity ligand, a cell penetrating peptide, an endosomal escape peptide, a subcellular targeting peptide, a nuclear targeting peptide, or a combination. One or more of the homing peptides can be independently an RGD peptide, iRGD, Lyp-1 peptide, NGR peptide, iNGR, RGR peptide, HER2 binding peptide, or a combination. The protein or peptide can comprise iRGD. The protein or peptide can comprise a Lyp-1 peptide. The protein or peptide can comprise iNGR. The protein or peptide can comprise RGR peptide.

The protein or peptide can selectively home to brain cells, tissue, or both, kidney cells, tissue, or both, skin and tendon cells, tissue, or both, lung cells, tissue, or both, pancreatic cells, tissue, or both, intestinal cells, tissue, or both, adrenal gland cells, tissue, or both, retinal cells, tissue, or both, liver cells, tissue, or both, prostate cells, tissue, or both, endometriosis cells, tissue, or both, ovary cells, tissue, or both, heart cells, tissue, or both, tumor cells, tumors, tumor blood vessels, or a combination. The protein or peptide can selectively home to a tumor. The protein or peptide can selectively home to tumor vasculature. The protein or peptide can selectively home to lung tissue. The protein or peptide can selectively home to heart tissue.

The amino acid sequence can be selected for internalization into a cell. The amino acid sequence can be selected for tissue penetration. The amino acid sequence can be selected for internalization into a cell and tissue penetration.

In some forms, the internalization, penetration, or both of the co-composition into or through a cell, tissue, or both can be enhanced when the cell, tissue, or both is exposed to the CendR element but not when the cell, tissue, or both is not exposed to the CendR element. In some forms, the penetration of the co-composition into or through tissue can be enhanced when the tissue is exposed to the CendR element but not when the tissue is not exposed to the CendR element. In some forms, the internalization and penetration of the co-composition into or through a cell and tissue can be enhanced when the cell and tissue are exposed to the CendR element but not when the cell and tissue is not exposed to the CendR element.

The CendR element can be comprised in a CendR composition. The CendR composition can comprise one or more accessory molecules. The CendR composition can comprise one or more cargo compositions. The CendR composition can comprise one or more homing molecules. The CendR element can be comprised in a CendR conjugate. The CendR conjugate can comprise one or more accessory molecules. The CendR conjugate can comprise one or more cargo compositions. The CendR conjugate can comprise one or more homing molecules.

The cell, tissue, or both can be exposed to a plurality of accessory molecules. The cell, tissue, or both can be exposed to a plurality of homing molecules. The cell, tissue, or both can be exposed to a plurality of cargo compositions. The cell, tissue, or both can be exposed to a plurality of CendR elements. The cell, tissue, or both can be exposed to a plurality of co-compositions.

As defined herein, a C-terminal element (CendR element) is either an arginine, a lysine, or a lysine-glycine (for a type 1 CendR element), or a histidine or an amino acid sequence having the sequence $X_1X_2X_3X_4$, where $X_1$ can be R, K or H, where $X_4$ can be R, K, H, or KG, and where $X_2$ and $X_3$ can each be, independently, any amino acid (for a type 2 CendR element).

As used herein, "selecting an amino acid sequence for internalization into a cell" refers to selecting, identifying designing or otherwise categorizing an amino acid sequence with the specific intention of obtaining entry into a cell of a protein or peptide that is comprised of the amino acid sequence. Thus, for example, selecting an amino acid sequence for some purpose or capability other than obtaining entry into a cell of a protein or peptide that is comprised of the amino acid sequence and in the absence of an intention of obtaining entry into a cell of a protein or peptide that is comprised of the amino acid sequence does not constitute "selecting an amino acid sequence for internalization into a cell." Selecting an amino acid sequence for some purpose or capability as well as for obtaining entry into a cell of a protein or peptide that is comprised of the amino acid sequence does constitute "selecting an amino acid sequence for internalization into a cell." Thus, the presence of additional goals or purposes does not alter that selection of an amino acid sequence at least with the specific intention of obtaining entry into a cell of a protein or peptide that is comprised of the amino acid sequence constitutes "selecting an amino acid sequence for internalization into a cell."

As used herein, "selecting an amino acid sequence for penetration of tissue" refers to selecting, identifying designing or otherwise categorizing an amino acid sequence with the specific intention of obtaining entry into tissue (that is, tissue penetration) of a protein or peptide that is comprised of the amino acid sequence. Thus, for example, selecting an amino acid sequence for some purpose or capability other than obtaining entry into tissue of a protein or peptide that is comprised of the amino acid sequence and in the absence of an intention of obtaining entry into tissue of a protein or peptide that is comprised of the amino acid sequence does not constitute "selecting an amino acid sequence for penetration of tissue." Selecting an amino acid sequence for some purpose or capability as well as for obtaining entry into tissue of a protein or peptide that is comprised of the amino acid sequence does constitute "selecting an amino acid sequence for penetration of tissue." Thus, the presence of additional goals or purposes does not alter that selection of an amino acid sequence at least with the specific intention of obtaining entry into tissue of a protein or peptide that is comprised of the amino acid sequence constitutes "selecting an amino acid sequence for penetration of tissue."

As used herein, "selecting an amino acid sequence for internalization into a cell and/or penetration of tissue" refers to selecting, identifying designing or otherwise categorizing an amino acid sequence with the specific intention of obtaining entry into either or both a cell and tissue of a protein or peptide that is comprised of the amino acid sequence. Thus, for example, selecting an amino acid sequence for some purpose or capability other than obtaining entry into a cell, tissue, or both of a protein or peptide that is comprised of the amino acid sequence and in the absence of an intention of obtaining entry into a cell, tissue, or both of a protein or peptide that is comprised of the amino acid sequence does not constitute "selecting an amino acid sequence for internalization into a cell and/or penetration of tissue." Selecting an amino acid sequence for some purpose or capability as well as for obtaining entry into either or both a cell and tissue of a protein or peptide that is comprised of the amino acid sequence does constitute "selecting an amino acid sequence for internalization into a cell and/or penetration of tissue." Thus, the presence of additional goals or purposes does not alter that selection of an amino acid sequence at least with the specific intention of obtaining entry into a cell, tissue, or both of a protein or peptide that is comprised of the amino acid sequence constitutes "selecting an amino acid sequence for internalization into a cell and/or penetration of tissue."

As used herein, unless the context indicates otherwise, "selecting a co-composition for internalization into a cell" refers to selecting, identifying designing or otherwise categorizing a co-composition and a CendR composition, CendR conjugate, CendR molecule, CendR compound, CendR protein, CendR peptide, or CendR element with the specific intention of obtaining entry into a cell of both the co-composition and the CendR composition, CendR conjugate, CendR molecule, CendR compound, CendR protein, CendR peptide, or CendR element. Thus, for example, selecting a co-composition for some purpose or capability other than obtaining entry into a cell in combination with entry of a selected CendR composition, CendR conjugate, CendR molecule, CendR compound, CendR protein, CendR peptide, or CendR element and in the absence of an intention of obtaining entry into a cell of both the co-composition and the CendR composition, CendR conjugate, CendR molecule, CendR compound, CendR protein, CendR peptide, or CendR element does not constitute "selecting co-composition for internalization into a cell." Selecting a co-composition for some purpose or capability as well as for obtaining entry into a cell of the co-composition does constitute "selecting co-composition for internalization into a cell." Thus, the presence of additional goals or purposes does not alter that selection of a co-composition at least with the specific intention of obtaining entry into a cell of a co-composition constitutes "selecting a co-composition for internalization into a cell."

As used herein, unless the context indicates otherwise, "selecting a co-composition for penetration of tissue" refers to selecting, identifying designing or otherwise categorizing a co-composition and a CendR composition, CendR conjugate, CendR molecule, CendR compound, CendR protein, CendR peptide, or CendR element with the specific intention of obtaining entry into tissue (that is, tissue penetration) of both the co-composition and the CendR composition, CendR conjugate, CendR molecule, CendR compound, CendR protein, CendR peptide, or CendR element. Thus, for example, selecting a co-composition for some purpose or capability other than obtaining entry into tissue in combination with entry of a selected CendR composition, CendR conjugate, CendR molecule, CendR compound, CendR protein, CendR peptide, or CendR element and in the absence of an intention of obtaining entry into tissue of both the co-composition and the CendR composition, CendR conjugate, CendR molecule, CendR compound, CendR protein, CendR peptide, or CendR element does not constitute "selecting co-composition for penetration of tissue." Selecting a co-composition for some purpose or capability as well as for obtaining entry into tissue of the co-composition does constitute "selecting co-composition for penetration of tissue." Thus, the presence of additional goals or purposes does not alter that selection of a co-composition at least with the specific intention of obtaining entry into tissue of a co-composition constitutes "selecting a co-composition for penetration of tissue."

As used herein, unless the context indicates otherwise, "selecting a co-composition for internalization into a cell and/or penetration of tissue" refers to selecting, identifying designing or otherwise categorizing a co-composition and a CendR composition, CendR conjugate, CendR molecule, CendR compound, CendR protein, CendR peptide, or CendR element with the specific intention of obtaining entry into either or both a cell and tissue of both the co-composition and the CendR composition, CendR conjugate, CendR molecule, CendR compound, CendR protein, CendR peptide, or CendR element. Thus, for example, selecting a co-composition for some purpose or capability other than obtaining entry into either or both a cell and tissue in combination with entry of a selected CendR composition, CendR conjugate, CendR molecule, CendR compound, CendR protein, CendR peptide, or CendR element and in the absence of an intention of obtaining entry into either or both a cell and tissue of both the co-composition and the CendR composition, CendR conjugate, CendR molecule, CendR compound, CendR protein, CendR peptide, or CendR element does not constitute "selecting co-composition for internalization into a cell and/or penetration of tissue." Selecting a co-composition for some purpose or capability as well as for obtaining entry into either or both a cell and tissue of the co-composition does constitute "selecting co-composition for internalization into a cell and/or penetration of tissue." Thus, the presence of additional goals or purposes does not alter that selection of a co-composition at least with the specific intention of obtaining entry into either or both a cell and tissue of a co-composition constitutes "selecting a co-composition for internalization into a cell and/or penetration of tissue."

As used herein, unless the context indicates otherwise, "selecting a cargo composition for internalization into a cell" refers to selecting, identifying designing or otherwise categorizing a cargo composition and a CendR composition, CendR conjugate, CendR molecule, CendR compound, CendR protein, CendR peptide, or CendR element with the specific intention of obtaining entry into a cell of both the cargo composition and the CendR composition, CendR conjugate, CendR molecule, CendR compound, CendR protein, CendR peptide, or CendR element. Thus, for example, selecting a cargo composition for some purpose or capability other than obtaining entry into a cell in combination with entry of a selected CendR composition, CendR conjugate, CendR molecule, CendR compound, CendR protein, CendR peptide, or CendR element and in the absence of an intention of obtaining entry into a cell of both the cargo composition and the CendR composition, CendR conjugate, CendR molecule, CendR compound, CendR protein, CendR peptide, or CendR element does not constitute "selecting cargo composition for internalization into a cell." Selecting a cargo composition for some purpose or capability as well as for obtaining entry into a cell of the cargo composition does constitute "selecting cargo composition for internalization into a cell." Thus, the presence of additional goals or purposes does not alter that selection of a cargo composition at least with the specific intention of obtaining entry into a cell of a cargo composition constitutes "selecting a cargo composition for internalization into a cell."

As used herein, unless the context indicates otherwise, "selecting a cargo composition for penetration of tissue" refers to selecting, identifying designing or otherwise categorizing a cargo composition and a CendR composition, CendR conjugate, CendR molecule, CendR compound, CendR protein, CendR peptide, or CendR element with the specific intention of obtaining entry into tissue (that is, tissue penetration) of both the cargo composition and the CendR composition, CendR conjugate, CendR molecule, CendR compound, CendR protein, CendR peptide, or CendR element. Thus, for example, selecting a cargo composition for some purpose or capability other than obtaining entry into tissue in combination with entry of a selected CendR composition, CendR conjugate, CendR molecule, CendR compound, CendR protein, CendR peptide, or CendR element and in the absence of an intention of obtaining entry into tissue of both the cargo composition and the CendR composition, CendR conjugate, CendR molecule, CendR compound, CendR protein, CendR peptide, or CendR element does not constitute "selecting cargo composition for penetration of tissue." Selecting a cargo composition for some purpose or capability as well as for obtaining entry into tissue of the cargo composition does constitute "selecting cargo composition for penetration of tissue." Thus, the presence of additional goals or purposes does not alter that selection of a cargo composition at least with the specific intention of obtaining entry into tissue of a cargo composition constitutes "selecting a cargo composition for penetration of tissue."

As used herein, unless the context indicates otherwise, "selecting a cargo composition for internalization into a cell and/or penetration of tissue" refers to selecting, identifying designing or otherwise categorizing a cargo composition and a CendR composition, CendR conjugate, CendR molecule, CendR compound, CendR protein, CendR peptide, or CendR element with the specific intention of obtaining entry into either or both a cell and tissue of both the cargo composition and the CendR composition, CendR conjugate, CendR molecule, CendR compound, CendR protein, CendR peptide, or CendR element. Thus, for example, selecting a cargo composition for some purpose or capability other than obtaining entry into either or both a cell and tissue in combination with entry of a selected CendR composition, CendR conjugate, CendR molecule, CendR compound, CendR protein, CendR peptide, or CendR element and in the absence of an intention of obtaining entry into either or both a cell and tissue of both the cargo composition and the CendR composition, CendR conjugate, CendR molecule, CendR compound, CendR protein, CendR peptide, or CendR element does not constitute "selecting cargo composition for internalization into a cell and/or penetration of tissue." Selecting a cargo composition for some purpose or capability as well as for obtaining entry into either or both a cell and tissue of the cargo composition does constitute "selecting cargo composition for internalization into a cell and/or penetration of tissue." Thus, the presence of additional goals or purposes does not alter that selection of a cargo composition at least with the specific intention of obtaining entry into either or both a cell and tissue of a cargo composition constitutes "selecting a cargo composition for internalization into a cell and/or penetration of tissue."

As used herein, "causing a compound or composition to be covalently coupled or non-covalently associated" with something else refers to any action that results in a compound or composition that is not covalently coupled or non-covalently associated with the something else becoming or coming into the state of being covalently coupled or non-covalently associated with the something else. As an example, covalently coupling a homing molecule to a CendR element constitutes "causing a homing molecule to be covalently coupled or non-covalently associated" with the CendR element. As another example, a CendR peptide that starts as a nonexistent concept and then is synthesized as part of a composition that includes the thing to which the CendR peptide is to be coupled or associated constitutes "causing a CendR peptide to be covalently coupled or non-covalently associated" with the thing. For example, synthesis of a peptide that includes both an amino acid sequence of interest and an amino acid sequence comprising a C-terminal element constitutes causing the amino acid sequence of interest to be covalently coupled or non-covalently associated with the amino acid sequence comprising a C-terminal element. However, and in general, synthesis of a protein or peptide that naturally includes both the amino acid sequence of interest and an amino acid sequence comprising a C-terminal element can be excluded as a process of "causing the amino acid sequence of interest to be covalently coupled or non-covalently associated" with the amino acid sequence comprising a C-terminal element.

As used herein, "causing a co-composition to be covalently coupled or non-covalently associated" with something else refers to any action that results in a co-composition that is not and the something else becoming or coming into the state of being and the something else. More clearly, "causing a co-composition to be covalently coupled or non-covalently associated" with something else refers to any action that results in a co-composition and the something else becoming or coming into the state of being covalently coupled or non-covalently associated. As an example, covalently coupling a co-composition to another co-composition constitutes "causing a co-composition to be covalently coupled or non-covalently associated" with the other co-composition. As another example, a co-composition that starts as a nonexistent concept and then is synthesized as part of a composition that includes the thing to which the co-composition is to be coupled or associated constitutes "causing a co-composition to be covalently coupled or non-covalently associated" with the thing.

As used herein, "causing a cargo composition to be covalently coupled or non-covalently associated" with something else refers to any action that results in a cargo composition that is not and the something else becoming or coming into the state of being and the something else. More clearly, "causing a cargo composition to be covalently coupled or non-covalently associated" with something else refers to any action that results in a cargo composition and the something else becoming or coming into the state of being covalently coupled or non-covalently associated. As an example, covalently coupling a cargo composition to another cargo composition constitutes "causing a cargo composition to be covalently coupled or non-covalently associated" with the other cargo composition. As another example, a cargo composition that starts as a nonexistent concept and then is synthesized as part of a composition that includes the thing to which the cargo composition is to be coupled or associated constitutes "causing a cargo composition to be covalently coupled or non-covalently associated" with the thing.

As used herein, "CendR element" refers to an amino acid sequence having a C-terminal arginine, lysine, or lysine-glycine sequence (for a type 1 CendR element), or a C-terminal histidine or a C-terminal amino acid sequence having the sequence $X_1X_2X_3X_4$, where $X_1$ can be R, K or H, where $X_4$ can be R, K, H, or KG, and where $X_2$ and $X_3$ can each be, independently, any amino acid (for a type 2 CendR element). Some type 2 CendR elements can also be described as R/K/HXXR/K/H (SEQ ID NO:20), R/KXXR/K (SEQ ID NO:23), and R/K/HXXKG (SEQ ID NO:21). The $X_1$, $X_2$ and $X_3$ amino acids can also be selected to recruit additional proteins to NRP-1 molecules at the cell surface, such as by inclusion of an overlapping accessory peptide or homing peptide. This can be applied, for example, to modulate the selectivity and internalization and/or tissue penetration potency of CendR elements (and the compositions, conjugates, proteins, and peptides containing CendR elements). A CendR element can, for example, comprise a protein or peptide comprising an amino acid sequence having a C-terminal element, comprise a protein or peptide consisting of an amino acid sequence having a C-terminal element, or consist of an amino acid sequence having a C-terminal element. Optionally, certain amino acids can also be excluded from use for $X_2$, $X_3$, or both in CendR elements of the form $X_1X_2X_3X_4$. For example, if desired, G and D can be excluded from simultaneous use as $X_2$ and $X_3$, respectively.

Examples of CendR elements include XXR/K/H, XXR/K, XXR/H, XXK/H, XXR, XXK, XXH, XXKG, RXXR/K/H, RXXR/K, RXXR/H, RXXK/H, RXXR, RXXK, RXXH, RXXKG, KXXR/K/H, KXXR/K, KXXR/H, KXXK/H, KXXR, KXXK, KXXH, KXXKG, HXXR/K/H, HXXR/K, HXXR/H, HXXK/H, HXXR, HXXK, HXXH, HXXKG, R/K/HXXR, R/KXXR, R/HXXR, K/HXXR, RXXR, KXXR, HXXR, R/K/HXXK, R/KXXK, R/HXXK, K/HXXK, RXXK, KXXK, HXXK, R/K/HXXH, R/KXXH, R/HXXH, K/HXXH, RXXH, KXXH, HXXH, R/K/HXXKG (SEQ ID NO:21), R/KXXKG, R/HXXKG, K/HXXKG, RXXKG, KXXKG, and HXXKG.

For the sake of convenience, amino acid motifs that would constitute a CendR element if an arginine, lysine, lysine-glycine pair, or histidine were at the C-terminus and where the exposure in the future of the arginine, lysine, lysine-glycine pair, or histidine at the C-terminus is planned or intended, can be referred to as CendR elements or latent CendR elements.

CendR elements can be composed of, for example amino acids, amino acid analogs, peptide analogs, amino acid mimetics, peptide mimetics, etc. Although structures, design, etc. of CendR elements and CendR peptides is described herein in terms of amino acids and peptides composed of amino acids for convenience, it is understood that analogous analogs, mimetics, modified forms, etc. of amino acids and peptides can also be used as CendR elements and CendR peptides and designed using similar principles.

As disclosed herein, certain components can overlap with CendR elements. Generally, a component that overlaps with a CendR element will be a component that comprises an amino acid sequence and all or part of the amino acid sequence of the component will overlap with amino acid(s) of the CendR element. Generally, such overlap is characterized by amino acids that are part of, within, or specifying the component are shared with or are in the range of amino acids constituting the CendR element. For type 1 CendR elements, a component overlaps with the CendR element if the C-terminal arginine, lysine, or lysine-glycine sequence is an amino acid that is part of, within, or specifies the component. For example, the homing peptide NGRAHA (SEQ ID NO:24) can be overlapped with a CendR element comprising arginine. In this example, the arginine residue in the homing peptide is the CendR element.

For type 2 CendR elements, a component overlaps with the CendR element if one or more of the amino acids $X_1$, $X_2$, $X_3$, and/or $X_4$ or if the C-terminal histidine is an amino acid that is part of, within, or specifies the component. For example, the homing peptide CREKA (SEQ ID NO:7) can be overlapped with a CendR element comprising RGCR (SEQ ID NO:19) to form RGCREKA (SEQ ID NO:18) (with the CendR element underlined). In this example, the last two amino acids of the CendR element (CR) also serve as the first two amino acids in the homing peptide. As another example, the homing peptide NGRAHA (SEQ ID NO:24) can be overlapped with a type 2 CendR element by adding an arginine (or lysine or histidine) and using the internal arginine resulting in the overlapped homing peptide and CendR element RNGRAHA (SEQ ID NO:25) (with the CendR element underlined). As another example, the homing peptide CREKA (SEQ ID NO:7) can be overlapped with a CendR element comprising RREK (SEQ ID NO:26) to form RREKA (SEQ ID NO:27) (with the CendR element underlined). The cysteine in the CREKA (SEQ ID NO:7) peptide is not critical to its homing function. As another example, the homing peptide NGR can be overlapped with the CendR element, a cleavable motif, GPDC (SEQ ID NO:28), can be added to make it activatable, and the peptide can be circularized using terminal cysteines to form CRN-GRGPDC (SEQ ID NO:41) (with the CendR element underlined). As another example, a urokinse activatable CendR peptide with affinity to angiogenic blood vessels (for tumor targeting) can be made by combining a CendR element (underlined), a urokinse cleavable sequence (bold), and a sequence that homes to angiogenic integrins (double underline): RPARSGRAGGSVACRGDC (SEQ ID NO:43). As another example, a furin activatable CendR peptide with affinity to angiogenic blood vessels (for tumor targeting) can be made by combining a CendR element (underlined), a furin cleavable sequence, and a CD13-homing sequence (double underline): RPARVKRNGRAHA (SEQ ID NO:42). As another example, a furin activatable CendR peptide with affinity to brain blood vessels (for CNS targeting) can be made by combining a CendR element (underlined), a furin cleavable sequence, and a brain microvasculature homing sequence (double underline): RPARVKRGGSCAGALCY (SEQ ID NO:44).

Components that have certain specified amino acid sequences and, for example, a specified spacer that does not have a specified amino acid sequence can still be said to overlap with a CendR element if all or part of the spacer of the component shared with or are in the range of amino acids constituting the CendR element. For example, if a component is defined by an amino acid sequence TGLTAXXXXW (SEQ ID NO:45), the component overlaps with a CendR element is the CendR element is within the XXXX region of the component. Components that overlap with CendR elements can, and usually will, extend beyond the CendR element at one or both ends (that is, beyond the N-terminal of the CendR element, beyond the C-terminal end of the CendR element, or both.

Using these principles, the structural specification of CendR elements as disclosed herein, and the structural specification of a component to be overlapped with the CendR element, numerous overlapping CendR elements can be designed and used. Where the structural specification of the CendR element and of components are compatible, multiple different components can be overlapped with a single CendR element. For example, both a homing peptide and a protease cleavage site can be overlapped with the same CendR element.

Components can also be adjacent to a CendR element. As used herein, components that are adjacent to a CendR element do not overlap a CendR element. Components that are adjacent to a CendR element can be adjacent to either end of the CendR element. A component is adjacent to a CendR element if an amino acid (or other molecule) of the component is covalently coupled to a terminal amino acid of a CendR element. A component that neither overlaps nor is adjacent to a CendR element but that is covalently coupled to the CendR element can be either can be upstream (N-terminal of), downstream (C-terminal of), or both (in circular molecules) of the CendR element.

Any component, such as the components disclosed herein, can overlap, be adjacent to, and/or be upstream, downstream, or both of a CendR element. Examples of such components include accessory molecules, homing molecules, protease cleavage sites, etc. It is useful to have some components coupled to or associated with a CendR element to be downstream (C-terminal) of the CendR element. For example, activatable CendR elements having an accessory protein or a homing peptide downstream of the CendR element (and thus downstream from the cleavage site for activation) will be separated from the CendR element when it is activated. As another example, activatable CendR elements having an accessory molecule or a homing molecule downstream of the CendR element (and thus downstream from the cleavage site for activation) will be separated from the CendR element when it is activated. This can have some advantages such as making the CendR element function more efficient or reducing the chance for extraneous effects of the eliminated component.

Any CendR element disclosed herein in any context, combination, or usage can be a CendR element in general, a type 1 CendR element, a type 2 CendR element, a specific CendR element, or a combination. In some forms, the CendR element is a type 1 CendR element. In some forms, the CendR element is a type 2 CendR element. In some forms, the CendR element is not a type 1 CendR element. An example of a CendR element that is not a type 1 CendR element is a CendR element having a C-terminal histidine. In some forms, the CendR element is not a type 2 CendR element. An example of a CendR element that is not a type 2 CendR element is a CendR element having a C-terminal arginine, lysine, or lysine-glycine pair where the amino acid three amino acids upstream of the arginine or lysine is not arginine, lysine, or histidine. In some forms, the CendR element is a type 1 CendR element and not a type 2 CendR element. An example of a CendR element that is a type 1 CendR element and not a type 2 CendR element is a CendR element having a C-terminal arginine, lysine, or lysine-glycine pair where the amino acid three amino acids upstream of the arginine or lysine is not arginine, lysine, or histidine. In some forms, the CendR element is a type 2 CendR element and not a type 1 CendR element. An example of a CendR element that is a type 2 CendR element and not a type 1 CendR element is a CendR element having a C-terminal histidine. Another example of a CendR element that is a type 2 CendR element and not a type 1 CendR element is a CendR element having a C-terminal arginine, lysine, histidine, or lysine-glycine pair where the amino acid three amino acids upstream of the arginine, lysine, or histidine is an arginine, lysine, or histidine. In some forms, the CendR element is a type 1 CendR element or a type 2 CendR element. Any type of CendR element, set of CendR elements, and/or specific CendR elements can be specifically included or excluded form any context, combination, or use. For example, any CendR element described in U.S. Patent Application Publication No. 20090226372 can be specifically included or excluded. U.S. Patent Application Publication No. 20090226372 is hereby incorporated herein by reference in its entirety, and specifically for its description of CendR elements.

A CendR element that can be internalized into a cell can be referred to as an internalization CendR element. A CendR element that can penetrate tissue can be referred to as a penetrating CendR element. A CendR element that can be internalized into a cell and that can penetrate tissue can be referred to as an internalization and penetrating CendR element. Unless the context clearly indicates otherwise, reference to "CendR element" refers to any of these, either individually, collectively, or in any combination.

As used herein, "CendR composition" refers to a composition that comprises a CendR element. The CendR element can be, for example, active, activatable, or blocked. For example, the CendR composition can comprise a protein or peptide comprising an amino acid sequence that comprises a CendR element where the amino acid sequence is at the C-terminal end of the protein or peptide.

As used herein, "activatable CendR element" refers to a CendR element having a molecule, moiety, nanoparticle, compound or other composition covalently coupled to the CendR element, such as to the terminal carboxyl group of the C-terminal element, where the molecule, moiety, nanoparticle, compound or other composition can block internalization and/or tissue penetration of the CendR composition, conjugate, molecule, protein, peptide, etc. and where the molecule, moiety, nanoparticle, compound or other composition can be removed (to expose the terminal carboxy group, for example). For example, the activatable CendR element can be on the C-terminal end of the peptide, and can prevent the CendR element from being internalized and/or from penetrating tissue. The molecule, nanoparticle, moiety, compound or other composition covalently coupled to the CendR element can be referred to as the "blocking group." For example, the blocking group can be coupled to the terminal carboxyl group of the C-terminal arginine or lysine or other C-terminal amino acid of the CendR element, to the C-terminal amino acid of the CendR element, or to an amino acid of the CendR element other than the C-terminal amino acid. The blocking group can also be coupled, or associated with a part of a CendR composition, conjugate, molecule, protein, peptide, etc. other than the CendR element so long as it can prevent the CendR element from being internalized and/or from penetrating tissue. A CendR composition comprising an activatable CendR element can be referred to as an activatable CendR composition. A CendR molecule comprising an activatable CendR element can be referred to as an activatable CendR molecule. A CendR conjugate comprising an activatable CendR element can be referred to as an activatable CendR conjugate. A CendR protein comprising an activatable CendR element can be referred to as an activatable CendR protein. A CendR peptide comprising an activatable CendR element can be referred to as an activatable CendR peptide.

An activatable CendR element can be blocked from internalization into a cell, from tissue penetration, or both. Generally, an activatable CendR element will be blocked from both internalization into a cell and penetration of tissue. Such activatable CendR elements can be referred to as activatable internalization and penetrating CendR elements. However, some activatable CendR elements could be blocked only from tissue penetration or only from internalization into a cell. Such activatable CendR elements can be referred to as activatable internalization CendR elements (for CendR elements that are blocked only from internalization into a cell) or as activatable internalization and penetrating CendR elements (for CendR elements that are blocked only from penetration of tissue). Generally, internalization CendR elements that are activatable will be activatable internalization CendR elements. Similarly, penetrating CendR elements that are activatable generally will be activatable penetrating CendR elements. Internalization and penetrating CendR elements that are activatable will be activatable internalization and penetrating CendR elements. Removal of the blocking group will allow the CendR element to be internalized into a cell, penetrate tissue, or both.

The cleavable bond of an activatable CendR element can be cleaved in any suitable way. For example, the cleavable bond can be cleaved enzymatically or non-enzymatically. For enzymatic cleavage, the cleaving enzyme can be supplied or can be present at a site where the CendR element is delivered, homes, travels or accumulates. For example, the enzyme can be present in proximity to a cell to which the CendR element is delivered, homes, travels, or accumulates. For non-enzymatic cleavage, the CendR element can be brought into contact with a cleaving agent, can be placed in cleaving conditions, or both. A cleaving agent is any substance that can mediate or stimulate cleavage of the cleavable bond. A non-enzymatic cleaving agent is any cleaving agent except enzymes. Cleaving conditions can be any solution or environmental conditions that can mediate or stimulate cleavage of the cleavable bond. For example, some labile bonds can be cleaved in acid conditions, alkaline conditions, in the presence of a reactive group, etc. Non-enzymatic cleaving conditions are any cleaving conditions except the presence of enzymes. Non-agent cleaving conditions are any cleaving conditions except the presence of cleaving agents.

Activatable CendR elements can be activatable in broad or narrow circumstances. Generally, activatable CendR elements are activatable relative to a specific agent or group of agents that can activate the CendR elements. Thus, for example, a particular activatable CendR element may only be activatable by certain proteases. Such a CendR element can be referred to as an activatable CendR element but can also be referred to as being activatable by the particular proteases.

A "protease-activatable CendR element" (or "protease-activated CendR element") refers to an activatable CendR element where the blocking group is coupled to the CendR element via a peptide bond and where the peptide bond can be cleaved by a protease. Cleavage of this peptide bond in a protease-activatable CendR element makes the CendR element capable of internalization into a cell and/or of tissue penetration. In one example, the blocking group can be coupled to the CendR element via a cleavable or labile bond. The cleavable bond can be cleaved by, for example, an enzyme or a chemical compound. Cleavage or 'labilization' of the bond in an activatable CendR element makes the CendR element capable of internalization into a cell and/or of tissue penetration. Such cleavage or 'labilization' can be referred to as activation of the CendR element. A protease-activatable CendR element is a form of activatable CendR element. The $X_2$ and $X_3$ amino acids of a CendR element of the form $X_1X_2X_3X_4$ can be selected for specific purposes. For example, $X_2$, $X_3$, or both can be chosen to form all or a portion of a protease recognition sequence. This would be useful, for example, to specify or enable cleavage of a peptide having the CendR element as a latent or cryptic CendR element that is activated by cleavage following the $X_4$ amino acid. Examples of such amino acid choices are shown in Tables 1 and 2. Protease cleavage sites can be predicted based on knowledge developed and known to those of skill in the art. For example, prediction of cleavage can be assessed at the website cbs.dtu.dk/services/ProP/. A useful class of CendR elements can consist of unblocked CendR elements and activatable CendR elements, which class excludes blocked CendR elements that are not activatable.

Useful proteases include enzymes that cleave on the C terminal side of basic residues (the C terminal residues of CendR elements can be basic residues) and enzymes that recognize sequence on the C terminal side of their cleavage site (thus allowing free choice of the C terminal sequence of the cleavage product). Examples of useful proteases include, for example, serine proteases (including, for example, plasmin and plasminogen activators), urokinase, proprotein convertases (see, for example, Duckert et al., Prediction of proprotein convertase cleavage sites Protein engineering Design and Selection 17(1):107-112 (2004)), furins, and carboxypeptidases, such as carboxypeptidase A (amino acids with aromatic or branched hydrocarbon side chains), glutamate-specific carboxypeptidase, proline-specific carboxypeptidase, and PSMA. Serine proteases are particularly useful for CendR elements and CendR compositions targeted to cancer cells and tumors. Examples of enzymes that cleave on the C terminal side of basic residues include Arg-C protease (which cleaves on the C terminal side of arginine residues; Keil, Specificity of Proteolysis (Springer-Verlag, Berlin-Heidelberg-New York (1992)), clostripain (which cleaves on the C terminal side of arginine residues; Keil, 1992), enterokinase (which cleaves after the sequence -Asp-Asp-Asp-Asp-Lys-; SEQ ID NO:22), Factor Xa (which cleaves after the sequence -Gly-Arg-; Fujikawa et al., Activation of bovine factor X (Stuart factor): conversion of factor Xa alpha to factor Xa beta, Proc. Natl. Acad. Sci. 72: 3359-3363 (1975)), Lys-C (which cleaves on the C terminal side of lysine residues; Keil, 1992), thrombin (which cleaves on the C terminal side of arginine residues; Keil, 1992), trypsin (which cleaves on the C terminal side of arginine and lysine residues; Keil, 1992), serine proteases, proprotein convertases (such as PC1, PC2, PC3, PC4, PC5, PC6, PC7, PC8, furin, Pace, PACE4, Site 1 protease, SIP, SKI, NARC-1, PCSK1, PCSK2, PCSK3, PCSK4, PCSK5, PCSK6, PCSK7, PCSK8, and PCSK9), plasmin, and plasminogen activators. Examples of enzymes that recognize sequence on the C terminal side of their cleavage site include Asp-N endopeptidase (which cleaves on the N terminal side of aspartic acid; Keil, 1992) and carboxypeptidases such as carboxypeptidase A (which cleaves C-terminal residues except proline, lysine and arginine).

Examples of proteases are also described in Hook, Proteolytic and cellular mechanisms in prohormone and proprotein processing, R G Landes Company, Austin, Texas, USA (1998); Hooper et al., Biochem. J. 321: 265-279 (1997); Werb, Cell 91: 439-442 (1997); Wolfsberg et al., J. Cell Biol. 131: 275-278 (1995); Murakami and Etlinger, Biochem. Biophys. Res. Comm 146: 1249-1259 (1987); Berg et al., Biochem. J. 307: 313-326 (1995); Smyth and Trapani, Immunology Today 16: 202-206 (1995); Talanian et al., J. Biol. Chem. 272: 9677-9682 (1997); and Thornberry et al., J. Biol. Chem. 272: 17907-17911 (1997).

TABLE 1

Protease-cleavable and control phage used for in vitro and in vivo targeting studies. Cleavage sites in substrate phage are indicated by arrow. Proteolytically exposed C-terminal residues are in bold.

| Substrate motif | Activating enzyme | Peptide sequence displayed in C-terminus of GP10 of T7 bacteriophage | |
|---|---|---|---|
| | | Substrate phage | Mimic of post-cleavage substrate phage |
| 1. Furin cleavage consensus | Furin | GGGRKKR↑STGGG- (SEQ ID NO: 8) Can be universally cleaved & internalized | GGGRKKR- (SEQ ID NO: 9) Can be universally internalized |
| 2. Thrombin substrate | Thrombin | GGGLVPR↑GSGGG (SEQ ID NO: 10) Can be universally cleaved & internalized upon addition of thrombin to the cultured cells | GGGLVPR (SEQ ID NO: 11) Can be universally internalized |
| 3. Plasminogen-derived sequence | uPA/tPA | GGGPCPGR↑VVGGG- (SEQ ID NO: 12) Can be cleaved & internalized by uPA/tPA-expressing cells | GGGPCPGR- (SEQ ID NO: 13) Can be universally internalized |
| 4. uPA minimum optimal substrate | uPA | GGGPGSGR↑SAGGG- (SEQ ID NO: 14) Can be cleaved & internalized by uPA-expressing cells | GGGPGSGR- (SEQ ID NO: 15) Can be universally internalized |
| 5. uPA alternative substrate | uPA | GGGPGSGK↑SAGGG- (SEQ ID NO: 16) Can be cleaved by uPA-expressing cells | GGGPGSGK- (SEQ ID NO: 17) Can be not internalized |

TABLE 2

Cleavage rules

Figure 21:
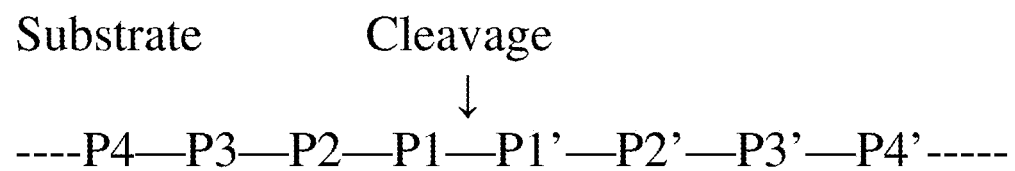
FIG. 21 is a schematic showing the cleavage rules summarized in Table 2. Cleavage occurs between P1 and P1'.

| Enzyme name | P4 | P3 | P2 | P1 | P1' | P2' |
|---|---|---|---|---|---|---|
| The following enzymes can cleave when the respective compositions of the cleavage sites are found (see FIG. 21). | | | | | | |
| Arg-C proteinase | — | — | — | R | — | — |
| Asp-N endopeptidase | — | — | — | — | D | — |
| Clostripain (Clostridiopeptidase B) | — | — | — | R | — | — |
| Enterokinase | D or N | D or N | D or N | K | — | — |
| Factor Xa | A, F, G, I, L, T, V or M | D or E | G | R | — | — |
| LysC | — | — | — | K | — | — |
| Thrombin | — | — | G | R | G | — |
|  | A, F, G, I, L, T, V or M | A, F, G, I, L, T, V, W or A | P | R | not D or E | not DE |
| Trypsin (please note the exceptions) | — | — | — | K or R | not P | — |
|  | — | — | W | K | P | — |
|  | — | — | M | R | P | — |
| The exception rules: The above cleavage rules do not apply, i.e. no cleavage occurs, with the following compositions of the cleavage sites: | | | | | | |
| Trypsin | — | — | C or D | K | D | — |
|  | — | — | C | K | H or Y | — |
|  | — | — | C | R | K | — |
|  | — | — | R | R | H or R | — |

Exopeptidases, such as carboxypeptidases, can be used to activate CendR elements. For example, carboxypeptidases are useful proteases for activating CendR elements. Carboxypeptidases remove the C-terminal amino acid from proteins and peptides. Carboxypeptidases can, within the limits of their substrate preferences, remove amino acids sequentially from a protein or peptide. Thus, for example, a carboxypeptidase could completely or nearly completely hydrolyze a protein of peptide. Because various carboxypeptidases have certain substrate preferences or limitations, and because carboxypeptidases generally only cleave peptide bonds, the presence of certain amino acids, modifications, and/or non-peptide bonds can control carboxypeptidase cleavage of a protein or peptide.

In the context of CendR elements, the structure of and/or modifications to a protein, peptide or amino acid sequence comprising a CendR element can be chosen to result in cleavage by a carboxypeptidase ending at the C-terminal amino acid of the CendR element. This can be accomplished by, for example, including as the penultimate amino acid in a CendR element an amino acid that is disfavored by or that blocks the carboxypeptidase from cleaving its bond with the C-terminal amino acids. Proline is an example of such an amino acid (for many carboxypeptidases). As another example, the bond between the C-terminal amino acid and the penultimate amino acid in the CendR element can be protected from protease cleavage. For example, the bond can be a non-peptide bond or can include a modification, such as methylation. As another example, a D-amino acid can be used as the C-terminal amino acid, the penultimate amino acid, or both, in a CendR element. As another example, a D-amino acid can be used as the C-terminal amino acid in a CendR element. CendR elements with limited use of D amino acids retain internalization and penetration activity.

As another example, an amino acid that serves as a substrate for a carboxypeptidase can be located C-terminal to the C-terminal amino acid in the CendR element. For example, for a glutamate-specific carboxypeptidase such as PSMA, a glutamic acid amino acid can be placed adjacent to and C-terminal of the C-terminal amino acid in the CendR element and at the C-terminal end of the protein or peptide containing the CendR element. Other amino acid-specific (or preferring) carboxypeptidases can be used in similar ways. In these cases, the C-terminal amino acid in the CendR element should not be a substrate (or should be a disfavored substrate) for the carboxypeptidase.

Bonds and modifications to amino acids that can reduce or eliminate protease cleavage at a bond are known and can be used in the disclosed CendR elements. For example, a variety of chemical modification techniques and moieties are described in, for example, U.S. Pat. Nos. 5,554,728, 6,869,932, 6,828,401, 6,673,580, 6,552,170, 6,420,339, U.S. Pat. Pub. 2006/0210526 and Intl. Pat. App. WO 2006/136586. Some examples of such modifications include peptide bond surrogates such as those described in Cudic and Stawikowski, Peptidomimetics: Fmoc Solid-Phase Pseudo-peptide Synthesis, in Methods in Molecular Biology, vol. 294, 223-246 (2008), and chemical modifications, such as maleimide capping, polyethylene glycol (PEG) attachment, maleidification, acylation, alkylation, esterification, and amidification, to produce structural analogs of the peptide. These and other modifications are further described elsewhere herein.

Some useful forms of activatable CendR elements can be, or can be in, circular proteins or peptides. The CendR element would be latent in such circular structures because the CendR element would not be at a free C-terminal end. Circular proteins and peptides can be formed in a variety of ways known in the art, such as by cysteine bonds, by covalent bonds, by reaction of active groups, and via linkers. Cysteine bonds are a useful way to circularize proteins and peptides. It should be understood that the circularizing linkage need not be at the C-terminal end of the CendR element. By placing the circularizing linkage away from the C-terminal end of the CendR element, the choice of circularizing bond and the choice of the cleavable bond of the latent CendR element each can be independently. For example, the circularizing linkage can be a cysteine bond while the cleavable bond of the latent CendR element can be a peptide bond (where the peptide bond can be, for example, at the cleavage site of a protease target).

The CendR element in a disclosed protein, peptide, amino acid sequence or CendR composition generally should be at a free C-terminal end or on the N-terminal side of the cleavage site in an activatable CendR element.

In some forms, a CendR element that is not at a free C-terminal end of a peptide or protein can mediate cell internalization and/or tissue penetration. When present, this effect is typically less efficient than internalization and tissue penetration using an unblocked CendR element. CendR elements that are not at a free C-terminal end of a peptide or protein but that can mediate cell internalization and/or tissue penetration can be referred to as internal CendR elements. Internal CendR elements are distinguished from blocked CendR elements because blocked CendR elements do not mediate cell internalization and/or tissue penetration (unless unblocked). Internal CendR elements can be used in linear, circular or branched peptides and proteins. Internal CendR elements can also be activatable by cleavage to expose the CendR element at the C-terminal end of a protein or peptide.

Such activation of an internal CendR element would serve to increase the internalization and/or tissue penetration activity.

In some forms, the peptide or protein of the CendR composition can be internalized into a cell when the selected amino acid sequence (CendR element) is present in the peptide or protein, but not when the selected amino acid is not present in the peptide or protein. This can be used to detect whether a protein or peptide comprises a CendR element, for example. The CendR element can be internalized into a cell without being associated with anything other than its own sequence, for example. The CendR element can be the only functional internalization element in the protein or peptide or the CendR composition, or there can be one or more additional functional internalization elements. In some forms, the CendR composition can be internalized into a cell when the selected amino acid sequence (CendR element) is present in the CendR composition, but not when the selected amino acid is not present in the CendR composition.

Similarly, in some forms, the peptide or protein of the CendR composition can penetrate tissue when the selected amino acid sequence (CendR element) is present in the peptide or protein, but not when the selected amino acid is not present in the peptide or protein. This can be used to detect whether a protein or peptide comprises a CendR element, for example. The CendR element can penetrate tissue without being associated with anything other than its own sequence, for example. The CendR element can be the only functional tissue penetration element in the protein or peptide or the CendR composition, or there can be one or more additional functional tissue penetration elements. In some forms, the CendR composition can penetrate tissue when the selected amino acid sequence (CendR element) is present in the CendR composition, but not when the selected amino acid is not present in the CendR composition.

Similarly, in some forms, the peptide or protein of the CendR composition can be internalized into a cell and penetrate tissue when the selected amino acid sequence (CendR element) is present in the peptide or protein, but not when the selected amino acid is not present in the peptide or protein. This can be used to detect whether a protein or peptide comprises a CendR element, for example. The CendR element can be internalized into a cell and penetrate tissue without being associated with anything other than its own sequence, for example. The CendR element can be the only functional internalization and tissue penetration element in the protein or peptide or the CendR composition, or there can be one or more additional functional internalization and/or tissue penetration elements. In some forms, the CendR composition can be internalized into a cell and penetrate tissue when the selected amino acid sequence (CendR element) is present in the CendR composition, but not when the selected amino acid is not present in the CendR composition.

"Internalization" refers to passage through a plasma membrane or other biological barrier. "Penetration" refers to passage into and through a cell, tissue, or other biological barrier. Penetration generally involves and includes internalization. The disclosed CendR elements generally promote and allow both internalization (such as internalization into a cell) and penetration (such as tissue penetration). Reference to internalization or to penetration should be understood to refer to both internalization and penetration unless the context indicates otherwise (such as separate or distinct discussion and description of internalization into a cell and tissue penetration separately—the present paragraph is an example of such).

By "internalization into a cell" is meant that that CendR element is capable of penetrating the plasma membrane, thereby being internalized into the cell. This internalization can occur with, for example, 10, 20, 30, 40, 50, 60, 70, 80, 90, or 100% efficiency for a given CendR element and a given cell. CendR elements generally an promote, mediate, cause, enhance, etc. internalization; penetration; internalization into and/or through cells, tissue, or both; penetration into and/or through cells, tissue, or both; permeabilization of cells and/or tissues; or a combination. By "permeabilization" is meant promoting, mediating, causing, enhancing, etc. the ability and/or condition of cells and/or tissues to allow compositions, conjugates, molecules, etc. in proximity to the cells and/or tissues to enter and or pass through the cells and/or tissues. Thus, the disclosed CendR elements, proteins, peptides, conjugates, compositions, etc. can be said to permeabilize the cells and/or tissues. By "permeable" is meant the ability and/or condition of cells and/or tissues to allow compositions, conjugates, molecules, etc. in proximity to the cells and/or tissues to enter and or pass through the cells and/or tissues.

Cells that can internalize a CendR element can be identified by, for example, (a) exposing a cell to a CendR element; and (b) determining if the CendR element was internalized. The cell can be in an assay, for example. The CendR element can be coupled to, or example, a homing molecule, thereby forming a CendR composition. Cells that can internalize an activatable CendR element can be identified by, for example, (a) exposing a cell to an activatable CendR element; (b) determining if the activatable CendR element was internalized. The activatable CendR element can be unblocked before exposure to the cell, but does not need to be. This can be used to test the blocking ability of the blocker, for example. The activatable CendR element can also be a protease-activated CendR element. Any form or type of CendR element, CendR peptide, CendR protein, CendR conjugate, or CendR composition can be used in these methods.

Cancer cells, or subjects harboring cancer cells, can be identified as candidates for CendR-based therapy by, for example, (a) exposing the cancer cell to a CendR element; and (b) determining if the CendR element was internalized by the cancer cell, wherein an internalized CendR element identifies the cancer cell or the subject as being a candidate for CendR-based therapy. The cell can be in an assay, or can be in a subject, for example. The CendR element can be coupled to, for example, a homing molecule, thereby forming a CendR composition. Any form or type of CendR element, CendR peptide, CendR protein, CendR conjugate, or CendR composition can be used in these methods.

Tumors, or subjects harboring a tumor, can be identified as a candidate for CendR-based therapy by, for example, (a) exposing tissue from the tumor to a CendR element; and (b) determining if the CendR element passed through the tissue or was internalized by cells in the tissue, wherein a passed-through or internalized CendR element identifies the tumor or the subject as being a candidate for CendR-based therapy. Any form or type of CendR element, CendR peptide, CendR protein, CendR conjugate, or CendR composition can be used in these methods.

An activatable CendR element that can be activated in proximity to a cell of interest can be made by, for example, forming an activatable CendR element wherein a blocking group is coupled to a CendR element via a cleavable bond, wherein the cleavable bond is cleavable by an enzyme, cleaving agent, and/or cleaving conditions present in proximity to the cell of interest. This can further comprise, prior to forming the activatable CendR element, identifying the enzyme, cleaving agent, and/or cleaving conditions present in proximity to the cell of interest. This can further comprise, prior to forming the activatable CendR element, selecting the cleavable bond based on the enzyme, cleaving agent, and/or cleaving conditions present in proximity to the cell of interest. Any form or type of CendR element, CendR peptide, CendR protein, CendR conjugate, or CendR composition can be used in these methods.

An activatable CendR element can be formed by, for example, (a) selecting an amino acid sequence for internalization into a cell, wherein the amino acid sequence comprises a C-terminal element, wherein the C-terminal element comprises a terminal carboxyl group, and (b) causing a blocking group to be covalently coupled to the terminal carboxyl group of the selected amino acid sequence, wherein the bond coupling the blocking group and the terminal carboxyl group is cleavable, wherein the activatable CendR element comprises the selected amino acid sequence and the blocking group. This can further comprise, prior to step (b), selecting the bond coupling the blocking group and the terminal carboxyl group to be cleavable by a protease, enzyme, cleaving agent, and/or cleaving conditions present in proximity to the cell of interest. Any form or type of CendR element, CendR peptide, CendR protein, CendR conjugate, or CendR composition can be used in these methods.

Activatable CendR elements can be made by, for example, the method comprising (a) selecting an amino acid sequence for internalization into a cell, wherein the amino acid sequence comprises a C-terminal element, wherein the C-terminal element comprises a terminal carboxyl group, and (b) causing a blocking group to be covalently coupled to the terminal carboxyl group of the selected amino acid sequence, wherein the bond coupling the blocking group and the terminal carboxyl group is cleavable, wherein the activatable CendR element comprises the selected amino acid sequence and the blocking group. The method can further comprise, prior to step (b), selecting the bond coupling the blocking group and the terminal carboxyl group to be cleavable by a protease, enzyme, cleaving agent, and/or cleaving conditions present in proximity to the cell of interest. Any form or type of CendR element, CendR peptide, CendR protein, CendR conjugate, or CendR composition can be used in these methods.

The CendR element can be an activatable CendR element. The CendR element can be a protease-activatable CendR element. The protein or peptide can be circular or can contain a loop. The CendR element can be at the C-terminal end of the protein or peptide. The CendR element can comprise a terminal carboxyl group. A blocking group can be coupled to the terminal carboxyl group. The bond coupling the blocking group and the terminal carboxyl group can be selected to be cleavable by a protease, enzyme, cleaving agent, and/or cleaving conditions present in proximity to the cell of interest. The blocking group can be coupled to the C-terminal amino acid of the CendR element. The blocking group can be coupled to an amino acid of the CendR element other than the C-terminal amino acid of the CendR element.

The co-composition can be, for example, a nanoparticle, or a molecule, or complex of molecules with therapeutic or diagnostic applications. Therapeutic co-compositions that can be targeted with CendR elements include but are not limited to a nanoparticle, a molecule, a complex of molecules, an anti-angiogenic agent, a pro-angiogenic agent, a cancer chemotherapeutic agent, a cytotoxic agent, a pro-cell survival agent, a cell differentiating agent, a neuroprotective agent, an immunomodulatory agent, an anti-inflammatory agent, an anti-arthritic agent, an anti-viral agent, or a combination of these. Therapeutic co-compositions that can be targeted with CendR elements include but are not limited to a therapeutic protein, a therapeutic compound, a therapeutic composition, an anti-angiogenic agent, a pro-angiogenic agent, a cancer chemotherapeutic agent, a toxin, a cytotoxic agent, an anti-inflammatory agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination. Diagnostic co-compositions that can be targeted with CendR elements include but are not limited to a nanoparticle, a molecule, a complex of molecules, a MRI imaging agent, a radioimaging agent, an optical imaging agent, a molecular tag (such as biotin), a fluorophore, an epitope tag (that can, for example, be detected using a specific molecular assay), or a combination of these.

The cargo composition can be, for example, a nanoparticle, or a molecule, or complex of molecules with therapeutic or diagnostic applications. Therapeutic cargo compositions that can be targeted with CendR elements include but are not limited to a nanoparticle, a molecule, a complex of molecules, an anti-angiogenic agent, a pro-angiogenic agent, a cancer chemotherapeutic agent, a cytotoxic agent, a pro-cell survival agent, a cell differentiating agent, a neuroprotective agent, an immunomodulatory agent, an anti-inflammatory agent, an anti-arthritic agent, an anti-viral agent, or a combination of these. Therapeutic cargo compositions that can be targeted with CendR elements include but are not limited to a therapeutic protein, a therapeutic compound, a therapeutic composition, an anti-angiogenic agent, a pro-angiogenic agent, a cancer chemotherapeutic agent, a toxin, a cytotoxic agent, an anti-inflammatory agent, an anti-arthritic agent, a growth factor, a cytokine, a chemokine, a compound that modulates one or more signaling pathways, an antibody, a nucleic acid, a nucleic acid analog, a cell, a virus, a phage, a viral particle, a phage particle, a viral capsid, a phage capsid, a virus-like particle, a liposome, a micelle, a bead, a nanoparticle, a microparticle, a chemotherapeutic agent, a contrast agent, an imaging agent, a label, a labeling agent, or a combination. Diagnostic cargo compositions that can be targeted with CendR elements include but are not limited to a nanoparticle, a molecule, a complex of molecules, a MRI imaging agent, a radioimaging agent, an optical imaging agent, a molecular tag (such as biotin), a fluorophore, an epitope tag (that can, for example, be detected using a specific molecular assay), or a combination of these.

A cell that can internalize a CendR element can be identified by, for example, (a) exposing a cell to a CendR element, and (b) determining if the CendR element was internalized. Also disclosed are methods of identifying a cancer cell as a candidate for CendR-based therapy, the method comprising (a) exposing the cancer cell to a CendR element, and (b) determining if the CendR element was internalized by the cancer cell, wherein an internalized CendR element identifies the cancer cell as being a candidate for CendR-based therapy. The cell can be in an assay. The CendR element can be coupled to a protein or peptide. The CendR element can be an activatable CendR element. The activatable CendR element can be activated before exposure to the cell. The activatable CendR element can be a protease-activatable CendR element. The protein or peptide can be circular. The protein or peptide can be linear. The CendR element can be at the C-terminal end of the protein or peptide. Any form or type of CendR element, CendR peptide, CendR protein, CendR conjugate, or CendR composition can be used in these methods.

A tissue that can be penetrated by a CendR element can be identified by, for example, (a) exposing a tissue to a CendR element, and (b) determining if the CendR element penetrated the tissue. Also disclosed are methods of identifying a tumor as a candidate for CendR-based therapy, the method comprising (a) exposing a cell from the tumor to a CendR element, and (b) determining if the CendR element was internalized by the cell, wherein an internalized CendR element identifies the tumor as being a candidate for CendR-based therapy. A tumor can be identified as a candidate for CendR-based therapy by, for example, (a) exposing the tumor to a CendR element, and (b) determining if the CendR element penetrated the tumor, wherein a CendR element that penetrated identifies the tumor as being a candidate for CendR-based therapy. The tumor can be in an assay. The CendR element can be coupled to a protein or peptide. The CendR element can be an activatable CendR element. The activatable CendR element can be activated before exposure to the tumor. The activatable CendR element can be a protease-activatable CendR element. The protein or peptide can be circular. The protein or peptide can be linear. The CendR element can be at the C-terminal end of the protein or peptide. Any form or type of CendR element, CendR peptide, CendR protein, CendR conjugate, or CendR composition can be used in these methods.

An activatable CendR element that can be activated in proximity to a cell of interest can be produced by, for example, forming an activatable CendR element wherein a blocking group is coupled to a CendR element via a cleavable bond, wherein the cleavable bond is cleavable by an enzyme, cleaving agent, and/or cleaving conditions present in proximity to the cell of interest. The cell can be in a subject. The enzyme, cleaving agent, and/or cleaving conditions present in proximity to the cell of interest can be identified. The enzyme, cleaving agent, and/or cleaving conditions present in proximity to the cell of interest can be identified prior to forming the activatable CendR element. The cleavable bond can be selected based on the enzyme, cleaving agent, and/or cleaving conditions present in proximity to the cell of interest. The cleavable bond can be selected based on the cleaving agent present at site where the CendR element is delivered, homes, travels or accumulates, such as the cell of interest. The cleavable bond can be selected based on the cleaving conditions present at site where the CendR element is delivered, homes, travels or accumulates, such as the cell of interest. The cleavable bond can be selected prior to forming the activatable CendR element. The CendR element can comprise a terminal carboxyl group, wherein the blocking group is coupled to the terminal carboxyl group. Any form or type of CendR element, CendR peptide, CendR protein, CendR conjugate, or CendR composition can be used in these methods.

An activatable CendR element can be formed by, for example, causing a blocking group to be covalently coupled to a CendR element, wherein a bond coupling the blocking group and the CendR element is cleavable. An activatable CendR element can be formed by, for example, causing a blocking group to be covalently coupled to an amino acid sequence, wherein the amino acid sequence comprises a CendR element the CendR element, and wherein a bond coupling the blocking group and the CendR element is cleavable. An activatable CendR element can be formed by, for example, (a) selecting an amino acid sequence for internalization into a cell and/or tissue penetration, wherein the amino acid sequence comprises a CendR element, and (b) causing a blocking group to be covalently coupled to the CendR element, wherein a bond coupling the blocking group and the CendR element is cleavable. The blocking group covalently coupled to the CendR element reduces or prevents internalization into a cell and/or tissue penetration. The blocking group covalently coupled to the CendR element can reduce or prevent internalization into a cell and/or tissue penetration compared to the same CendR element with no blocking group. The activatable CendR element can comprise the selected amino acid sequence and the blocking group. The cell can be in a subject. The enzyme, cleaving agent, and/or cleaving conditions that is present in proximity to the cell of interest can be identified. The enzyme, cleaving agent, and/or cleaving conditions present in proximity to the cell of interest can be identified prior to forming the activatable CendR element. The cleavable bond can be selected based on the enzyme, cleaving agent, and/or cleaving conditions present in proximity to the cell of interest. The cleavable bond can be selected based on the cleaving agent present at site where the CendR element is delivered, homes, travels or accumulates, such as the cell of interest. The cleavable bond can be selected based on the cleaving conditions present at site where the CendR element is delivered, homes, travels or accumulates, such as the cell of interest. The cleavable bond can be selected prior to forming the activatable CendR element. The CendR element can comprise a terminal carboxyl group, wherein the blocking group is coupled to the terminal carboxyl group. Any form or type of CendR element, CendR peptide, CendR protein, CendR conjugate, or CendR composition can be used in these methods.

The CendR element can have a length of up to 10, 20, 30, 40, 50, 100, 150, 200, 250, 300, 400, 500, 1000 or 2000 residues. In particular embodiments, a CendR element can have a length of at least 1, 2, 3, 4, 5, 6, 7, 8, 9, 10, 15, 20, 25, 30, 40, 50, 60, 70, 80, 90, 100 or 200 residues. In further embodiments, a CendR element can have a length of 2 to 200 residues, 2 to 100 residues, 2 to 90 residues, 2 to 80 residues, 2 to 70 residues, 2 to 60 residues, 2 to 50 residues, 2 to 40 residues, 2 to 30 residues, 2 to 20 residues, 2 to 15 residues, 2 to 10 residues, 3 to 200 residues, 3 to 100 residues, 3 to 90 residues, 3 to 80 residues, 3 to 70 residues, 3 to 60 residues, 3 to 50 residues, 3 to 40 residues, 3 to 30 residues, 3 to 20 residues, 3 to 15 residues, 3 to 10 residues, 4 to 200 residues, 4 to 100 residues, 4 to 90 residues, 4 to 80 residues, 4 to 70 residues, 4 to 60 residues, 4 to 50 residues, 4 to 40 residues, 4 to 30 residues, 4 to 20 residues, 4 to 15 residues, 4 to 10 residues, 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

A protein or peptide containing a CendR element can have a length of up to 50, 100, 150, 200, 250, 300, 400, 500, 1000 or 2000 residues. In particular embodiments, the protein or peptide portion of a CendR composition can have a length of at least 10, 20, 30, 40, 50, 60, 70, 80, 90, 100 or 200 residues. In further embodiments, the protein or peptide containing a CendR element can have a length of 2 to 200 residues, 2 to 100 residues, 2 to 90 residues, 2 to 80 residues, 2 to 70 residues, 2 to 60 residues, 2 to 50 residues, 2 to 40 residues, 2 to 30 residues, 2 to 20 residues, 2 to 15 residues, 2 to 10 residues, 3 to 200 residues, 3 to 100 residues, 3 to 90 residues, 3 to 80 residues, 3 to 70 residues, 3 to 60 residues, 3 to 50 residues, 3 to 40 residues, 3 to 30 residues, 3 to 20 residues, 3 to 15 residues, 3 to 10 residues, 4 to 200 residues, 4 to 100 residues, 4 to 90 residues, 4 to 80 residues, 4 to 70 residues, 4 to 60 residues, 4 to 50 residues, 4 to 40 residues, 4 to 30 residues, 4 to 20 residues, 4 to 15 residues, 4 to 10 residues, 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

The CendR conjugate can have a length of up to 50, 100, 150, 200, 250, 300, 400, 500, 1000 or 2000 residues. In particular embodiments, a CendR conjugate can have a length of at least 10, 20, 30, 40, 50, 60, 70, 80, 90, 100 or 200 residues. In further embodiments, a CendR conjugate can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

The protein or peptide portion of a CendR composition can have a length of up to 50, 100, 150, 200, 250, 300, 400, 500, 1000 or 2000 residues. In particular embodiments, the protein or peptide portion of a CendR composition can have a length of at least 10, 20, 30, 40, 50, 60, 70, 80, 90, 100 or 200 residues. In further embodiments, the protein or peptide portion of a CendR composition can have a length of 2 to 200 residues, 2 to 100 residues, 2 to 90 residues, 2 to 80 residues, 2 to 70 residues, 2 to 60 residues, 2 to 50 residues, 2 to 40 residues, 2 to 30 residues, 2 to 20 residues, 2 to 15 residues, 2 to 10 residues, 3 to 200 residues, 3 to 100 residues, 3 to 90 residues, 3 to 80 residues, 3 to 70 residues, 3 to 60 residues, 3 to 50 residues, 3 to 40 residues, 3 to 30 residues, 3 to 20 residues, 3 to 15 residues, 3 to 10 residues, 4 to 200 residues, 4 to 100 residues, 4 to 90 residues, 4 to 80 residues, 4 to 70 residues, 4 to 60 residues, 4 to 50 residues, 4 to 40 residues, 4 to 30 residues, 4 to 20 residues, 4 to 15 residues, 4 to 10 residues, 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

The CendR composition can have a length of up to 50, 100, 150, 200, 250, 300, 400, 500, 1000 or 2000 residues. In particular embodiments, a CendR composition can have a length of at least 10, 20, 30, 40, 50, 60, 70, 80, 90, 100 or 200 residues. In further embodiments, a CendR composition can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

CendR (and other) peptides can be stabilized against proteolysis. For example, the stability and activity of peptides, such as tumor-homing peptides CREKA (SEQ ID NO:7) (Simberg et al., 2007), by protecting some of the peptide bonds with N-methylation or C-methylation. The most important bond to protect in order to enhance activity is the R-G bond because it would prevent a cleavage that would inactivate both the integrin-binding and CendR activities. For example, the peptides C(CMe)RGDKGPDC (SEQ ID NO:92) and CR(NMe)GDKGPDC (SEQ ID NO:93) compounds are stable against unwanted proteolysis. Accessory peptides and homing peptides can also or similarly be stabilized against proteolysis.

Figure 5A:
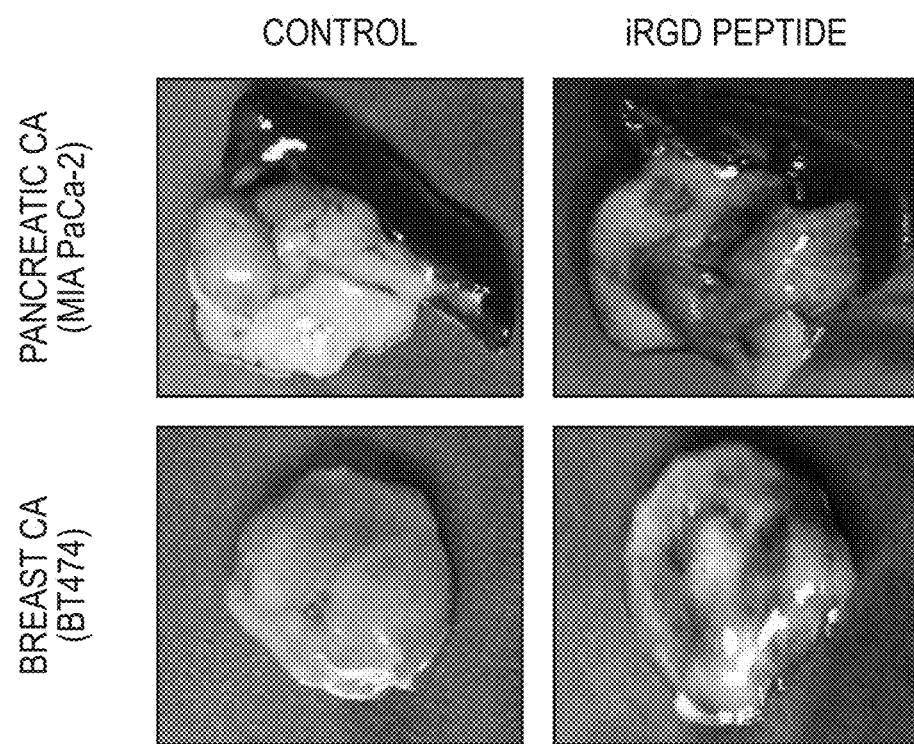

The activity of LyP-1 peptides and any other CendR peptide can be tested using the same Evans Blue assay used for iRGD (FIG. 5). The MDA-MB-435 human carcinoma can be used for testing the activity of LyP-1 peptides because this tumor shows the highest expression of cell surface p32, the primary receptor for LyP-1 (Fogal et al., 2008). RGR was identified in a phage library screen with RIP-Tag pancreatic islet cell carcinomas (Joyce et al., 2003), which can be used to test the activity of RGR peptides. The primary target of LyP-1 is tumor lymphatics, tumor macrophages, and tumor cells in hypoxic/low nutrient areas, not the blood vessels (Laakkonen et al., 2004; Fogal et al., 2008). Because of this, a compound co-injected with LyP-1 can be expected to preferentially accumulate in the areas favored by the peptide.

iRGD can increase the accumulation of co-compositions of a variety of sizes: a 1.3-kDa FAM-CRGDC (SEQ ID NO:36) peptide (which lacks a CendR motif and on its own only minimally penetrates tumor tissue), an albumin-binding dye (Evans Blue), an antibody, and two types of nanoparticles: T7 phage (65 nm in diameter) and iron oxide nanoworms (80 nm in length and 30 nm in thickness). Any co-composition can be tested using, for example iRGD and a non-CendR RGD peptide (which serves as a control for tumor accumulation that involves homing to tumor-associated integrins, but not the CendR mechanism). An inert D to E variant of this RGD peptide can be used as a control peptide that does not bind to integrins. The dose of the CendR peptide can be titrated to find the range that is maximally effective. Internalization and tissue penetration of co-compositions mediated by CendR peptides can also be tested by, for example, staining perfused, iRGD-treated tumors with a labeled form of the co-composition.

The disclosed CendR peptides (and other CendR forms) and co-compositions can be administered together or separately; in the same form and manner or in different forms and/or manners; at the same time or at different times; with the CendR peptide (or other CendR form) administered first or second. Administration can be, for example, co-administration (at the same time and by the same or different route/means/form), separate administration (parallel administration by the same or different route/means/form), sequential administration (at different times by the same or different route/means/form), etc. When the co-composition and CendR peptide (or other CendR form) are administered at different times, a variety of different delays can be used between the administrations. For example, the CendR peptide (or other CendR form) can be administered 1, 2, 3, 4, 5, 6, 7, 8, 9, 10, 11, 12, 13, 15, 20, 30, 40, 45, 50, 60, 70, 80, 90, 100, 110, or 120 minutes or more before administering a co-composition. The CendR peptide (or other CendR form) can be administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours or more before administering a co-composition. The CendR peptide (or other CendR form) can be administered 1, 2, 3, 4, 5, 6, or 7 days or more before administering a co-composition. The CendR peptide (or other CendR form) can be administered 1, 2, 3, 4, 5, 6, 7, 8, 9, 10, 11, 12, 13, 15, 20, 30, 40, 45, 50, 60, 70, 80, 90, 100, 110, or 120 minutes or more after administering a co-composition. The CendR peptide (or other CendR form) can be administered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours or more after administering a co-composition. The CendR peptide (or other CendR form) can be administered 1, 2, 3, 4, 5, 6, or 7 days or more after administering a co-composition.

The CendR peptide (or other CendR form) can be administered within 1, 2, 3, 4, 5, 6, 7, 8, 9, 10, 11, 12, 13, 15, 20, 30, 40, 45, 50, 60, 70, 80, 90, 100, 110, or 120 minutes before administering a co-composition. The CendR peptide (or other CendR form) can be administered within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours before administering a co-composition. The CendR peptide (or other CendR form) can be administered within 1, 2, 3, 4, 5, 6, or 7 days before administering a co-composition. The CendR peptide (or other CendR form) can be administered within 1, 2, 3, 4, 5, 6, 7, 8, 9, 10, 11, 12, 13, 15, 20, 30, 40, 45, 50, 60, 70, 80, 90, 100, 110, or 120 minutes after administering a co-composition. The CendR peptide (or other CendR form) can be administered within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 54, 60, 66, or 72 hours after administering a co-composition. The CendR peptide (or other CendR form) can be administered within 1, 2, 3, 4, 5, 6, or 7 days after administering a co-composition. Administration within the same day or hour is particularly useful.

The CendR composition, CendR conjugate, CendR molecule, CendR compound, CendR protein, CendR peptide, or CendR element and the co-composition can be administered to the subject simultaneously. By simultaneously is meant during overlapping or contiguous time periods. The CendR composition, CendR conjugate, CendR molecule, CendR compound, CendR protein, CendR peptide, or CendR element and the co-composition can be administered to the subject in a single composition comprising the CendR composition, CendR conjugate, CendR molecule, CendR compound, CendR protein, CendR peptide, or CendR element and the co-composition. The CendR composition, CendR conjugate, CendR molecule, CendR compound, CendR protein, CendR peptide, or CendR element and the co-composition can be administered to the subject in separate compositions. The CendR element and the co-composition can be administered to the subject at different times. The CendR element and the co-composition can be administered to the subject in separate compositions. By separate compositions is meant compositions that are not mixed or in contact with each other (except as may occur following administration). The CendR element and the co-composition can be administered to the subject by separate routes. By separate routes is meant in separate locations, by different means or mode.

CendR peptides can be made in the form of stabilized peptides and/or formulated as long-circulating forms. For example, a polyethylene glycol conjugate can be used. CendR peptides and/or co-compositions can also be administered over a period of time. For example, CendR peptides and/or co-compositions can be delivered with an osmotic pump. This can extend the permeability of the target cells and tissues. Modified forms of CendR peptides can be used. For example, CendR peptides can be methylated (which can stabilize the peptides against proteolysis). Stability against cleavage is desirable, except for bonds to be cleaved to activate CendR elements. Modifications to CendR elements generally should leave them functional or capable of function after activation.

It is understood that there are numerous amino acid and peptide analogs which can be incorporated into the disclosed CendR compositions, conjugates, molecules, proteins, peptides, and elements. For example, there are numerous D amino acids or other non-natural amino acids which can be used. The opposite stereoisomers of naturally occurring peptides are disclosed, as well as the stereo isomers of peptide analogs. These amino acids can readily be incorporated into polypeptide chains by chemical synthesis or by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH-$, $-CH_2S-$, $-CH_2-CH_2-CH=CH-$ (cis and trans), $-COCH_2-CH(OH)CH_2-$, and $-CHH_2SO-$ (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) ($-CH_2NH-$, $CH_2CH_2-$); Spatola et al. Life Sci 38:1243-1249 (1986) ($-CH\ H_2-S$); Hann J. Chem. Soc Perkin Trans. I 307-314 (1982) ($-CH-CH-$, cis and trans); Almquist et al. J. Med. Chem. 23:1392-1398 (1980) ($-COCH_2-$); Jennings-White et al. Tetrahedron Lett 23:2533 (1982) (—COCH$_2$—); Szelke et al. European Appln, EP 45665 CA (1982): 97:39405 (1982) (—CH(OH) CH$_2$—); Holladay et al. Tetrahedron. Lett 24:4401-4404 (1983) (—C(OH)CH$_2$—); and Hruby Life Sci 31:189-199 (1982) (—CH$_2$—S—); each of which is incorporated herein by reference. A particularly preferred non-peptide linkage is —CH$_2$NH—. It is understood that peptide analogs can have more than one atom between the bond atoms, such as b-alanine, g-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides as long as activity is preserved. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Disclosed are polyfunctional CendR compositions which, in addition to the CendR element, contain, for example, an accessory peptide, an accessory peptide fused to the CendR element, an accessory molecule covalently coupled to or non-covalently associated with the CendR element or CendR peptide, a homing peptide fused to the CendR element, a homing molecule covalently coupled to or non-covalently associated with the CendR element or CendR peptide, a cargo composition fused to the CendR element, and/or a cargo composition covalently coupled to or non-covalently associated with the CendR element or CendR peptide. Additional compounds having separate functions can be added to the composition. Such polyfunctional conjugates have at least two functions conferred by different portions of the composition and can, for example, display anti-angiogenic activity or pro-apoptotic activity in addition to selective homing activity.

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as that from which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

CendR elements bind to neuropilin-1 (NRP-1) present on the cell surface. Binding of CendR elements to NRP-1 mediates internalization of the CendR element, anything attached to the CendR element, and co-compositions. Non-peptide compounds can also be used to bind NRP-1 and mediate internalization and tissue penetration. Such non-peptide compounds are referred to herein as CendR compounds. CendR compounds can be used in all of the ways and in all of the compositions described herein where CendR elements are used (the only exception is where a particular use or composition requires that the CendR component be a peptide).

A design principle for homing peptides has been developed that combines three functions: tissue-specific homing, spreading within the target tissue, and internalization into cells in that tissue. These peptides contain both a tissue-specific homing sequence and a tissue-penetrating and internalizing motif embodied in a CendR element. Activatable CendR elements can be activated by, for example, a proteolytic cleavage at the target tissue. This example provides proof of principle for this platform technology by targeting selected tissues.

1. Using the disclosed principles and examples, peptides that combine specific homing to a normal or diseased tissue, tissue-penetration, and cell internalization can be screened for and synthesized. Also disclosed are peptides that combine tissue-specific homing, tissue-penetration, and cell internalization. The peptides can use various combinations of homing and tissue-penetration elements and will target the heart, lungs, or prostate.
2. The disclosed peptides can be used to tissue-specific homing, spreading within the target tissue, and internalization into cells in that tissue and this use can be established and validated by performing in vitro cell binding and internalization, and in vivo homing assays.

The disclosed compounds are useful tools for introducing materials into the target tissues. They can allow disease-specific or cell type and tissue-specific targeting of diagnostic and therapeutic compounds to increase efficacy and decrease side effects. The principles disclosed herein are applicable to any cells or tissues for which specific homing peptides can be obtained and that express a CendR receptor (which most cells do).

Recent studies have revealed extensive molecular heterogeneity in the vasculature of different normal tissues. In addition, pathological lesions, such as tumors, impose their own changes on the vasculature. This system of molecular markers can be referred to as 'vascular zip codes' (Ruoslahti, 2004). The zip codes enable docking-based ('synaphic') targeting to selectively deliver diagnostics and therapeutics into a specific tissue. This approach can produce greater efficacy and diminished side effects. The targeted delivery principle has been established, particularly in cancer: targeting of radioisotopes to leukemic cells with antibodies is an established therapy, and several products aimed at diagnosis and treatment of solid tumors are in clinical trials; many of them use early generation tumor-homing peptides or their derivatives. However, one issue in making the synaphic delivery more generally useful is that efficacy has tended to be low. It has been realized that it may be more effective to target the delivery to blood vessels because their inner endothelial lining is readily available to circulating probes, whereas penetration into tumor parenchyma has been a problem in the past (Jain, 1990). Thus, while it has been easy to demonstrate binding of the targeted material to the target vessels, a substantially higher concentration of the material in the target tissue has not necessarily been achieved (e.g. Liu et al., 2007).

A new class of homing peptides has been discovered that is more effective and specific than the currently available peptides in delivering payloads to a target. As described herein, an important feature of these peptides (and the basis for their to the superior performance) is that having arrived at the target tissue, they actively extravasate and penetrate into the tissue and cells within it. The principle and molecular mechanisms of this activity has been established with tumor-homing peptides. However, the principles can be used and applied with any cells and tissues and using any cell or tissue targeting or homing compound.

The ability to deliver a higher concentration or amount of material to and into a specific target in the body beyond what is now possible has tremendous implications in medicine. The disclosed technology can benefit all in vivo diagnostic compounds, parenterally administered drugs, nanomedical compounds, gene and cell therapies, etc. It can increase the potency by concentrating the material to be delivered at the target, and reduces the side effects in other tissues that receive relatively less of the material. Selective penetration into the target tissue further increases efficacy. Finally, the disclosed tissue-penetrating peptides can be modified and formulated into a drug-like chemistry, which makes the technology applicable to orally administered therapies as well.

A tissue/cell penetration system was recently discovered that makes it possible to derive peptides that not only home to a specific target tissue, but also penetrate into that tissue. The tissue-penetration motif has to be exposed at the C-terminus of a peptide (or protein) to be active. Hence it has been dubbed CendR for C-end Rule. FIG. 1 depicts the principle of the CendR system. A CendR homing peptide contains both a tissue-specific homing sequence and a CendR sequence (which can be a cryptic or activatable CendR sequence, as depicted in FIG. 1). The homing sequence takes the peptide to the vascular endothelium in the target tissue where, if it has a cryptic CendR sequence, the peptide is proteolytically processed by an endogenous protease, such that the CendR motif becomes C-terminal and active. The activated CendR motif then binds to a receptor (neuropilin-1), which mediates extravasation, tissue penetration, and cell entry of the CendR peptide and any payload attached to it (Teesalu et al., 2009; U.S. Patent Application Publication No. 20090226372).

The multi-step homing, processing, and tissue penetration process makes CendR more specific than peptides and other probes that rely on receptor binding only. The tissue and cell penetration facilitates delivery to all parts and cell types within the target tissue.

It was first noted that a disproportionate number of peptides T7 phage library screens for cell binding and tissue homing peptides had an arginine (or sometimes lysine or histidine) as the C-terminal residue. (The peptide insert is displayed at the C-terminus of the phage coat protein in the T7 system). The C-terminal arginine was usually in the context of an RXXR sequence (R, arginine; X, any amino acid). It was realized that this sequence motif could trigger cellular internalization of the phage particles to cells, leading to the enrichment. Extensive data has been generated to demonstrate this system and its mechanism. First, phage displaying the R(K)XXR motif were recovered from cells (PPC1 prostate cancer cells) that had been incubated at 37° C. and washed with an acidic (pH 2.5) buffer. As the T7 phage is not stable at pH 2.5, this result indicated internalization of the phage. Binding studies using individual phage from selected pools showed that, whereas the presence of C-terminal arginine (as in $G_6R$) alone is sufficient for weak phage binding to the PPC1 cells, robust binding and internalization require the presence of a C-terminal RXXR motif, as in, for example, RPARPAR (SEQ ID NO:2), the most frequently represented sequence in the selected phage pool.

An alanine scan of the RPARPAR (SEQ ID NO:2) peptide showed that the C-terminal arginine (or lysine) is critical for phage binding, and the other two basic amino acids increase the interaction in a dose and position dependent manner. The interaction with cells did not involve other phage elements, as RPARPAR (SEQ ID NO:2)-functionalized quantum dots (qdots) bound and were internalized in a manner indistinguishable from the phage particles. The qdot internalization was seen with live, unfixed cells, excluding that the intracellular accumulation is due to a processing artifact. Interestingly, a peptide comprised of D-amino acids (D-rparpar; SEQ ID NO:2) had a greatly reduced ability to trigger uptake of quantum dots, indicating the involvement of a chiral binding site. Masking the C-terminal RXXR element with an additional C-terminal amino acid (as in RPARPARA; SEQ ID NO:94) or an amidation of the C-terminal carboxyl group abolished cell binding and internalization. Treating the RPARPARA (SEQ ID NO:94) phage with trypsin (which cleaves after basic residues and presumably exposes a C-terminal arginine) restored PPC-1 cell binding. These findings indicate that cell binding and internalization requires the presence of a terminal basic amino acid with a free carboxyl group. Each cell line in a panel of tumor and normal cell lines and primary cells derived from normal mouse organs also bound RPARPAR (SEQ ID NO:2) phage.

Intravenously injected RPARPAR (SEQ ID NO:2) phage strongly accumulated in the first-met vascular beds: the lungs and, to a lesser extent, the heart. The RPARPAR (SEQ ID NO:2) phage spread throughout lung tissue, whereas a control phage was not detected in the lungs. This result indicates that the CendR phage was able to penetrate into tissue parenchyma. Thus, RPARPAR (SEQ ID NO:2) peptide is cell-penetrating peptide that is capable of entering into various types of cells and can also promote tissue penetration. None of the available inhibitors of the various cell internalization pathways inhibited internalization mediated by the RPARPAR (SEQ ID NO:2) CendR peptide, indicating a new pathway.

Neuropilin-1 is the cellular receptor for CendR peptides. To identify RPARPAR (SEQ ID NO:2) binding proteins, PPC-1 tumor extracts were fractionated by affinity chromatography on the RPARPAR (SEQ ID NO:2) peptide immobilized on agarose beads. Elution with a buffer containing free RPARPAR (SEQ ID NO:2) peptide released a 130-kDa protein, identified by MALDI-TOF mass spectroscopy as NRP-1. The identification was confirmed by immunoblotting.

Several lines of evidence supported the role of NRP-1 as the CendR receptor: The M21 melanoma cells, which do not bind nor internalize the RPARPAR (SEQ ID NO:2) peptide, also do not to express NRP-1. Forced expression of NRP-1 rendered in these cells capable of binding and internalizing RPARPAR (SEQ ID NO:2) phage, whereas cells transfected with an NRP-1 binding pocket mutant did not confer RPARPAR (SEQ ID NO:2) binding. Finally, immunofluorescent co-staining showed that RPARPAR (SEQ ID NO:2) phage and qdots co-localize with NRP-1 at the cell surface and inside the cells.

One of the alternative forms of vascular endothelial growth factor, VEGF-165, binds to NRP-1 using its C-terminal CendR-like sequence encoded by exon 8 (CRCDKPRR; SEQ ID NO:95; Jia et al., 2006). Several peptides such as A7R (ATWLPPR; SEQ ID NO:96; Starzec et al., 2006), immunomodulatory peptide tuftsin (TKPR; SEQ ID NO:97) and its variant enhanced tuftsin (TKPPR; SEQ ID NO:98; von Wronski et al., 2006) also bind to the same site on the NRP-1 (Geretti et al., 2008). Semaphorin 3A, which also binds to this site, enhances vascular permeability (Acevedo et al., 2008). T7 phage displaying seven C-terminal amino acids of VEGF-165, enhanced tuftsin or A7R bound to and were taken up by PPC-1 cells, and both activities were reduced when unlabeled RPARPAR (SEQ ID NO:2) peptide was included in the binding buffer or an alanine residue was added to the C-terminus of VEGF-C7. These experiments show that CendR peptides are internalized via a pathway that involves NRP-1 as a critical component.

Homeodomain transcription factors such as Antennapedia, the herpes simplex virus-1 protein VP22, and the human immunodeficiency virus-1 transactivator TAT protein are known to internalize into cells. Short cationic cell penetrating peptides (CPP) derived from these proteins retain their ability to internalize. However, these peptides are different from CendR peptides in that they are independent of the chirality of the amino acids in the peptide, require cell surface heparan sulfate for activity, and have not been assigned tissue-penetrating activity (Langel, 2007).

Cryptic CendR sequences in tumor-homing peptides from phage screens. The activation of the C-terminally blocked RPARPARA peptide by trypsin indicated that internal CendR motifs could be activated by proteases, triggering internalization and tissue penetration. Indeed, examination of the cell-penetrating peptides from the tumor homing screens revealed several potential CendR peptides. These peptides include LyP-1 (CGNKRTRGC; SEQ ID NO:99) containing the KRTR sequence (SEQ ID NO:100; Laakkonen et al., 2002, 2004; PCT Publication No. WO 2007/090194; U.S. Patent Application Publication No. 2008/0014143), CRGRRST (SEQ ID NO:101; RGRR (SEQ ID NO:102; Joyce et al., 2003), and a newly discovered RGD peptide with exceptional cell and tissue penetrating activities, iRGD (Sugahara et al., 2009; U.S. patent application Ser. No. 12/355,672, filed Jan. 19, 2009).

Each of the tumor-homing peptides listed above contains a CendR motif, R/KXXK/R, but this motif is not C-terminal. It was postulated that proteolytic processing could activate the CendR motif in these peptides. Indeed, treatment of iRGD phage or LyP-1 phage with trypsin enhanced the binding of the phage to PPC1 cells. Trypsin had no effect on the non-internalizing peptides CRGDC (SEQ ID NO:36) or RGD-4C. The binding at 4° C. of the trypsin-treated iRGD phage, but not of intact iRGD phage, was blocked by non-infectious phage expressing a prototypic CendR peptide, RPARPAR (SEQ ID NO:2), but not by phage displaying a peptide in which the CendR motif was masked by addition of an alanine residue to the C-terminus (RPARPARA; SEQ ID NO:2). Intracellular products have also been isolated from cells treated with iRGD peptide and shown by mass spectrometry that the expected CendR-active fragment, CRGDK (SEQ ID NO:34), could be recovered from the cells (Sugahara et al., 2009; U.S. patent application Ser. No. 12/355,672, filed Jan. 19, 2009).

Figure 4A:
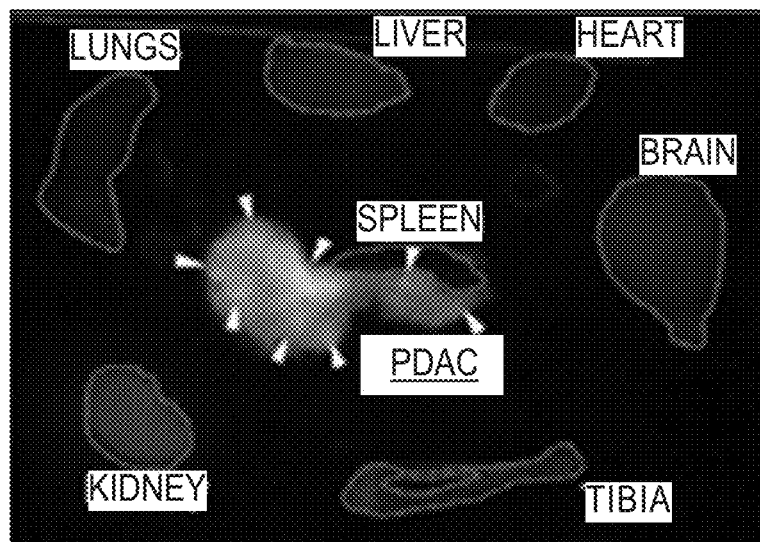
FIGS. 4A-4C shows in vivo tumor homing of iRGD peptide.
Figure 4B:
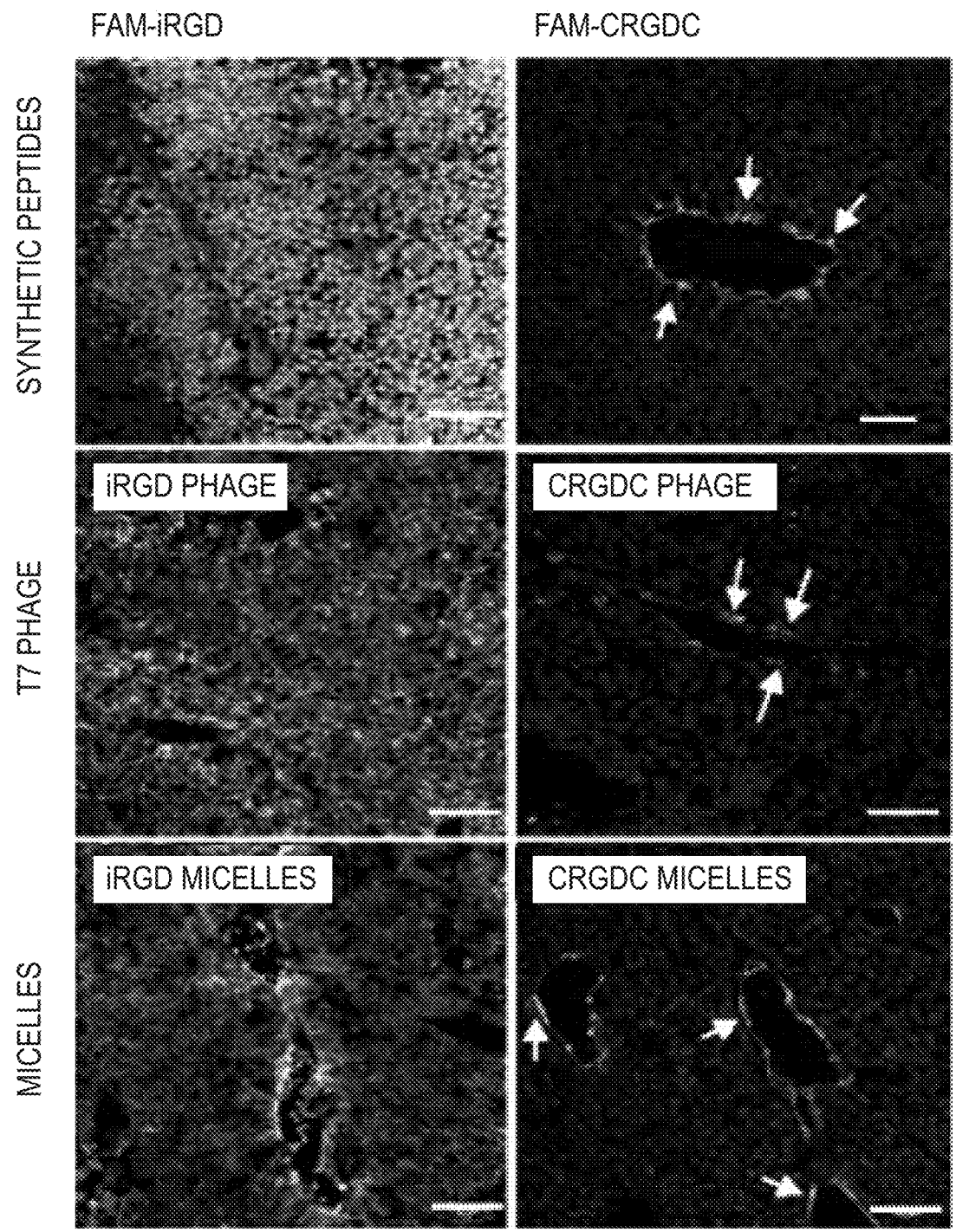
Figure 4C:
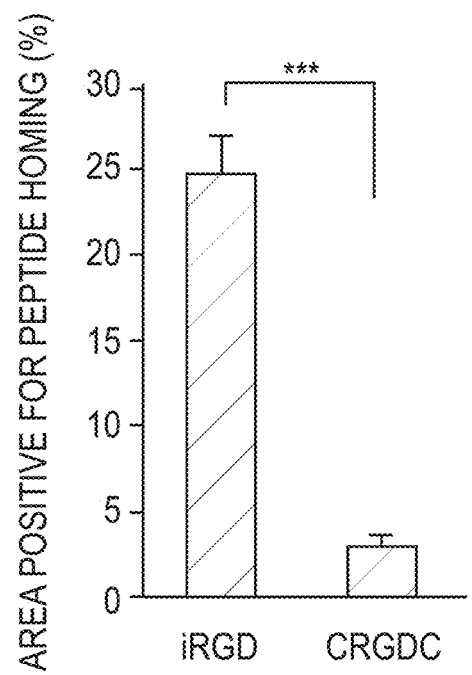

The iRGD peptide is uniquely effective in promoting extravasation and tissue penetration; iRGD peptide and iRGD phage spread within tumor tissue, whereas conventional RGD peptides lacking a cryptic CendR motif only reach the tumor blood vessels (see FIG. 4). The iRGD peptide does not detectably home to any normal tissue. Nanoparticles coated with the iRGD peptide impressively spread into tissues, allowing optical imaging, MRI and enhancing the activity of abraxane, which is a nanoparticle drug composed of paclitaxel and albumin. The increase in homing by iRGD was on the average 12 fold over untargeted controls (Sugahara et al. 2009; U.S. patent application Ser. No. 12/355,672, filed Jan. 19, 2009). The LyP-1 peptide also takes nanoparticles and other co-compositions deep into extravascular tumor tissue (Laakkonen et al., 2004; Karmali et al., 2009; PCT Publication No. WO 2007/090194; U.S. Patent Application Publication No. 2008/0014143). These results demonstrate that the CendR element mediates tissue penetration and cell internalization, and that tumor-homing peptides containing a cryptic CendR element can be uniquely effective in specific delivery of payloads into tumors. As disclosed herein, the use of CendR elements and CendR homing peptides can be extended for tissues other than tumors.

Organ-specific CendR homing peptides. Most, perhaps all, normal tissues put on their vasculature a tissue-specific molecular signature defined by specific molecular markers (reviewed in Ruoslahti, 2004). As with tumors, these differences can be probed with peptides from phage display screens, and can be exploited as targets for delivery of compounds and compositions such as CendR elements and CendR peptides.

All normal tissues that have been analyzed by in vivo phage display so far have turned out to express tissue-specific endothelial markers. These tissues include both major organs, such as the brain, lungs, heart, and kidneys, as well as small ones such as the prostate (Ruoslahti and Rajotte, 2000; Arap et al., 2002; Zhang et al., 2005). The early work was done with filamentous phage libraries, in which the insert is expressed as an N-terminal extension on a phage surface protein. These libraries do not favor CendR peptides, and consequently, the tissue-specific homing peptides recovered from these screens did not contain CendR motifs.

Examination of organ-specific homing peptides from recent work with T7 has revealed a number of peptides with cryptic CendR sequences. A collection of heart-homing peptides (Zhang et al., 2005; U.S. Patent Application Publication nos. 2006/0160743 and 2009/0092548) contains three such peptides; the two most potent ones among them being CGRKSKTVC (SEQ ID NO:103) (proposed receptor, cysteine-rich protein 2) and CPKTRRVPC (SEQ ID NO:104) (receptor, bladder cancer-associated protein bc10). Quite recently, T7-based screening with normal prostate tissue has been performed, and unlike earlier filamentous phage screens (Arap et al., 2002), the T7 screens also revealed a preponderance of CendR peptides. Nine out of twenty-one peptides from a screen that consisted of: three ex vivo screening rounds on cells isolated from mouse prostate, and one in vivo round for prostate homing, contained a cryptic CendR motif. Interestingly, eight out of the nine were quite similar to one another in that they all conformed to a CRXTRXXRC consensus (SEQ ID NO:105). A rabies virus-derived peptide with an apparent CendR motif has been used to deliver siRNA to the brain through the blood-brain barrier (Kumar et al., 2007). These results suggest that organ-specific peptides with CendR properties can be produced and used.

As disclosed herein, peptides can be screened for and synthesized that combine tissue-specific homing, tissue-penetration, and cell internalization. The peptides can use various combinations of vascular-homing and tissue-penetration elements and can target, for example, the heart, lungs, or prostate.

The normal organs can be used as the target because the tissue-specific properties of the vasculature and parenchyma can be expected to be retained even in a diseased tissue, especially early in a disease process, when intervention is likely to be of most benefit. For example, the heart, lungs, and prostate, can be targeted. Both conventional and candidate CendR peptides for the vasculature of these tissues are in hand. The heart and lungs are of a particular interest as targets for therapies that could use specific targeting and tissue penetration (cystic fibrosis is an example of such diseases). Moreover, the right side of the heart and the lungs are the tissues first encountered by intravenously injected peptides. Indeed pre-activated CendR peptides (peptides with an exposed R/KXXR/K sequence; SEQ ID NO:23) are selectively retained by these tissues. Thus, they can be somewhat selectively targeted with peptides like RPARPAR (SEQ ID NO:2) and CRPPR (SEQ ID NO:106; Zhang et al., 2005). Transgenic prostate cancer mice have been previously used to show that targeted destruction of prostate tissue before the tumors developed significantly delayed the development of tumors in these mice (Arap et al., 2002). The disclosed peptides will be more effective to improve the procedure. In addition, the prostate represents a small organ and one in which first pass effects are not a factor. Neuropilin-1 is ubiquitously expressed in endothelial cells and various parenchymal cells, and a large number of apparent CendR peptides were obtained in a prostate screen, so the CendR approach can be used with the prostate as well.

For example, three approaches can be used for tissue-penetrating peptides for the selected organs: (1) testing of the CendR motif peptides already at hand for the heart and prostate; (2) constructing chimeric peptides that incorporate a previously identified homing sequence and a generic CendR motif; and (3) phage screening for new peptides.

Existing CendR motif homing peptides. Peptides are in hand that home to the lungs (Rajotte and Ruoslahti, 1999; Brown and Ruoslahti, 2004), heart (Zhang et al., 2005, and unpublished results), and prostate (Arap et al., 2002; unpublished). Some of these peptides have a CendR motif. Homing of peptides can be established in several way. One example is by using a screening method called "play off screening." The candidate phage are combined at equal ratios, the pool is injected into mice, the target organ or tissue along with several other organs or tissues are collected, and it is determined by quantitative PCR whether any of the phage display peptides have preferentially homed to the target. The lungs (and the heart) can be to some extent targeted with activated CendR peptides (e.g. RPARPAR; SEQ ID NO:2). The homing is based on a first pass effect, and includes the heart (right side in particular). There is also substantial accumulation of these peptides in other organs; as a result, they are best if stringent targeting is desired.

Chimeric peptides. Previously identified (and future) non-CendR homing peptides can be combined with activated or activatable CendR elements. For example, homing peptides for the lungs (Rajotte and Ruoslahti, 1999; Brown and Ruoslahti, 2004) and prostate (Arap et al., 2002) can be combined with RPARPAR (SEQ ID NO:2) (or RPAR; SEQ ID NO:5) such that the homing peptide is C-terminal of RPARPAR (SEQ ID NO:2) (to block the CendR activity), and separated by a sequence that provides a protease cleavage site for CendR activation. The cryptic CendR elements in such peptides can be activated by furins, as these enzymes prefer to cleave after the C-terminal arginine in an RXXR context, particularly if one of the Xs is a basic amino acid. However, as demonstrated by the activation of RPARPARA (SEQ ID NO:2) and iRGD by trypsin, any enzyme that cleaves after a basic amino acid can potentially activate a cryptic CendR sequence. The location of the enzyme relative to the primary receptor for a CendR homing peptide may affect the activation. Known cleavage sites can be made by duplicating sequences from existing activatable CendR peptides. The constructs can be tested as phage-displayed peptides using phage titration as the readout. If desired, the protease cleavage site can be optimized by preparing a phage library with the structure RPARPXRXXXX-homing peptide (SEQ ID NO:107) and screening it for binding to and internalization into cells isolated from the target tissue.

For lung homing, the sequence CGFELETC (SEQ ID NO:108; Rajotte and Ruoslahti, 1999; target molecule: membrane dipeptidyl peptidase), for example, can be used to construct a chimeric peptide library.

As another strategy for heart homing, non-CendR peptides heart-homing peptides collection (Zhang et al., 2005) can be used to construct chimeric peptides and libraries. As another strategy, activated CendR peptide CRPPR (SEQ ID NO:106), which shows a preference for the heart (Zhang et al., 2005), can be used. Additional heart-homing CendR-motif peptides can be produced by testing, for example, a CRPPRA sequence (SEQ ID NO:109) for activation and/or internalization (the C-terminal amino acid needs to be cleaved off in order to activate the CendR element—other amino aicds can be used as well), or by screening a phage library with, for example, the structure CRPPRXXXX (SEQ ID NO:110).

For the prostate, the prostate-homing peptide (SMSIARL (SEQ ID NO:112); target molecule unknown; Arap et al., 2002), for example, can be used as the starting point in the construction of a chimeric peptide library. Prostate specific membrane antigen (PSMA) offers another interesting source for a CendR peptide that is activated in the prostate. PSMA is a glutamyl-preferring carboxypeptidase (e.g., Liu et al., 2002). Blocking the RPARPAR peptide with a C-terminal glutamic acid (RPARPARE; SEQ ID NO:111) will give a CendR peptide that is selectively activated in the prostate. Expression of the carboxypeptidase is upregulated in cancer cells, making it particularly useful for activation in the cancer-treatment context. To increase the concentration of the peptide in the prostate, a construct in which, for example, the prostate-homing SMSIARL sequence (SEQ ID NO:112) is added, in this case to the N-terminal side of, for example, a RPARE sequence (amino acids 4-8 of SEQ ID NO:111) (SMSIARLARPARE; SEQ ID NO:113). Inserting one amino acid (for example, alanine) in between the two peptides creates a double CendR motif similar to that in RPARPAR (SEQ ID NO:2).

The disclosed peptides can be validated by, for example, testing in vitro cell binding and internalization, and in vivo homing. Synthetic peptides can be used to show that the activities associated with the selected phage are reproduced by the peptide the phage displays. Techniques for this are well known (e.g. Zhang et al., 2005; Simberg et al., 2007; Karmali et al., 2008). The peptides generally can be labeled with a fluorophore to allow detection in tissues, and both the free peptide and a multimeric conjugate on nanoparticles (which more closely resembles the multivalent presentation on phage) can be tested.

Disclosed are homing molecules coupled to a CendR element in order to selectively deliver the CendR element to a given cell, thereby forming a homing CendR composition. A variety of homing molecules can be used in the disclosed compositions, conjugates and methods. Such homing molecules include, without limitation, peptides as disclosed herein. The disclosed compounds, compositions, conjugates and methods can include or use the disclosed homing molecules in various forms, including peptides and peptidomimetics as disclosed. For convenience of expression, in many places herein the use or inclusion of peptides will be recited. It is understood that, in such cases, it is considered that homing molecules in various forms can also be used or included in the same or similar ways as is described in terms of peptides, and such use and inclusion is specifically contemplated and disclosed thereby. A homing CendR peptide, molecule, etc. refers to a CendR element that is combined with one or more homing peptides or molecules.

The term "homing molecule" as used herein, means any molecule that selectively homes in vivo to specific cells or specific tissue in preference to normal tissue. Similarly, the term "homing peptide" or "homing peptidomimetic" means a peptide that selectively homes in vivo to specific cells or specific tissue in preference to normal tissue. It is understood that a homing molecule that selectively homes in vivo to specific cells or specific tissue or can exhibit preferential homing to r specific cells or specific tissue.

By "selectively homes" is meant that, in vivo, the homing molecule binds preferentially to the target as compared to non-target. For example, the homing molecule can bind preferentially to tumors, as compared to non-tumors. Selective homing to, for example, tumor cells generally is characterized by at least a two-fold greater localization within tumor cells, as compared to several tissue types of non-tumor cells. A homing molecule can be characterized by 5-fold, 10-fold, 20-fold or more preferential localization to target cells, as compared to-most or all non-target cells. Thus, it is understood that, in some cases, a homing molecule homes, in part, to one or more normal cells, tissues, and organs in addition to homing to target cells and tissues. Selective homing can also be referred to as targeting.

Binding in the context of a homing molecule recognizing and/or binding to its target can refer to both covalent and non-covalent binding, for example where a homing molecule can bind, attach or otherwise couple to its target by covalent and/or non-covalent binding. Binding can be either high affinity or low affinity, preferably high affinity. Examples of binding forces that can be useful include, but are not limited to, covalent bonds, dipole interactions, electrostatic forces, hydrogen bonds, hydrophobic interactions, ionic bonds, and/or van der Waals forces. This binding can occur in addition to that binding which occurs with the CendR element.

Many homing molecules and homing peptides home to the vasculature of the target tissue. However, for the sake of convenience homing is referred to in some places herein as homing to the tissue associated with the vasculature to which the homing molecule or homing peptide may actually home. Thus, for example, a homing peptide that homes to tumor vasculature can be referred to herein as homing to tumor tissue or to tumor cells. By including or associating a homing molecule or homing peptide with, for example, a protein, peptide, amino acid sequence, co-composition, cargo composition, or CendR element the protein, peptide, amino acid sequence, co-composition, cargo composition, or CendR element can be targeted or can home to the target of the homing molecule or homing peptide. In this way, the protein, peptide, amino acid sequence, co-composition, cargo composition, or CendR element can be said to home to the target of the homing molecule or homing peptide. For convenience and unless otherwise indicated, reference to homing of a protein, peptide, amino acid sequence, co-composition, cargo composition, CendR element, etc. is intended to indicate that the protein, peptide, amino acid sequence, co-composition, cargo composition, CendR element, etc. includes or is associated with an appropriate homing molecule or homing peptide.

The disclosed amino acid sequences, co-compositions, cargo compositions, proteins or peptides (and CendR elements that are coupled to or associated with a homing molecule) can, for example, home to brain cells, brain stem cells, brain tissue, and/or brain vasculature, kidney cells, kidney stem cells, kidney tissue, and/or kidney vasculature, skin cells, skin stem cells, skin tissue, and/or skin vasculature, lung cells, lung tissue, and/or lung vasculature, pancreatic cells, pancreatic tissue, and/or pancreatic vasculature, intestinal cells, intestinal tissue, and/or intestinal vasculature, adrenal gland cells, adrenal tissue, and/or adrenal vasculature, retinal cells, retinal tissue, and/or retinal vasculature, liver cells, liver tissue, and/or liver vasculature, prostate cells, prostate tissue, and/or prostate vasculature, endometriosis cells, endometriosis tissue, and/or endometriosis vasculature, ovary cells, ovary tissue, and/or ovary vasculature, tumor cells, tumors, tumor blood vessels, and/or tumor vasculature, bone cells, bone tissue, and/or bone vasculature, bone marrow cells, bone marrow tissue, and/or bone marrow vasculature, cartilage cells, cartilage tissue, and/or cartilage vasculature, stem cells, embryonic stem cells, pluripotent stem cells, induced pluripotent stem cells, adult stem cells, hematopoietic stem cells, neural stem cells, mesenchymal stem cells, mammary stem cells, endothelial stem cells, olfactory adult stem cells, neural crest stem cells, cancer stem cells, blood cells, erythrocytes, platelets, leukocytes, granulocytes, neutrophils, eosinphils, basophils, lymphoid cells, lymphocytes, monocytes, wound vasculature, vasculature of injured tissue, vasculature of inflamed tissue, atherosclerotic plaques, or a combination.

Examples of homing molecules and homing peptides are known. Examples include: Brain homing peptides such as: CNSRLHLRC (SEQ ID NO:114), CENWWGDVC (SEQ ID NO:115), WRCVLREGPAGGCAWFNRHRL (SEQ ID NO:116), CLSSRLDAC (SEQ ID NO:117), CVLRGGRC (SEQ ID NO:118), CNSRLQLRC (SEQ ID NO:119), CGVRLGC (SEQ ID NO:120), CKDWGRIC (SEQ ID NO:121), CLDWGRIC (SEQ ID NO:122), CTRITESC (SEQ ID NO:123), CETLPAC (SEQ ID NO:124), CRTGTLFC (SEQ ID NO:125), CGRSLDAC (SEQ ID NO:126), CRHWFDVVC (SEQ ID NO:127), CANAQSHC (SEQ ID NO:128), CGNPSYRC (SEQ ID NO:129), YPCGGEAVAGVSSVRTMCSE (SEQ ID NO:130), LNCDYQGTNPATSVSVPCTV (SEQ ID NO:131); kidney homing peptides such as: CLPVASC (SEQ ID NO:132), CGAREMC (SEQ ID NO:133), CKGRSSAC (SEQ ID NO:134), CWARAQGC (SEQ ID NO:135), CLGRSSVC (SEQ ID NO:136), CTSPGGSC (SEQ ID NO:137), CMGRWRLC (SEQ ID NO:138), CVGECGGC (SEQ ID NO:139), CVAWLNC (SEQ ID NO:140), CRRFQDC (SEQ ID NO:141), CLMGVHC (SEQ ID NO:142), CKLLSGVC (SEQ ID NO:143), CFVGHDLC (SEQ ID NO:144), CRCLNVC (SEQ ID NO:145), CKLMGEC (SEQ ID NO:146); skin homing peptides such as: CARSKNKDC (SEQ ID NO:147), CRKDKC (SEQ ID NO:148), CVAL-CREACGEGC (SEQ ID NO:149), CSSGCSKNCLEMC (SEQ ID NO:150), CIGEVEVC (SEQ ID NO:151), CKWSRLHSC (SEQ ID NO:152), CWRGDRKIC (SEQ ID NO:153), CERVVGSSC (SEQ ID NO:154), CLAKENVVC (SEQ ID NO:155); lung homing peptides such as: CGFECVRQCPERC (SEQ ID NO:156), CGFELETC (SEQ ID NO:157), CTLRDRNC (SEQ ID NO:158), CIGEVEVC (SEQ ID NO:159), CTLRDRNC (SEQ ID NO:160), CGKRYRNC (SEQ ID NO:161), CLRPYLNC (SEQ ID NO:162), CTVNEAYKTRMC (SEQ ID NO:163), CRLRSYGTLSLC (SEQ ID NO:164), CRPWHNQAHTEC (SEQ ID NO:165); pancreas homing peptides such as: SWCEPGWCR (SEQ ID NO:166), CKAAKNK (SEQ ID NO:167), CKGAKAR (SEQ ID NO:168), VGVGEWSV (SEQ ID NO:169); intestine homing peptides such as: YSGKWGW (SEQ ID NO:170); uterus homing peptides such as: GLSGGRS (SEQ ID NO:171); adrenal gland homing peptides such as: LMLPRAD (SEQ ID NO:172), LPRYLLS (SEQ ID NO:173); retina homing peptides such as: CSCFRDVCC (SEQ ID NO:174), CRDVVSVIC (SEQ ID NO:175); gut homing peptides such as: YSGKWGK (SEQ ID NO:176), GISALVLS (SEQ ID NO:177), SRRQPLS (SEQ ID NO:178), MSPQLAT (SEQ ID NO:179), MRRDEQR (SEQ ID NO:180), QVRRVPE (SEQ ID NO:181), VRRGSPQ (SEQ ID NO:182), GGRGSWE (SEQ ID NO:183), FRVRGSP (SEQ ID NO:184), RVRGPER (SEQ ID NO:185); liver homing peptides such as: VKSVCRT (SEQ ID NO:186), WRQNMPL (SEQ ID NO:187), SRRFVGG (SEQ ID NO:188), ALERRSL (SEQ ID NO:189), ARRGWTL (SEQ ID NO:190); prostate homing peptides such as: SMSIARL (SEQ ID NO:191), VSFLEYR (SEQ ID NO:192), RGRWLAL (SEQ ID NO:193); ovary homing peptides such as: EVRSRLS (SEQ ID NO:194), VRARLMS (SEQ ID NO:195), RVGLVAR (SEQ ID NO:196), RVRLVNL (SEQ ID NO:197); Clot binding homing peptide such as: CREKA (SEQ ID NO:7), CLOT1, and CLOT2; heart homing peptides such as: CRPPR (SEQ ID NO:198), CGRKSKTVC (SEQ ID NO:199), CARPAR (SEQ ID NO:200), CPKRPR (SEQ ID NO:201), CKRAVR (SEQ ID NO:202), CRNSWKPNC (SEQ ID NO:203), RGSSS (SEQ ID NO:204), CRSTRANPC (SEQ ID NO:205), CPKTRRVPC (SEQ ID NO:206), CSGMARTKC (SEQ ID NO:207), GGGVFWQ (SEQ ID NO:208), HGRVRPH (SEQ ID NO:209), VVLVTSS (SEQ ID NO:210), CLHRGNSC (SEQ ID NO:211), CRSWNKADNRSC (SEQ ID NO:212), CGRKSKTVC (SEQ ID NO:213), CKRAVR (SEQ ID NO:214), CRNSWKPNC (SEQ ID NO:215), CPKTRRVPC (SEQ ID NO:216), CSGMARTKC (SEQ ID NO:217), CARPAR (SEQ ID NO:218), CPKRPR (SEQ ID NO:219); tumor blood vessel homing peptide such as: CNGRC (SEQ ID NO:220) and other peptides with the NGR motif (U.S. Pat. Nos. 6,177,542 and 6,576,239; U.S. Patent Application Publication No. 20090257951); RGD peptides, and RGR peptides. Other homing peptides include CSRPRRSEC (SEQ ID NO:221), CSRPRRSVC (SEQ ID NO:222) and CSRPRRSWC (SEQ ID NO:223) (Hoffman et al., Cancer Cell, vol. 4 (2003)), F3 (KDEPQRRSARLSAKPAPPKPEPKPKKAPAKK; (SEQ ID NO:224)), PQRRSARLSA (SEQ ID NO:225), PKRRSARLSA (SEQ ID NO:226) (U.S. Pat. No. 7,544,767), and CGRECPRLCQSSC (SEQ ID NO:62), which home to tumors.

It is understood that, although many homing and targeting motifs and sequences are shown with cysteine residues at one or both ends, such cysteine residues are generally not required for homing function. Generally, such cysteines are present due to the methods by which the homing and targeting sequences were identified. Such terminal cysteines can be used to, for example, circularize peptides, such as those disclosed herein. For these reasons, it is also understood that cysteine residues can be added to the ends of any of the disclosed peptides.

Useful NGR peptides include peptide such as $X_2CNGRCX_2$ (SEQ ID NO:89), $CX_2(C/X) NGR(C/X)X_2C$ (SEQ ID NO:90), and $CNGRCX_6$ (SEQ ID NO:91) (where "X" is any amino acid), which can be linear or circular. Examples of NGR peptides include CNGRCVSGCAGRC (SEQ ID NO:63), NGRAHA (SEQ ID NO:24), CVLNGRMEC (SEQ ID NO:67), CNGRC (SEQ ID NO:68), ALNGREESP (SEQ ID NO:66), CVLNGRME (SEQ ID NO:87), CKVCNGRCCG (SEQ ID NO:88), CEMCNGRCMG (SEQ ID NO:69), CPLCNGRCAL (SEQ ID NO:70), CPTCNGRCVR (SEQ ID NO:71), CGVCNGRCGL (SEQ ID NO:72), CEQCNGRCGQ (SEQ ID NO:73), CRNCNGRCEG (SEQ ID NO:74), CVLCNGRCWS (SEQ ID NO:75), CVTCNGRCRV (SEQ ID NO:76), CTECNGRCQL (SEQ ID NO:77), CRTCNGRCLE (SEQ ID NO:78), CETCNGRCVG (SEQ ID NO:79), CAVCNGRCGF (SEQ ID NO:80), CRDLNGRKVM (SEQ ID NO:81), CSCCNGRCGD (SEQ ID NO:82), CWGCNGRCRM (SEQ ID NO:83), CPLCNGRCAR (SEQ ID NO:84), CKSCNGRCLA (SEQ ID NO:85), CVPCNGRCHE (SEQ ID NO:86), CQSCNGRCVR (SEQ ID NO:47), CRTCNGRCQV (SEQ ID NO:48), CVQCNGRCAL (SEQ ID NO:49), CRCCNGRCSP (SEQ ID NO:50), CASNNGRVVL (SEQ ID NO:51), CGRCNGRCLL (SEQ ID NO:52), CWLCNGRCGR (SEQ ID NO:53), CSKCNGRCGH (SEQ ID NO:54), CVWCNGRCGL (SEQ ID NO:55), CIRCNGRCSV (SEQ ID NO:56), CGECNGRCVE (SEQ ID NO:57), CEGVNGRRLR (SEQ ID NO:58), CLSCNGRCPS (SEQ ID NO:59), CEVCNGRCAL (SEQ ID NO:60).

Useful peptides for tumor targeting include, for example, iRGD, LyP-1, iNGR, and RGR peptides. The prototypic tumor-homing CendR peptide, iRGD, which was used in generating the results described herein. LyP-1, is a peptide that contains a putative CendR element and has tumor-penetrating properties. This peptide has a unique target within tumors; it preferentially accumulates in the hypoxic/low nutrient areas of tumors (Laakkonen et al., 2002; 2004; Karmali et al., 2009). CRGRRST (SEQ ID NO:101) (RGR; Joyce et al., 2003) is a peptide that has been successfully used in targeting a cytokine antibody combination into tumors (Hamzah et al., 2008). This peptide is linear, which simplifies the synthesis. NGR peptides home to angiogenic vasculature, including angiogenic vasculature associated with tumors, and αv integrin and α5β1 integrin (U.S. Pat. Nos. 6,576,239 and 6,177,542 and U.S. Patent Application Publication No. 20090257951). Like LyP-1, RGR is at least to some extent tumor type-specific (Joyce et al., 2003), but the tumor types recognized by the two peptides seem to be partially different, which may be an advantage in testing combinations with the pan-tumor iRGD. Table 3 shows examples of tumor-homing CendR peptides.

TABLE 3

Examples of Tumor-Homing Peptides with CendR Elements

| Sequence following MLGDPNS | Reference |
|---|---|
| CRKDKC | Jarvinen et al., Am. J. Pathol. 171(2): 702-711 (2007); SEQ ID NO: 148 |
| CGNKRTRGC | Laakkonen et al., Nature Medicine 8: 751-755 (2002); SEQ ID NO: 99 |

TABLE 3-continued

Examples of Tumor-Homing Peptides with CendR Elements

| Sequence following MLGDPNS | Reference |
|---|---|
| AKVKDEPQRR SARLSAKPAPP KPEPKPKKAPA KK | Christian et al., JCB, 163(4): 871-878 (2003); U.S. Pat. No. 7,544,767; SEQ ID NO: 35 |
| CSRPRRSEC CSRPRRSVC CSRPRRSWC | Hoffman et al., Cancer Cell, vol. 4 (2003); SEQ ID NOs: 221, 222, and 223 |
| CNRRTKAGC | Zhang et al., Cancer Res. 66(11): 5696-5706 (2006); SEQ ID NO: 227 |
| CRGRRST CRSRKG CKAAKNK CKGAKAR | Joyce et al., 4(5):393-403 (2003); SEQ ID NOs: 101, 228, 167, 168 |
| PQRRSARLSA | Porkka et al., Proc. Natl. Acad. Sci. USA 99(11): 7444-7449 (2002); U.S. Pat. No. 7,544,767; SEQ ID NO: 225 |
| PKRRSARLSA | U.S. Pat. No. 7,544,767; SEQ ID NO: 226 |
| CRGDKGPDC | iRGD, Sugahara et al., 2009; U.S. Patent Application No. 12/355,672, filed Jan. 19, 2009; SEQ ID NO: 3 |

RGD peptides are peptides that contain the RGD (Arg-Gly-Asp) motif and that home to angiogenesis and tumor vasculature. NGR peptides are peptides that contain the NGR (Asn-Gly-Arg) motif and that home to angiogenesis and tumor vasculature. Examples of NGR peptides include CNGRCVSGCAGRC (SEQ ID NO:63), NGRAHA (SEQ ID NO:24), CVLNGRMEC (SEQ ID NO:67), and CNGRC (SEQ ID NO:68). GSL peptides are peptides that contain the GSL (Gly-Ser-Leu) motif and that home to tumor vasculature. Examples of a GSL peptide include CGSLVRC (SEQ ID NO:65) and CLSGSLSC (SEQ ID NO:64).

Internalizing RGD (iRGD) refers to peptides that combine an RGD motif and a CendR element. For example, cyclic RGD peptide having the sequence CRGDK/RGPD/EC (SEQ ID NOs:71) is exceptionally effective in orchestrating extravasation and spreading of linked payloads within tumor tissue, and subsequently internalizing within tumor cells. The iRGD peptide incorporates two functional elements: the RGD motif that gives tumor specificity (Pierschbacher and Ruoslahti, E. Cell attachment activity of fibronectin can be duplicated by small synthetic fragments of the molecule. Nature 309, 30-33 (1984); Ruoslahti (2003); Eliceiri and Cheresh (2001); Ruoslahti (2002); Arap et al. (1998); Curnis et al. (2004); Sipkins et al. (1998); Murphy et al. (2008)), and a CendR motif that mediates penetration. iRGD readily adheres to cultured cells expressing αv integrins, and is internalized far more effectively than other RGD peptides. Internalization was dependent on expression of neuropilin-1, the receptor for the CendR motif. iRGD coupled to a payload of fluorescein, phage, or artificial nanoparticles, accumulated around tumor vessels in vivo, spread through the tumor interstitium, and became internalized within tumor cells in various tumor models. Systemic administration of iRGD micelles labeled with a near infrared dye produced a strong and specific tumor signal in whole body imaging of mice. The CendR element in iRGD is an activatable CendR element that is activated, likely by cleavage after the Lys/Arg, to allow the peptide to mediate internalization.

Internalizing NGR (iNGR) refers to peptides that combine a NGR motif and a CendR element. For example, NGR peptide having the sequence K/RNGR (SEQ ID NO:46) can be effective in orchestrating extravasation and spreading of linked payloads within tumor tissue, and subsequently internalizing within tumor cells. The iNGR peptide incorporates two functional elements: the NGR motif that gives tumor specificity, and a CendR motif that mediates penetration. Another example of an iNGR peptide is NGRAHA (SEQ ID NO:24). The CendR element in the iNGR peptide NGRAHA (SEQ ID NO:24) is an activatable CendR element that is activated, likely by cleavage after the Arg, to allow the peptide to mediate internalization.

Accessory molecules can be any molecule, compound, component, etc. that has a useful function and that can be used in combination with a CendR element, CendR composition, CendR conjugate, CendR molecule, CendR compound, CendR protein, CendR peptide, composition, co-composition, and/or cargo composition. Examples of useful accessory molecules include homing molecules, targeting molecules, affinity ligands, cell penetrating molecules, endosomal escape molecules, subcellular targeting molecules, nuclear targeting molecules. Different accessory molecules can have similar or different functions from each other.

Molecules that target, home, or have affinity for certain molecules, structures, cells, tissues, etc. are particularly useful as accessory molecules. In addition to the homing peptides described elsewhere herein, there are numerous molecules and compounds known that have affinity for particular target molecules, structures, cells, tissues, etc. and can aid in accumulating and/or directing the disclosed components and compositions to desired targets. For convenience, such affinity effects can be referred to as homing. Descriptions of homing and homing effects elsewhere herein can be applied to these molecules.

An affinity ligand is a molecule that interacts specifically with a particular molecule, moiety, cell tissue, etc. The molecule, moiety, cell tissue, etc. that interacts specifically with an affinity ligand is referred to herein as a target or target molecule, moiety, cell tissue, etc. It is to be understood that the term target molecule refers to both separate molecules and to portions of such molecules, such as an epitope of a protein, that interacts specifically with an affinity ligand. Antibodies, either member of a receptor/ligand pair, synthetic polyamides (Dervan and Burli, *Sequence-specific DNA recognition by polyamides*. Curr Opin Chem Biol, 3(6):688-93 (1999); Wemmer and Dervan, *Targeting the minor groove of DNA*. Curr Opin Struct Biol, 7(3):355-61 (1997)), and other molecules with specific binding affinities are examples of affinity ligands.

An affinity ligand that interacts specifically with a particular target molecule is said to be specific for that target molecule. For example, where the affinity ligand is an antibody that binds to a particular antigen, the affinity ligand is said to be specific for that antigen. The antigen is the target molecule. The affinity ligand can also be referred to as being specific for a particular target molecule. Examples of useful affinity ligands are antibodies, ligands, binding proteins, receptor proteins, haptens, aptamers, carbohydrates, lectins, folic acid, synthetic polyamides, and oligonucleotides. Useful binding proteins include DNA binding proteins. Useful DNA binding proteins include zinc finger motifs, leucine zipper motifs, and helix-turn-helix motifs. These motifs can be combined in the same affinity ligand.

Antibodies are useful as the affinity ligands. Antibodies can be obtained commercially or produced using well established methods. For example, Johnstone and Thorpe, *Immunochemistry In Practice* (Blackwell Scientific Publications, Oxford, England, 1987) on pages 30-85, describe general methods useful for producing both polyclonal and monoclonal antibodies. The entire book describes many general techniques and principles for the use of antibodies in assay systems. Numerous antibodies and other affinity ligands are known that bind to particular proteins, carbohydrates, glycoproteins, molecules, cells, tissues, etc. Such antibodies can be used in the disclosed components and compositions.

Examples of cell penetrating peptides are described in, for example, U.S. Patent Application Publication Nos. 20100061942, 20100061932, 20100048487, 20100022466, 20100016215, 20090280058, 20090186802, 20080234183, 20060014712, 20050260756, and 20030077289, which are hereby incorporated by reference in their entirety and specifically for their description of cell penetrating peptides and motifs. Examples of endosomal escape molecules are described in, for example, U.S. Patent Application Publication Nos. 20090325866, 20090317802, 20080305119, 20070292920, 20060147997, 20050038239, 20040219169, 20030148263, 20030082143, 20020132990, and 20020068272, which are hereby incorporated by reference in their entirety and specifically for their description of endosomal escape molecules and motifs. Examples of subcellular targeting molecules are described in, for example, U.S. Patent Application Publication Nos. 2009031733, 20090258926, 20090176660, 20080311136, 20070287680, 20070157328, 20070111270, 20070111251, 20060257942, 20060154340, 20060014712, 20050281805, 20050233356, 20040005309, 20030082176, and 20010021500, which are hereby incorporated by reference in their entirety and specifically for their description of subcellular targeting molecules and motifs. Examples of nuclear targeting molecules are described in, for example, U.S. Patent Application Publication Nos. 10100143454, 20100099627, 20090305329, 20090176710, 20090087899, 20070231862, 20070212332, 20060242725, 20060233807, 20060147922, 20060070133, 20060051315, 20050147993, 20050071088, 20030166601, 20030125283, 20030083261, 20030003100, 20020068272, and 20020055174, which are hereby incorporated by reference in their entirety and specifically for their description of nuclear targeting molecules and motifs.

As disclosed herein, the term "co-composition" refers to any composition of matter that can be used with the CendR element. Similarly, the term "cargo composition" refers to any composition of matter that can be used with the CendR element. Generally, for example, a co-composition or cargo composition can be any composition to be internalized and/or to penetrate into cells and/or tissues. For example, a co-composition or cargo composition can be a molecule, a conjugate, an association of molecules, a composition, a mixture. Examples of co-compositions and cargo compositions include, but are not limited to, cancer chemotherapeutic agents, cytotoxic agents, anti-inflammatory agents, anti-arthritic agents, polypeptides, nucleic acid molecules, small molecules, nanoparticles, microparticles, fluorophores, fluorescein, rhodamine, a radionuclide, Lutetium-177 ($^{177}$Lu), Rhenium-188 ($^{188}$Re), Gallium-68 ($^{68}$Ga), Yttrium-90 ($^{99}$Y), Technetium-99m ($^{99m}$Tc), Holmium-166 ($^{166}$Ho), Iodine-131 ($^{131}$I), Indium-111 ($^{111}$In), Flourine-18 Carbon-11 ($^{11}$C), Nitrogen-13 ($^{13}$N), Oxygen-15 ($^{15}$O), Bromine-75 ($^{75}$Br), Bromine-76 ($^{76}$Br), Iodine-124 ($^{124}$I), Thalium-201 ($^{291}$Tl), Technetium-99 ($^{99}$Tc), Iodine-123 ($^{123}$I), an anti-angiogenic agents, pro-angiogenic agents, or a combination thereof.

The disclosed CendR components can be used with any therapeutic agents since they represent a general mode and platform for aiding in delivery of therapeutic agents to cells and tissues. Thus, any therapeutic agent can be used in or with the disclosed compositions. Comprehensive lists of therapeutic agents and drugs can be found in a number of places, such as the Orange Book and other lists maintained by the U.S. Food and Drug Administration and similar lists maintained by other countries.

Co-compositions and cargo compositions can be moieties. As used herein, the term "moiety" is used broadly to mean a physical, chemical, or biological material that generally imparts a biologically useful function to a linked co-composition or a linked cargo composition. A moiety can be any natural or nonnatural material including, without limitation, a biological material, such as a cell, phage or other virus; an organic chemical such as a small molecule; a nanoparticle, a radionuclide; a nucleic acid molecule or oligonucleotide; a polypeptide; or a peptide. For example, moieties that affect the target, such as moieties with therapeutic effect, or that facilitate detection, visualization or imaging of the target, such as fluorescent molecule or radionuclides.

Components of the disclosed co-compositions and cargo compositions can be combined, linked and/or coupled in any suitable manner. For example, moieties and other molecules can be associated covalently or non-covalently, directly or indirectly, with or without a linker moiety.

In some embodiments, a co-composition or cargo composition can comprise a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab; paclitaxel such as Abraxane; Doxil.

A co-composition or cargo composition can comprise a therapeutic agent. Useful therapeutic agents can be, for example, a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, Pseudomonas exotoxin A, cholera toxin, ligand fusion toxins such as DAB389EGF, *Ricinus communis* toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:175 (1996). One skilled in the art understands that these and additional cytotoxic agents described herein or known in the art can be useful in the disclosed compositions and methods.

In some forms, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. As non-limiting examples, useful therapeutic polypeptides can be a cytokine such as tumor necrosis factor-α (TNF-α), tumor necrosis factor-O (TNF-β), granulocyte macrophage colony stimulating factor (GM-CSF), granulocyte colony stimulating factor (G-CSF), interferon-α. (IFN-α); interferon-γ (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase, for example, diphtheria toxin A chain, Pseudomonas exotoxin A, cholera toxin, a ligand fusion toxin such as DAB389EGF or ricin; or an anti-angiogenic polypeptide such as angiostatin, endostatin, thrombospondin, platelet factor 4; anastellin; or one of those described further herein or known in the art. It is understood that these and other polypeptides with biological activity can be a "therapeutic polypeptide."

A therapeutic agent useful in the disclosed co-compositions and cargo compositions can be an anti-angiogenic agent. As used herein, the term "anti-angiogenic agent" means a molecule that reduces or prevents angiogenesis, which is the growth and development of blood vessels. The co-compositions and cargo compositions can be used to treat or diagnose any disease, condition, or disorder associated with angiogenesis. For example, macular degeneration and diabetic vascular complications can be diagnosed and/or treated. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof. See, for example, Hagedorn and Bikfalvi, Crit. Rev. Oncol. Hematol. 34:89-110 (2000), and Kirsch et al., J. Neurooncol. 50:149-163 (2000).

Some other examples of useful therapeutic agents include nitrogen mustards, nitrosoureas, ethyleneimine, alkane sulfonates, tetrazine, platinum compounds, pyrimidine analogs, purine analogs, antimetabolites, folate analogs, anthracyclines, taxanes, *vinca* alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Chlomaphazine, Cholophosphamide, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Estramustine, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, mechlorethamine oxide hydrochloride, Melphalan, Mercaptopurine, Methotrexate, Mitomycin, Mitotane, Mitoxantrone, Novembiehin, Oxaliplatin, Paclitaxel, Pamidronate, Pentostatin, Phenesterine, Plicamycin, Prednimustine, Procarbazine, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Trofosfamide, Vinblastine, Vincristine, Vindesine, Vinorelbine, VP-16, and Xeloda. Alkylating agents such as Thiotepa and; alkyl sulfonates such as Busulfan, Improsulfan and Piposulfan; aziridines such as Benzodopa, Carboquone, Meturedopa, and Uredopa; ethylenimines and methylamelamines including altretamine, triethylenemelamine, trietylenephosphoramide, triethylenethiophosphaoramide and trimethylolomelamine; nitroureas such as Cannustine, Chlorozotocin, Fotemustine, Lomustine, Nimustine, and Ranimustine; antibiotics such as Aclacinomysins, Actinomycin, Authramycin, Azaserine, Bleomycins, Cactinomycin, Calicheamicin, Carabicin, Caminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; anti-metabolites such as Methotrexate and 5-fluorouracil (5-FU); folic acid analogues such as Denopterin, Methotrexate, Pteropterin, and Trimetrexate; purine analogs such as Fludarabine, 6-mercaptopurine, Thiamiprine, and Thioguanine; pyrimidine analogs such as Ancitabine, Azacitidine, 6-azauridine, Carmofur, Cytarabine, Dideoxyuridine, Doxifluridine, Enocitabine, Floxuridine, and 5-FU; androgens such as Calusterone, Dromostanolone Propionate, Epitiostanol, Rnepitiostane, and Testolactone; anti-adrenals such as aminoglutethimide, Mitotane, and Trilostane; folic acid replenisher such as frolinic acid; aceglatone; aldophosphamide glycoside; aminolevulinic acid; Amsacrine; Bestrabucil; Bisantrene; Edatraxate; Defofamine; Demecolcine; Diaziquone; Elfornithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone; 2,2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotEPa; taxoids, e.g., Paclitaxel (TAXOL®, Bristol-Myers Squibb Oncology, Princeton, N.J.) and Doxetaxel (TAXO- TERE®, Rhone-Poulenc Rorer, Antony, France); Gemcitabine; 6-thioguanine; Mercaptopurine; Methotrexate; platinum analogs such as Cisplatin and Carboplatin; Vinblastine; platinum; etoposide (VP-16); Ifosfamide; Mitomycin C; Mitoxantrone; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylornithine (DMFO); retinoic acid; Esperamicins; Capecitabine; and pharmaceutically acceptable salts, acids or derivatives of any of the above. Also included are anti-hormonal agents that act to regulate or inhibit hormone action on tumors such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above. Useful co-compositions and cargo compositions include, for example, doxorubicin, Herceptin, and liposomal doxorubicin.

The co-composition or cargo composition can also comprise a boron containing compound. Boron containing compounds have received increasing attention as therapeutic agents over the past few years as technology in organic synthesis has expanded to include this atom (Boron Therapeutics on the horizon, Groziak, M. P.; American Journal of Therapeutics (2001) 8, 321-328). The most notable boron containing therapeutic is the boronic acid bortezomib which was recently launched for the treatment of multiple myeloma. This breakthrough demonstrates the feasibility of using boron containing compounds as pharmaceutical agents. Boron containing compounds have been shown to have various biological activities including herbicides (Organic boron compounds as herbicides. Barnsley, G. E.; Eaton, J. K.; Airs, R. S.; (1957), DE 1016978 19571003), boron neutron capture therapy (Molecular Design and Synthesis of B-10 Carriers for Neutron Capture Therapy. Yamamoto, Y.; Pure Appl. Chem., (1991) 63, 423-426), serine protease inhibition (Borinic acid inhibitors as probes of the factors involved in binding at the active sites of subtilisin Carlsberg and .alpha.-chymotrypsin. Simpelkamp, J.; Jones, J. B.; Bioorganic & Medicinal Chemistry Letters, (1992), 2(11), 1391-4; Design, Synthesis and Biological Evaluation of Selective Boron-containing Thrombin Inhibitors. Weinand, A.; Ehrhardt, C.; Metternich, R.; Tapparelli, C.; Bioorganic and Medicinal Chemistry, (1999), 7, 1295-1307), acetylcholinesterase inhibition (New, specific and reversible bifunctional alkylborinic acid inhibitor of acetylcholinesterase. Koehler, K. A.; Hess, G. P.; Biochemistry (1974), 13, 5345-50) and as antibacterial agents (Boron-Containing Antibacterial Agents: Effects on Growth and Morphology of Bacteria Under Various Culture Conditions. Bailey, P. J.; Cousins, G.; Snow, G. A.; and White, A. J.; Antimicrobial Agents and Chemotherapy, (1980), 17, 549-553). The boron containing compounds with antibacterial activity can be sub-divided into two main classes, the diazaborinines, which have been known since the 1960's, and dithienylborinic acid complexes. This latter class has been expanded to include many different diarylborinic acid complexes with potent antibacterial activity (Preparation of diarylborinic acid esters as DNA methyl transferase inhibitors. Benkovic, S. J.; Shapiro, L.; Baker, S. J.; Wahnon, D. C.; Wall, M.; Shier, V. K.; Scott, C. P.; Baboval, J.; PCT Int. Appl. (2002), WO 2002044184).

The co-composition or cargo composition can also have one or more isotopes. Such isotopes can be useful, for example, as a therapeutic agent, as a detectable agent, or both. Examples of useful isopes include Lutetium-177 ($^{177}$Lu), Rhenium-188 ($^{188}$Re), Gallium-68 ($^{68}$Ga), Yttrium-90 ($^{90}$Y), Technetium-99m ($^{99m}$Tc), Holmium-166 ($^{166}$Ho), Iodine-131 ($^{131}$I), Indium-111 ($^{111}$In), Flourine-18 Carbon-11 ($^{11}$C), Nitrogen-13 CND, Oxygen-15 ($^{15}$O), Bromine-75 ($^{75}$Br), Bromine-76 ($^{76}$Br), Iodine-124 ($^{124}$I), Thalium-201 ($^{201}$Tl), Technetium-99 ($^{99}$Tc), and Iodine-123 ($^{123}$I).

The co-composition or cargo composition can also comprise a detectable agent. A variety of detectable agents are useful in the disclosed methods. As used herein, the term "detectable agent" refers to any molecule which can be detected. Useful detectable agents include moieties that can be administered in vivo and subsequently detected. Detectable agents useful in the disclosed compositions and imaging methods include yet are not limited to radiolabels and fluorescent molecules. The detectable agent can be, for example, any moiety that facilitates detection, either directly or indirectly, preferably by a non-invasive and/or in vivo visualization technique. For example, a detectable agent can be detectable by any known imaging techniques, including, for example, a radiological technique. Detectable agents can include, for example, a contrast agent. The contrast agent can be, for example, Feridex. In some embodiments, for instance, the detectable agent comprises a tantalum compound. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, e.g., a non-radioactive isotope. For example, iron oxide and Gd can be used as a non-radioactive detectable agent in certain embodiments. Detectable agents can also include radioactive isotopes, enzymes, fluorophores, and quantum dots (Qdot®). For example, the detection moiety can be an enzyme, biotin, metal, or epitope tag. Other known or newly discovered detectable markers are contemplated for use with the provided compositions. In some embodiments, for instance, the detectable agent comprises a barium compound, e.g., barium sulfate.

The detectable agent can be (or the co-composition or cargo composition can include) one or more imaging agents. Examples of imaging agents include radiologic contrast agent, such as diatrizoic acid sodium salt dihydrate, iodine, and barium sulfate, a fluorescing imaging agent, such as Lissamine Rhodamine PE, a fluorescent or non-fluorescent stain or dye, for example, that can impart a visible color or that reflects a characteristic spectrum of electromagnetic radiation at visible or other wavelengths, for example, infrared or ultraviolet, such as Rhodamine, a radioisotope, a positron-emitting isotope, such as $^{18}$F or $^{124}$I (although the short half-life of a positron-emitting isotope may impose some limitations), a metal, a ferromagnetic compound, a paramagnetic compound, such as gadolinium, a superparamagnetic compound, such as iron oxide, and a diamagnetic compound, such as barium sulfate Imaging agents can be selected to optimize the usefulness of an image produced by a chosen imaging technology. For example, the imaging agent can be selected to enhance the contrast between a feature of interest, such as a gastrointestinal polyp, and normal gastrointestinal tissue. Imaging can be accomplished using any suitable imaging techniques such as X-Ray, computed tomography (CT), MRI, Positron Emission Tomography (PET) or SPECT. In some forms, the co-composition or cargo composition can be coupled to a nuclear medicine imaging agent such as Indium-III or Technetium-99, to PET imaging agents, or to MRI imaging agents such as nanoparticles.

Examples of imaging techniques include magnetic resonance imaging (MRI), computerized tomography (CT), single photon emission computerized tomography (SPECT), and positron emission tomography (PET) Imaging agents generally can be classified as either being diagnostic or therapeutic in their application. Because of radiation's damaging effect on tissues, it is useful to target the biodistribution of radiopharmaceuticals as accurately as possible. PET can use imaging agents labeled with, for example, the positron-emitters such as $^{18}$F, $^{11}$C, $^{13}$N and $^{15}$O, $^{75}$Br, $^{76}$Br and $^{124}$I. SPECT can use imaging agents labeled with, for example, the single-photon-emitters such as $^{201}$Tl, $^{99}$Tc, $^{123}$I, and $^{131}$I.

Glucose-based and amino acid-based compounds can be used as imaging agents. Amino acid-based compounds are more useful in analyzing tumor cells, due to their faster uptake and incorporation into protein synthesis. Of the amino acid-based compounds, $^{11}$C- and $^{18}$F-containing compounds have been used with success. $^{11}$C-containing radiolabeled amino acids suitable for imaging include, for example, L-[1-$^{11}$C]leucine (Keen et al. J. Cereb. Blood Flow Metab. 1989 (9):429-45), L-[1-$^{11}$C]tyrosine (Wiesel et al. J. Nucl. Med. 1991 (32):2041-49), L[methyl-$^{11}$C]methionine (Comar et al. Eur. J. Nucl. Med. 1976 (1):11-14) and L-[1-$^{11}$C]methionine (Bolster et al. Appl. Radiat. Isot. 1986 (37):1069-70).

PET involves the detection of gamma rays in the form of annihilation photons from short-lived positron emitting radioactive isotopes including, but not limited to, $^{18}$F with a half-life of approximately 110 minutes, $^{11}$C with a half-life of approximately 20 minutes, $^{13}$N with a half-life of approximately 10 minutes and $^{15}$O with a half-life of approximately 2 minutes, using the coincidence method. For PET imaging studies, compounds such as [$^{11}$C]meta-hydroxyephedrine (HED) and 2-[$^{18}$F]fluoro-2-deoxy-D-glucose (FDG) can be used. SPECT can use longer-lived isotopes including, but not limited to, $^{99m}$Tc with a half-life of approximately 6 hours and $^{201}$Tl with a half-life of approximately 74 hours. Radio-iodinated meta-iodobenzylguanidine (MIBG) is a radiotracing agent that can be used in nuclear medicine imaging studies.

The disclosed CendR compositions and co-compositions and cargo compositions can be administered in vivo in a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, or cells).

The CendR compositions and co-compositions and cargo compositions can be used therapeutically in combination with a pharmaceutically acceptable carrier. Suitable carriers and their formulations are described in Remington: The Science and Practice of Pharmacy (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

The preparation can be administered to a subject or organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to a subject or organism.

Herein the term "active ingredient" refers to the preparation accountable for the biological effect.

As used herein, the phrases "physiologically acceptable carrier" and "pharmaceutically acceptable carrier" which can be interchangeably used refer to a carrier or a diluent that does not cause significant irritation to a subject or organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in Remington's Pharmaceutical Sciences, Mack Publishing Co., Easton, Pa., latest edition, which is incorporated herein by reference.

Any suitable route of administration can be used for the disclosed compositions. Suitable routes of administration can, for example, include topical, enteral, local, systemic, or parenteral. For example, administration can be epicutaneous, inhalational, enema, conjunctival, eye drops, ear drops, alveolar, nasal, intranasal, vaginal, intravaginal, transvaginal, enteral, oral, intraoral, transoral, intestinal, rectal, intrarectal, transrectal, injection, infusion, intravenous, intraarterial, intramuscular, intracerebral, intraventricular, intracerebroventricular, intracardiac, subcutaneous, intraosseous, intradermal, intrathecal, intraperitoneal, intravesical, intracavernosal, intramedullar, intraocular, intracranial, transdermal, transmucosal, transnasal, inhalational, intracisternal, epidural, piridrol, intravitreal, etc. The disclosed compositions can be used in and with any other procedure. For example, the disclosed compositions can be administered as part of HIPEC therapy. In HIPEC a heated sterile solution containing a composition of interest is continuously circulated throughout the peritoneal cavity.

Pharmaceutical compositions can be manufactured by processes well known in the art, e.g., by means of conventional mixing, dissolving, granulating, dragee-making, levigating, emulsifying, encapsulating, entrapping or lyophilizing processes.

Pharmaceutical compositions for use in the disclosed methods thus can be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients can be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents can be added, such as cross-linked polyvinyl pyrrolidone, agar, or alginic acid or a salt thereof such as sodium alginate.

Dragee cores are provided with suitable coatings. For this purpose, concentrated sugar solutions can be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments can be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules can contain the active ingredients in admixture with filler such as lactose, binders such as starches, lubricants such as talc or magnesium stearate and, optionally, stabilizers. In soft capsules, the active ingredients can be dissolved or suspended in suitable liquids, such as fatty oils, liquid paraffin, or liquid polyethylene glycols. In addition, stabilizers can be added. All formulations for oral administration should be in dosages suitable for the chosen route of administration.

For buccal administration, the compositions can take the form of tablets or lozenges formulated in conventional manner.

For administration by nasal inhalation, the active ingredients for use in the disclosed methods can be conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit can be determined by providing a valve to deliver a metered amount. Capsules and cartridges of, e.g., gelatin for use in a dispenser can be formulated containing a powder mix of the compound and a suitable powder base such as lactose or starch.

The preparations described herein can be formulated for parenteral administration, e.g., by bolus injection or continuous infusion. Formulations for injection can be presented in unit dosage form, e.g., in ampoules or in multidose containers with optionally, an added preservative. The compositions can be suspensions, solutions or emulsions in oily or aqueous vehicles, and can contain formulatory agents such as suspending, stabilizing and/or dispersing agents.

Pharmaceutical compositions for parenteral administration include aqueous solutions of the active preparation in water-soluble form. Additionally, suspensions of the active ingredients can be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions can contain substances, which increase the viscosity of the suspension, such as sodium carboxymethyl cellulose, sorbitol or dextran. Optionally, the suspension can also contain suitable stabilizers or agents which increase the solubility of the active ingredients to allow for the preparation of highly concentrated solutions.

Alternatively, the active ingredient can be in powder form for constitution with a suitable vehicle, e.g., sterile, pyrogen-free water based solution, before use.

The preparations can also be formulated in rectal compositions such as suppositories or retention enemas, using, e.g., conventional suppository bases such as cocoa butter or other glycerides.

The disclosed compositions can be provided in any suitable formulation. For example, solid, liquid, solution, gel, patch, slow release, timed release, etc.

Pharmaceutical compositions for use in the disclosed methods include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any preparation used in the disclosed methods, the therapeutically effective amount or dose can be estimated initially from in vitro and cell culture assays. For example, a dose can be formulated in animal models to achieve a desired circulating antibody concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl et al in The Pharmacological Basis of Therapeutics, Ch. 1 p. 1. (1975)).

Dosage amount and interval can be adjusted individually to provide plasma of antibodies which are sufficient to prevent or reduce viral entry (minimal effective concentration, MEC). The MEC will vary for each preparation, but can be estimated from in vitro data. Dosages necessary to achieve the MEC will depend on individual characteristics and route of administration. Binding assays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Fatty acids (i.e., lipids) that can be conjugated to the disclosed CendR compositions and co-compositions and cargo compositions include those that allow the efficient incorporation of the peptide into liposomes. Generally, the fatty acid is a polar lipid. Thus, the fatty acid can be a phospholipid. The provided compositions can comprise either natural or synthetic phospholipid. The phospholipids can be selected from phospholipids containing saturated or unsaturated mono or disubstituted fatty acids and combinations thereof. These phospholipids can be, for example, dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Alabaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the provided compositions can comprise palmitoyl 16:0.

The co-composition or cargo composition can be a microparticle or a nanoparticle, such as a nanosphere, nanoshell, nanoworm, heat generating nanoshell, and the like. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Nanoshells can be formed with, for example, a core of a dielectric or inert material such as silicon, coated with a material such as a highly conductive metal which can be excited using radiation such as near infrared light (approximately 800 to 1300 nm). Upon excitation, the nanoshells emit heat. The resulting hyperthermia can kill the surrounding cell(s) or tissue. The combined diameter of the shell and core of the nanoshells ranges from the tens to the hundreds of nanometers. Near infrared light is advantageous for its ability to penetrate tissue. Other types of radiation can also be used, depending on the selection of the nanoparticle coating and targeted cells. Examples include x-rays, magnetic fields, electric fields, and ultrasound. The particles can also be used to enhance imaging, especially using infrared diffuse photon imaging methods. Targeting molecules can be antibodies or fragments thereof, ligands for specific receptors, or other proteins specifically binding to the surface of the cells to be targeted.

The other molecules, elements, moieties, etc. can be covalently linked to or non-covalently associated with, for example, the disclosed co-compositions, cargo compositions, CendR composition, protein, peptide, amino acid sequence, or CendR element. Such molecules, elements, moieties, etc. can be linked, for example, to the amino terminal end of the disclosed protein, peptide, amino acid sequence, or CendR element; to an internal amino acid of the disclosed protein, peptide, amino acid sequence, or CendR element; to the carboxy terminal end of the disclosed protein, peptide, amino acid sequence, or CendR element; to the protein, peptide, amino acid sequence on the N terminal side of the CendR element; via a linker to the disclosed protein, peptide, amino acid sequence, or CendR element; or a combination. The disclosed CendR compositions can further comprise a linker connecting such molecules, elements, moieties, etc. and disclosed CendR composition, protein, peptide, amino acid sequence, or CendR element. The disclosed CendR composition, protein, peptide, amino acid sequence, or CendR element can also be conjugated to a coating molecule such as bovine serum albumin (BSA; see Tkachenko et al., (2003) J Am Chem Soc, 125, 4700-4701) that can be used to coat nanoparticles, nanoworms, nanoshells, and the like with the protein, peptide, amino acid sequence, or CendR element.

Protein crosslinkers that can be used to crosslink other molecules, elements, moieties, etc. to the disclosed co-compositions, cargo compositions, CendR composition, protein, peptide, amino acid sequence, etc. are known in the art and are defined based on utility and structure and include DSS (Disuccinimidylsuberate), DSP (Dithiobis(succinimidylpropionate)), DTS SP (3,3'-Dithiobis (sulfosuccinimidylpropionate)), SULFO BSOCOES (Bis[2-(sulfosuccinimdooxycarbonyloxy) ethyl]sulfone), BS OCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di[3'-(2'-pyridyldithio) propionamido]butane), BSSS (Bis(sulfosuccinimdyl) suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl) aminobenzoate), SULFO SIAB (N-Sulfosuccinimidyl(4-iodoacetyl)aminobenzoate), SMCC (Succinimidyl-4-(N-maleimidomethyl) cyclohexane-1-carboxylate), SULFO SMCC (Sulfosuccinimidyl-4-(N-maleimidomethyl) cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio) propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl) cyclohexane-1-carboxylic acid hydrazide hydrochloride), MBH (m-Maleimidobenzoic acid hydrazidehydrochloride), SULFO EMCS (N-(epsilon-Maleimidocaproyloxy) sulfosuccinimide), EMCS (N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent; Methyl-p-hydroxybenzimidate hydrochloride, 98%), DMA (Dimethyladipimidate hydrochloride).

Components of co-compositions or cargo composition can also be coupled using, for example, maleimide coupling. By way of illustration, components can be coupled to lipids by coupling to, for example, 1,2-distearoyl-sn-glycero-3-phosphoethanolamine-N-[maleimide(polyethylene glycol)$_{2000}$; DSPE-PEG$_{2000}$-maleimide] (Avanti Polar Lipids) by making use of a free cysteine sulfhydryl group on the component. The reaction can be performed, for example, in aqueous solution at room temperature for 4 hours. This coupling chemistry can be used to couple components of co-compositions and cargo compositions.

The disclosed compounds, components, and compositions can also be coupled using, for example, amino group-functionalized dextran chemistry. Particles, such as, for example, nanoparticles, nanoworms, and micelles, can be coated with amino group functionalized dextran. Attachment of PEG to aminated particles increases the circulation time, presumably by reducing the binding of plasma proteins involved in opsonization (Moghimi et al., 2001). The particles can have surface modifications, for example, for reticuloendothelial system avoidance (PEG) and homing (homing molecules), endosome escape (pH-sensitive peptide; for example, Pirello et al., 2007), a detectable agent, a therapeutic compound, or a combination. To accommodate all these functions on one particle, optimization studies can be conducted to determine what proportion of the available linking sites at the surface of the particles any one of these elements should occupy to give the best combination of targeting and payload delivery. The cell internalization and/or tissue penetration of such co-compositions and cargo compositions can be mediated by the disclosed CendR elements, amino acid sequences, peptides, proteins, molecules, conjugates, and compositions.

The CendR elements, amino acid sequences, peptides, proteins, molecules, conjugates, and compositions themselves can be coupled to other components as disclosed herein using any known technique or the techniques described herein (although generally not, as described elsewhere herein, to the disclosed co-compositions). The disclosed CendR elements can be used in cyclic peptides. To allow such cyclic peptides to be coupled to other components, selective side group protection can be used to synthesize cyclic peptides with an extra cysteine that presents a free sulfhydryl group. These peptides are stable with no detectable scrambling of the disulfide bond. A maleimide function can also be used as a coupling group. These chemistries can be used to couple CendR elements, amino acid sequences, peptides, proteins, molecules, conjugates, and compositions to each other and to other components.

CendR elements, amino acid sequences, peptides and proteins can also be coupled to other components using, for example, maleimide coupling. By way of illustration, CendR elements, amino acid sequences, peptides and proteins can be coupled to lipids by coupling to, for example, 1,2-distearoyl-sn-glycero-3-phosphoethanolamine-N-[maleimide(polyethylene glycol)$_{2000}$; DSPE-PEG$_{2000}$-maleimide] (Avanti Polar Lipids) by making use of a free cysteine sulfhydryl group on the CendR elements, amino acid sequence, peptide or protein. The reaction can be performed, for example, in aqueous solution at room temperature for 4 hours. This coupling chemistry can be used to couple the disclosed CendR elements, amino acid sequences, peptides and proteins to many other components, molecules and compositions.

By "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, "subject" includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. In particular, pets and livestock can be a subject. The subject can be an invertebrate, such as a worm or an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. In the context of endometriosis and endometriosis cells, it is understood that a subject is a subject that has or can have endometriosis and/or endometriosis cells.

Tumor-penetrating CendR peptides can be used to augment tumor imaging and tumor treatment with anti-cancer drugs. The effect of CendR peptides on imaging can be tested. For example, optical imaging with, for example, near infrared fluorphores using a Kodak IN VIVO Fx imager and Li-Cor Odyssey imager (e.g. Simberg et al., 2007; Sugahara et al., 2009), and MRI imaging can be used. For MRI imaging, the co-composition or cargo composition can be an MRI contrast agent such as Feridex iron oxide nanoparticles and gadolinium compounds. These compounds will be injected into tumor-bearing mice with and without a tumor-homing CendR peptide or a combination of peptides, followed by imaging. The results can be use to determine effectiveness of treatments and to assess different treatment protocols for using CendR peptides with therapeutics as the co-composition or cargo composition.

Combinations of different CendR peptides and different co-compositions and/or cargo compositions can be tested for optimal accumulation and distribution of the co-composition or cargo composition in the target cells and tissue by, for example, varying the dose of the drug and using the dose of the peptide that gives the maximal effect. The disclosed results show that CendR-drug combinations can reduce the amount of drug needed and therefore, the side effects, while producing the same anti-tumor effect. CendR peptides can also produce effects not achievable by using the co-composition or cargo composition alone. For example, use of CendR peptides can allow higher concentrations of the co-composition or cargo composition in cells and tissues that is otherwise possible. In such cases, the effectiveness of the co-composition or cargo composition can be beyond that obtainable with conventional therapy.

U.S. patent application Ser. No. 12/355,672, filed Jan. 19, 2009, and Ser. No. 12/390,061, filed Feb. 20, 2009, are hereby incorporated by reference in their entirety and specifically for their disclosure of iRGD peptides and CendR elements, peptides and conjugates.

EXAMPLES

The following example is put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Figure 2:
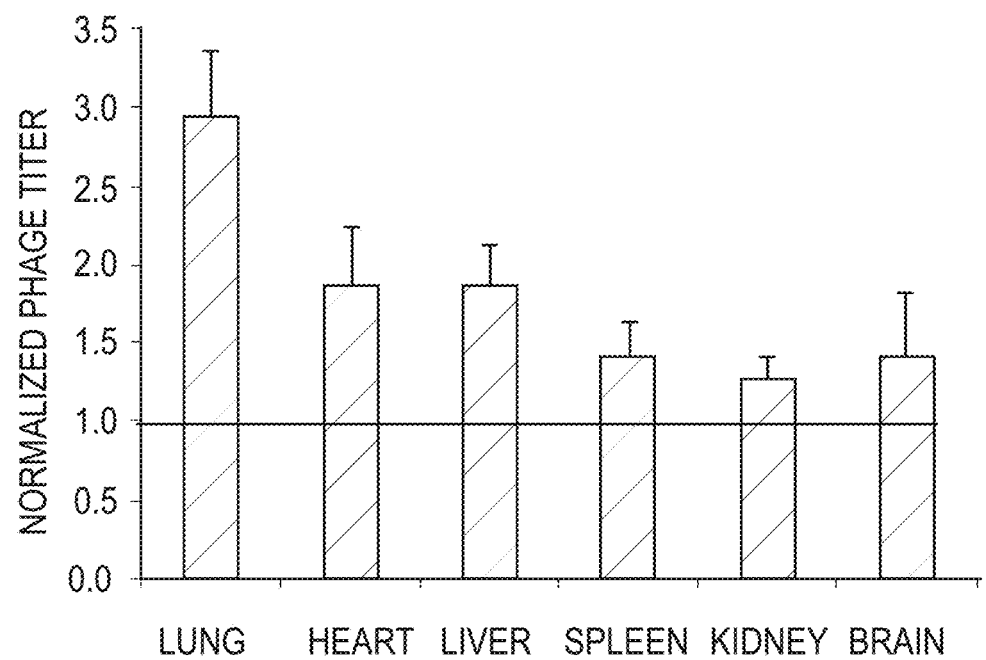
FIG. 2 shows a graph of phage titer in various tissues following injection of peptide RPARPAR (SEQ ID NO:2). Systemic oligomeric RPARPAR (SEQ ID NO:2) increases leakiness of blood vessels to circulating untargeted tracer phage. Mice were intravenously injected with 150 µl of PBS containing 1010 pfu of a control phage and 8 µM RPARPAR (SEQ ID NO:2) (or control) peptide oligomerized using neutravidin scaffold. After 30 min of circulation, mice were perfused, and the number of phage retained in tissues was determined. The values on y-axis represent RPARPAR (SEQ ID NO:2)/control ratio. Statistical analysis was performed by Student's t-test, n=4; error bars indicate s.e.m.; double asterisk, $p<0.01$, triple asterisk, $p<0.001$. Scale bars: 20 µ.m (B,C) and 50 µm (F).

A. Example 1: Cell Internalization and Tissue Penetration of Co-Composition Mediated by CendR Peptide To demonstrate the ability of systemically administered CendR peptides to cause vascular leakage (and thus enhance cell internalization and tissue penetration of a co-composition), oligomeric RPARPAR-neutravidin complexes (SEQ ID NO:2) were intravenously injected and tissue distribution of co-injected tracer phage was determined. In this assay, the blood is removed by perfusion, and the extravasated blood constituents, including the tracer phage, remain in tissues. Oligomeric RPARPAR (SEQ ID NO:2), but not oligomeric control peptide, caused increased retention of the phage in lungs and other organs, in line with increased extravasation of the phage particles (FIG. 2). These data show that RPARPAR peptides are able to promote tissue penetration of both attached payloads and to permeabilize tissues to allow entry of macromolecules, such as co-compositions administered or present.

Figure 3:
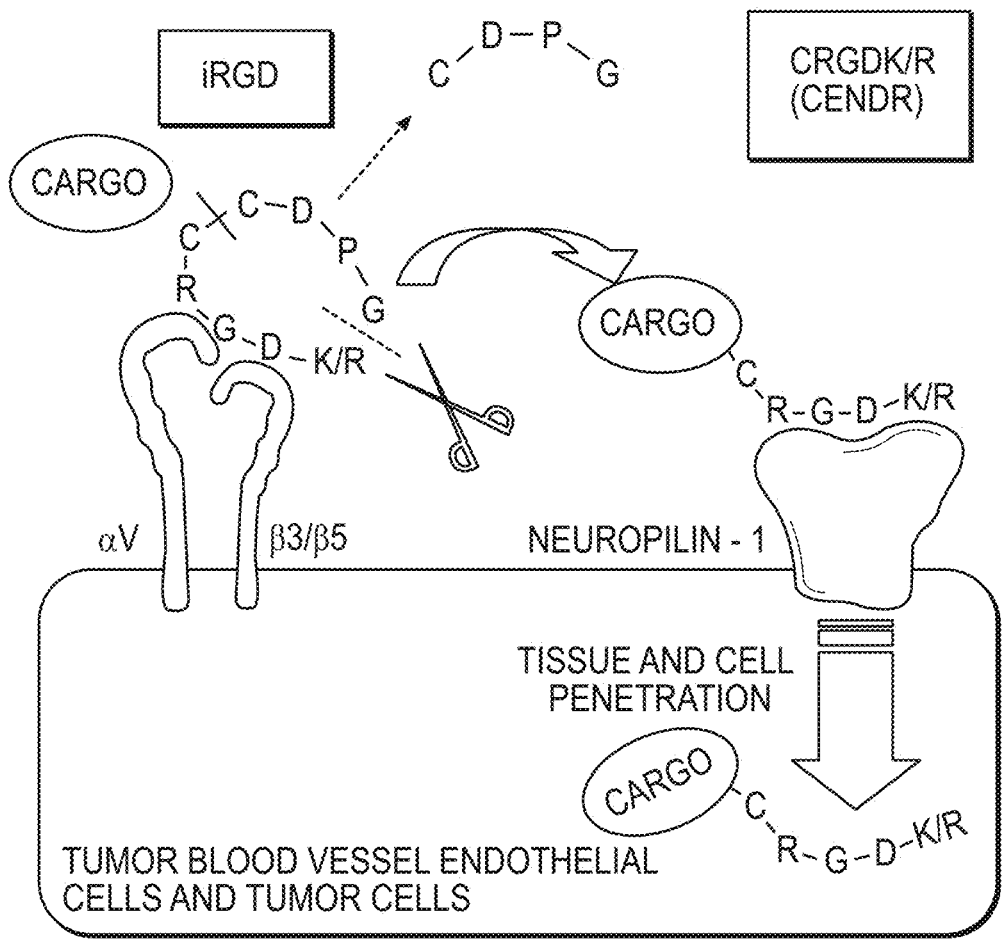
FIG. 3 shows a diagram of an example of a multi-step binding and penetration mechanism of iRGD. Sequences are SEQ ID NO:1 and SEQ ID NO:37.

B. Example 2: Tumor Penetration and Permeabilization Using Homing CendR Peptides FIG. 3 depicts the principle of the CendR system as it applies to a tumor-homing RGD peptide dubbed iRGD (sequence: CRGDK/RGPD/EC; SEQ ID NO:61). The two motifs in iRGD are the RGD motif (Ruoslahti, 2002), which mediates the binding of the peptide to αv integrins on tumor endothelium and a cryptic CendR sequence RGDK (or RGDR; SEQ ID NO:229). The RGD homing sequence directs the peptide to tumor endothelium (angiogenic vasculature expresses αv integrins), where the peptide is proteolytically processed by an endogenous protease, such that the CendR motif becomes C-terminal and active. The activated CendR motif then binds to a different receptor (neuropilin-1; Teesalu et al., 2009; U.S. patent Ser. No. 12/355, 672, filed Jan. 19, 2009), which mediates extravasation, tumor penetration, and cell entry of the C-terminally truncated peptide (and any payload attached to it). Each of these steps has been documented in biochemical experiments, which include isolation of the expected N-terminal fragment of iRGD from inside the cells (Sugahara et al., 2009; U.S. patent application Ser. No. 12/390,061, filed Feb. 20, 2009). The multi-step homing and tissue penetration process makes CendR more specific than peptides and other probes that rely on receptor binding only. Neuropilin-1 is widely expressed in various kinds of cells, but tumors often express this protein at higher levels than normal tissues.

The remarkable tumor-penetrating properties of iRGD are illustrated in FIG. 4, which compares iRGD with two RGD peptides that bind to αv integrins with affinities similar to that of iRGD (Sugahara et al., 2009), but lack a CendR motif.

The CendR motif is present at the C-terminus of some proteins. One of the alternative forms of vascular endothelial growth factor, VEGF-165, binds to NRP-1 using its C-terminal CendR-like sequence encoded by exon 8 (CRCDKPRR; SEQ ID NO:95). Several peptides such as A7R (ATWLPPR; SEQ ID NO:96), the immunomodulatory peptide tuftsin (TKPR; SEQ ID NO:97) and its variant enhanced tuftsin (TKPPR; SEQ ID NO:98) also bind to the same site on the NRP-1 (Geretti et al., 2008). Semaphorin 3A, which also contains a C-terminal CendR motif and binds to this site, enhances vascular permeability (Acevedo et al., 2008). Some tumor-penetrating peptides reproduce the vascular permeability effect of these compounds. The effect can be tumor specific because it requires accumulation at target cell surface and proteolytic activation.

Homeodomain transcription factors such as Antennapedia, the herpes simplex virus-1 protein VP22, and the human immunodeficiency virus-1 transactivator TAT protein are known to internalize into cells. Short cationic cell-penetrating peptides derived from these proteins retain their ability to internalize. However, these peptides are different from the disclosed CendR peptides in that they are independent of the chirality of the amino acids in the peptide, require cell surface heparan sulfate for activity (which our peptides do not), and have not been assigned tissue-penetrating activity (Langel, 2007).

Figure 7:
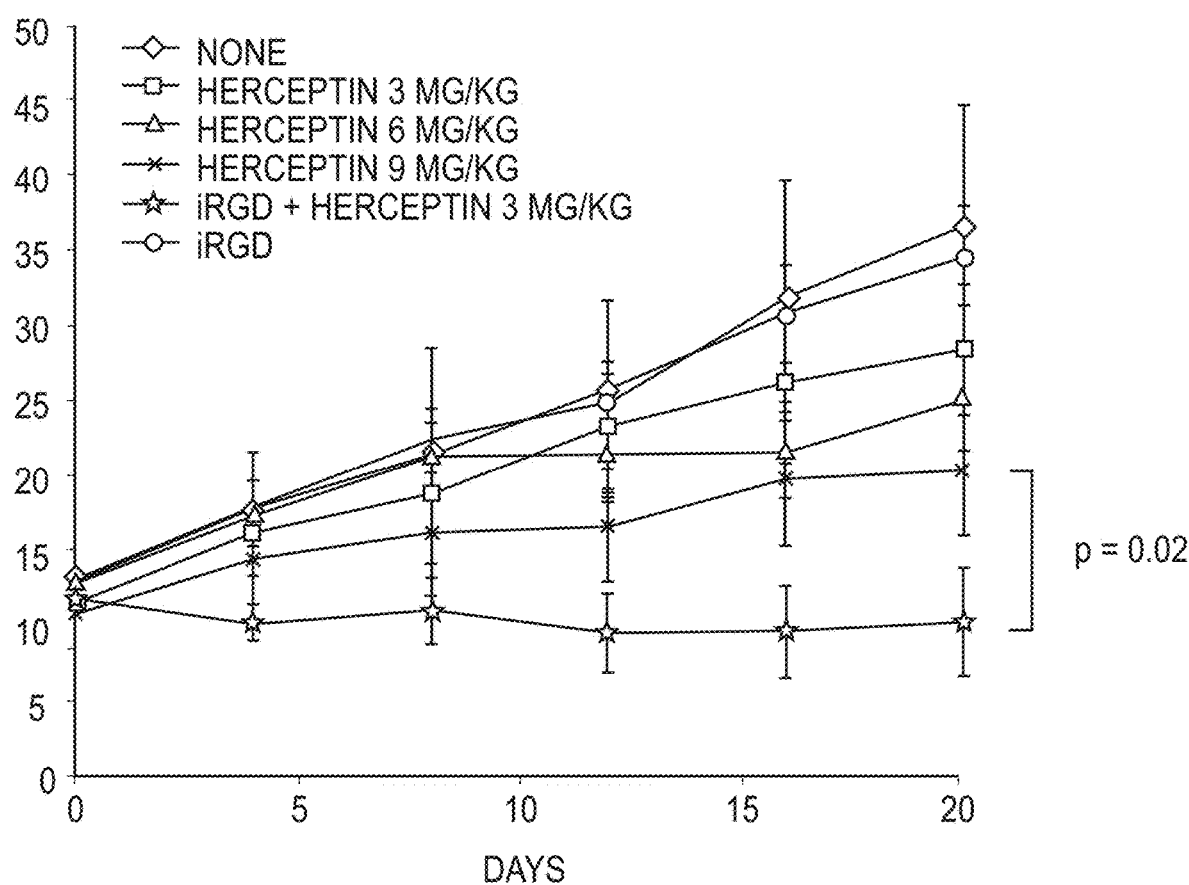
FIG. 7 is a graph of tumor volume (in mm³) versus time (in days) after injection of different compositions and shows enhanced anti-tumor effect in mice treated with a combination of Herceptin and iRGD peptide. Mice bearing orthotopic xenografts of human breast cancer with elevated HER2 expression (BT474) were treated with weekly injections of Herceptin at 3 mg/kg (first injection at day 21 after tumor cell inoculation=day 0 in the graph) or 1.5 mg/kg (subsequent injections) in combination with daily injections of 4 mg/kg iRGD or PBS as indicated in the figure.
Figure 8:
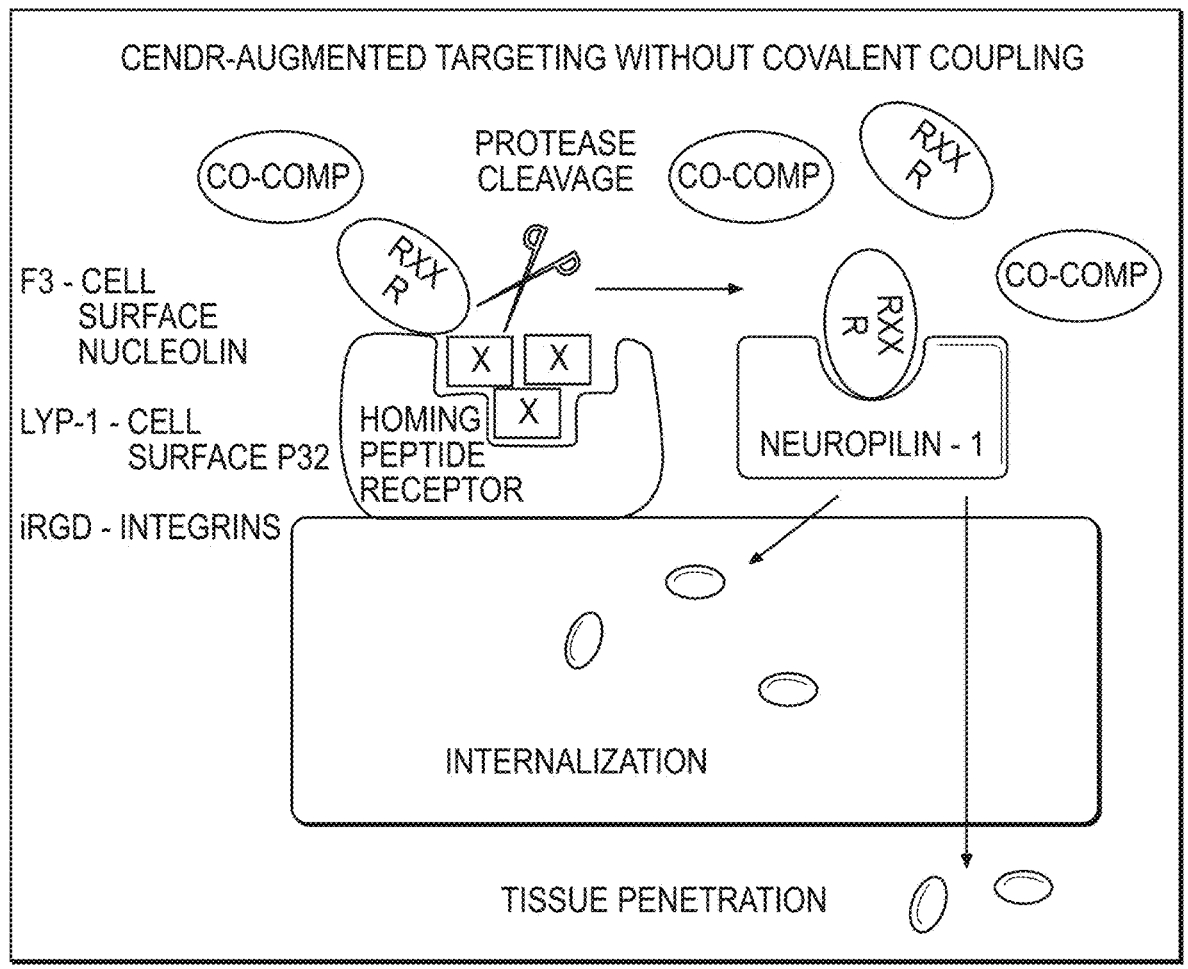
FIG. 8 shows a diagram of CendR-augmentation of targeting, internalization, and tissue penetration of un-coupled co-compositions. Three example homing peptides are listed, but CendR elements can be used without targeting or homing and can be used with any other targeting or homing molecules, agents, peptides, or sequences.

Cryptic CendR sequences in tumor-homing peptides from phage screens. In addition to iRGD, a number of other homing peptides contain CendR elements. These peptides include LyP-1 (CGNKRTRGC; SEQ ID NO:99) containing the KRTR sequence (SEQ ID NO:100; Laakkonen et al., 2002, 2004) and CRGRRST with RGRR (SEQ ID NOs:101 and 102; Joyce et al., 2003). Like in iRGD, the CendR motif of these peptides is not C-terminal. It has been discovered that proteolytic processing is needed to activate the CendR motifs. Indeed, treatment of iRGD phage or LyP-1 phage with trypsin enhanced the binding of the phage to neuropilin-1 on PPC1 cells. Trypsin had no effect on the non-CendR peptides CRGDC (SEQ ID NO:36) and RGD-4C. Lyp-1 homes to hypoxic/low nutrient areas in tumors that are far from blood vessels and delivers nanoparticle sized payloads to these locations (Laakkonen et al., 2002; 2004; Karmali et al., 2009). Thus, LyP-1 is a tumor-penetrating CendR peptide.

iRGD enhances vascular permeability in tumors. It has been discovered that the tumor-penetrating properties of iRGD include an ability to increase vascular permeability in tumors. Tumor-bearing mice were injected with Evans Blue, an albumin-binding dye commonly used in vascular permeability studies, followed by an injection of iRGD peptide. As shown in FIG. 5, iRGD caused more leakage of the dye into the tumor than the control peptide, the leakage was specific for tumor tissue, and it was not elicited by RGD peptides that do not contain a CendR motif. Four tumor types have been tested, including tumor metastases, in multiple experiments with consistent results. The involvement of the CendR system in the vascular leakage was demonstrated by experiments, in which the RGD effect on vascular permeability was blocked by using an inhibitory antibody against NRP-1.

iRGD enhances iron oxide nanoparticle entry into tumors. Nanoparticle entry into tumors was tested by injecting tumor mice with a clinically used MRI contrast agent, Feridex, which is a paramagnetic, dextran-coated iron oxide nanoparticle with a diameter approximately 150 nm. Combining Feridex with iRGD resulted in stronger MRI contrast in the tumors than Feridex alone.

iRGD induces tissue penetration. The rapid penetration of iRGD and LyP-1 into tumor tissue distant from blood vessels (Laakkonen et al., 2004; Sugahara et al., 2009) indicated that iRGD, in addition to promoting extravasation, could increase transport through parenchymal tumor tissue. To demonstrate this, the effect of circulation was eliminated by incubating freshly excised tumors in culture media containing phage. The iRGD phage rapidly penetrated into the tumor tissue, traveling about 4 mm in 90 min whereas control phage was found only at the tumor surface in trace amounts (FIG. 6). Thus, CendR peptides induce tissue penetration and the penetration is dependent on an active transport process. This process can be referred to as CendR-Induced Transendothelium & tissue (CendIT) effect.

iRGD increases tumor accumulation and anti-cancer activity of Herceptin. It has also been demonstrated that iRGD enhances drug delivery in tumors. Herceptin was used as the co-composition drug. Herceptin is an antibody against the HER2 receptor that is in wide clinical use as an anticancer agent. Administration of both iRGD and Herceptin was significantly more effective in suppressing tumor growth than an equivalent dose of Herceptin alone (FIG. 7).

These results demonstrate a conceptually new approach to tumor treatment: tumor-specific enhancement of drug penetration into tumor tissue. Tumor blood vessels tend to be leaky, which allows extravasation of materials into the tissue surrounding tumor vessels (so called enhanced permeability and retention—EPR—effect). The effect of CendR peptides, which can be referred to as CendIT, is clearly much more effective than the EPR effect (for example, see FIG. 4). Also, because CendIT is an active process, not leakage, and because it is receptor (NRP-1)-dependent, it results in deep tumor penetration, which passive diffusion and convection in the absence of circulation cannot accomplish (FIG. 6).

1. Discussion

The studies reveal a previously unrecognized cellular internalization pathway, termed CendR. Salient features of CendR are: (i) R/KXXR/K (SEQ ID NO:23) recognition motif, (ii) C-terminal exposure of the motif for binding and internalizing activity, (iii) NRP-1 involvement in the binding and internalization, and (iv) conversion of cryptic CendR motifs into active ones through proteolytic processing.

A group of heart-homing peptides contain an exposed CendR motif (Zhang, L. et al. 2005) but the CendR motif can also be cryptic. Several tumor-homing peptides with cell-penetrating properties contain cryptic CendR motifs (Laakkonen, P., et al. 2002b; Porkka, K. et al., 2002; Jarvinen, T. A. et al. 2007; Zhang, L. et al. 2006). In addition to the CendR motif, these peptides possess a sequence that binds to a specific receptor. An integrin-binding iRGD peptide described in Sugahara et al., 2009 and U.S. patent application Ser. No. 12/390,061, filed Feb. 20, 2009, provides an explanation of how such peptides work; the specific homing element concentrates the peptide at the target (tumor), a protease exposes the CendR motif and subsequent NRP-1 binding causes cellular uptake of the peptide (and its payload, if any).

Many of cationic CPP contain active or cryptic CendR elements (Langel, 2007). The basic domain of HIV-1 TAT protein with a CendR motif inhibits VEGFA-165 binding to NRP-1 (Jia, H. et al. 2001), but the mechanism of binding and uptake of cationic CPP is still not clear. The most important difference between cationic CPP and CendR peptides is that CCP composed of D-amino acids are active (Polyakov, V. et al. 2000, Gammon, S. T. et al. 2003), whereas the results herein show that CendR uptake is dependent on specific recognition of L-peptides only. Also, many of the CPP can internalize C-terminally anchored cargo, in clear contradiction to the core CendR concept. It is possible that CendR is one of several parallel pathways that could be involved in the uptake of cationic CPP.

The physiological significance of the CendR-mediated internalization system is not well understood, but CendR elements are present throughout the proteome, and many serine and cysteine proteases are capable of activating them (Barrett, Alan et al. 1998). Proprotein convertases and membrane proteases such as matriptase could be particularly relevant, as cleavage by these enzymes exposes an RXXR sequence at the C-terminus of various endogenous proteins (peptide hormones, growth factors, adhesion molecules, proteases; Thomas, G., 2002, Uhland, K. 2006). Enabling the NRP-1 co-receptor function, receptor activation, and cellular uptake of active proteins are possible functions of the physiological CendR sequences.

Viruses and other micro-organisms appear to have hijacked the CendR mechanism as a facilitator of infection. Proteolytic cleavage of viral coat proteins with concomitant exposure of CendR elements appears to be a recurring theme in the infectivity of many viral pathogens (Table 4).

TABLE 4

Examples of human pathogenic viruses with surface CendR elements

| Virus | Protein | Sequence [* - cleavage] | SEQ ID NO: | Reference |
|---|---|---|---|---|
| Human cytomegalovirus | Envelope glycoprotein B (UL55) | LNITHRTRR*STSDN | 1 | Vey, M. et al., 1995; SEQ ID NO: 230 |
| Measles virus | Fusion protein | SVASSRRHKR*FAGVV | 3 | Varsanyi, T. M., et al. 1985; SEQ ID NO: 231 |
| Tick-born encephalitis virus | PreM protein | KQEGSRTRR*SVLIP | 4 | Chambers, T. J., et al. 1990; SEQ ID NO: 232 |
| Respiratory syncytial virus | Fusion protein | PATNNRARR*ELPRF | 5 | Gonzalez-Reyes, L. et al. 2001; SEQ ID NO: 233 |
| Influenza A virus (H5N1) | Hemagglutinin | PQRERRRKKR*GLFGA | 6 | Steinhauer, D. A., 1999; SEQ ID NO: 234 |
| HIV-1 | Envelope precursor gp160 | RRVVQREKR*AVGIG | 7 | Moulard, M. et al. 2000; SEQ ID NO: 235 |
| Zaire ebolavirus | Virion spike glycoprotein precursor | LITGGRRTR*REAIV | 18 | Wool-Lewis, R. J. et al. 1999; SEQ ID NO: 236 |
| Mumps virus | Fusion protein | PSSGSRRHKR*FAGIA | 19 | Elango, N. et al. 1989; SEQ ID NO: 237 |
| Yellow fever virus | PreM protein | CDSAGRSRR*SRRAI | 24 | Ruiz-Linares, A. et al. 1989; SEQ ID NO: 238 |
| Human herpesvirus 4 | BALF4 (glycoprotein B) | AAVLRRRR*RDAGN | 25 | Johannsen, E. et al. 2004; SEQ ID NO: 239 |
| Human metapneumo-virus | Fusion glycoprotein precursor | QIENPRQSR*FVLGA | 26 | Biacchesi, S. et al., 2006; SEQ ID NO: 240 |
| Human T-lymphotropic virus-2 | Env propeptide | PPPATRRRR*AVPIA | 27 | Sjoberg, M. et al. 2006; SEQ ID NO: 241 |
| Crimean-congo hemorrhagic fever virus | Glycoprotein precursor | PSPTNRSKR*NLKME | 28 | Sanchez, A. J., et al. 2006; SEQ ID NO: 242 |

Cleavage of viral surface proteins by the ubiquitously expressed protease, furin, is an important contributing factor to the systemic spread of several viruses, whereas infectivity of viruses that are sensitive to proteases with a restricted expression pattern can limit infection to the tissues that express the appropriate protease. This concept is exemplified in influenza virus (Steinhauer, D. A. et al. 1999). Haemagglutinins of locally infective mammalian and avirulent avian-influenza viruses are cleaved at a single arginine residue; such cleavage is restricted to limited cell types, such as those of the respiratory and alimentary tracts. In contrast, virulent avian-influenza viruses that cause systemic infection are activated by furin to expose a polybasic CendR element. It is indicated herein that inhibiting CendR-mediated internalization and tissue penetration of pathogens and their products can provide a novel way of combating infectious diseases.

The CendR technology could have many other biotechnology applications, for example, improvements in the delivery of cell type-specific nanoparticle. Nanoparticles coated with pre-exposed CendR peptides would be taken up in the first vascular beds that the particles encounter (heart and lungs, after intravenous injection of RPARPAR (SEQ ID NO:2) phage). As shown by Sugahara et al. 2008, cryptic CendR sequences could be useful in delivering cargos to peripheral tissues. Blood plasma contains high concentrations of general (e.g. alpha-2-macroglobulin) and enzyme-specific (e.g. alpha-2 antiplasmin, antithrombin) protease inhibitors. This likely provides protection against premature CendR activation in the blood. Active proteases are typically confined to the immediate pericellular area. These proteases can activate cryptic CendR peptides on nanoparticles that have reached a target tissue through passive accumulation or by homing peptide-mediated delivery. Tissue-specific proteases capable of unmasking a cryptic CendR sequence can further enhance in vivo target selectivity. The cellular uptake mediated by the activated CendR element provides a mechanism for the processed peptide and its cargo to accumulate at the target tissue or cell. Another important conclusion from the studies is that CendR elements could promote the spreading of nanoparticles in tissues, and that selective CendR mediated internalization and tissue penetration can be achieved by combining docking-based and protease-sensitive CendR targeting elements. The iRGD peptide (Sugahara et al., 2009), and possibly other internalizing vascular homing peptides with cryptic CendR elements discussed above, illustrate this paradigm. It is also indicated that in analogy with the phage and other nanoparticles studied, various infectious agents could use the CendR system to facilitate their spreading through tissues.

2. Methods

Animal procedures. All the animal experimentation was performed using BALB/c nude mice (Harlan Sprague Dawley, Inc., Indianapolis, IN) according to procedures approved by the Animal Research Committee at University of California, Santa Barbara.

Phage display. For in vivo phage display, mice were injected intravenously with $10^{10}$ plaque-forming units (pfu) of T7 phage followed by perfusion of the circulatory system and determination of the bound phage in target organs by titration. For cell binding studies on cultured cells (in vitro display) and organ-derived cell suspensions (ex vivo display), the cells were incubated with $10^9$ pfu of phage at 4° C., washed, lysed, and quantified by titration. Incubation at 37° C. followed by low pH wash (glycine-HCl, pH 2.5) was used to assess the amount of internalized phage.

Labeling of qdots. Biotinylated peptides were used to functionalize the 605 ITK streptavidin qdots (Invitrogen, Carlsbad, CA) according to the manufacturer's instructions.

Immunofluorescence. Cultured cells and tissue sections were fixed with 4% buffered paraformaldehyde or cold (−20° C.) methanol followed by incubations with appropriate primary and Alexa-labelled secondary antibodies and nuclear staining with DAPI or Hoechst 342 DNA dyes.

Affinity chromatography. PPC-1 tumors were lysed in PBS containing 200 mM n-octyl-beta-D-glucopyranoside, followed by incubation with RPARPAR (SEQ ID NO:2)-coated Sulfolink-beads (Pierce, Rockford, IL) and elution in lysis buffer containing 2 mM free RPARPAR (SEQ ID NO:2) peptide. Gel fragments excised from silver stained gel of eluted fractions were subjected to MALDI-TOF mass spectrometry at the Burnham Institute for Medical Research Proteomics Resource.

Mice and tissues. All animal experimentation was performed according to procedures approved by the Animal Research Committee at the University of California, Santa Barbara. For tumor injections and before sacrificing, the mice were anesthetized with intraperitoneal injections of xylazine (10 mg/kg) and ketamine (50 mg/kg). BALB/c athymic nude mice (Harlan Sprague Dawley, Inc., Indianapolis, IN) were used for tumor xenografts and in vivo and ex vivo phage display experiments. Orthotopic prostate tumor xenografts were generated by injecting $10^6$ PPC-1 cells (Zhang, L. et al. 2006) into the ventral lobe of the prostate. For histological analysis, tissues were fixed in 4% paraformaldehyde, cryoprotected in phosphate buffered saline solution containing 30% sucrose, and sectioned at 10 µm.

Cell lines. PPC-1, PC-3, Du-145, 4T1, MIA PaCa-2, PDAC1.3, B 16F10, M21, and MDA-MB-435 cell lines were maintained in the Dulbecco's Modified Eagle Medium (DMEM) supplemented with 10% fetal bovine serum and penicillin/streptomycin. Human umbilical vein endothelial cells were cultured according to the manufacturer's instructions.

Phage display. T7-select phage display system was used for phage library construction (library diversity—$10^8$) and individual phage cloning according the manufacturer's instructions (EMD Biosciences, Gibbstown, NJ). Phage was purified by precipitation with PEG-8000 (Sigma, St. Louis, MO) followed by $CsCl_2$ gradient ultracentrifugation and dialysis. The sequences of displayed peptides were determined from the DNA encoding the insert-containing region at the C-terminus of the T7 major coat protein gp10.

For biopanning and phage binding studies (Hoffman, J. A. et al., 2004), cultured cells were grown to confluence and harvested with trypsin and mouse organs were dissociated using Medimachine (BD Biosciences, San Jose, CA). To measure phage binding, $10^6$ cells in binding buffer (DMEM containing 1% BSA) were incubated with $10^9$ pfu/ml of T7 phage for 1 hour at 4° C. The cells were washed 4 times with the binding buffer, lysed in LB bacterial growth medium containing 1% NP-40, and titrated. Phage internalization assays used the same procedure, except that the cells were incubated with the phage at 37° C., and that an acidic buffer (500 mM sodium chloride, 0.1 M glycine, 1% BSA, pH 2.5) was used instead of binding buffer in the second wash.

Centrifugation on a silicone oil cushion (1.03 g/ml) was used to separate unbound phage from cells during time course experiments. Inhibitors of phage binding and internalization (heparin, chondroitin, glycocalyx removal enzymes, endocytosis inhibitors, free peptides, quantum dots and UV-inactivated phage) were added to the cells 20 minutes prior to incubation with phage. Endocytosis inhibitors used in this study were the following: nystatin (50 µg/ml), genistein (100 µg/ml), chlorpromazine (5 µg/ml), 5-(N-ethyl-N-isopropyl)amiloride (100 µM), wortmannin (10 µM).

In vivo phage homing studies in mice were carried out by injecting $10^{10}$ pfu of T7 phage into tail vein and 10 minutes to 1 hour later, the mice were perfused with DMEM through the left ventricle of the heart. The organs of interest were collected, homogenized in 1% NP40 and the phage was quantified by titration.

Peptide synthesis and qdot labeling. The peptides were synthesized using Fmoc/t-Bu chemistry on a microwave assisted automated peptide synthesizer (Liberty, CEM Corporation). Peptides were purified by HPLC using 0.1% TFA in acetonitrile-water mixtures to 90%-95% purity by HPLC and validated by Q-TOF mass spectral analysis.

Streptavidin ITK-605 quantum dots (Invitrogen, Carlsbad, CA) were functionalized with biotinylated peptides by incubation with 100 fold molar excess of peptide followed by removal of free peptide by dialysis.

Affinity chromatography. Orthotopic PPC-1 tumors were homgenized in PBS containing 400 mM n-octyl-beta-D-glucopyranoside, 1 mM $MgSO_4$, 1 mM $MnCl_2$, 1 mM $CaCl_2$ and 1 tablet/5 ml of EDTA-free protease inhibitors cocktail (Sigma, St. Louis, MO). After 6 hours of extraction on a rotating platform at 4° C., the lysate was cleared by centrifugation (20 minutes at 14,000 rpm in refrigerated microcentrifuge) and loaded to an affinity column prepared by coupling cysteine-tagged RPARPAR (SEQ ID NO:2) peptide to Sulfolink coupling gel according to the manufacturer's instructions (Pierce, Rockford, IL). After overnight binding, the column was washed with a column wash buffer containing 200 mM n-octyl-beta-D-glucopyranoside, but otherwise identical to the lysis buffer, followed by elution with 2 mM free RPARPAR (SEQ ID NO:2) peptide in the same buffer.

Samples of the wash and elution fractions were separated using Novex 4-20% Tris-glycine polyacrylamide gels (Invitrogen, Carlsbad, CA), silver stained using Silver Snap kit (Pierce, Rockford, IL) and subjected to MALDI-TOF mass spectrometry at the Burnham Institute for Medical Research Proteomics Facility. Affinity chromatography samples were immunoblotted and probed with antibodies followed by chemiluminescent detection of binding.

Immunofluorescence staining. Cultured cells ($2 \times 10^5$ cells) were grown in 6-well tissue culture plates on collagen-I coated coverslips (BD Biosciences, San Jose, CA) overnight at 37° C. in 5% $CO_2$, and incubated with $10^8$ pfu of T7 phage. The cells were fixed in 4% paraformaldehyde or cold (−20° C.) methanol, and stained with antibodies. Nuclei were stained with DAPI or Hoechst 542. A polyclonal rabbit anti-T7 antibody was generated in-house as described previously (Laakkonen, P. et al. 2002b), except that an additional phage purification step using $CsCl_2$ centrifugation was included. Other primary antibodies used were rat anti-mouse CD31 monoclonal antibody (BD Biosciences), rabbit anti-NRP-1, mouse anti-human Lamp-1, mouse anti-human caveolin (Millipore, Temecula, CA), mouse anti-NRP-1 (Miltenyi Biotec Inc., Auburn, CA), mouse anti-human EEA-1 (BD Biosciences, San Jose, CA). The secondary antibodies, Alexa594 goat antibodies to mouse, rat, and rabbit immunoglobulins and Alexa488 donkey anti-rabbit antibody were from Invitrogen (Carlsbad, CA). Cells and tissue sections were examined by confocal microscopy (Fluoview 500, Olympus America Inc., Center Valley, PA).

DNA constructs and transfection. Expression construct of the wild type NRP-1 cDNA in pcDNA3.1(+) was a kind gift of Dr. Michael Klagsbrun. Site directed mutagenesis was used to generate triple mutation of the VEGF-165 binding site in the b1 domain of NRP-1 (S346A-E348A-349A) by replacing TCAAAAGAAACC (SEQ ID NO:29; encoding amino acids SKET) with GCTAAAGCTGCT (SEQ ID NO:30; encoding AKAA).

M21 melanoma cells were transiently transfected with these constructs using lipofectamine according to manufacturer's instructions (Invitrogen, Carlsbad, CA). Protease treatment of phage and qdots. $10^9$ phage particles or 50 μl of peptide-coated qdots phage were treated with 50 iu of uPA, 25 μg of crystalline trypsin, 50 iu of thrombin, or 25 μg of collagenase type I (all Sigma, St. Louis, Mo).

C. Example 3: Targeting Tumors by Inducing a Tumor-Selective Vascular Permeabilization A major problem of cancer therapy is that anti-cancer agents do not adequately penetrate into tumor tissue. Here, a conceptually new approach is introduced that overcomes this limitation. A tumor-penetrating peptide, iRGD (CRGDK/RGPD/EC; SEQ ID NO:61), that selectively increases vascular escape and tumor penetration of co-administered compounds of various sizes is disclosed. This activity depends on two sequence motifs within iRGD, the RGD binding motif for ow integrins, which are expressed in tumor vessels (and often on tumor cells) and the RXXR/K C-end Rule motif that binds to a tissue-penetration receptor, neuropilin-1. Co-administration with iRGD increased the anti-tumor activity of two drugs (doxorubicin liposomes and Herceptin). iRGD can be utilized as a generic booster of cancer diagnostics and therapeutics.

Current anti-cancer agents suffer from two main problems: poor penetration into tumor tissue and high toxicity to normal tissues. In solid tumors, anti-cancer agents only penetrate 3-5 cell diameters from the blood vessels, leaving some areas of the tumor with no drug or a low concentration of the drug (Hambley et al., 2009; Minchinton et al., 2006). Tumors have a high interstitial pressure, presumably because the blood vessels tend to be leaky and the lymphatic vessels are poorly functional in tumors, which works against penetration of drugs into tumor tissue (Jain, 1990; Heldin et al., 2004). These circumstances reduce the efficacy of the therapy and promote the development of drug resistance.

A tumor-penetrating peptide, iRGD (CRGDK/RGPD/EC; SEQ ID NO:61; cyclized by a disulfide bond between the cysteines), has recently been identified that specifically binds to tumor blood vessels, penetrates into tumor tissue, and can carry an attached payload, such as a fluorophore, drug, or nanoparticle contrast agent deep into extravascular tumor tissue (Sugahara, 2009). It is not necessary to couple a payload to the tumor-penetrating peptide; the peptide increases the vascular permeability specifically in the tumor, allowing a co-injected compound(s) to extravasate and penetrate into tumor tissue Sugahara et al., 2010). This procedure makes it possible to increase the efficacy of drugs that act within a tumor, without having to modify the drugs for targeting, and without increasing the side effects of the drugs.

The iRGD peptide selectively homes to tumors because it binds to ow integrins, which are specifically expressed in tumor vasculature and often on the tumor cells (Ruoslahti et al., 2002; Eliceiri et al., 2001; Sugahara et al., 2009). RGD peptides and their mimics are being used in various medical applications such as tumor diagnosis and treatment, and are evaluated in clinical trials (Tucker et al., 2003). The iRGD peptide differs from such currently used RGD peptides in that while it initially binds to ow integrins on angiogenic tumor endothelium, a proteolytic cleavage subsequently exposes a C-terminal RGDK/R sequence (SEQ ID NO:31; CendR sequence; Sugahara et al., 2009; Teesalu et al., 2009). The truncated peptide no longer binds to integrins, but has gained affinity for neuropilin-1, which mediates the extravasation and tissue penetration activity (Sugahara et al., 2009; Teesalu et al., 2009). Such properties confer on iRGD a highly efficient, and tumor-selective, tissue penetration that occurs within minutes after the injection of the peptide in the blood stream (Sugahara, 2009).

Figure 9A:
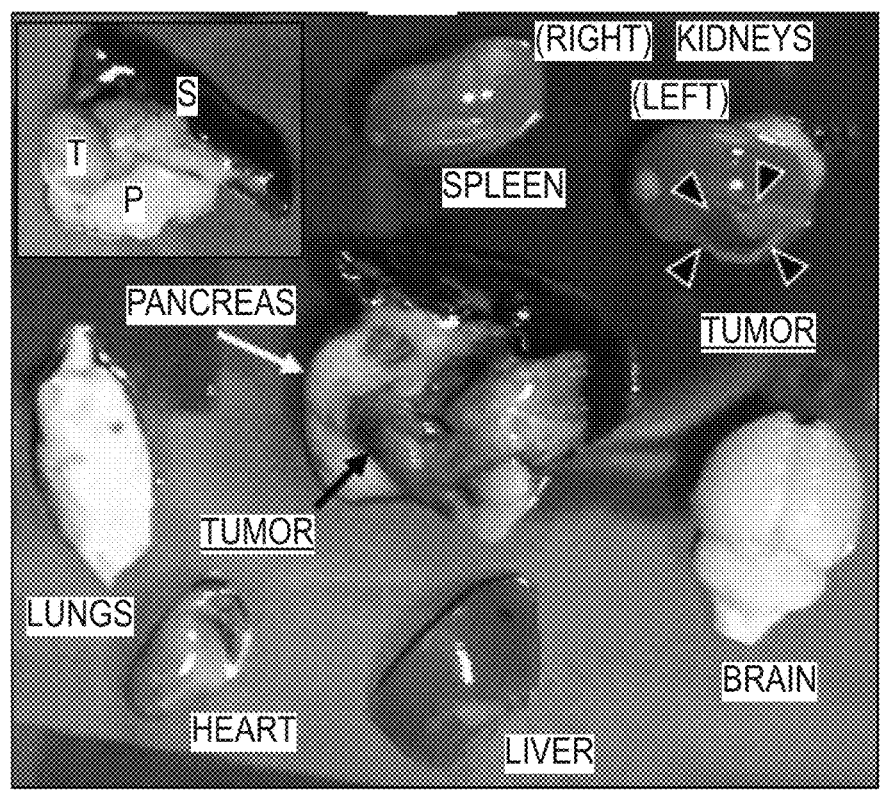
FIGS. 9A-9D show a tumor-specific entry of Evans Blue into extravascular tumor tissue in iRGD-injected mice. iRGD is SEQ ID NO:3. iRGDD is SEQ ID NO:4. Mice bearing orthotopic MIA PaCa-2 human pancreatic carcinoma xenografts were intravenously injected with 1 µg of the albumin-binding dye Evans Blue, followed 5 min later by 100 nmol iRGD peptide or control peptides in PBS, or PBS alone. Tissues were collected 30 min later.
Figure 9B:
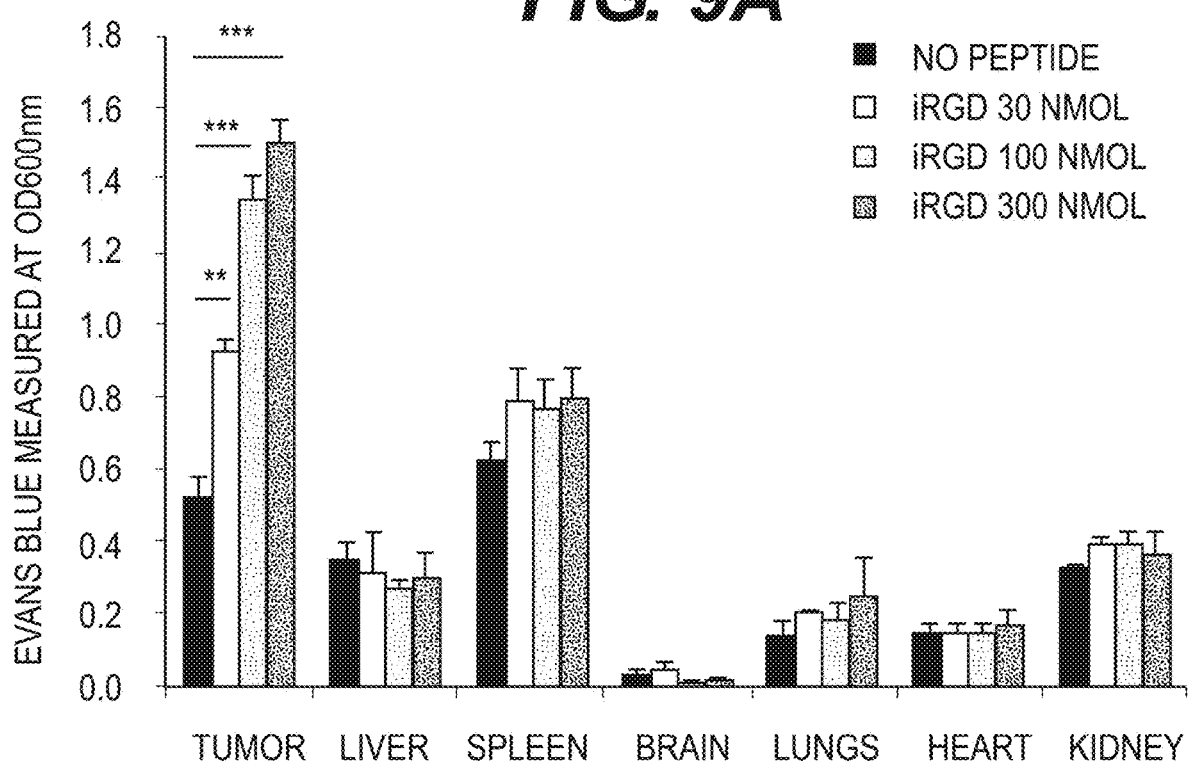
Figure 10A:
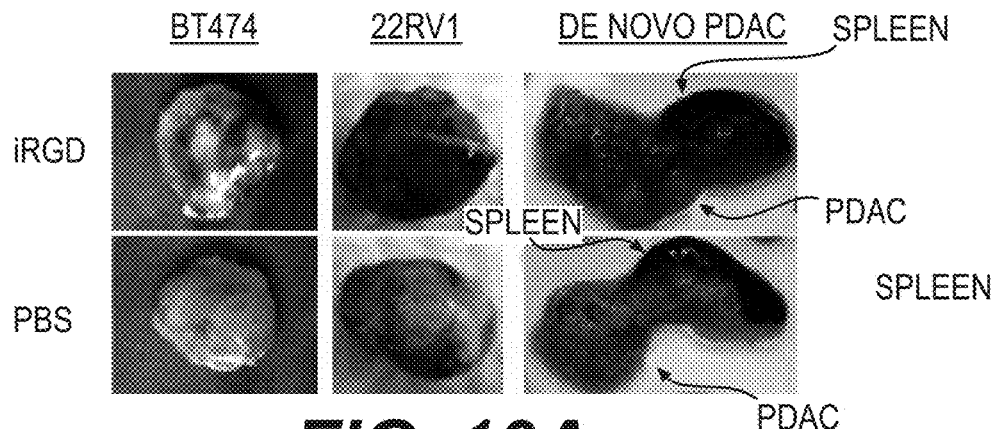
FIGS. 10A-10C shows the tumor-specific entry of Evans Blue into extravascular tumor tissue in various tumor models. Sequences are SEQ ID NO:3, SEQ ID NO:4, and SEQ ID NO:40. Tumor mice were injected with 1 µg of the albumin-binding dye Evans Blue, followed 5 min later by 100 nmol iRGD peptide or control peptides in PBS, or PBS alone. Tissues were collected 30 min later.
Figure 10B:
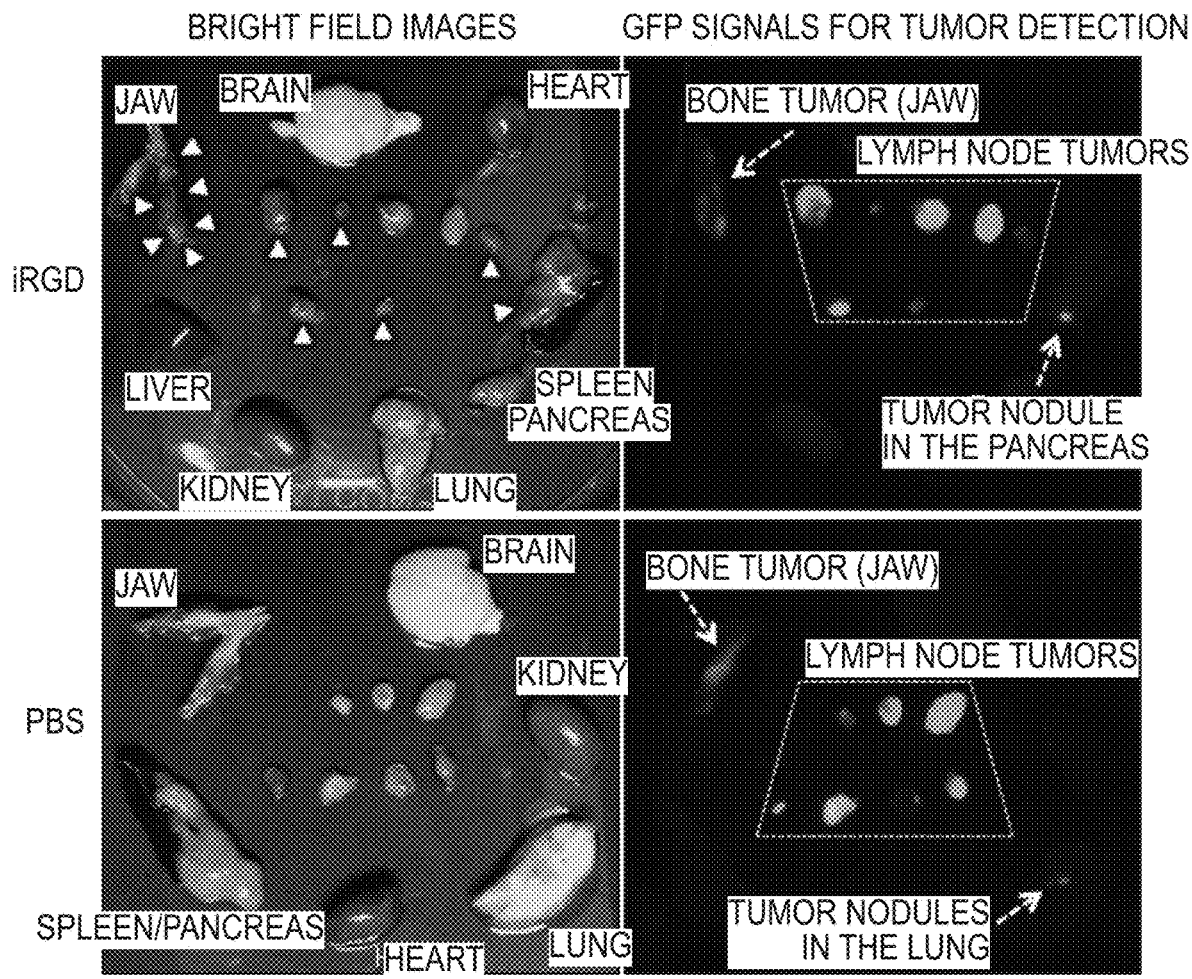

Peptides and proteins with a C-terminal R/KXXR/K (SEQ ID NO:23) sequence increase vascular permeability through binding to neuropilin-1 (Acevedo et al., 2008; Jia et al., 2006; Soker et al., 1998; Teesalu et al., 2009). The rapid extravasation and tissue penetration of iRGD in the tumor can be caused by a tumor-specific increase in vascular permeability induced by the CendR sequence of iRGD. Tumor-bearing mice were injected with Evans Blue, an albumin-binding dye commonly used to study vascular permeability (Miles et al., 1952; Murohara et al., 1998). Chemically synthesized iRGD peptide, when co-injected with the dye, caused specific accumulation of the dye in orthotopic MIA PaCa-2 human pancreatic carcinoma xenografts (FIG. 9A) and secondary sites invaded by this tumor (FIG. 9A, arrowheads). The induced permeabilization was also observed in other tumor types, which iRGD was shown to efficiently home to (Sugahara et al., 2010); orthotopic xenografts of BT474 human breast and 22Rv1 human prostate tumors, disseminated human GFP-PC-3 prostate tumors that mimic metastases, and a genetically engineered model of de novo pancreatic ductal adenocarcinoma (Hezel et al., 2006; FIG. 9A and FIGS. 10, A and B). Quantification of the dye in the tissues confirmed that the permeabilization was specific to the tumors and dependent on the dose of iRGD administered. The increase in the tumor accumulation was about 4 fold (FIG. 9B).

Figure 9C:
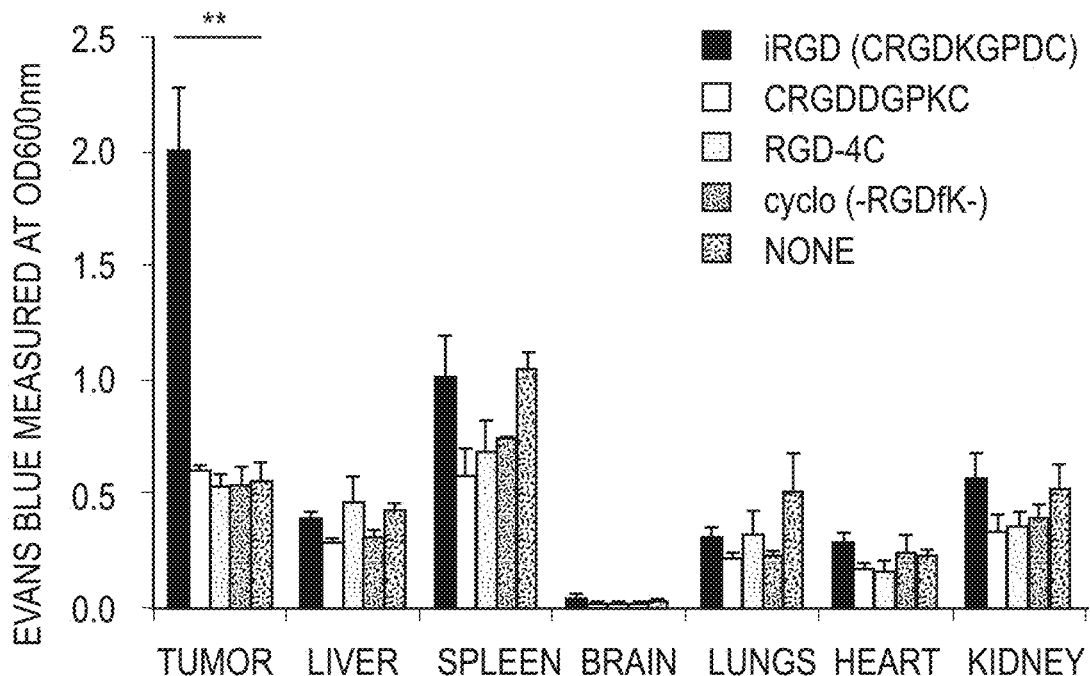
Figure 9D:
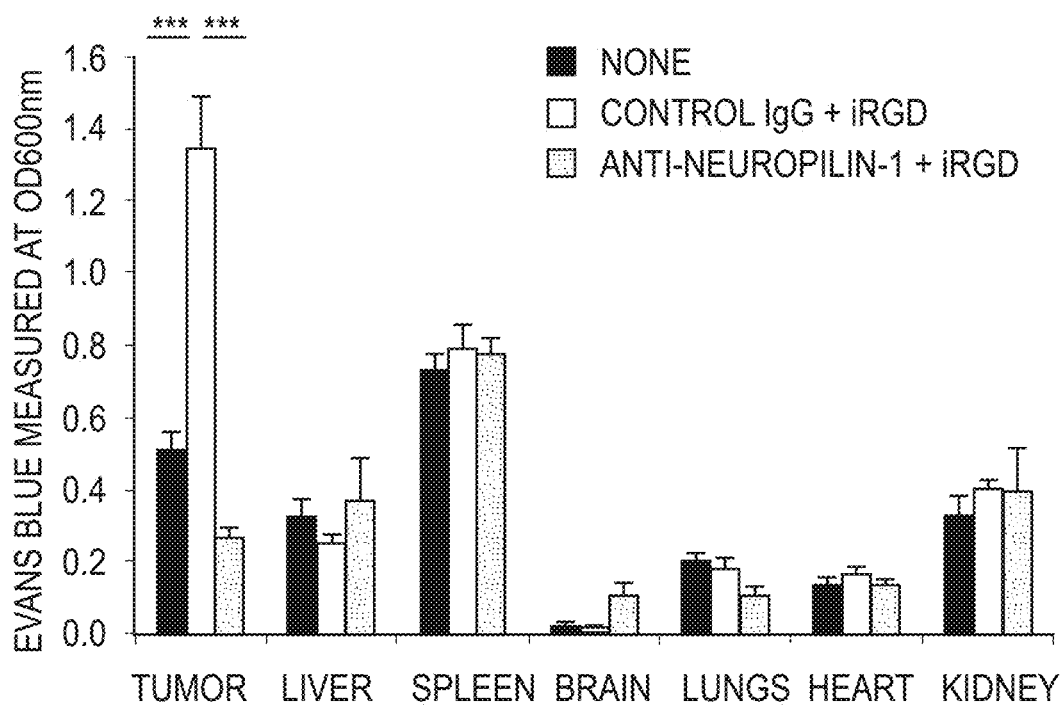
Figure 10C:
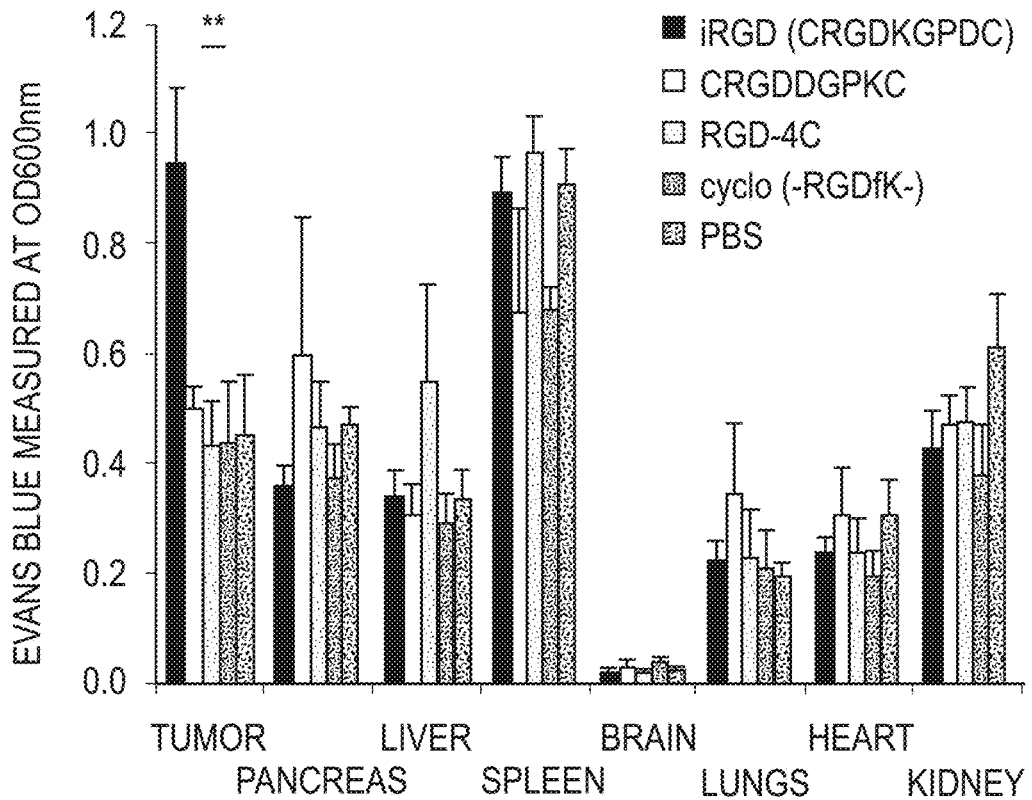
Figure 11:
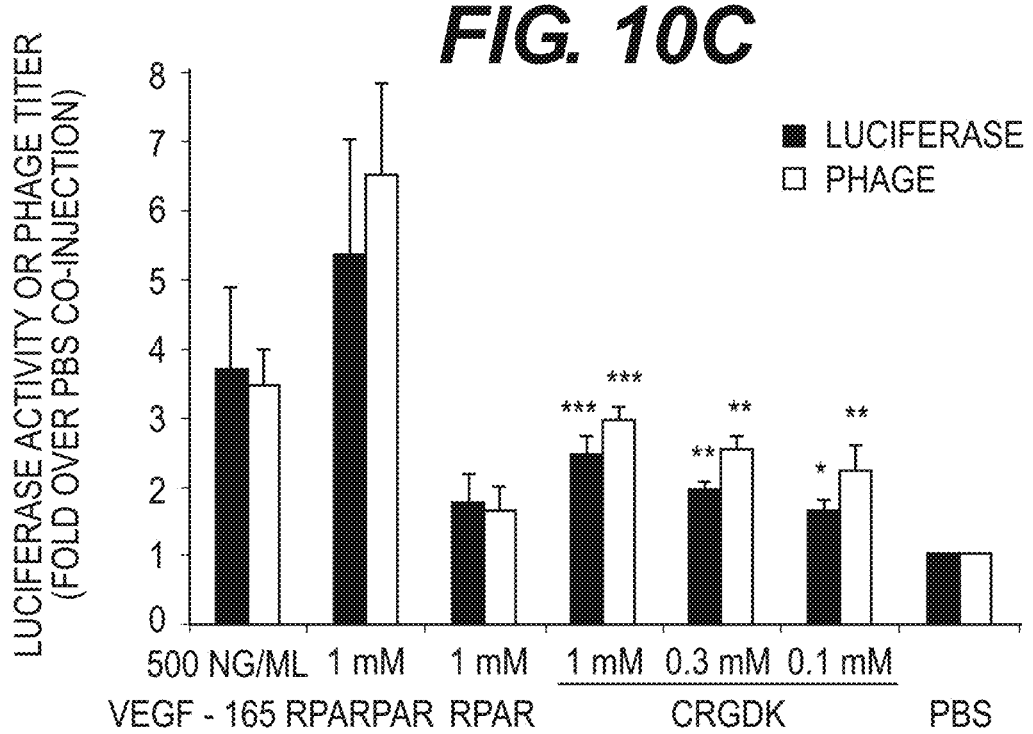
FIG. 11 shows the CendR element of iRGD (CRGDK; SEQ ID NO:34) induces local vascular permeabilization in the skin. Modified Miles assay was performed (Miles and Miles, 1952, Murohara et al., 1998, Teesalu et al., 2009). Mice were intravenously injected with 150 µl of PBS containing a mixture of 0.5% Evans Blue, 13 µg of Quantilum recombinant luciferase, and 10⁹ pfu of untargeted phage particles. Ten min later, the mice received intradermal injections of 30 µl of PBS containing VEGF-165, RPARPAR peptide (SEQ ID NO:2), RPAR (SEQ ID NO:5) peptide, CRGDK peptide (SEQ ID NO:34), or only PBS at the indicated concentrations. After 30 min, the skin samples were collected with a 4 mm puncher. Luciferase activity and phage titer were measured to quantify the retention of the agents in the extravascular tissue of the skin. The values were normalized to the skin samples injected with PBS. Statistical analyses were performed with ANOVA; n=3; error bars, s.e.m.; single asterisk, $p<0.05$; double asterisk, $p<0.01$; triple asterisk, $p<0.001$. RPAR is SEQ ID NO:5.

To test the relevance of the CendR element in iRGD-induced vascular permeabilization, two commonly used RGD peptides that do not carry a CendR motif, RGD-4C (CDCRGDCFC; SEQ ID NO:32; Koivunen et al., 1995) and cyclo(-RGDfK-) (SEQ ID NO:40; Murphy et al., 2008), were examined for the permeability effect and found to be inactive (FIG. 9C and FIG. 10C). In addition, a scrambled iRGD variant that carries an RGD but no CendR motif (CRGDDGPKC; SEQ ID NO:33) also failed to enhance the permeability in the tumors (FIG. 9C and FIG. 10C). Pre-injection into tumor mice of an antibody that functionally blocks neuropilin-1, the receptor for CendR peptides, inhibited the iRGD-induced increase in permeability (FIG. 9D). When iRGD targets a tumor, it is proteolytically cleaved to become CRGDK (SEQ ID NO:34), which acts as a neuropilin-1-binding CendR peptide (Sugahara et al., 2009). A chemically synthesized CRGDK (SEQ ID NO:34) peptide enhanced local vascular permeability in the skin in a dose-dependent manner similar to VEGF-165 and prototypic CendR peptides, RPARPAR (SEQ ID NO:2) and RPAR (SEQ ID NO:5; Teesalu et al., 2009; FIG. 11). Collectively, these results show that the enhanced permeability by iRGD in the tumor is CendR-dependent.

Figure 12:
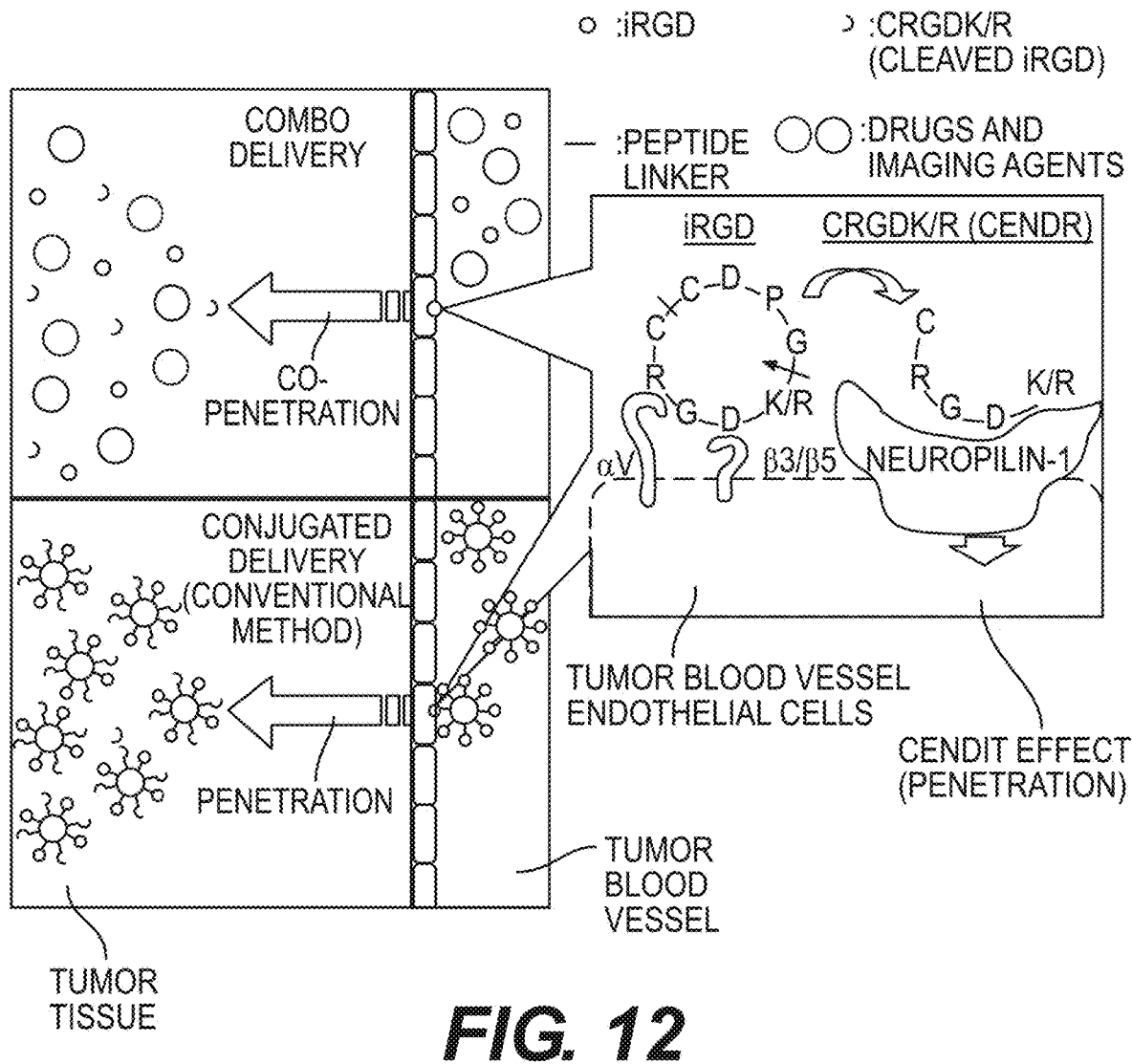
FIG. 12 shows the iRGD-combo delivery system. Sequences are SEQ ID NO:1 and SEQ ID NO:37. The intravenously injected iRGD peptide penetrates tumor tissue in a 3-step process (right panel, see Sugahara et al., 2009 for more details); (1) iRGD recognizes the αv integrins on tumor blood vessel endothelial cells with the RGD motif, (2) it is then proteolysed to expose the cryptic CendR element, RGDK/R (SEQ ID NO:31), at the C-terminus (small, skinny arrow in right panel), and the disulfide bond breaks (narrow line in right panel), (3) the CendR element mediates binding to neuropilin-1, to induce the CendR-Induced Transendothelium & tissue (CendIT) effect with resulting penetration of cells and tissues. In conventional conjugated delivery methods, cargos (e.g. drugs, diagnostics) are chemically attached to the N-terminal cysteine ("C" underneath the narrow line representing the disulfide break, right panel). With the combo delivery method, the cargos are co-administered with the peptide separately. The CendIT effect that iRGD induces allows penetration of the co-administered cargos into the extravascular tumor tissue.
Figure 13A:
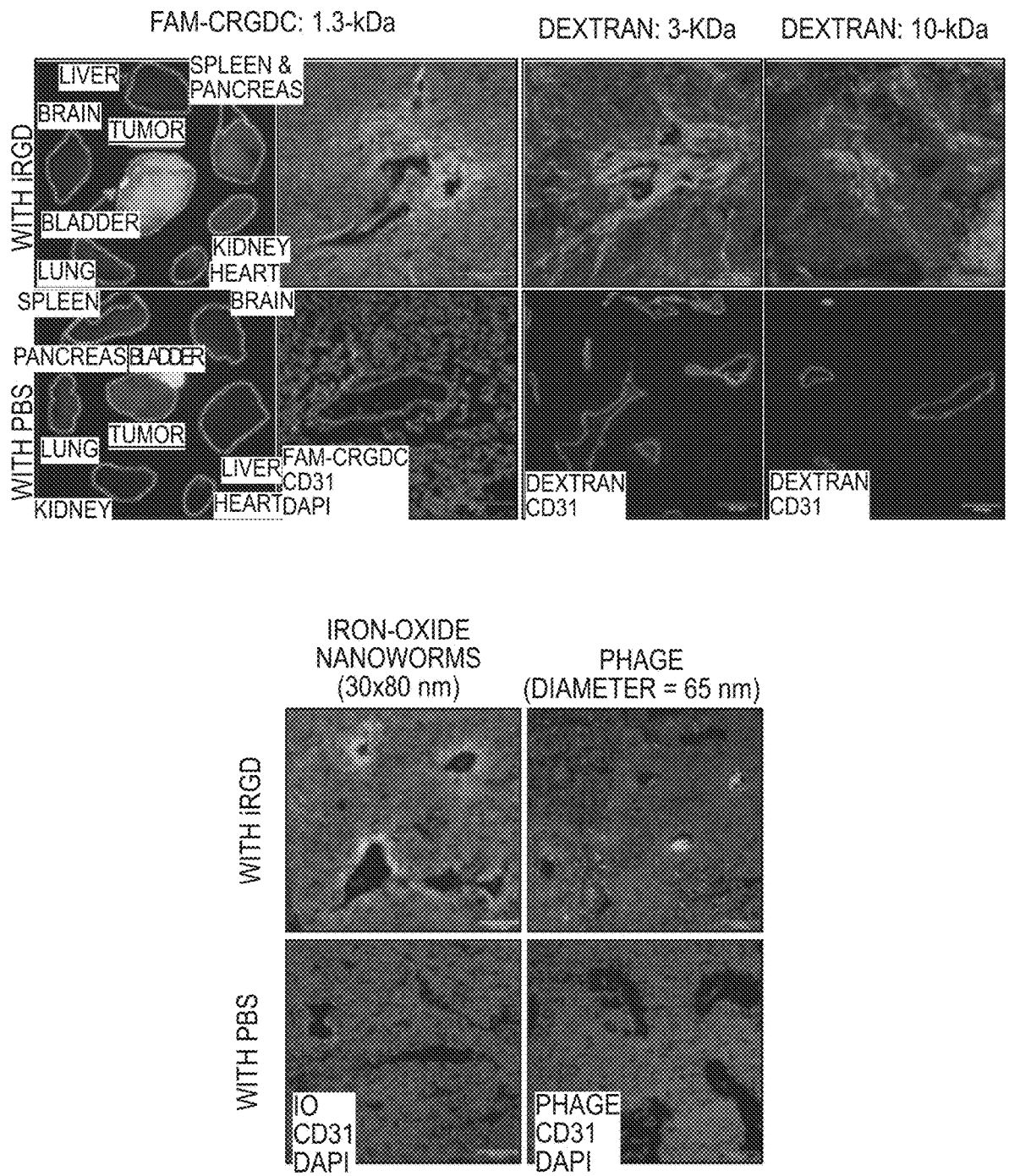
FIGS. 13A-13C show the accumulation of molecules and nanoparticles within extravascular tumor tissue in iRGD-injected mice. Mice bearing orthotopic 22Rv1 human prostate tumors were injected with 200 nmol of fluorescein-labeled CRGDC peptide (FAM-CRGDC, SEQ ID NO:36), 0.2 mg of Texas red-labeled 3-kDa or 10-kDa dextran, 5 mg iron/kg of fluorescein-labeled iron-oxide nanoworms, or 10⁹ plaque forming units (pfu) of untargeted phage, followed 5 min later by 100 nmol iRGD peptide in PBS or PBS alone. Tissues were collected 30 min later for the dextrans and phage, and 2 hours later for the FAM-CRGDC (SEQ ID NO:36) and nanoworms.
Figure 13B:
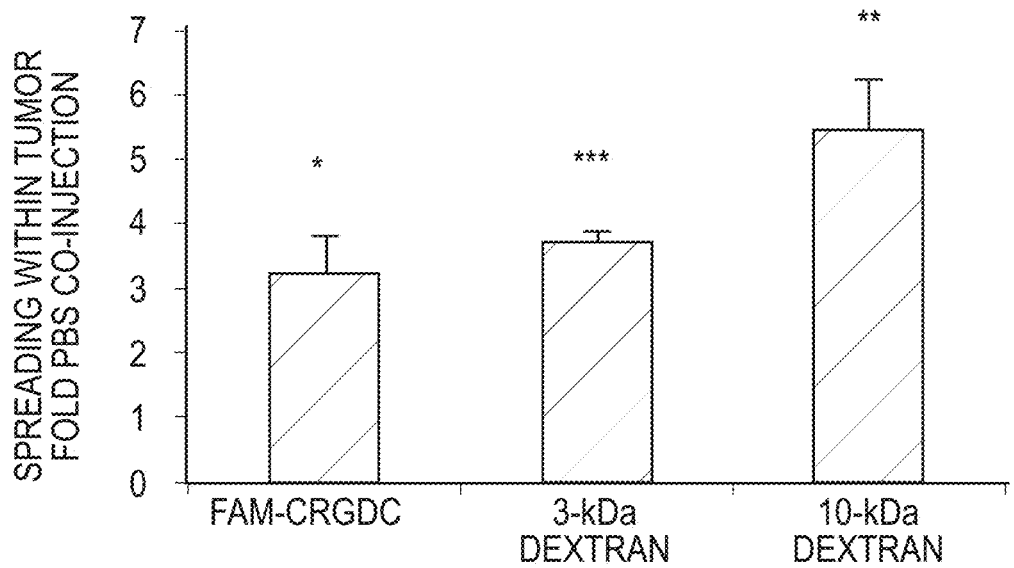
Figure 13C:
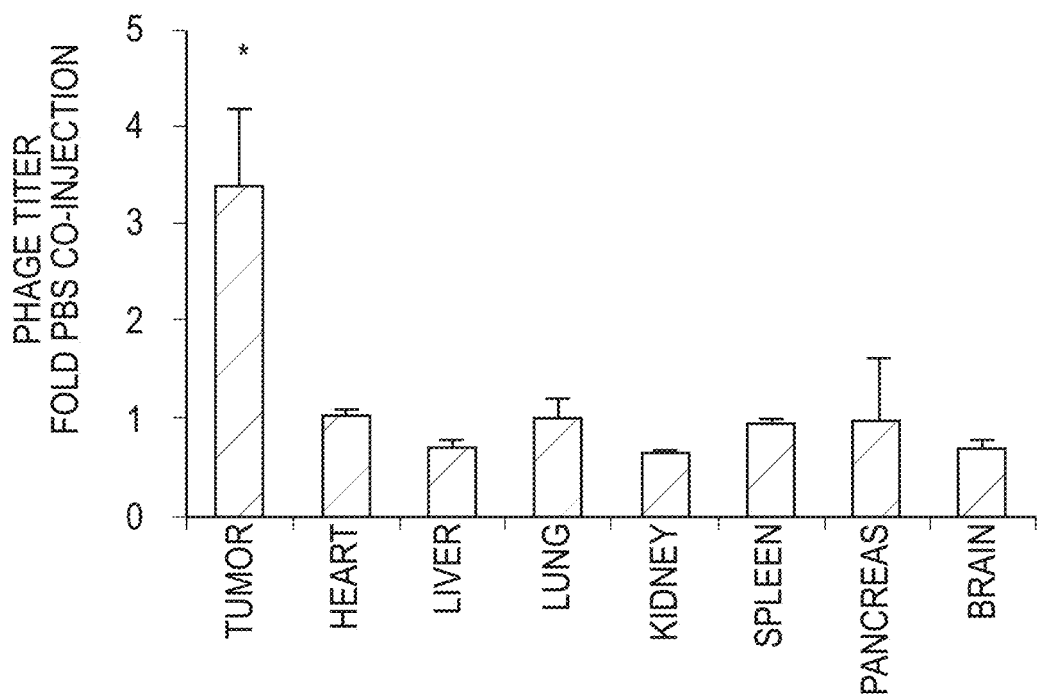

The tumor-specific increase in tissue access mediated by iRGD led to a novel approach to improve the delivery of drugs and imaging agents to tumor parenchyma (schematized in FIG. 12). A number of compounds were injected in combination with iRGD. A 1.3-kDa peptide, fluorescein-labeled CRGDC (FAM-CRGDC, SEQ ID NO:36), which does not contain a CendR motif and only minimally penetrates into tumor tissue by itself (Koivunen et al., 1993; Sugahara et al., 2009), showed extensive extravascular distribution when co-injected with iRGD (FIG. 13A). Similar results were obtained with 3-kDa and 10-kDa dextran, superparamagnetic iron-oxide nanoworms (about 80 nm long and 30 nm thick (Park et al., 2009)), and T7 phage (diameter about 65 nm (Sokoloff et al., 2000)). Quantification of the area of spreading in histology sections revealed that FAM-CRGDC (SEQ ID NO:36) and the dextrans spread within the tumor 3 to 5 fold more in the presence of iRGD than without it (FIG. 13B). The T7 phage accumulated in the tumor 3 fold more when co-injected with iRGD than the control as evidenced by phage titer (FIG. 13C). These results show that the iRGD combo system can increase the tumor accumulation of compounds with vastly different sizes and chemical properties, ranging from a 1-kDa peptide to nanoparticles of about 70 nm in size. This tissue-specific penetration of molecules induced by co-administered CendR peptides, such as iRGD, has been termed the CendR-Induced Transendothelium & tissue effect (CendIT—pronounced like 'send it'—effect).

Figure 14A:
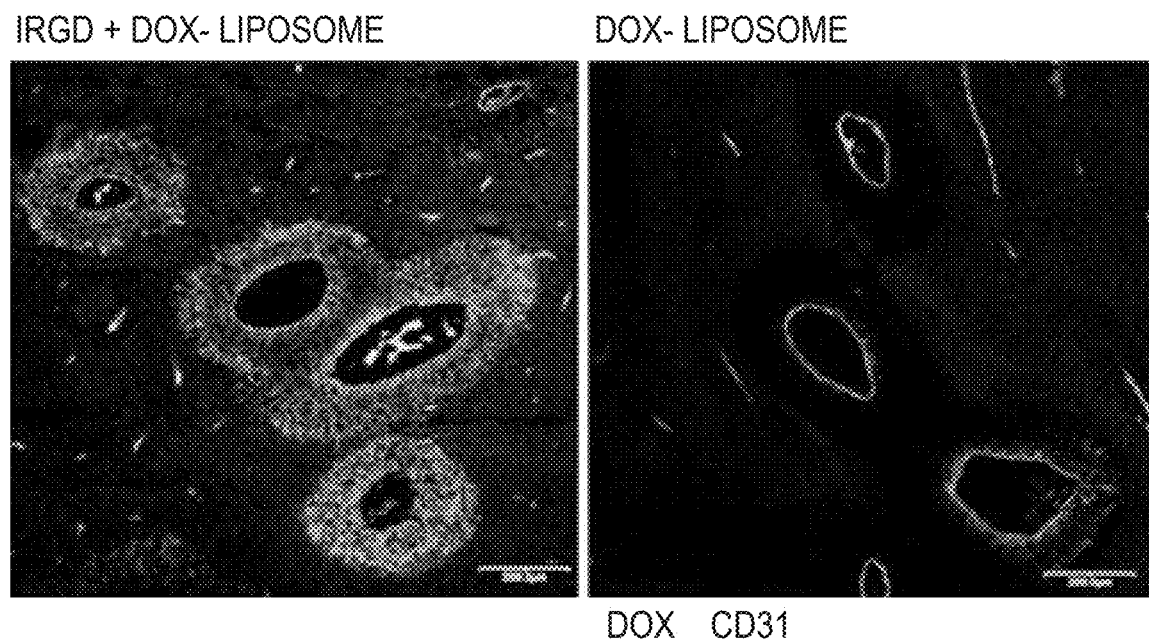
FIGS. 14A-14D show enhanced anti-tumor effect of doxorubicin (DOX)-liposomes co-injected with iRGD.
Figure 14B:
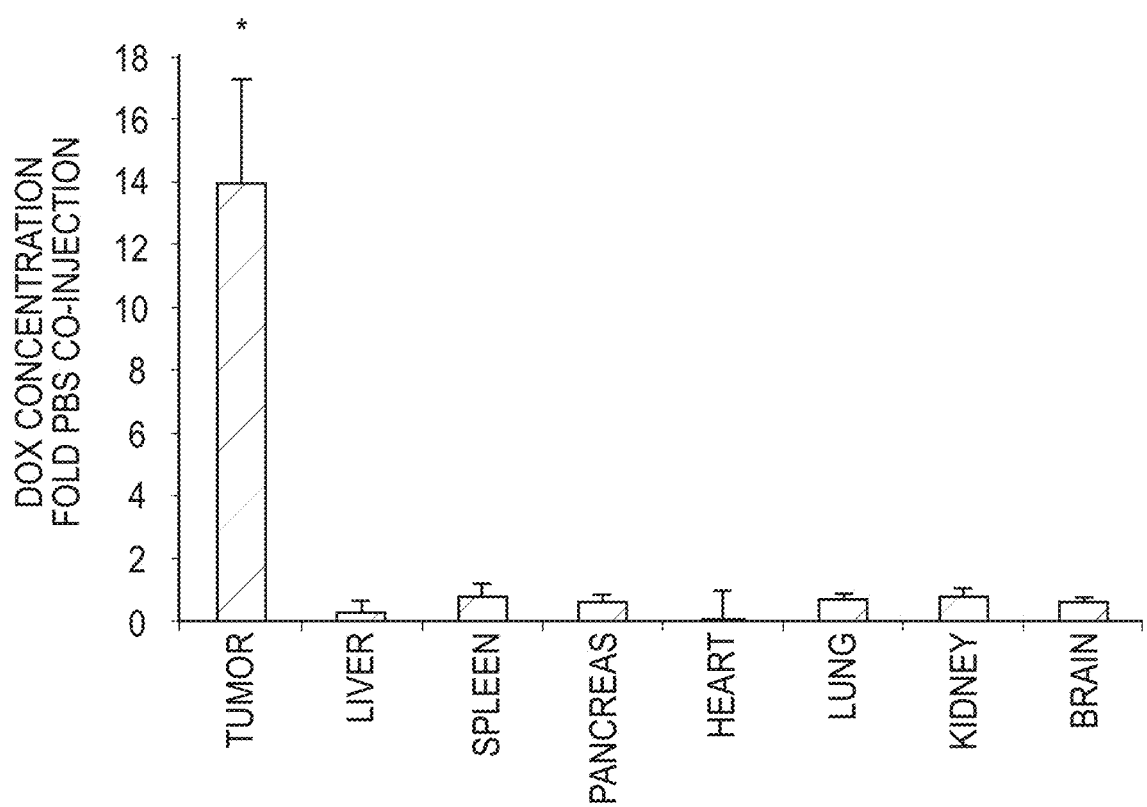
Figure 14C:
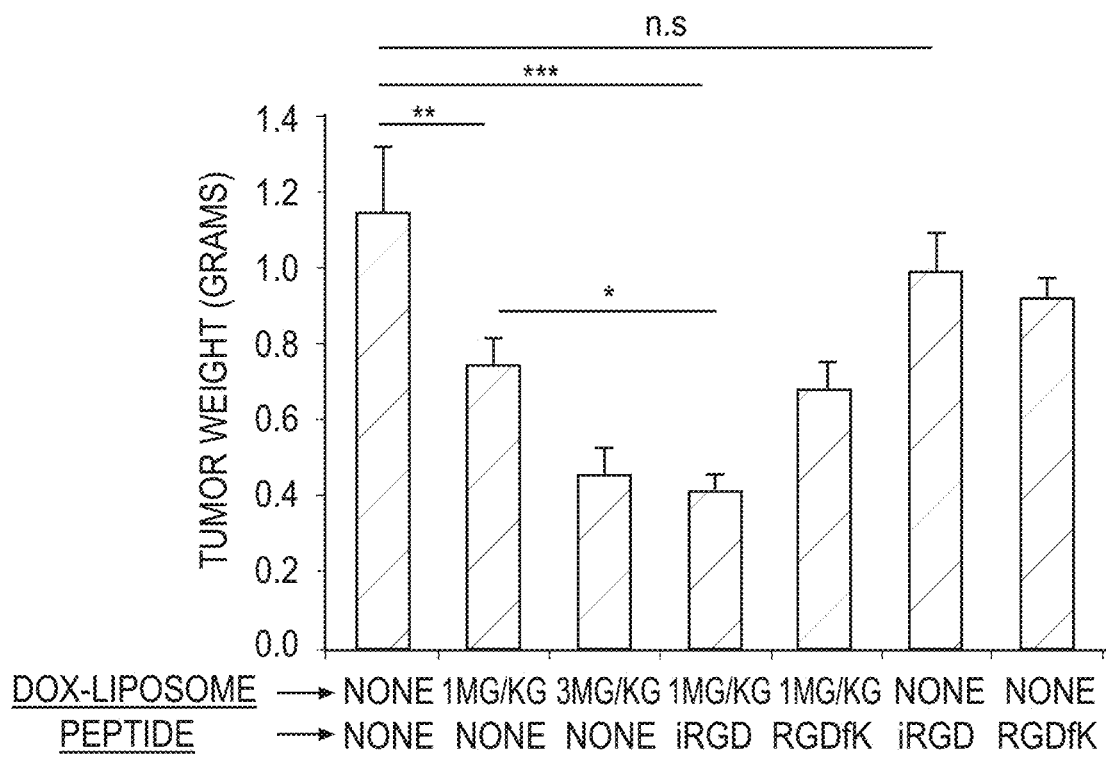
Figure 15:
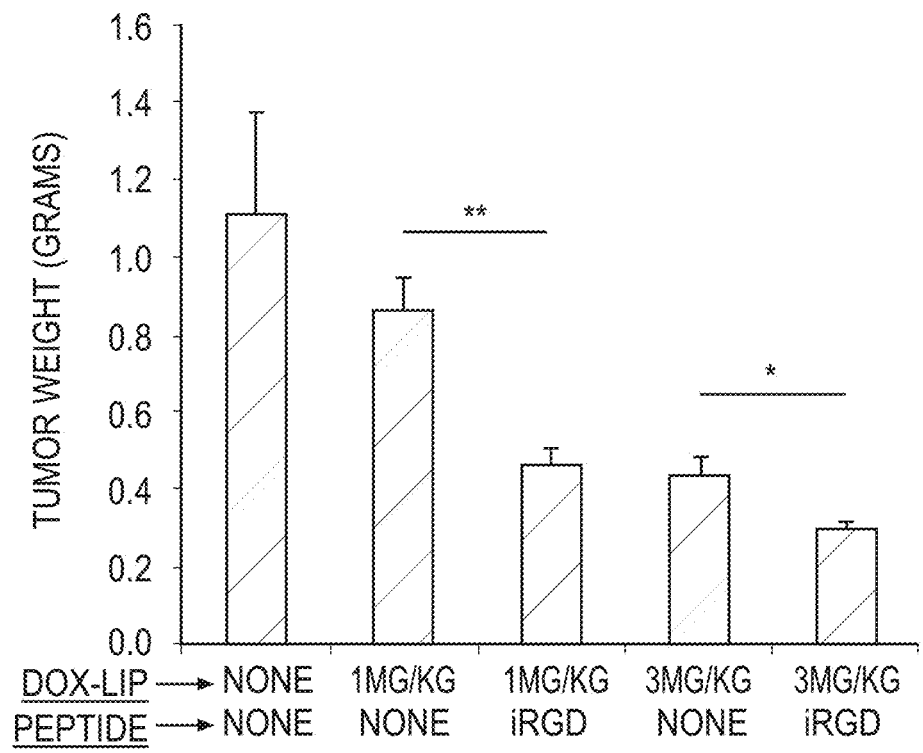
FIG. 15 shows the enhanced anti-tumor effect of a combination of iRGD and DOX-liposomes at 3 mg DOX/kg. Nude mice bearing 2 week-old orthotopic 22Rv1 tumors received daily intravenous injections of DOX-liposomes (3 mg DOX/kg) or PBS, combined with 2 µmol/kg iRGD or PBS. The tumors were harvested and weighed after 17 days of treatment. The number of animals in each group was 13. Statistical analysis was performed with Student's t-test; error bars, s.e.m.; single asterisk, $p<0.05$; double asterisk, $p<0.01$.

To investigate the applicability of the iRGD-combo regimen to tumor treatment, orthotopic 22Rv1 tumors were treated with a combination of iRGD and doxorubicin (DOX)-liposomes (diameter about 120 nm). The liposomes spread much wider and accumulated more in the tumor tissue with iRGD than without it (FIGS. 14A and 14B). Tumor treatment studies showed that the iRGD-combo regimen (1 mg DOX/kg+iRGD) was as potent as the DOX-liposomes given alone at a dose 3-times higher (FIG. 14C). A cyclic RGD peptide that does not contain a CendR motif failed to enhance the effect of the drug. Certain RGD peptides have been shown to inhibit tumor growth (Brooks et al., 1994; Tucker et al., 2003). An iRGD alone control at the dose used for the combo regimen showed no effect on the tumor growth, supporting the notion that the combo regimen is more effective than the drug alone because iRGD improves the access of the drug to tumor cells. Daily administration of the liposomes at 3 mg DOX/kg for 17 days reaches the cumulative maximum tolerated dose of the drug in mice (Parr et al., 1997). Combining iRGD with this dose (3 mg DOX/kg+iRGD) further improved the efficacy of the drug (FIG. 15).

Figure 14D:
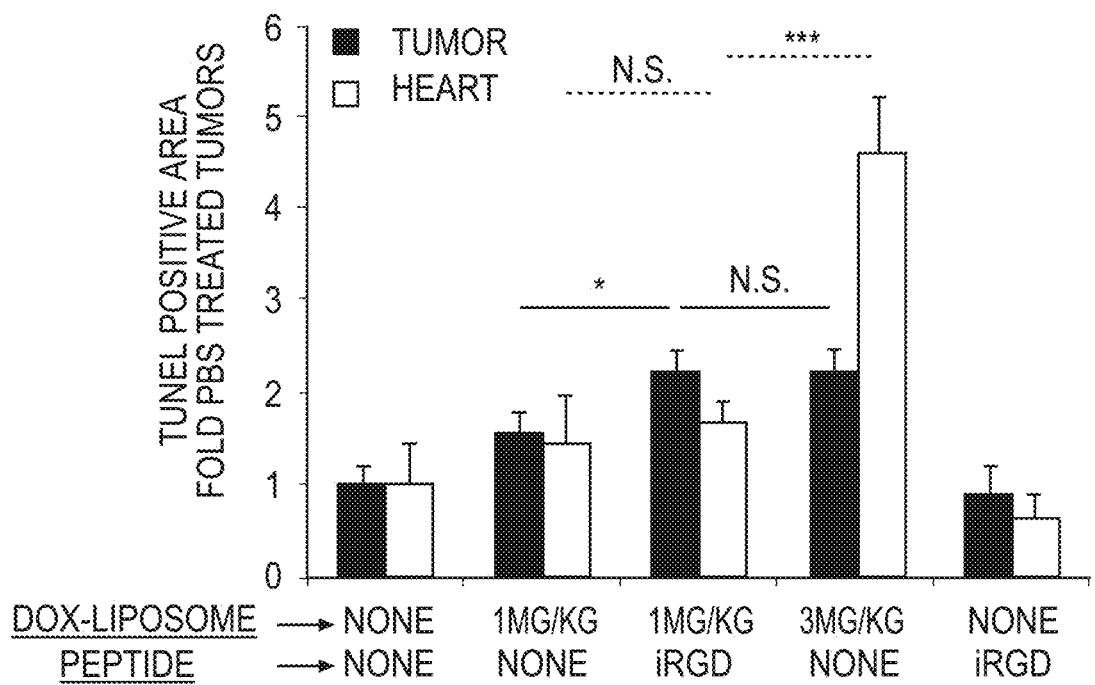
Figure 16:
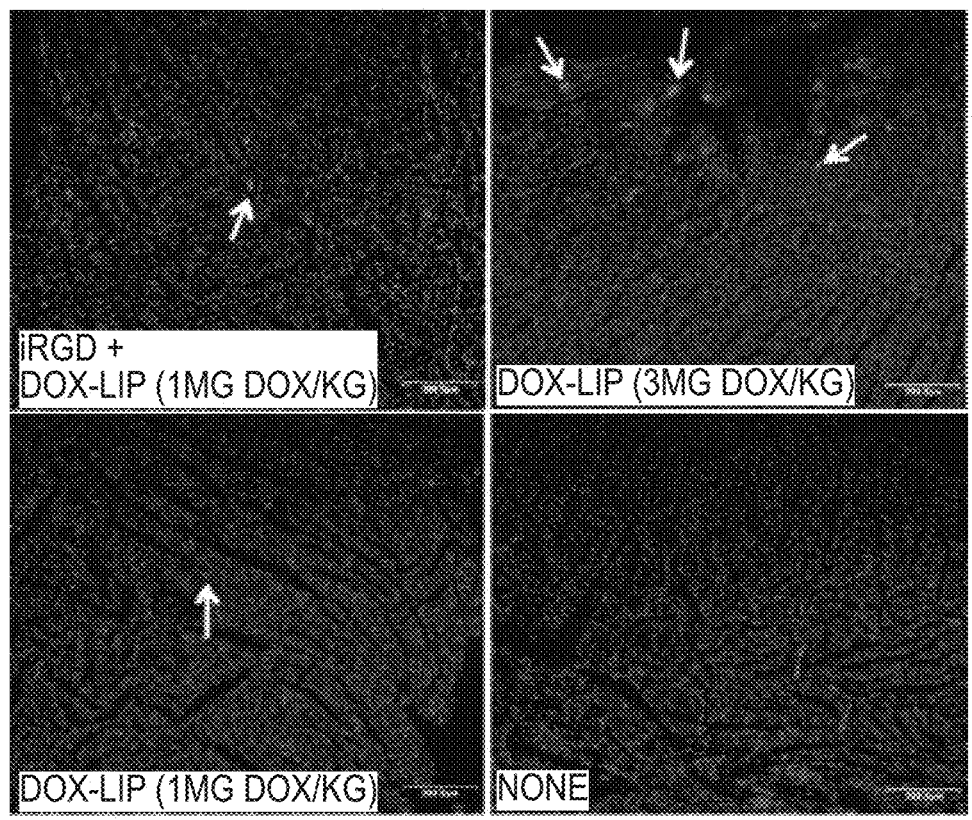
FIG. 16 shows TUNEL staining performed on tissue sections of the heart after treatment with the combination of iRGD and DOX-liposomes. The heart samples collected after the treatment study shown in FIG. 14C were sectioned, immunofluorescently stained with a TUNEL assay kit and DAPI (blue), and viewed with a confocal microscope. The red dots that appear fuzzy (arrows point to examples) represent the TUNEL signals. Scale bars=200 µm.
Figure 17:
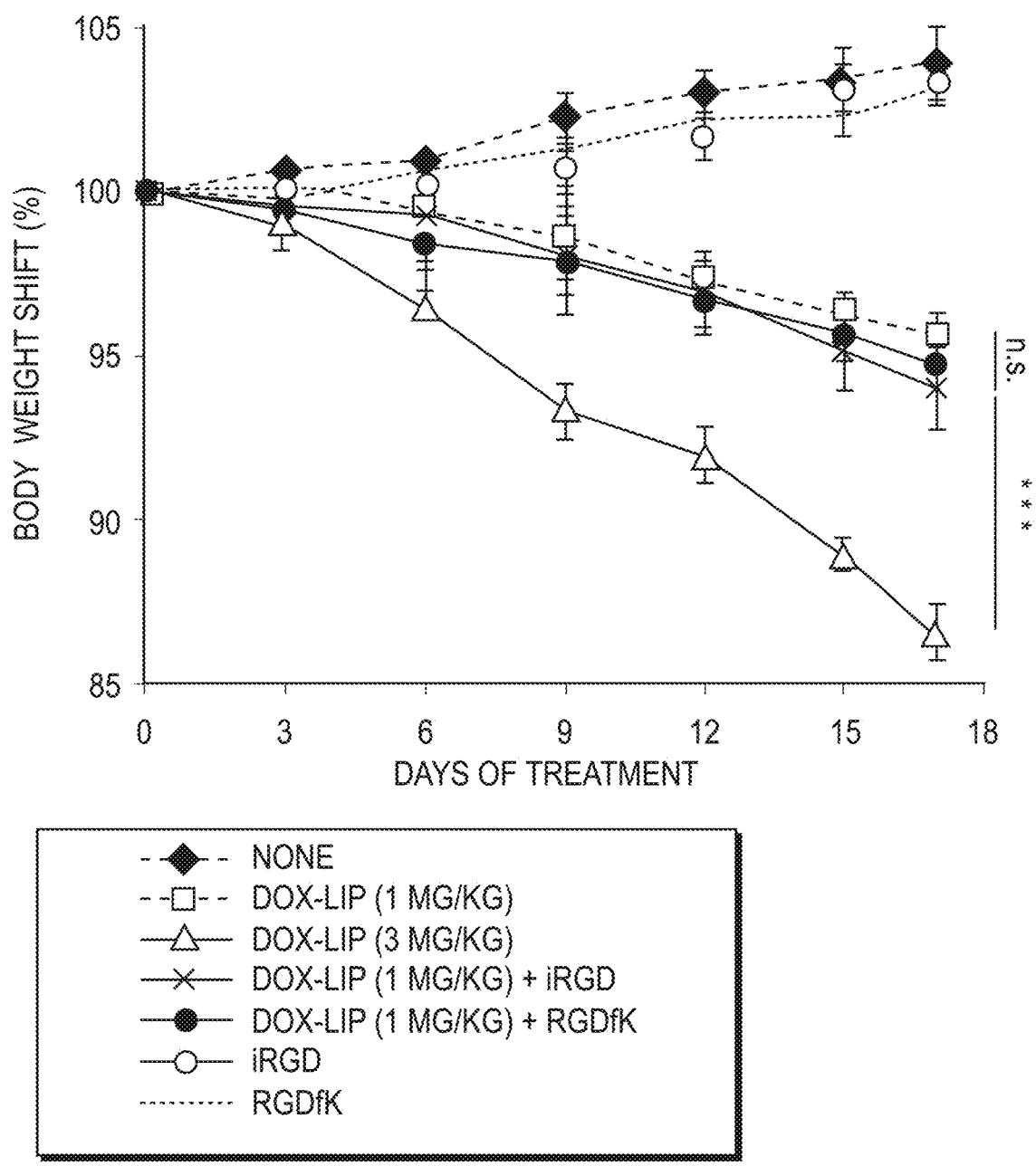
FIG. 17 shows the body weight shift of the tumor mice treated with the combination of iRGD and DOX-liposomes. The mice in the treatment study shown in FIG. 14C were weighed every 4 days during the treatment study. The percent body weight shift is shown. Statistical analysis was performed with ANOVA; error bars, s.e.m.; n.s., not significant; triple asterisk, $p<0.001$.

While the combo regimen significantly increased the potency of the drug, it did not increase the side effects. Cardiotoxicity, the major side effect of DOX, is evidenced by cardiomyocyte apoptosis at molecular levels (Arola et al., 2000). Abundant cardiomyocyte apoptosis, detected by TUNEL staining, was observed in the 3 mg DOX/kg group, while it was minimally present in the combo group (1 mg DOX/kg+iRGD) at a level similar to the 1 mg DOX/kg group (FIG. 14D and FIG. 16). In contrast, tumors from the combo group (1 mg DOX/kg+iRGD) showed strong TUNEL staining at a level comparable to the 3 mg DOX/kg group, supporting the treatment data (FIG. 14D). In addition, the 3 mg DOX/kg group steeply lost weight, whereas the combo group (1 mg DOX/kg+iRGD) showed mild weight loss comparable to the 1 mg DOX/kg group (FIG. 17). These results indicate that the combo regimen provides equivalent anti-tumor effects as treatment with higher dose of the drug alone without increasing the side effects.

Figure 18A:
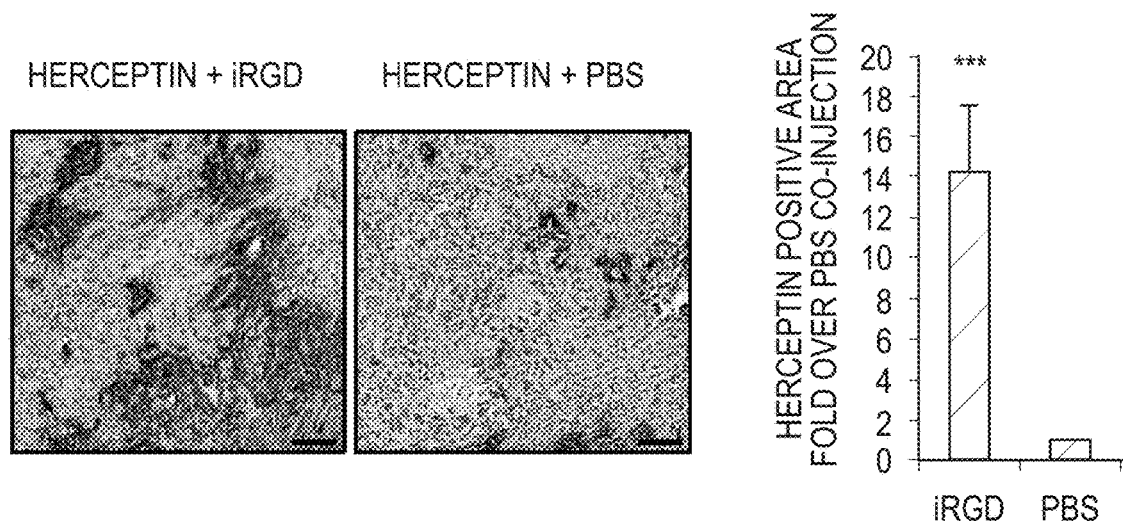
FIGS. 18A-18C show the enhanced anti-tumor effects of Herceptin co-injected with iRGD.
Figure 18B:
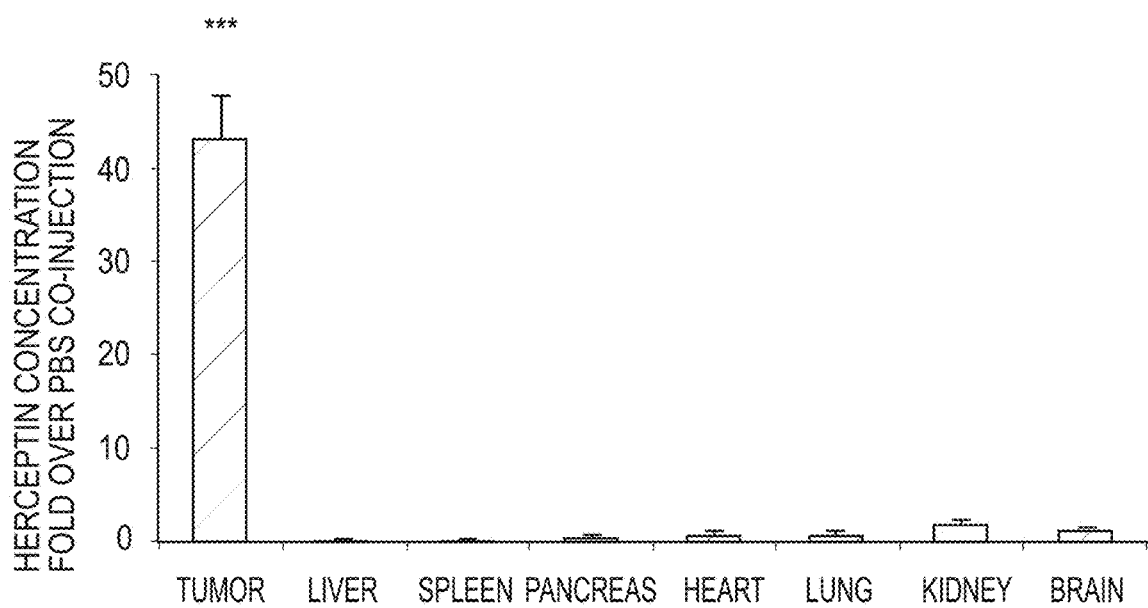
Figure 18C:
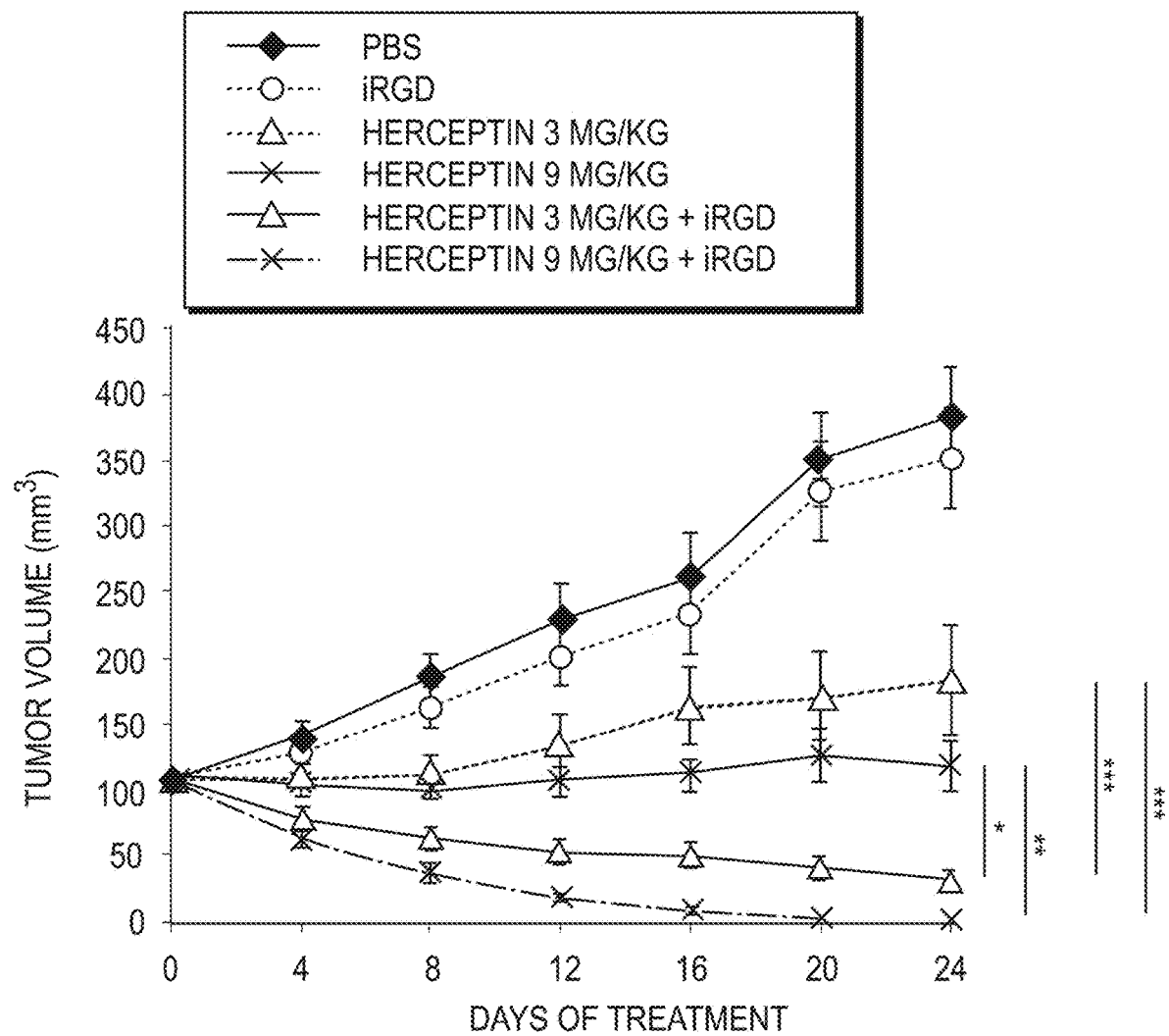

The iRGD-combo regimen was then tested in another orthotopic tumor model created with BT474 cells. The BT474 cells highly express HER2, the target of the 148-kDa anti-HER2 antibody, Herceptin (Spiridon et al., 2002). Herceptin, when injected together with iRGD, spread much more efficiently within the tumor tissue than the control injection (FIG. 18A). ELISA quantification showed that iRGD dramatically enhanced the accumulation of Herceptin in the tumors by 40 fold, possibly due to its affinity to the HER2-expressing tumor cells (FIG. 18B). Accordingly, treatment of orthotopic BT474 tumors with combining iRGD with Herceptin greatly increased the potency of the drug (FIG. 18C). The iRGD peptide alone at the dose used in the combo regimen did not affect the tumor growth. The combo regimen was significantly more effective than treatment with the same or 3-fold higher dose of Herceptin alone. Combining iRGD with the 3-fold higher dose of Herceptin improved the efficacy of the drug even more. Treatment with this combination resulted in an eradication of all tumors (FIG. 18C). The tumors did not relapse without any treatment during a 2-week observation period after they disappeared.

Figure 19:
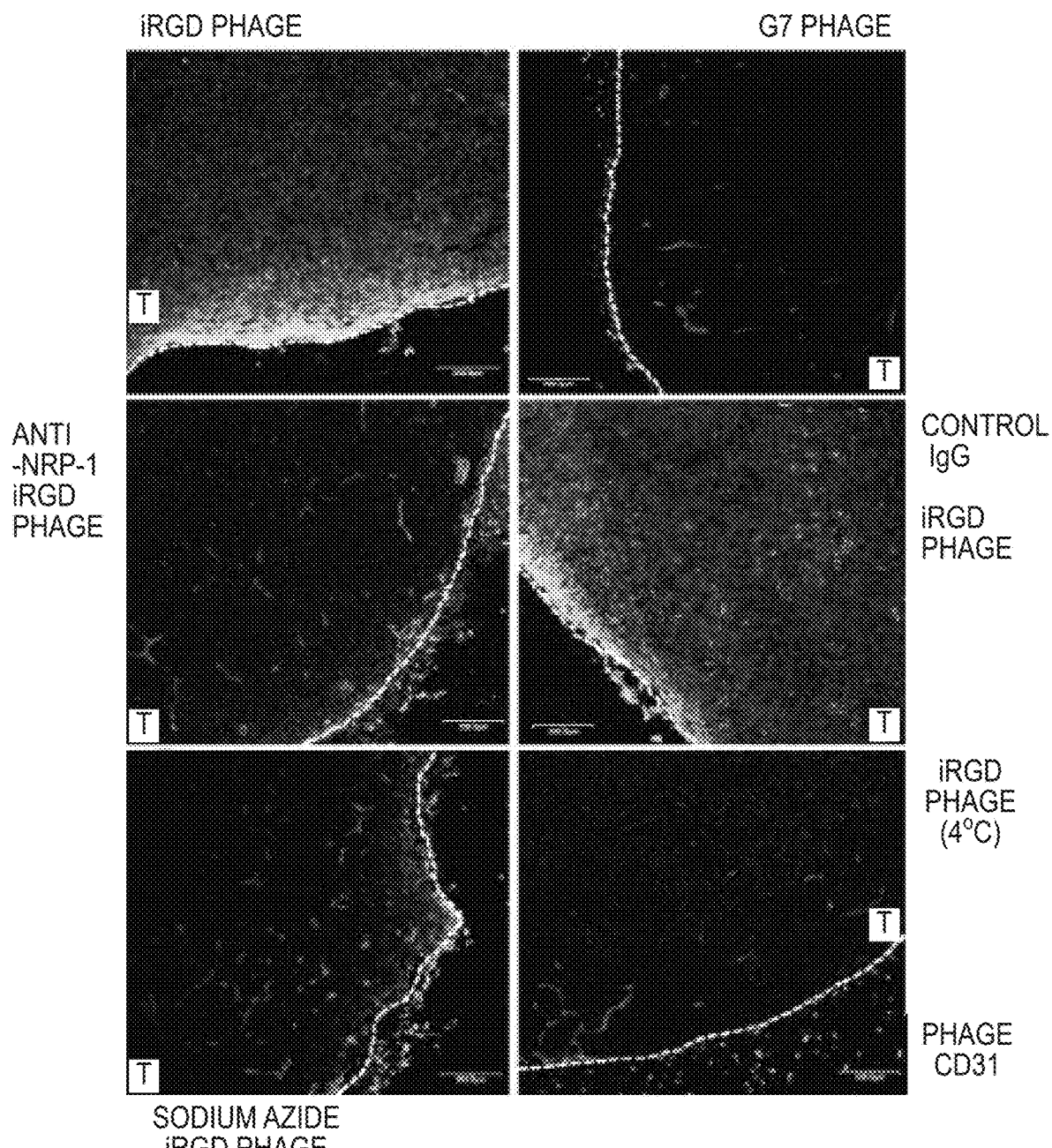
FIG. 19 shows ex vivo tumor penetration of T7 phage expressing iRGD. PPC1 human prostate cancer subcutaneous tumors were excised and maintained in short-term culture containing the following combinations of $10^9$ pfu/ml phage and inhibitors; (upper left), phage expressing iRGD peptides (iRGD phage) with no inhibitors; (upper right), untargeted phage expressing control $G_7$ peptides ($CG_7C$ phage) with no inhibitors; (middle left), iRGD phage with 10 mM sodium azide; (middle right), iRGD phage with no inhibitors, but incubated at 4° C.; (lower left), iRGD phage with a function-blocking anti-neuropilin-1 antibody; (lower right), iRGD phage with a control goat IgG. The tumors were first incubated with the inhibitors for 20 min at 4° C. The indicated phage were then added to the solution and the tumors were further incubated for 90 min at 37° C. (4° C. in panel D). After the incubation, tumors were washed, fixed, and sectioned. The sections were stained with an anti-T7 phage antibody (light colored staining), an anti-CD31 antibody (medium shade staining—none visible in A, very little present in B), and DAPI (gray staining), and viewed with a confocal microscope. Note that the iRGD phage has penetrated deep into the tumor, and that the process was inhibited by sodium azide, low temperature, or an anti-neuropilin-1 antibody. Scale bar=200 μm.

The CendIT effect, that the new tumor targeting methodology is based on, is distinct from the so-called Enhanced Permeability and Retention (EPR) effect. The EPR is due to leakiness of tumor vessels, which allows extravasation of materials into the tissue surrounding tumor vessels (Maeda et al., 2003). The CendIT effect is clearly much more effective than the EPR (for example, see FIG. 13). The CendIT effect can possibly be an active process and not a passive vascular leakage phenomenon, because (i) CendIT is receptor (neuropilin-1)-mediated, and EPR is not (ii) the CendIT causes extravasation within minutes, whereas EPR shows a slow onset and gradually peaks within 6-8 hours (Maeda et al., 2003), (iii) CendIT is effective with small molecules, whereas EPR prolongs the retention within the tumor of molecules larger than 45-kDa (Maeda et al., 2003), and (iv) phage expressing iRGD penetrates into the tumor tissue even in the absence of circulation, and that this process is neuropilin-1 and energy dependent (FIG. 19). However, there can be a CendlT component in EPR (and vascular permeability in general) because VEGF-165, which is involved in these processes, has an active CendR motif at the C-terminus (Maeda et al., 2003; Jia et al., 2006; Soker et al., 1998; Teesalu et al., 2009).

The CendlT-based iRGD-combo system is a conceptually new approach to tumor treatment; co-administering a peptide with a free drug enhances drug access to tumors. Conventional drug delivery systems often require extensive chemistry to attach the targeting elements (e.g. peptides and antibodies) to the drug. The disclosed system provides a significant advantage over such systems that the activity of a drug can be enhanced without any modification (see FIG. 12). In addition, conventional systems rely on antigen-receptor docking at the target (synaphic targeting), thus suffer from being saturated due to the limited amount of receptors available on the tumor vasculature. In contrast, the combo system is not saturable. Once the penetration signal (CendlT effect) is triggered, any given concentration of molecules is likely to extravasate and reside within the tumor tissue as shown with different doses of drugs in this study.

The iRGD-combo system is highly tumor selective. The tumor specificity stems from the 3-step tumor targeting mechanism of iRGD (Sugahara et al., 2009 and 2010; FIG. 12); the iRGD peptide (i) targets the tumor vasculature with its RGD, (ii) is then cleaved to become a CendR (the CRGDK/R fragment, SEQ ID NO:37), (iii) and binds to neuropilion-1 to trigger the CendlT effect. Unless it is cleaved, iRGD does not display CendR characters or have a measurable affinity to the tissue-penetration receptor, neuropilin-1, thus gives minimal background in normal tissues (Sugahara et al., 2009). Similar attempts were made with VEGF to increase the vascular permeability to accomplish deeper penetration of molecules and nanoparticles into tumor tissue (Monsky et al., 1999). VEGF, when locally superfused on tumors, successfully enhanced extravasation of albumin and nanoparticles within the tumor up to 4-fold. However, similar effects were observed in the skin with local injection of VEGF (Monsky et al., 1999; Murohara et al., 1998; Teesalu et al., 2009) and in the lung with systemic injection of untargeted CendR peptides (Teesalu et al., 2009), demonstrating the requirement of a targeting element for successful tumor-selective CendlT effects.

Figure 20:
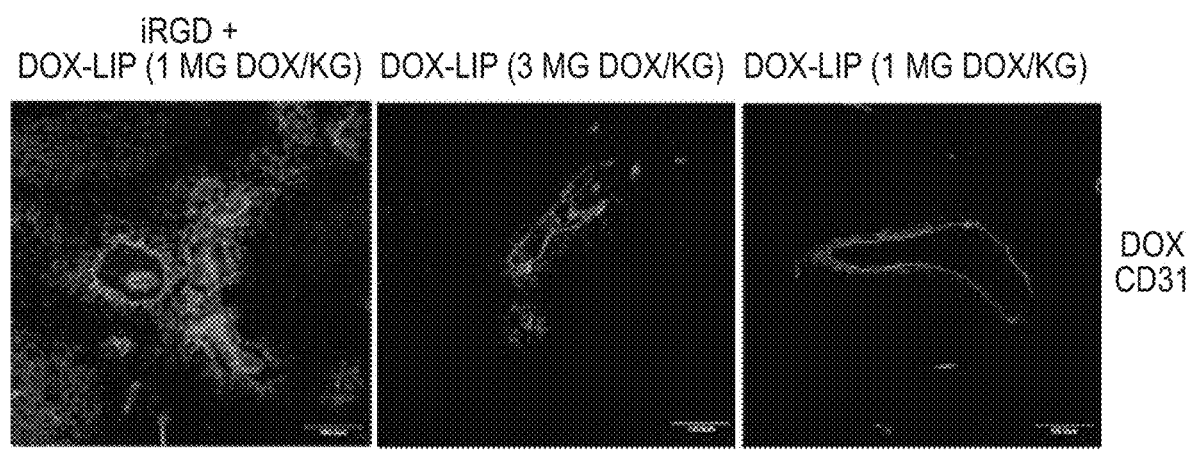
FIG. 20 shows the spreading of DOX-liposomes within tumor tissue after treatment with the iRGD-combo regimen. Tumors collected after the treatment studies in FIG. 14C were fixed and sectioned. The sections of the tumors from FIG. 14C were immunofluorescently stained with an anti-CD31 antibody. The gray specs seen all over in the left panel represent Dox staining. Note the wide spreading of DOX after 2-3 weeks of treatment with the iRGD-combo regimen. Representative images from each of 5 tumors are shown. Scale bars=200 μm.

The 4-fold increase in the accumulation of molecules in tumors, but not elsewhere, was achieved with little optimization work; it is likely that this ratio can be improved, for example, by employing multimeric iRGD on nanoparticles, structurally stabilized iRGD, other tumor-homing CendR peptides (Hoffman et al., 2003; Joyce et al., 2003; Laakkonen et al., 2002; Porkka et al., 2002), or peptide combinations, or by optimizing the dose and administration schedules. Interestingly, tumors collected after treatment with the combo regimen (FIG. 14B) showed strikingly wide distribution of the drugs within the tumors compared to those treated with the drugs alone at the same or higher doses (FIG. 20). Tumors collected from the herceptin combo regimen (FIG. 18C) showed wide distribution of herceptin within the tumors compared to those treated with the drugs alone at the same or higher doses. Therefore, multiple injections of the combo regimen or a long circulation time can help increase the accumulation of compounds in the tumor. In addition, as demonstrated with Herceptin, using anti-cancer agents with affinity to the tumor tissue can help improve this system.

The accumulation of molecules in tumors makes it possible to achieve greater anti-tumor activity. This point has been demonstrated in 2 tumor models using different drugs with tissue penetration issues (Yuan et al., 1994; Thurber et al., 2008). As tumor delivery of every one of the 8 vastly different compounds we tested could be enhance (from a 1-kDa molecule up to a nanoparticle of about 120 nm in diameter), it is possible that the activity of any drug can be improved with this system. Alternatively, lowering the dose makes it possible to reduce side effects while achieving the same level of anti-tumor activity as with conventional treatment. Thus, it can even be possible to revive drugs that have been previously rejected because of toxicity. Substantial advances in cancer treatment (and diagnosis) can ensue.

1. Methods

Cells and tumor models. MIA PaCa-2 human pancreatic ductal cancer, and 22Rv1, GFP-PC-3, and PPC1 human prostate cancer cell lines were cultured in Dulbecco's Modified Eagle Medium (DMEM) supplemented with 10% fetal bovine serum and penicillin/streptomycin. BT474 human breast cancer cell line was cultured in SFM4MAB medium supplemented with 10% fetal bovine serum and penicillin/streptomycin. Xenografts were created by injecting BALB/c athymic nude mice (Harlan Sprague Dawley, Inc., Indianapolis, IN) orthotopically with $10^6$ human cancer cells. For the BT474 xenografts, 17β-estradiol pellets (Innovative Research of America, Sarasota, FL) were implanted subcutaneously into the back of the mice one day prior to the orthotopic inoculation of $5 \times 10^6$ tumor cells suspended in matrigel (BD Biosciences, San Jose, CA). Disseminated prostate tumors were generated by injecting $2 \times 10^6$ GFP-PC-3 cells into the left ventricle of the heart. The disseminated tumor nodules were detected under UV light with an Illumatool Bright Light System LT-9900 (Lightools Research, Encinitas, CA). Transgenic mice for de novo pancreatic ductal adenocarcinoma were kindly provided by Dr. Douglas Hanahan at the University of California, San Francisco, CA. All animal experimentation was performed according to procedures approved by the Animal Research Committee at the University of California, Santa Barbara.

Preparation of compounds. Synthetic peptides (Teesalu et al., 2009), untargeted T7 phage expressing $G_7$ (SEQ ID NO:38) or $CG_7C$ (SEQ ID NO:39) peptides and iRGD phage (Teesalu et al., 2009), and fluorescein-labeled untargeted iron oxide nanoworms (Park et al., 2009) were prepared as described. DOX-liposomes were composed of 1,2-distearoyl-sn-glycero-3-phosphocholine, cholesterol, 1,2-dioleoyl-sn-glycero-3-phosphoethanolamine and 1,2-distearoyl-sn-glycero-3-phosphoethanolamine-N-[methoxy (polyethylene glycol)-2000] at 2:1.5:1.25:0.25 molar ratios. The lipids (from Avanti Polar Lipids, Alabaster, AL) were dissolved in chloroform and the solvent was evaporated with a thin film of moisture free nitrogen gas. The dried lipid film was hydrated with 300 mM ammonium phosphate (pH 7.4) for 1 hour at 60° C. The vial was then briefly vortexed and occasionally sonicated in a bath sonicator. The multilamellar vesicles, thus formed, were further sonicated using a Ti probe sonicator for 2-3 minutes until a translucent solution of small unilamellar vesicles was obtained. The small unilamellar vesicles were then sequentially extruded 11 times through polycarbonate membrane filters with pore diameters of 200 nm and 100 nm using an Avanti mini extruder (Avanti Polar Lipids). The buffer was then exchanged with Hepes-buffered saline (20 mM Hepes, 150 mM NaCl, pH 7.4) by gel filtration using NAP-10 or NAP-25 columns (GE Healthcare, Milwaukee, WI). DOX (Sigma-Aldrich, St. Louis, MO) was encapsulated in these liposomes through a trans-membrane phosphate gradient as described previously (Murphy et al., 2008). The DOX-liposomes were 119.8±7.6 nm in diameter (± indicates standard deviation) as measured by dynamic laser light scattering (refractive index, 1.59; viscosity, 0.89) on a Malvern Zetasizer Nano (Malvern, UK).

In vivo systemic permeability assay (iRGD-combo system). Tumor mice were injected intravenously with 100 µl of PBS containing either 1 µg of Evans Blue, 200 nmol of fluorecein-labeled CRGDC peptide (FAM-CRGDC, SEQ ID NO:36), 200 µg of fixable dextran (Molecular Probes, Eugene, OR), $10^9$ plaque-forming units (pfu) of $G_7$-expressing phage, 5 mg iron/kg of fluorecein-labeled untargeted iron-oxide nanoworms, 1 mg DOX/kg of DOX-liposomes, or 3 mg/kg of Herceptin (Genentech, South San Francisco, CA). Five min later, the mice received an intravenous injection with 100 µl of PBS with or without iRGD or control peptides at various concentrations. After the indicated time of circulation, the mice were perfused with 20 ml of PBS containing 1% BSA, and tissues were collected. For Evans Blue quantification, the dye was extracted from tissues using N,N-dimethylformamide for 24 hours at 37° C. and the dye content was quantified by measuring the absorbance at 600 nm with a spectrophotometer. Tissues from mice that received FAM-CRGDC (SEQ ID NO:36) were imaged under UV light with the Illumatool Bright Light System LT-9900 before being processed for immunofluorescence and immunohistochemistry. Tissues with dextran, nanoworms, DOX-liposomes, or Herceptin were processed for either or both immunofluorescence and immunohistochemistry. Quantification of the positive area in immunohistochemically stained sections, and total amount of antibodies within the tissues are described elsewhere in this manuscript.

In vivo skin permeability assay (modified Miles assay). Anesthetized nude mice were injected intravenously with a 3-tracer mixture consisting of 0.5% Evans Blue (MP Biomedicals, Irvine, CA), 13 µg of Quantilum recombinant luciferase (Promega, Madison, Wi) and $10^9$ pfu of $G_7$ (SEQ ID NO:38)-expressing phage particles in 150 µl of PBS. Ten minutes later, the mice were injected intradermally on the ventral side in two rows with 30 µl of PBS containing either 15 ng of VEGF-165 (Calbiochem, San Diego, CA) or peptides at various concentrations. Thirty minutes later, the mice were perfused through the heart and the skin containing the injection sites detected with Evans Blue was removed and extensively cleaned. Samples of the skin (4 mm in diameter) were punched out from the injection sites, homogenized in lysogeny broth with 1% NP40, and assayed for luciferase activity and phage titer.

Immunofluorescence. Tissue preparation and staining of the cryo-sections were performed as described (Sugahara et al., 2009). The primary antibodies were rat anti-mouse CD31 monoclonal (BD Biosciences) and rabbit anti-T7 phage polyclonal (Teesalu et al., 2009) antibodies. The secondary antibodies, Alexa Fluor 594 goat anti-rat, 647 goat anti-rat, and 488 donkey anti-rabbit antibodies were from Molecular Probes. In some experiments, tissue sections were stained with a TUNEL assay kit (In Situ Cell Death Detection Kit, TMR red; Roche Applied Science, Indianapolis, IN). The tissue sections were examined with a Fluoview 500 confocal microscope (Olympus America, Center Valley, PA).

Immunohistochemistry. Cryo-sections were immunohistochemically stained, scanned with a Scanscope CM-1 scanner, and positively stained areas were quantified with the ImageScope software (Aperio Technologies, Vista, CA; Sugahara et al., 2009). The primary antibodies used were biotinylated rabbit anti-FITC/Oregon green polyclonal (Molecular Probes), mouse anti-dextran monoclonal (Stemcell Technologies, Vancouver, BC, Canada), and biotinylated rat anti-mouse CD31 monoclonal (BD Biosciences). Secondary antibodies were biotinylated goat anti-rabbit (Pierce Biotechnology, Rockford, IL), goat anti-mouse (Vector laboratories, Burlingame, CA), and rabbit anti-human (Pierce Biotechnology) polyclonal antibodies. In some experiments, tissue sections were stained with a TUNEL assay kit (In Situ Cell Death Detection Kit, POD; Roche Applied Science).

Quantification of DOX in tumors and normal tissues. The quantification was performed as described elsewhere (Mayer et al., 1997). Briefly, mice bearing 22Rv1 orthotopic tumors were intravenously injected with DOX-liposomes (5 mg DOX/kg) with or without iRGD (4 µmol/kg), or with empty liposomes. After 3 hrs, the mice were perfused through the heart, and the tumors and organs of interest were collected. The tissues were mechanically homogenized in a mixture of 1% sodium dodecyl sulfate and 1 mM $H_2SO_4$ in water. Subsequently, DOX was extracted by adding 2 ml of chloroform/isopropyl alcohol (1:1, v/v) followed by vortexing and freeze/thaw cycles. The samples were centrifuged at 14,000×g for 15 min and the organic phase (lowest phase) was measured for DOX at OD490 nm with a spectrophotometer.

22Rv1 xenograft treatment with DOX-liposomes. Nude mice bearing 2 week-old 22Rv1 orthotopic xenografts (typically about 250 mm$^3$ in tumor volume) received daily intravenous injections of DOX-liposomes (1 or 3 mg DOX/kg) or PBS, combined with daily intravenous injections of 2 µmol/kg iRGD, cyclo(-RGDfK-, SEQ ID NO:40), or PBS. The mice were weighed every 4 days during the treatment. After 17 days of treatment, the mice were perfused through the heart and tissues were harvested. The tumors were weighed and heart samples were processed for histology as described elsewhere in this study.

Competitive ELISA for quantification of Herceptin. The ELISA is based on a competitive binding principle between Herceptin and a biotinylated human IgG. A standard curve was created each time when a measurement was performed. For the standard curve, microtiter wells coated with 5 µg/ml rabbit anti-human IgG (SouthernBiotech) were incubated with a mixture of various concentrations of Herceptin (ranging from 0.01 to 10 µg/ml) and 1 µg/ml at final concentration of biotinylated human IgG (Rockland Immunochemicals, Gilbertsville, PA). After 2 hours of incubation at room temperature, the wells were washed with PBS containing 0.01% Tween 20, added with streptavidin-conjugated horseradish peroxidase, and incubated for 30 min at room temperature. The amount of biotinylated human IgG captured on the microtiter wells was quantified with 2,2-azino-bis(3-etylbenzthiazoline-6-sulfonic acid) as a substrate and the absorbance at 405 nm was measured. A standard curve was drawn by plotting the absorbance against the concentration of Herceptin, and used to calculate the concentration of Herceptin in tissue extracts. The amount of Herceptin that entered the BT474 xenografts and tissues was measured in the same competitive ELISA system by substituting the standard Herceptin samples with tissue extracts. The tissue extracts were prepared as follows. Tissues from BT474 tumor mice that received Herceptin injections were homogenized in 1 ml of 0.1M Glycine pH2 with 1% Tween-20 and protease inhibitors (Complete Mini EDTA-free; Roche Applied Science) followed by a centrifugation (4° C., 10 min, 14,000 rpm). Six hundred microliters of supernatant was collected, and added with 150 µl of 1M Tris pH8 and 50 µl of 5M NaCl.

BT474 xenograft treatment with Herceptin. Nude mice bearing BT474 orthotopic xenografts (about 100 mm³ in tumor volume) were intravenously treated every 4 days with Herceptin at 3 mg/kg for the first injection at day 21 after tumor cell inoculation (=day 0 in the graph) and 1.5 mg/kg for subsequent injections. The Herceptin treatment was combined with daily injections of 4 µmol/kg iRGD or PBS on the days of Herceptin injections, and 2 µmol/kg iRGD or PBS on the other days. In some groups, Herceptin of 3-times higher dose than in the iRGD-combo regimen was used. After 24 days of treatment, the mice were perfused through the heart and tissues were harvested. Tumor volume was calculated using the following formula: volume (mm³)=x D)/2, where d is the smallest and D is the largest tumor diameters (Karmali et al., 2009).

Ex vivo tumor penetration assay (tumor dipping assay). PPC1 human prostate subcutaneous tumors (about 1 cm in diameter) were excised and maintained in DMEM containing $10^9$ pfu/ml of T7 phage expressing iRGD or $G_7$ (SEQ ID NO:38) peptides and various inhibitors. The tumors were first incubated with the inhibitors for 20 min at 4° C. The indicated phage were added to the solution and the tumors were further incubated for 90 min at 37° C. or 4° C. After the incubation, tumors were washed with cold DMEM containing 1% BSA, fixed, sectioned, immunofluorescently stained, and viewed with a confocal microscope.

Statistical analysis. Data were analyzed by two-tailed Student's t-test or one-way analysis of variance (ANOVA) followed by suitable post-hoc test. The results are summarized in table 5.

Throughout this application, various publications are referenced. The disclosures of these publications in their entireties are hereby incorporated by reference into this application in order to more fully describe the state of the art to which this invention pertains.

REFERENCES

Abi-Habib R J, Liu S, Bugge T H, Leppla S H, Frankel A E. (2004) A urokinase-activated recombinant diphtheria toxin targeting the granulocyte-macrophage colony-stimulating factor receptor is selectively cytotoxic to human acute myeloid leukemia blasts. Blood. 104, 2143-8.

Acevedo, L M., Barillas S., Weis, S M., Gothert, J R. and Cheresh., D A. Semaphorin 3A suppresses VEGF-mediated angiogenesis yet acts as a vascular permeability factor. *Blood* 111: 2674-2680, 2008.

Akerman, M. E., Chan, W. C. W., Laakkonen, P., Bhatia, S. N., and Ruoslahti, E. (2002) Nanocrystal targeting in vivo. Proc. Natl. Acad. Sci. USA 99, 12617-12621.

Allen, J. W., Johnson, R. S., and Bhatia, S. N. (2005). Hypoxic inhibition of 3-methylcholanthrene-induced CYP1A1 expression is independent of HIF-1alpha. Toxicol Lett 155, 151-159.

Altin J G, Pagler E B. (1995) A one-step procedure for biotinylation and chemical cross-linking of lymphocyte surface and intracellular membrane-associated molecules. Anal Biochem. 224, 382-9.

Andreasen, P. A., Egelund, R., and Petersen, H. H., The plasminogen activation system in tumor growth, invasion, and metastasis. Cell. Mol. Life Sci. 57, 25-40 (2000).

Arap, W., Pasqualini, R., and Ruoslahti, E. (1998) Cancer treatment by targeted drug delivery to tumor vasculature in a mouse model. Science 279, 377-380.

Arap, W., W. Haedicke, M. Bernasconi, R. Kain, D. Rajotte, S. Krajewski, H. M. Ellerby, D. E. Bredesen, R. Pasqualini, and E. Ruoslahti, (2002) Targeting the prostate for destruction through a vascular address. Proc. Natl Acad. Sci. USA 99, 1527-1531.

Arola, O. J., Saraste, A., Pulkki, K., Kallajoki, M., Parvinen, M., and Voipio-Pulkki, L. M. (2000). Acute doxorubicin cardiotoxicity involves cardiomyocyte apoptosis. Cancer Res 60, 1789-1792.

Assa-Munt, N., Jia, X., Laakkonen, P., and Ruoslahti, E. (2001) Solution structures and integrin binding activities of an RGD peptide with two isomers. Biochemistry 40, 2373-2378.

Backhaus, R., Zehe, C., Wegehingel, S., Kehlenbach, A., Schwappach, B., and Nickel, W. (2004) Unconventional protein secretion: membrane translocation of FGF-2 does not require protein unfolding. J. Cell Sci. 117, 1727-1736.

Bagri, A., Tessier-Lavigne, M., Watts, R. J. Neuropilins in tumor biology. Clin Cancer Res. 15:1860-4, 2009.

Barinaga, M., Peptide-guided cancer drugs show promise in mice. Science. 279:323-324 (1998).

Barrett, Alan J., Rawlings, Neil D., and Woessner, J. F., Handbook of proteolytic enzymes. (Academic Press, San Diego, 1998).

Bartlett, D W., Su, H., Hildebrandt, I J., Weber, W. A., Davis, M E. (2007). Impact of tumor-specific targeting on the biodistribution and efficacy of siRNA nanoparticles measured by multimodality in vivo imaging. Proc. Natl. Acad. Sci USA. 104, 15549-15554.

Biacchesi, S. et al., Modification of the trypsin-dependent cleavage activation site of the human metapneumovirus fusion protein to be trypsin independent does not increase replication or spread in rodents or nonhuman primates. J. Virol. 80, 5798-5806 (2006).

Blasi F, Carmeliet P. (2002) uPAR: a versatile signalling orchestrator. Nat Rev Mol Cell Biol. 3, 932-43.

Brewis, N. D., Phelan, A., Normand, N., Choolun, E., and O'Hare, P. (2003) Particle assembly incorporating a VP22-BH3 fusion protein, facilitating intracellular delivery, regulated release, and apoptosis. Mol. Ther. 7, 262-270.

Brooks, P. C., Montgomery, A. M., Rosenfeld, M., Reisfeld, R. A., Hu, T., Klier, G., and Cheresh, D. A. (1994). Integrin alpha v beta 3 antagonists promote tumor regression by inducing apoptosis of angiogenic blood vessels. Cell 79, 1157-1164.

Brown, D. and Ruoslahti, E. Metadherin, a cell-surface protein in breast tumors that mediates lung metastasis. *Cancer Cell* 5: 365-374 (2004).

Chambers, T. J., Hahn, C. S., Galler, R., and Rice, C. M., Flavivirus genome organization, expression, and replication. Annu. Rev. Microbiol. 44, 649-688 (1990).

Chatterjee, J., Gilon, C., Hoffman, A. and Kessler, H. N-Methylation of Peptides: A New Perspective in Medicinal Chemistry. Accounts Chem. Res. 41:1331-1342, 2008.

Choi Y, McCarthy J R, Weissleder R, Tung C H. (2006) Conjugation of a photosensitizer to an oligoarginine-based cell-penetrating peptide increases the efficacy of photodynamic therapy. ChemMedChem. 1, 458-463.

Christian, S., Pilch, J., Porkka, K., Laakkonen, P., and Ruoslahti, E. (2003) Nucleolin expressed at the cell surface is a marker of endothelial cells in tumor blood vessels. J Cell Biol. 163, 871-878.

Curnis, F., Gasparri, A., Sacchi, A., Longhi, R. & Corti, A. Coupling tumor necrosis factor-a with $a_v$ integrin ligands improves its antineoplastic activity. *Cancer Res.* 64, 565-571 (2004).

Debela M, Magdolen V, Schechter N, Valachova M, Lottspeich F, Craik C S, Choe Y, Bode W, Goettig P. (2006)

Specificity profiling of seven human tissue kallikreins reveals individual subsite preferences J Biol Chem. 281, 25678-88.

Derfus, A., Chen A., Dal-Hee M., Ruoslahti, E., Bhatia, S., (2007) Targeted Quantum Dot Conjugates for siRNA Delivery Bioconjug Chem. 18, 1391-6.

Derossi D, Chassaing G, Prochiantz A. (1998) Trojan peptides: the penetratin system for intracellular delivery. Trends Cell Biol. 8, 84-7.

Deshayes S. Morris M C. Divita G. Heitz F. 2005 Interactions of primary amphipathic cell penetrating peptides with model membranes: consequences on the mechanisms of intracellular delivery of therapeutics. Current Pharmaceutical Design. 11, 3629-38.

Devine, D. V. and Bradley, A. J. (1998) The complement system in liposome clearance: can complements deposition be inhibited? Adv Drug Delivery Rev 32, 19-39.

Dharap S S, Minko T. (2003) Targeted proapoptotic LHRH-BH3 peptide. Pharm Res. 20, 889-96.

Duchardt F. Fotin-Mleczek M. Schwarz H. Fischer R. Brock R. (2007) A comprehensive model for the cellular uptake of cationic cell-penetrating peptides. Traffic. 8, 848-66.

Dykxhoorn, D. M., Palliser, D., and Lieberman, J. (2006) The silent treatment: siRNAs as small molecule drugs. Gene Ther. 13, 541-552.

Elango, N., Varsanyi, T. M., Kovamees, J., and Norrby, E., The mumps virus fusion protein mRNA sequence and homology among the paramyxoviridae proteins. J. Gen. Virol. 70, 801-807 (1989).

Eliceiri, B. P., and Cheresh, D. A. (2001). Adhesion events in angiogenesis. Curr Opin Cell Biol 13, 563-568.

Elliott, G. and O'Hare, P. (1997) Intercellular trafficking and protein delivery by a herpesvirus structural protein. Cell 88, 223-233.

Esmon, C. T., Cell mediated events that control blood coagulation and vascular injury. Annu. Rev. Cell. Biol. 9, 1-26 (1993).

Fenart, L. and Cecchelli R. (2003) Protein transport in cerebral endothelium. In vitro transcytosis of transferrin. Meth. Mol. Med. 89, 277-290.

Fogal, V., Zhang, L., and Ruoslahti, E. Mitochondrial/Cell surface protein p32/gC1qR as a molecular target in tumor cells and tumor stroma. *Cancer Res.* 68: 7210-7218, 2008.

Frankel, A. D. and Pabo, C. O., Cellular uptake of the tat protein from human immunodeficiency virus. Cell 55, 1189-1193 (1988).

Gammon, S. T. et al., Quantitative Analysis of Permeation Peptide Complexes Labeled with Technetium-99m: Chiral and Sequence-Specific Effects on Net Cell Uptake Bioconjugate Chem. 14, 368-376 (2003).

Geier, M. R., Trigg, M. E., and Merril, C. R. (1973) Fate of bacteriophage lambda in non-immune germ-free mice. Nature 246, 221-223.

Geretti, E., Shimizu, A., and Klagsbrun, M., Neuropilin structure governs VEGF and semaphorin binding and regulates angiogenesis. Angiogenesis 11, 31-39 (2008).

Ghebrehiwet, B., Jesty, J., and Peerschke, E. I. (2002). gC1q-R/p33: structure-function predictions from the crystal structure. Immunobiology 205, 421-432.

Gonzalez-Reyes, L. et al., Cleavage of the human respiratory syncytial virus fusion protein at two distinct sites is required for activation of membrane fusion. Proc. Natl. Acad. Sci. USA 98, 9859-9864 (2001).

Gordon, V. M. et al., Proteolytic activation of bacterial toxins by eukaryotic cells is performed by furin and by additional cellular proteases. Infect. Immun 63, 82-87 (1995).

Green, M. and Loewenstein, P. M., Autonomous functional domains of chemically synthesized human immunodeficiency virus tat trans-activator protein. Cell 55, 1179-1188 (1988).

Gump J M. And Dowdy S F. TAT transduction: the molecular mechanism and therapeutic prospects. *Trends Molec. Med.* 13:443-448, 2007.

Hambley, T. W. and Hait, W. N. Is Anticancer Drug Development Heading in the Right Direction? *Cancer Res.* 69: 1259-1262, 2009.

Hamzah J, Nelson D., Moldenhauer G., Arnold B., Hammerling G. and Ganss R. Vascular Targeting of Anti-CD40/IL2 into Autochthonous Tumors Enhances Immunotherapy, J. Clin. Invest. 118: 1691-1699, 2008.

Hansen M, Wind T, Blouse G E, Christensen A, Petersen H H, Kjelgaard S, Mathiasen L, Holtet T L, Andreasen P A. (2005) A urokinase-type plasminogen activator-inhibiting cyclic peptide with an unusual P2 residue and an extended protease binding surface demonstrates new modalities for enzyme inhibition. J Biol Chem. 280, 38424-37.

Heldin, C. H., Rubin, K., Pietras, K., and Ostman, A. (2004). High interstitial fluid pressure—an obstacle in cancer therapy. Nat Rev Cancer 4, 806-813.

Hezel, A. F., Kimmelman, A. C., Stanger, B. Z., Bardeesy, N., and Depinho, R. A. (2006). Genetics and biology of pancreatic ductal adenocarcinoma. Genes Dev 20, 1218-1249.

Hoffman, J. A., Giraudo E., Singh, M., Inoue, M., Porkka, K., Hanahan D., and Ruoslahti E. (2003) Progressive vascular changes in a transgenic mouse model of squamous cell carcinoma. Cancer Cell 4, 383-391.

Hoffman, J. A., Laakkonen, P., Porkka, K., Bernasconi, M., and Ruoslahti, E. (2004) In vivo and ex vivo selections using phage-displayed libraries. In Phage Display: A Practical Approach, T. Clarkson and H. Lowman, eds. (Oxford, U.K.: Oxford University Press), Chap 10, p 171.

Hood, J. D., Bednarski, M., Frausto, R., Guccione, S., Reisfeld, R. A., Xiang, R., and Cheresh, D. A. (2002) Tumor regression by targeted gene delivery to the neovasculature. Science 296, 2404-2407.

Jain R K. Vascular and interstitial barriers to delivery of therapeutic agents in tumors, Cancer Metastasis Rev, 1990, 9: 253-266.

Jain R K., Tong, R. T. and Munn, L. L. Effect of vascular normalization by antiangiogenic therapy on interstitial hypertension, peritumor edema, and lymphatic metastasis: insights from a mathematical model. *Cancer Res.* 67: 2729-2735, 2007.

Jain, R K. (2005) Normalization of tumor vasculature: An emerging concept in anti-angiogenic therapy. Science 307, 58-62.

Jarvinen T. and Ruoslahti E. (2007). Molecular changes in the vasculature of injured tissues. Am. J. Path. 171:702-711.

Jia et al. Characterization of a bicyclic peptide neuropilin-1 (NP-1) antagonist (EG3287) reveals importance of vascular endothelial growth factor exon 8 for NP-1 binding and role of NP-1 in KDR signaling. *J. Biol.* Chem. 281: 13493-13502, 2006.

Jia, H. et al., Cysteine-rich and basic domain HIV-1 Tat peptides inhibit angiogenesis and induce endothelial cell apoptosis. Biochem. Biophys. Res. Commun. 283, 469-479 (2001).

Jiang, T., Olson, E. S., Nguyen, Q. T., Roy, M., Jennings, P. A., and Tsien, R. Y. (2004). Tumor imaging by means of proteolytic activation of cell-penetrating peptides. Proc. Natl. Acad. Sci. USA 101, 17867-17872.

Johannsen, E. et al., Proteins of purified Epstein-Barr virus. Proc. Natl. Acad. Sci. USA 101, 16286-16291 (2004).

Joliot, A., Pernelle, C., Deagostini-Bazin, H., and Prochiantz, A., Antennapedia homeobox peptide regulates neural morphogenesis. Proc. Natl. Acad. Sci. USA 88, 1864-1868 (1991).

Joyce, J. A., Laakkonen P., Bernasconi, M., Bergers, G., Ruoslahti, E., and Hanahan, D. (2003) Stage-specific vascular markers revealed by phage display in a mouse model of pancreatic islet tumorigenesis. Cancer Cell 4, 393-403.

Karmali, P. P., Kotamraju, V. R., Kastantin, M., Black, M., Missirlis, D., Tirrell, M., and Ruoslahti, E. (2009). Targeting of albumin-embedded paclitaxel nanoparticles to tumors. Nanomedicine 5, 73-82.

Ke, S. H. et al., Optimal subsite occupancy and design of a selective inhibitor of urokinase. J. Biol. Chem. 272, 20456-20462 (1997).

Kelly K A. Nahrendorf M. Yu A M. Reynolds F. Weissleder R. (2006). In vivo phage display selection yields atherosclerotic plaque targeted peptides for imaging Molecular Imaging & Biology. 8(4):201-207.

Kerbel, R. S. and B A Kamen, (2004) The anti-angiogenic basis of metronomic chemotherapy. Nat Rev Cancer 4, 423-436.

Kirpotin, D. B. et al. Antibody Targeting of Long-Circulating Lipidic Nanoparticles Does Not Increase Tumor Localization but Does Increase Internalization in Animal Models. *Cancer Res.* 66, 6732-6740 (2006).

Klenk H D, Garten W. (1994) Host cell proteases controlling virus pathogenicity. Trends Microbiol. 1994 2, 39-43.

Koivunen, E., Gay, D. A., and Ruoslahti, E. (1993). Selection of peptides binding to the alpha 5 beta 1 integrin from phage display library. J Biol Chem 268, 20205-20210.

Koivunen, E., Wang, B., and Ruoslahti, E. (1995). Phage libraries displaying cyclic peptides with different ring sizes: ligand specificities of the RGD-directed integrins. Biotechnology (NY) 13, 265-270.

Kruithof E K. (1988) Plasminogen activator inhibitors—a review. Enzyme. 40, 113-21. Kumar P, Wu H, McBride J L, Jung K E, Kim M H, Davidson B L, Lee S K, Shankar P, Manjunath N. Transvascular delivery of small interfering RNA to the central nervous system. Nature 448: 39-43, 2007.

Laakkonen, P., Akerman, M. E., Biliran, H., Yang, M., Ferrer, F., Karpanen, T., Hoffman, R. M., and Ruoslahti, E. (2004) Antitumor activity of a homing peptide that targets tumor lymphatics and tumor cells. Proc. Natl. Acad. Sci. USA. 101, 9381-9386.

Laakkonen, P., Porkka, K., Hoffman, J. A., and Ruoslahti, E., A tumor-homing peptide with a targeting specificity related to lymphatic vessels. Nature Med. 8, 751-755 (2002b).

Laakkonen, P., Porkka, K., Hoffman, J. A., and Ruoslahti, E. (2002a) A tumor-homing peptide with a lymphatic vessel-related targeting specificity. Nature Med 8, 743-751.

Langel, Ülo, Handbook of cell-penetrating peptides, 2nd ed. (CRC/Taylor & Francis, Boca Raton, 2007).

Li, H., Sun, H., and Qian, Z. M. (2002) The role of the transferrin-transferrin-receptor system in drug delivery and targeting. Trends Pharmacol. Sci. 23, 206-209.

Li, S-D. and Huang, L. (2006). Ann N.Y. Acad. Sci. 1082, 1-8.

Liu S, Bugge T H, Leppla S H. (2001) Targeting of tumor cells by cell surface urokinase plasminogen activator-dependent anthrax toxin. J Biol Chem. 276, 17976-84.

Liu, C., Huang, H., Donate, F., Dickinson, C., Santucci, R., Sheikh, A., Vessella, R. and Edgington, T. S. Prostate-specific Membrane Antigen Directed Selective Thrombotic Infarction of Tumors. *Cancer Res.* 62: 5470-5475, 2002.

Liu, Z. et al. In vivo biodistribution and highly efficient tumour targeting of carbon nanotubes in mice. *Nat. Nanotech.* 2, 47-52 (2007).

Mae M. Langel U. (2006). Cell-penetrating peptides as vectors for peptide, protein and oligonucleotide delivery. Current Opinion in Pharmacology. 6, 509-514.

Maeda, H., Fang, J., Inutsuka, T., and Kitamoto, Y. (2003). Vascular permeability enhancement in solid tumor: various factors, mechanisms involved and its implications. Int Immunopharmacol 3, 319-328.

Mayer, L. D., Dougherty, G., Harasym, T. O., and Bally, M. B. (1997). The role of tumor-associated macrophages in the delivery of liposomal doxorubicin to solid murine fibrosarcoma tumors. J Pharmacol Exp Ther 280, 1406-1414.

McCarthy J R. Kelly K A. Sun E Y. Weissleder R. (2007). Targeted delivery of multifunctional magnetic nanoparticles. Nanomedicine. 2, 153-167.

Meade B R. Dowdy S F. (2007). Exogenous siRNA delivery using peptide transduction domains/cell penetrating peptides. Advanced Drug Delivery Reviews. 59(2-3):134-40.

Medarova Z, Pham W, Farrar C, Petkova V, Moore A. (2007) In vivo imaging of siRNA delivery and silencing in tumors. Nat Med. 13, 372-7.

Merril, C. R., Biswas, B., Carlton, R., Jensen, N. C., Creed, G. J., Zullo, S., and Adhya, S. (1996) Long-circulating bacteriophage as antibacterial agents. Proc. Natl. Acad. Sci. USA 93, 3188-3192.

Miles, A. A., and Miles, E. M. (1952). Vascular reactions to histamine, histamine-liberator and leukotaxine in the skin of guinea-pigs. J Physiol 118, 228-257.

Minchinton, A. I., and Tannock, I. F. (2006). Drug penetration in solid tumours. Nat Rev Cancer 6, 583-592.

Moghimi, S. M., Hunter, A. C. & Murray, J. C. (2001). Long-circulating and target-specific nanoparticles: Theory to practice. Pharm. Rev. 53, 283-318.

Monsky, W. L., Fukumura, D., Gohongi, T., Ancukiewcz, M., Weich, H. A., Torchilin, V. P., Yuan, F., and Jain, R. K. (1999). Augmentation of transvascular transport of macromolecules and nanoparticles in tumors using vascular endothelial growth factor. Cancer Res 59, 4129-4135.

Moulard, M. and Decroly, E., Maturation of HIV envelope glycoprotein precursors by cellular endoproteases. Biochim. Biophys. Acta 1469, 121-132 (2000).

Murohara, T., Horowitz, J. R., Silver, M., Tsurumi, Y., Chen, D., Sullivan, A., and Isner, J. M. (1998). Vascular endothelial growth factor/vascular permeability factor enhances vascular permeability via nitric oxide and prostacyclin. Circulation 97, 99-107.

Murphy, E. A., Majeti, B. K., Barnes, L. A., Makale, M., Weis, S. M., Lutu-Fuga, K., Wrasidlo, W., and Cheresh, D. A. (2008). Nanoparticle-mediated drug delivery to tumor vasculature suppresses metastasis. Proc Natl Acad Sci USA 105, 9343-9348.

Newton J R. Kelly K A. Mahmood U. Weissleder R. Deutscher S L. (2006). In vivo selection of phage for the optical imaging of PC-3 human prostate carcinoma in mice. Neoplasia (New York). 8, 772-780.

Nyberg P, Ylipalosaari M, Sorsa T, Salo T. (2006) Trypsins and their role in carcinoma growth. Exp Cell Res. 312, 1219-28.

Pakalns. T., Haverstick, K. L., Fields, G. B., McCarthy, J. B., Mooradian, D. L., and Tirrell, M. (1999) Cellular recognition of synthetic peptide amphiphiles in self-assembled monolayer films. Biomaterials. 20, 2265-2279.

Palmacci, S. and Josephson, L. (Advanced Magnetics, Inc. (Cambridge, MA) USA, 1993).

Park, J-H., v Maltzahn G. A., Zhang, L., Schwartz, M. P., Ruoslahti, E., Bhatia, S. N., and Sailor, M. J. Magnetic iron oxide nanoworms for tumor targeting and imaging. Adv. Mater. 20: 1630-1635 (2008).

Park, J. H., von Maltzahn, G., Zhang, L., Derfus, A. M., Simberg, D., Harris, T. J., Ruoslahti, E., Bhatia, S. N., and Sailor, M. J. (2009). Systematic surface engineering of magnetic nanoworms for in vivo tumor targeting. Small 5, 694-700.

Parr, M. J., Masin, D., Cullis, P. R., and Bally, M. B. (1997). Accumulation of liposomal lipid and encapsulated doxorubicin in murine Lewis lung carcinoma: the lack of beneficial effects by coating liposomes with poly(ethylene glycol). J Pharmacol Exp Ther 280, 1319-1327.

Pasqualini R. Koivunen E. Ruoslahti E. (1997). Alpha v integrins as receptors for tumor targeting by circulating ligands. Nat. Biotech. 15, 542-546.

Pasqualini, R. and Ruoslahti, E. Organ targeting in vivo using phage display peptide libraries. Nature 380:364-366 (1996).

Pilch J, Brown D M, Komatsu M, Jarvinen T A, Yang M, Peters D, Hoffman R M, Ruoslahti E. (2006) Peptides selected for binding to clotted plasma accumulate in tumor stroma and wounds. Proc Natl Acad Sci USA. 103, 2800-4.

Pirollo K F, Rait A, Zhou Q, Hwang S H, Dagata J A, Zon G, Hogrefe R I, Palchik G, Chang E H. (2007) Materializing the potential of small interfering RNA via a tumor-targeting nanodelivery system. Cancer Res. 67, 2938-43.

Polyakov, V. et al., Novel Tat-Peptide Chelates for Direct Transduction of Technetium-99m and Rhenium into Human Cells for Imaging and Radiotherapy Bioconjugate Chem. 11, 762-771 (2000).

Poon G M, Gariepy J. (2007) Cell-surface proteoglycans as molecular portals for cationic peptide and polymer entry into cells. Biochem Soc Trans. 35, 788-93.

Porkka, K., Laakkonen, P., Hoffman, J. A., Bernasconi, M., and Ruoslahti, E. (2002) Targeting of peptides to the nuclei of tumor cells and tumor endothelial cells in vivo. Proc. Natl. Acad. Sci. USA. 99, 7444-7449.

Puente X S, Sanchez L M, Overall C M, Lopez-Otin C. (2003) Human and mouse proteases: a comparative genomic approach. Nat Rev Genet. 4, 544-58.

Rajotte, D. and Ruoslahti, E. Membrane dipeptidase is the receptor for a lung-targeting peptide identified by in vivo phage display. J. Biol. Chem. 274:11593-11598 (1999).

Reynolds, A. R., Hart, I. R. et al. Stimulation of tumor growth and angiogenesis by low concentrations of RGD-mimetic integrin inhibitors. Nat. Med. published online 22 Mar. 2009.

Rijken D C. (1995) Plasminogen activators and plasminogen activator inhibitors: biochemical aspects. Baillieres Clin Haematol. 8, 291-312.

Rubinstein, D. B., Stortchevoi, A., Boosalis, M., Ashfaq, R., Ghebrehiwet, B., Peerschke, E. I., Calvo, F., and Guillaume, T. (2004). Receptor for the globular heads of C1q (gC1q-R, p33, hyaluronan-binding protein) is preferentially expressed by adenocarcinoma cells. Int J Cancer 110, 741-750.

Ruiz-Linares, A. et al., Processing of yellow fever virus polyprotein: role of cellular proteases in maturation of the structural proteins. J. Virol. 63, 4199-4209 (1989).

Ruoslahti, E. Vascular zip codes in angiogenesis and metastasis. Biochem. Soc. Transact. 32: 397-402 (2004).

Ruoslahti, E. (2002) Specialization of tumour vasculature. Nat. Rev. Cancer 2, 83-90.

Ruoslahti, E. and Rajotte, D. An address system in the vasculature of normal tissues and tumors. Annu. Rev. Immunol. 18:813-827 (2000).

Sanchez, A. J., Vincent, M. J., Erickson, B. R., and Nichol, S. T., Crimean-congo hemorrhagic fever virus glycoprotein precursor is cleaved by Furin-like and SKI-1 proteases to generate a novel 38-kilodalton glycoprotein. J. Virol. 80, 514-525 (2006).

Sandgren, S., Cheng, F., and Belting, M., Nuclear targeting of macromolecular polyanions by an HIV-Tat derived peptide. Role for cell-surface proteoglycans. J. Biol. Chem. 277, 38877-38883 (2002).

Simberg, D., Duza T., Park, J. H., Essler M., Pilch, J., Zhang, L., Derfus A. M., Yang M., Hoffman R. M., Bhatia, S., Sailor, M. J. and Ruoslahti, E. Biomimetic amplification of nanoparticle homing to tumors. Proc. Natl. Acad. Sci. USA 104: 932-936 (2007).

Sjoberg, M., Wallin, M., Lindqvist, B., and Garoff, H., Furin cleavage potentiates the membrane fusion-controlling intersubunit disulfide bond isomerization activity of leukemia virus Env. J. Virol. 80, 5540-5551 (2006).

Soker, S. et al., Neuropilin-1 is expressed by endothelial and tumor cells as an isoform-specific receptor for vascular endothelial growth factor. Cell 92, 735-745 (1998).

Sokoloff, A. V., Bock, I., Zhang, G., Sebestyen, M. G., and Wolff, J. A. (2000) The interactions of peptides with the innate immune system studied with use of T7 phage peptide display. Mol. Ther. 2, 131-139.

Sokoloff, A. V., Wong, S. C., Ludtke, J. J., Sebestyen, M. G., Subbotin, V. M., Zhang, G., Budker, T., Bachhuber, M., Sumita, Y., and Wolff, J. A. (2003) A new peptide ligand that targets particles and heterologous proteins to hepatocytes in vivo. Mol. Ther. 8, 867-872.

Spiridon, C. I., Ghetie, M. A., Uhr, J., Marches, R., Li, J. L., Shen, G. L., and Vitetta, E. S. (2002). Targeting multiple Her-2 epitopes with monoclonal antibodies results in improved antigrowth activity of a human breast cancer cell line in vitro and in vivo. Clin Cancer Res 8, 1720-1730.

Starzec, A., Vassy, R., Martin, A., Lecouvey, M., Di Benedetto, M., Crepin, M. and Perret, G Y. Antiangiogenic and antitumor activities of peptide inhibiting the vascular endothelial growth factor binding to neuropilin-1. Life Sci 79: 2370-2381, 2006.

Steinhauer, D. A., Role of hemagglutinin cleavage for the pathogenicity of influenza virus. Virology 258, 1-20 (1999).

Sternlicht, M. D. and Werb, Z., How matrix metalloproteinases regulate cell behavior. Annu. Rev. Cell. Dev. Biol. 17, 463-513 (2001).

Sugahara, K. N., Teesalu, T., Karmali, P. P., Kotamraju, V. R., Agemy, L., Girard, O. M., Hanahan, D., Mattrey, R. F., and Ruoslahti, E. (2009). Tissue-penetrating delivery of compounds and nanoparticles into tumors. Cancer Cell, 16(6):510-20 (2009)

Sugahara K N, Teesalu T, Karmali P P, Kotamraju V R, Agemy L, Greenwald D R, Ruoslahti E. Coadministration of a Tumor-Penetrating Peptide Enhances the Efficacy of Cancer Drugs. Science. 2010:328:1031-5.

Teesalu, T., Sugahara, K. N., Kotamraju, V. R., and Ruoslahti, E. (2009). C-end rule peptides mediate neuropilin-1-dependent cell, vascular, and tissue penetration. PNAS 106(38):16157-16162 (2009).

Thomas, G., Furin at the cutting edge: from protein traffic to embryogenesis and disease. Nature Rev. Mol. Cell. Biol. 3, 753-766 (2002).

Thurber, G. M., Schmidt, M. M., and Wittrup, K. D. (2008). Antibody tumor penetration: transport opposed by systemic and antigen-mediated clearance. Adv Drug Deliv Rev 60, 1421-1434.

Torgersen, M. L., Skretting, G., van Deurs, B., and Sandvig, K., Internalization of cholera toxin by different endocytic mechanisms. J. Cell. Sci. 114, 3737-3747 (2001).

Tucker, G. C. (2003). Alpha v integrin inhibitors and cancer therapy. Curr Opin Investig Drugs 4, 722-731.

Tyagi, M., Rusnati, M., Presta, M., and Giacca, M., Internalization of HIV-1 tat requires cell surface heparan sulfate proteoglycans. J. Biol. Chem. 276, 3254-3261 (2001).

Uhland, K., Matriptase and its putative role in cancer. Cell. Mol. Life Sci. 63, 2968-2978 (2006).

Uprichard, S. L. (2005) The therapeutic potential of RNA interference. FEBS Lett. 579, 5996-6007.

Vander Kooi, C. W. et al., Structural basis for ligand and heparin binding to neuropilin B domains. Proc. Natl. Acad. Sci. USA 104, 6152-6157 (2007).

Varsanyi, T. M., Jornvall, H., and Norrby, E., Isolation and characterization of the measles virus F1 polypeptide: comparison with other paramyxovirus fusion proteins. Virology 147, 110-117 (1985).

Vey, M. et al., Proteolytic processing of human cytomegalovirus glycoprotein B (gpUL55) is mediated by the human endoprotease furin. Virology 206, 746-749 (1995).

von Wronski, M. A., Raju, N., Pillai, R. et al. Tuftsin binds neuropilin-1 through a sequence similar to that encoded by exon 8 of vascular endothelial growth factor. *J Biol Chem* 281: 5702-5710, 2006.

Wadia, J. S., and Dowdy, S. F. (2002) Protein transduction technology. Curr. Opin. Biotech. 13, 52-56.

Waisman, David Morton, Plasminogen: structure, activation, and regulation. (Kluwer Academic/Plenum Publishers, New York, 2003).

Weissleder, R., Bogdanov, A., Neuwelt, E. A. & Papisov, M. (1995). Long-circulating iron oxide for MR imaging. Adv. Drug Deliv. Rev. 16, 321-334.

Weissleder, R., Kelly, K., Sun, E. Y., Shtatland, T. & Josephson, L. Cell-specific targeting of nanoparticles by multivalent attachment of small molecules. *Nat. Biotechnol.* 23, 1418-1423 (2005).

Wool-Lewis, R. J. and Bates, P., Endoproteolytic processing of the ebola virus envelope glycoprotein: cleavage is not required for function. J. Virol. 73, 1419-1426 (1999).

Yuan, F., Leunig, M., Huang, S. K., Berk, D. A., Papahadjopoulos, D., and Jain, R. K. (1994). Microvascular permeability and interstitial penetration of sterically stabilized (stealth) liposomes in a human tumor xenograft. Cancer Res 54, 3352-3356.

Zhang, H., Jiro Kusunose, J., Kheirolomoom, A., Seo, J. W., Qi, J., Watson, K. D., Lindfors, H. A., Ruoslahti, E., Julie L. Sutcliffe, J. L. and Ferrara, K. W. Dynamic imaging of arginine-rich heart-targeted vehicles in a mouse model. Biomaterials 29: 1976-1988, 2008.

Zhang, L. et al., Lymphatic zip codes in premalignant lesions and tumors. Cancer Res. 66, 5696-5706 (2006).

Zhang, L., Hoffman, J. A., and Ruoslahti, E. Molecular profiling of heart endothelial cells. *Circulation.* 112:1601-1611 (2005).

Zorko M, Langel U. (2005) Cell-penetrating peptides: mechanism and kinetics of cargo delivery. Adv Drug Deliv Rev. 57, 529-45.

It must be noted that as used herein and in the appended claims, the singular forms "a", "an", and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the method and compositions described herein. Such equivalents are intended to be encompassed by the following claims.

What is claimed is:

1. A composition comprising a CendR element and a co-composition, wherein the CendR element and the co-composition are not covalently coupled and not directly non-covalently associated with each other,
   wherein the CendR element comprises the sequence $X_1X_2X_3X_4$, wherein $X_1$ is selected from the group consisting of R, K or H,
   wherein $X_4$ is selected from the group consisting of R, K, H, or KG,
   wherein $X_2$ and $X_3$ can each be, independently, any amino acid, and
   wherein the CendR element does not comprise RRLR (SEQ ID NO:248), RRRR (SEQ ID NO:249), CRCDKPRR (SEQ ID NO:95), or TKPPR (SEQ ID NO:98).

2. A method of enhancing internalization, penetration, or both of a co-composition into or through a cell, tissue, or both, the method comprising:
   exposing the cell, tissue, or both to the composition of claim 1, thereby enhancing internalization, penetration, or both of the co-composition into or through the cell, tissue, or both.

3. The method of claim 2, wherein the cell, tissue, or both is in a subject.

4. The method of claim 3, wherein the cell, tissue, or both are exposed to the CendR element and the co-composition by administering the CendR element and the co-composition to the subject.

5. The method of claim 2, wherein the CendR element is associated with one or more accessory molecules.

6. The method of claim 5, wherein one or more of the accessory molecules are independently a homing molecule, a targeting molecule, an affinity ligand, a cell penetrating peptide, an endosomal escape molecule, a subcellular targeting molecule, a nuclear targeting molecule, or a combination thereof.

7. The method of claim 5, wherein the CendR element selectively homes to a tumor.

8. The method of claim 4, wherein the CendR element and the co-composition are administered to the subject simultaneously.

9. The method of claim 8, wherein the CendR element and the co-composition are administered to the subject in a single composition comprising the CendR element and the co-composition,
   wherein the CendR element and the co-composition are indirectly non-covalently associated with each other.

10. The method of claim 2, wherein the co-composition comprises a therapeutic agent.

11. The composition of claim 1, wherein the CendR element is associated with one or more accessory molecules.

12. The composition of claim 11, wherein one or more of the accessory molecules are independently a homing molecule, a targeting molecule, an affinity ligand, a cell penetrating peptide, an endosomal escape molecule, a subcellular targeting molecule, a nuclear targeting molecule, or a combination thereof.

13. The composition of claim 11, wherein the CendR element selectively homes to a tumor.

14. The composition of claim 1, wherein the CendR element is an activatable CendR element.

15. The composition of claim 14, wherein the activatable CendR element is a protease-activatable CendR element.

16. The composition of claim 1, wherein the co-composition comprises a therapeutic agent.

17. The composition of claim 1, wherein the CendR element is comprised in an amino acid sequence,
wherein the amino acid sequence is comprised in a protein or peptide.

18. The composition of claim 17, wherein the protein or peptide is circular.

19. A method of enhancing internalization, penetration, or both of a cargo composition into or through a cell, tissue, or both, the method comprising:
exposing the cell, tissue, or both to a composition comprising
(i) a co-composition; and
(ii) a CendR element conjugated to a cargo composition,
wherein the co-composition and the CendR element are not covalently coupled and not directly non-covalently associated with each other,
wherein the cargo composition and the CendR element are covalently coupled or non-covalently associated with each other,
wherein the CendR element comprises the sequence $X_1X_2X_3X_4$,
wherein $X_1$ is selected from the group consisting of R, K or H,
wherein $X_4$ is selected from the group consisting of R, K, H, or KG,
wherein $X_2$ and $X_3$ can each be, independently, any amino acid,
wherein the CendR element enhances internalization, penetration, or both of the cargo composition into or through the cell, tissue, or both, and
wherein the CendR element does not comprise RRLR (SEQ ID NO:248), RRRR (SEQ ID NO:249), CRCDKPRR (SEQ ID NO:95), or TKPPR (SEQ ID NO:98).

* * * * *

```
                         SEQUENCE LISTING

<160> NUMBER OF SEQ ID NOS: 267

<210> SEQ ID NO 1
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 1

Cys Arg Gly Asp Lys Arg Gly Pro Asp Cys
1               5                   10

<210> SEQ ID NO 2
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 2

Arg Pro Ala Arg Pro Ala Arg
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 3

Cys Arg Gly Asp Lys Gly Pro Asp Cys
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 4

Cys Arg Gly Asp Asp Gly Pro Asp Cys
1               5

<210> SEQ ID NO 5
<211> LENGTH: 4
<212> TYPE: PRT
<213> ORGANISM: Artificial Sequence
<220> FEATURE:
```

```
<223> OTHER INFORMATION: synthetic sequence
<220> FEATURE:
<221> NAME/KEY: MISC_FEATURE
<222> LOCATION: (1)..(4)

<400> SEQUENCE: 5

Arg Pro Ala Arg
1

<210> SEQ ID NO 6
<211> LENGTH: 4
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(4)
<220> FEATURE:
<221> NAME/KEY: MISC_FEATURE
<222> LOCATION: (2)..(3)
<223> OTHER INFORMATION: X can be any amino acid
<220> FEATURE:
<221> NAME/KEY: MISC_FEATURE
<222> LOCATION: (4)..(4)
<223> OTHER INFORMATION: X can be Lys or Arg

<400> SEQUENCE: 6

Arg Xaa Xaa Xaa
1

<210> SEQ ID NO 7
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(5)

<400> SEQUENCE: 7

Cys Arg Glu Lys Ala
1               5

<210> SEQ ID NO 8
<211> LENGTH: 12
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(12)

<400> SEQUENCE: 8

Gly Gly Gly Arg Lys Lys Arg Ser Thr Gly Gly Gly
1               5                   10

<210> SEQ ID NO 9
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 9
```

```
Gly Gly Gly Arg Lys Lys Arg
1               5

<210> SEQ ID NO 10
<211> LENGTH: 12
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(12)

<400> SEQUENCE: 10

Gly Gly Gly Leu Val Pro Arg Gly Ser Gly Gly Gly
1               5                   10

<210> SEQ ID NO 11
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 11

Gly Gly Gly Leu Val Pro Arg
1               5

<210> SEQ ID NO 12
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(13)

<400> SEQUENCE: 12

Gly Gly Gly Pro Cys Pro Gly Arg Val Val Gly Gly Gly
1               5                   10

<210> SEQ ID NO 13
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 13

Gly Gly Gly Pro Cys Pro Gly Arg
1               5

<210> SEQ ID NO 14
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(13)

<400> SEQUENCE: 14
```

```
Gly Gly Gly Pro Gly Ser Gly Arg Ser Ala Gly Gly Gly
1               5                   10
```

<210> SEQ ID NO 15
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 15

```
Gly Gly Gly Pro Gly Ser Gly Arg
1               5
```

<210> SEQ ID NO 16
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(13)

<400> SEQUENCE: 16

```
Gly Gly Gly Pro Gly Ser Gly Lys Ser Ala Gly Gly Gly
1               5                   10
```

<210> SEQ ID NO 17
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 17

```
Gly Gly Gly Pro Gly Ser Gly Lys
1               5
```

<210> SEQ ID NO 18
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 18

```
Arg Gly Cys Arg Glu Lys Ala
1               5
```

<210> SEQ ID NO 19
<211> LENGTH: 4
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (1)..(4)

```
<400> SEQUENCE: 19

Arg Gly Cys Arg
1

<210> SEQ ID NO 20
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: PEPTIDE
<222> LOCATION: (1)..(4)
<220> FEATURE:
<221> NAME/KEY: MISC_FEATURE
<222> LOCATION: (1)..(1)
<223> OTHER INFORMATION: X can be Arg, Lys, or His
<220> FEATURE:
<221> NAME/KEY: MISC_FEATURE
<222> LOCATION: (2)..(3)
<223> OTHER INFORMATION: X can be any amino acid
<220> FEATURE:
<221> NAME/KEY: MISC_FEATURE
<222> LOCATION: (4)..(4)
<223> OTHER INFORMATION: X can be Arg, Lys, or His

<400> SEQUENCE: 20

Xaa Xaa Xaa Xaa
1

<210> SEQ ID NO 21
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(5)
<220> FEATURE:
<221> NAME/KEY: MISC_FEATURE
<222> LOCATION: (1)..(1)
<223> OTHER INFORMATION: X can be Arg, Lys, or His
<220> FEATURE:
<221> NAME/KEY: MISC_FEATURE
<222> LOCATION: (2)..(3)
<223> OTHER INFORMATION: X can be any amino acid

<400> SEQUENCE: 21

Xaa Xaa Xaa Lys Gly
1               5

<210> SEQ ID NO 22
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(5)

<400> SEQUENCE: 22

Asp Asp Asp Asp Lys
1               5

<210> SEQ ID NO 23
<211> LENGTH: 4
<212> TYPE: PRT
<213> ORGANISM: Artificial Sequence
<220> FEATURE:
```

```
<223> OTHER INFORMATION: synthetic sequence
<220> FEATURE:
<221> NAME/KEY: PEPTIDE
<222> LOCATION: (1)..(4)
<220> FEATURE:
<221> NAME/KEY: MISC_FEATURE
<222> LOCATION: (1)..(1)
<223> OTHER INFORMATION: X can be Arg or Lys
<220> FEATURE:
<221> NAME/KEY: MISC_FEATURE
<222> LOCATION: (2)..(3)
<223> OTHER INFORMATION: X can be any amino acid
<220> FEATURE:
<221> NAME/KEY: MISC_FEATURE
<222> LOCATION: (4)..(4)
<223> OTHER INFORMATION: X can be Arg or Lys

<400> SEQUENCE: 23

Xaa Xaa Xaa Xaa
1

<210> SEQ ID NO 24
<211> LENGTH: 6
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(6)

<400> SEQUENCE: 24

Asn Gly Arg Ala His Ala
1               5

<210> SEQ ID NO 25
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 25

Arg Asn Gly Arg Ala His Ala
1               5

<210> SEQ ID NO 26
<211> LENGTH: 4
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(4)

<400> SEQUENCE: 26

Arg Arg Glu Lys
1

<210> SEQ ID NO 27
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
```

<222> LOCATION: (1)..(5)

<400> SEQUENCE: 27

Arg Arg Glu Lys Ala
1               5

<210> SEQ ID NO 28
<211> LENGTH: 4
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(4)

<400> SEQUENCE: 28

Gly Pro Asp Cys
1

<210> SEQ ID NO 29
<211> LENGTH: 12
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(12)
<223> OTHER INFORMATION: VEGF-165 binding site in the b1 domain of NRP-1

<400> SEQUENCE: 29
tcaaaagaaa cc                                                         12

<210> SEQ ID NO 30
<211> LENGTH: 12
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (1)..(12)
<223> OTHER INFORMATION: triple mutation of VEGF-165 binding site of b1
      domain of NRP-1

<400> SEQUENCE: 30
gctaaagctg ct                                                         12

<210> SEQ ID NO 31
<211> LENGTH: 4
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(4)
<220> FEATURE:
<221> NAME/KEY: MISC_FEATURE
<222> LOCATION: (4)..(4)
<223> OTHER INFORMATION: X can be Lys or Arg

<400> SEQUENCE: 31

Arg Gly Asp Xaa
1

<210> SEQ ID NO 32
<211> LENGTH: 9

```
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 32

Cys Asp Cys Arg Gly Asp Cys Phe Cys
1               5

<210> SEQ ID NO 33
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 33

Cys Arg Gly Asp Asp Gly Pro Lys Cys
1               5

<210> SEQ ID NO 34
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(5)

<400> SEQUENCE: 34

Cys Arg Gly Asp Lys
1               5

<210> SEQ ID NO 35
<211> LENGTH: 34
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(34)

<400> SEQUENCE: 35

Ala Lys Val Lys Asp Glu Pro Gln Arg Arg Ser Ala Arg Leu Ser Ala
1               5                   10                  15

Lys Pro Ala Pro Pro Lys Pro Glu Pro Lys Pro Lys Lys Ala Pro Ala
            20                  25                  30

Lys Lys

<210> SEQ ID NO 36
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(5)

<400> SEQUENCE: 36
```

```
Cys Arg Gly Asp Cys
1               5

<210> SEQ ID NO 37
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(5)
<220> FEATURE:
<221> NAME/KEY: MISC_FEATURE
<222> LOCATION: (5)..(5)
<223> OTHER INFORMATION: X can be Lys or Arg

<400> SEQUENCE: 37

Cys Arg Gly Asp Xaa
1               5

<210> SEQ ID NO 38
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 38

Gly Gly Gly Gly Gly Gly Gly
1               5

<210> SEQ ID NO 39
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 39

Cys Gly Gly Gly Gly Gly Gly Gly Cys
1               5

<210> SEQ ID NO 40
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(5)

<400> SEQUENCE: 40

Arg Gly Asp Phe Lys
1               5

<210> SEQ ID NO 41
<211> LENGTH: 9
<212> TYPE: PRT
<213> ORGANISM: Artificial Sequence
<220> FEATURE:
<223> OTHER INFORMATION: synthetic sequence
<220> FEATURE:
```

```
<221> NAME/KEY: PEPTIDE
<222> LOCATION: (1)..(9)

<400> SEQUENCE: 41

Cys Arg Asn Gly Arg Gly Pro Asp Cys
1               5

<210> SEQ ID NO 42
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(13)

<400> SEQUENCE: 42

Arg Pro Ala Arg Val Lys Arg Asn Gly Arg Ala His Ala
1               5                   10

<210> SEQ ID NO 43
<211> LENGTH: 17
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(17)

<400> SEQUENCE: 43

Arg Pro Ala Arg Ser Gly Arg Ala Gly Gly Ser Val Ala Cys Arg Gly
1               5                   10                  15

Asp

<210> SEQ ID NO 44
<211> LENGTH: 17
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(14)

<400> SEQUENCE: 44

Arg Pro Ala Arg Val Lys Arg Gly Gly Ser Cys Ala Gly Ala Leu Cys
1               5                   10                  15

Tyr

<210> SEQ ID NO 45
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)
<220> FEATURE:
<221> NAME/KEY: MISC_FEATURE
<222> LOCATION: (6)..(9)
<223> OTHER INFORMATION: X can be any amino acid

<400> SEQUENCE: 45

Thr Gly Leu Thr Ala Xaa Xaa Xaa Xaa Trp
1               5                   10
```

```
<210> SEQ ID NO 46
<211> LENGTH: 4
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(4)
<220> FEATURE:
<221> NAME/KEY: MISC_FEATURE
<222> LOCATION: (1)..(1)
<223> OTHER INFORMATION: X can be Lys or Arg

<400> SEQUENCE: 46

Xaa Asn Gly Arg
1

<210> SEQ ID NO 47
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 47

Cys Gln Ser Cys Asn Gly Arg Cys Val Arg
1               5                   10

<210> SEQ ID NO 48
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 48

Cys Arg Thr Cys Asn Gly Arg Cys Gln Val
1               5                   10

<210> SEQ ID NO 49
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 49

Cys Val Gln Cys Asn Gly Arg Cys Ala Leu
1               5                   10

<210> SEQ ID NO 50
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)
```

```
<400> SEQUENCE: 50

Cys Arg Cys Cys Asn Gly Arg Cys Ser Pro
1               5                   10

<210> SEQ ID NO 51
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 51

Cys Ala Ser Asn Asn Gly Arg Val Val Leu
1               5                   10

<210> SEQ ID NO 52
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 52

Cys Gly Arg Cys Asn Gly Arg Cys Leu Leu
1               5                   10

<210> SEQ ID NO 53
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 53

Cys Trp Leu Cys Asn Gly Arg Cys Gly Arg
1               5                   10

<210> SEQ ID NO 54
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 54

Cys Ser Lys Cys Asn Gly Arg Cys Gly His
1               5                   10

<210> SEQ ID NO 55
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
```

```
<222> LOCATION: (1)..(10)

<400> SEQUENCE: 55

Cys Val Trp Cys Asn Gly Arg Cys Gly Leu
1               5                   10

<210> SEQ ID NO 56
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 56

Cys Ile Arg Cys Asn Gly Arg Cys Ser Val
1               5                   10

<210> SEQ ID NO 57
<211> LENGTH: 11
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(11)

<400> SEQUENCE: 57

Cys Thr Gly Glu Cys Asn Gly Arg Cys Val Glu
1               5                   10

<210> SEQ ID NO 58
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 58

Cys Glu Gly Val Asn Gly Arg Arg Leu Arg
1               5                   10

<210> SEQ ID NO 59
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 59

Cys Leu Ser Cys Asn Gly Arg Cys Pro Ser
1               5                   10

<210> SEQ ID NO 60
<211> LENGTH: 10
<212> TYPE: PRT
<213> ORGANISM: Artificial Sequence
<220> FEATURE:
<223> OTHER INFORMATION: synthetic sequence
<220> FEATURE:
```

```
<221> NAME/KEY: PEPTIDE
<222> LOCATION: (1)..(10)

<400> SEQUENCE: 60

Cys Glu Val Cys Asn Gly Arg Cys Ala Leu
1               5                   10

<210> SEQ ID NO 61
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)
<220> FEATURE:
<221> NAME/KEY: MISC_FEATURE
<222> LOCATION: (5)..(5)
<223> OTHER INFORMATION: X can be Lys or Arg
<220> FEATURE:
<221> NAME/KEY: MISC_FEATURE
<222> LOCATION: (8)..(8)
<223> OTHER INFORMATION: X can be Asp or Glu

<400> SEQUENCE: 61

Cys Arg Gly Asp Xaa Gly Pro Xaa Cys
1               5

<210> SEQ ID NO 62
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(13)

<400> SEQUENCE: 62

Cys Gly Arg Glu Cys Pro Arg Leu Cys Gln Ser Ser Cys
1               5                   10

<210> SEQ ID NO 63
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(13)

<400> SEQUENCE: 63

Cys Asn Gly Arg Cys Val Ser Gly Cys Ala Gly Arg Cys
1               5                   10

<210> SEQ ID NO 64
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 64

Cys Leu Ser Gly Ser Leu Ser Cys
1               5
```

```
<210> SEQ ID NO 65
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 65

Cys Gly Ser Leu Val Arg Cys
1               5

<210> SEQ ID NO 66
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 66

Ala Leu Asn Gly Arg Glu Glu Ser Pro
1               5

<210> SEQ ID NO 67
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 67

Cys Val Leu Asn Gly Arg Met Glu Cys
1               5

<210> SEQ ID NO 68
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(5)

<400> SEQUENCE: 68

Cys Asn Gly Arg Cys
1               5

<210> SEQ ID NO 69
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 69

Cys Glu Met Cys Asn Gly Arg Cys Met Gly
```

```
1               5                  10

<210> SEQ ID NO 70
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 70

Cys Pro Leu Cys Asn Gly Arg Cys Ala Leu
1               5                  10

<210> SEQ ID NO 71
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 71

Cys Pro Thr Cys Asn Gly Arg Cys Val Arg
1               5                  10

<210> SEQ ID NO 72
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 72

Cys Gly Val Cys Asn Gly Arg Cys Gly Leu
1               5                  10

<210> SEQ ID NO 73
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 73

Cys Glu Gln Cys Asn Gly Arg Cys Gly Gln
1               5                  10

<210> SEQ ID NO 74
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 74
```

```
Cys Arg Asn Cys Asn Gly Arg Cys Glu Gly
1               5                   10
```

<210> SEQ ID NO 75
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 75

```
Cys Val Leu Cys Asn Gly Arg Cys Trp Ser
1               5                   10
```

<210> SEQ ID NO 76
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 76

```
Cys Val Thr Cys Asn Gly Arg Cys Arg Val
1               5                   10
```

<210> SEQ ID NO 77
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 77

```
Cys Thr Glu Cys Asn Gly Arg Cys Gln Leu
1               5                   10
```

<210> SEQ ID NO 78
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 78

```
Cys Arg Thr Cys Asn Gly Arg Cys Leu Glu
1               5                   10
```

<210> SEQ ID NO 79
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 79

```
Cys Glu Thr Cys Asn Gly Arg Cys Val Gly
1               5                   10

<210> SEQ ID NO 80
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 80

Cys Ala Val Cys Asn Gly Arg Cys Gly Phe
1               5                   10

<210> SEQ ID NO 81
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 81

Cys Arg Asp Leu Asn Gly Arg Lys Val Met
1               5                   10

<210> SEQ ID NO 82
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 82

Cys Ser Cys Cys Asn Gly Arg Cys Gly Asp
1               5                   10

<210> SEQ ID NO 83
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 83

Cys Trp Gly Cys Asn Gly Arg Cys Arg Met
1               5                   10

<210> SEQ ID NO 84
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)
```

```
<400> SEQUENCE: 84

Cys Pro Leu Cys Asn Gly Arg Cys Ala Arg
1               5                   10

<210> SEQ ID NO 85
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 85

Cys Lys Ser Cys Asn Gly Arg Cys Leu Ala
1               5                   10

<210> SEQ ID NO 86
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 86

Cys Val Pro Cys Asn Gly Arg Cys His Glu
1               5                   10

<210> SEQ ID NO 87
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 87

Cys Val Leu Asn Gly Arg Met Glu
1               5

<210> SEQ ID NO 88
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 88

Cys Lys Val Cys Asn Gly Arg Cys Cys Gly
1               5                   10

<210> SEQ ID NO 89
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)
```

```
<220> FEATURE:
<221> NAME/KEY: MISC_FEATURE
<222> LOCATION: (1)..(2)
<223> OTHER INFORMATION: X can be any amino acid
<220> FEATURE:
<221> NAME/KEY: MISC_FEATURE
<222> LOCATION: (8)..(9)
<223> OTHER INFORMATION: X can be any amino acid

<400> SEQUENCE: 89

Xaa Xaa Cys Asn Gly Arg Cys Xaa Xaa
1               5

<210> SEQ ID NO 90
<211> LENGTH: 11
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(11)
<220> FEATURE:
<221> NAME/KEY: MISC_FEATURE
<222> LOCATION: (2)..(4)
<223> OTHER INFORMATION: X can be any amino acid
<220> FEATURE:
<221> NAME/KEY: MISC_FEATURE
<222> LOCATION: (8)..(10)
<223> OTHER INFORMATION: X can be any amino acid

<400> SEQUENCE: 90

Cys Xaa Xaa Xaa Asn Gly Arg Xaa Xaa Xaa Cys
1               5                   10

<210> SEQ ID NO 91
<211> LENGTH: 11
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(11)
<220> FEATURE:
<221> NAME/KEY: MISC_FEATURE
<222> LOCATION: (6)..(11)
<223> OTHER INFORMATION: X can be any amino acid

<400> SEQUENCE: 91

Cys Asn Gly Arg Cys Xaa Xaa Xaa Xaa Xaa Xaa
1               5                   10

<210> SEQ ID NO 92
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)
<220> FEATURE:
<221> NAME/KEY: MISC_FEATURE
<222> LOCATION: (2)..(2)
<223> OTHER INFORMATION: C is methylated

<400> SEQUENCE: 92

Cys Cys Arg Gly Asp Lys Gly Pro Asp Cys
1               5                   10
```

```
<210> SEQ ID NO 93
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)
<220> FEATURE:
<221> NAME/KEY: MISC_FEATURE
<222> LOCATION: (3)..(3)
<223> OTHER INFORMATION: Asn is methylated

<400> SEQUENCE: 93

Cys Arg Asn Gly Asp Lys Gly Pro Asp Cys
1               5                   10

<210> SEQ ID NO 94
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 94

Arg Pro Ala Arg Pro Ala Arg Ala
1               5

<210> SEQ ID NO 95
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 95

Cys Arg Cys Asp Lys Pro Arg Arg
1               5

<210> SEQ ID NO 96
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 96

Ala Thr Trp Leu Pro Pro Arg
1               5

<210> SEQ ID NO 97
<211> LENGTH: 4
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(4)

<400> SEQUENCE: 97
```

Thr Lys Pro Arg
1

<210> SEQ ID NO 98
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(5)

<400> SEQUENCE: 98

Thr Lys Pro Pro Arg
1               5

<210> SEQ ID NO 99
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 99

Cys Gly Asn Lys Arg Thr Arg Gly Cys
1               5

<210> SEQ ID NO 100
<211> LENGTH: 4
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(4)

<400> SEQUENCE: 100

Lys Arg Thr Arg
1

<210> SEQ ID NO 101
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 101

Cys Arg Gly Arg Arg Ser Thr
1               5

<210> SEQ ID NO 102
<211> LENGTH: 4
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(4)

```
<400> SEQUENCE: 102

Arg Gly Arg Arg
1

<210> SEQ ID NO 103
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 103

Cys Gly Arg Lys Ser Lys Thr Val Cys
1               5

<210> SEQ ID NO 104
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 104

Cys Pro Lys Thr Arg Arg Val Pro Cys
1               5

<210> SEQ ID NO 105
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (6)..(7)
<223> OTHER INFORMATION: X can be any amino acid

<400> SEQUENCE: 105

Cys Arg Xaa Thr Arg Xaa Xaa Arg Cys
1               5

<210> SEQ ID NO 106
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(5)

<400> SEQUENCE: 106

Cys Arg Pro Pro Arg
1               5

<210> SEQ ID NO 107
```

```
<211> LENGTH: 11
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(11)
<220> FEATURE:
<221> NAME/KEY: MISC_FEATURE
<222> LOCATION: (6)..(6)
<223> OTHER INFORMATION: X can be any amino acid
<220> FEATURE:
<221> NAME/KEY: MISC_FEATURE
<222> LOCATION: (8)..(11)
<223> OTHER INFORMATION: X can be any amino acid

<400> SEQUENCE: 107

Arg Pro Ala Arg Pro Xaa Arg Xaa Xaa Xaa Xaa
1               5                   10

<210> SEQ ID NO 108
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 108

Cys Gly Phe Glu Leu Glu Thr Cys
1               5

<210> SEQ ID NO 109
<211> LENGTH: 6
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(6)

<400> SEQUENCE: 109

Cys Arg Pro Pro Arg Ala
1               5

<210> SEQ ID NO 110
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)
<220> FEATURE:
<221> NAME/KEY: MISC_FEATURE
<222> LOCATION: (6)..(9)
<223> OTHER INFORMATION: X can be any amino acid

<400> SEQUENCE: 110

Cys Arg Pro Pro Arg Xaa Xaa Xaa Xaa
1               5

<210> SEQ ID NO 111
<211> LENGTH: 8
<212> TYPE: PRT
<213> ORGANISM: Artificial Sequence
```

```
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 111

Arg Pro Ala Arg Pro Ala Arg Glu
1               5

<210> SEQ ID NO 112
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 112

Ser Met Ser Ile Ala Arg Leu
1               5

<210> SEQ ID NO 113
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(13)

<400> SEQUENCE: 113

Ser Met Ser Ile Ala Arg Leu Ala Arg Pro Ala Arg Glu
1               5                   10

<210> SEQ ID NO 114
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 114

Cys Asn Ser Arg Leu His Leu Arg Cys
1               5

<210> SEQ ID NO 115
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 115

Cys Glu Asn Trp Trp Gly Asp Val Cys
1               5

<210> SEQ ID NO 116
<211> LENGTH: 21
<212> TYPE: PRT
```

```
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(21)

<400> SEQUENCE: 116

Trp Arg Cys Val Leu Arg Glu Gly Pro Ala Gly Gly Cys Ala Trp Phe
1               5                   10                  15

Asn Arg His Arg Leu
            20

<210> SEQ ID NO 117
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 117

Cys Leu Ser Ser Arg Leu Asp Ala Cys
1               5

<210> SEQ ID NO 118
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 118

Cys Val Leu Arg Gly Gly Arg Cys
1               5

<210> SEQ ID NO 119
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 119

Cys Asn Ser Arg Leu Gln Leu Arg Cys
1               5

<210> SEQ ID NO 120
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 120

Cys Gly Val Arg Leu Gly Cys
1               5
```

```
<210> SEQ ID NO 121
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 121

Cys Lys Asp Trp Gly Arg Ile Cys
1               5

<210> SEQ ID NO 122
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 122

Cys Leu Asp Trp Gly Arg Ile Cys
1               5

<210> SEQ ID NO 123
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 123

Cys Thr Arg Ile Thr Glu Ser Cys
1               5

<210> SEQ ID NO 124
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 124

Cys Glu Thr Leu Pro Ala Cys
1               5

<210> SEQ ID NO 125
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 125

Cys Arg Thr Gly Thr Leu Phe Cys
1               5
```

```
<210> SEQ ID NO 126
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 126

Cys Gly Arg Ser Leu Asp Ala Cys
1               5

<210> SEQ ID NO 127
<211> LENGTH: 9
<212> TYPE: PRT
<213> ORGANISM: Artificial Sequence
<220> FEATURE:
<223> OTHER INFORMATION: synthetic sequence

<400> SEQUENCE: 127

Cys Arg His Trp Phe Asp Val Val Cys
1               5

<210> SEQ ID NO 128
<211> LENGTH: 8
<212> TYPE: PRT
<213> ORGANISM: Artificial Sequence
<220> FEATURE:
<223> OTHER INFORMATION: synthetic sequence

<400> SEQUENCE: 128

Cys Ala Asn Ala Gln Ser His Cys
1               5

<210> SEQ ID NO 129
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 129

Cys Gly Asn Pro Ser Tyr Arg Cys
1               5

<210> SEQ ID NO 130
<211> LENGTH: 20
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(20)

<400> SEQUENCE: 130

Tyr Pro Cys Gly Gly Glu Ala Val Ala Gly Val Ser Ser Val Arg Thr
1               5                   10                  15

Met Cys Ser Glu
            20
```

```
<210> SEQ ID NO 131
<211> LENGTH: 20
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(20)

<400> SEQUENCE: 131

Leu Asn Cys Asp Tyr Gln Gly Thr Asn Pro Ala Thr Ser Val Ser Val
1               5                   10                  15

Pro Cys Thr Val
            20

<210> SEQ ID NO 132
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 132

Cys Leu Pro Val Ala Ser Cys
1               5

<210> SEQ ID NO 133
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 133

Cys Gly Ala Arg Glu Met Cys
1               5

<210> SEQ ID NO 134
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 134

Cys Lys Gly Arg Ser Ser Ala Cys
1               5

<210> SEQ ID NO 135
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 135
```

```
Cys Trp Ala Arg Ala Gln Gly Cys
1               5

<210> SEQ ID NO 136
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 136

Cys Leu Gly Arg Ser Ser Val Cys
1               5

<210> SEQ ID NO 137
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 137

Cys Thr Ser Pro Gly Gly Ser Cys
1               5

<210> SEQ ID NO 138
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 138

Cys Met Gly Arg Trp Arg Leu Cys
1               5

<210> SEQ ID NO 139
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 139

Cys Val Gly Glu Cys Gly Gly Cys
1               5

<210> SEQ ID NO 140
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 140
```

```
Cys Val Ala Trp Leu Asn Cys
1               5

<210> SEQ ID NO 141
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 141

Cys Arg Arg Phe Gln Asp Cys
1               5

<210> SEQ ID NO 142
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 142

Cys Leu Met Gly Val His Cys
1               5

<210> SEQ ID NO 143
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 143

Cys Lys Leu Leu Ser Gly Val Cys
1               5

<210> SEQ ID NO 144
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 144

Cys Phe Val Gly His Asp Leu Cys
1               5

<210> SEQ ID NO 145
<211> LENGTH: 7
<212> TYPE: PRT
<213> ORGANISM: Artificial Sequence
<220> FEATURE:
<223> OTHER INFORMATION: synthetic sequence

<400> SEQUENCE: 145

Cys Arg Cys Leu Asn Val Cys
```

```
1               5

<210> SEQ ID NO 146
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 146

Cys Lys Leu Met Gly Glu Cys
1               5

<210> SEQ ID NO 147
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 147

Cys Ala Arg Ser Lys Asn Lys Asp Cys
1               5

<210> SEQ ID NO 148
<211> LENGTH: 6
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(6)

<400> SEQUENCE: 148

Cys Arg Lys Asp Lys Cys
1               5

<210> SEQ ID NO 149
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(13)

<400> SEQUENCE: 149

Cys Val Ala Leu Cys Arg Glu Ala Cys Gly Glu Gly Cys
1               5                   10

<210> SEQ ID NO 150
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(13)

<400> SEQUENCE: 150
```

```
Cys Ser Ser Gly Cys Ser Lys Asn Cys Leu Glu Met Cys
1               5                   10
```

<210> SEQ ID NO 151
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 151

```
Cys Ile Gly Glu Val Glu Val Cys
1               5
```

<210> SEQ ID NO 152
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 152

```
Cys Lys Trp Ser Arg Leu His Ser Cys
1               5
```

<210> SEQ ID NO 153
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 153

```
Cys Trp Arg Gly Asp Arg Lys Ile Cys
1               5
```

<210> SEQ ID NO 154
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 154

```
Cys Glu Arg Val Val Gly Ser Ser Cys
1               5
```

<210> SEQ ID NO 155
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 155

```
Cys Leu Ala Lys Glu Asn Val Val Cys
1               5

<210> SEQ ID NO 156
<211> LENGTH: 13
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(13)

<400> SEQUENCE: 156

Cys Gly Phe Glu Cys Val Arg Gln Cys Pro Glu Arg Cys
1               5                   10

<210> SEQ ID NO 157
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 157

Cys Gly Phe Glu Leu Glu Thr Cys
1               5

<210> SEQ ID NO 158
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 158

Cys Thr Leu Arg Asp Arg Asn Cys
1               5

<210> SEQ ID NO 159
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 159

Cys Ile Gly Glu Val Glu Val Cys
1               5

<210> SEQ ID NO 160
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)
```

```
<400> SEQUENCE: 160

Cys Thr Leu Arg Asp Arg Asn Cys
1               5

<210> SEQ ID NO 161
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 161

Cys Gly Lys Arg Tyr Arg Asn Cys
1               5

<210> SEQ ID NO 162
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 162

Cys Leu Arg Pro Tyr Leu Asn Cys
1               5

<210> SEQ ID NO 163
<211> LENGTH: 12
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(12)

<400> SEQUENCE: 163

Cys Thr Val Asn Glu Ala Tyr Lys Thr Arg Met Cys
1               5                   10

<210> SEQ ID NO 164
<211> LENGTH: 12
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(12)

<400> SEQUENCE: 164

Cys Arg Leu Arg Ser Tyr Gly Thr Leu Ser Leu Cys
1               5                   10

<210> SEQ ID NO 165
<211> LENGTH: 12
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(12)
```

```
<400> SEQUENCE: 165

Cys Arg Pro Trp His Asn Gln Ala His Thr Glu Cys
1               5                   10

<210> SEQ ID NO 166
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 166

Ser Trp Cys Glu Pro Gly Trp Cys Arg
1               5

<210> SEQ ID NO 167
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 167

Cys Lys Ala Ala Lys Asn Lys
1               5

<210> SEQ ID NO 168
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 168

Cys Lys Gly Ala Lys Ala Arg
1               5

<210> SEQ ID NO 169
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 169

Val Gly Val Gly Glu Trp Ser Val
1               5

<210> SEQ ID NO 170
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
```

```
<222> LOCATION: (1)..(7)

<400> SEQUENCE: 170

Tyr Ser Gly Lys Trp Gly Trp
1               5

<210> SEQ ID NO 171
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 171

Gly Leu Ser Gly Gly Arg Ser
1               5

<210> SEQ ID NO 172
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 172

Leu Met Leu Pro Arg Ala Asp
1               5

<210> SEQ ID NO 173
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 173

Leu Pro Arg Tyr Leu Leu Ser
1               5

<210> SEQ ID NO 174
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 174

Cys Ser Cys Phe Arg Asp Val Cys Cys
1               5

<210> SEQ ID NO 175
<211> LENGTH: 9
<212> TYPE: PRT
<213> ORGANISM: Artificial Sequence
<220> FEATURE:
<223> OTHER INFORMATION: synthetic sequence
<220> FEATURE:
```

```
<221> NAME/KEY: PEPTIDE
<222> LOCATION: (1)..(9)

<400> SEQUENCE: 175

Cys Arg Asp Val Val Ser Val Ile Cys
1               5

<210> SEQ ID NO 176
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 176

Tyr Ser Gly Lys Trp Gly Lys
1               5

<210> SEQ ID NO 177
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 177

Gly Ile Ser Ala Leu Val Leu Ser
1               5

<210> SEQ ID NO 178
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 178

Ser Arg Arg Gln Pro Leu Ser
1               5

<210> SEQ ID NO 179
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 179

Met Ser Pro Gln Leu Ala Thr
1               5

<210> SEQ ID NO 180
<211> LENGTH: 7
<212> TYPE: PRT
<213> ORGANISM: Artificial Sequence
<220> FEATURE:
<223> OTHER INFORMATION: synthetic sequence
```

```
<220> FEATURE:
<221> NAME/KEY: PEPTIDE
<222> LOCATION: (1)..(7)

<400> SEQUENCE: 180

Met Arg Arg Asp Glu Gln Arg
1               5

<210> SEQ ID NO 181
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 181

Gln Val Arg Arg Val Pro Glu
1               5

<210> SEQ ID NO 182
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 182

Val Arg Arg Gly Ser Pro Gln
1               5

<210> SEQ ID NO 183
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 183

Gly Gly Arg Gly Ser Trp Glu
1               5

<210> SEQ ID NO 184
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 184

Phe Arg Val Arg Gly Ser Pro
1               5

<210> SEQ ID NO 185
<211> LENGTH: 7
<212> TYPE: PRT
<213> ORGANISM: Artificial Sequence
<220> FEATURE:
```

```
<223> OTHER INFORMATION: synthetic sequence
<220> FEATURE:
<221> NAME/KEY: PEPTIDE
<222> LOCATION: (1)..(7)

<400> SEQUENCE: 185

Arg Val Arg Gly Pro Glu Arg
1               5

<210> SEQ ID NO 186
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 186

Val Lys Ser Val Cys Arg Thr
1               5

<210> SEQ ID NO 187
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 187

Trp Arg Gln Asn Met Pro Leu
1               5

<210> SEQ ID NO 188
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 188

Ser Arg Arg Phe Val Gly Gly
1               5

<210> SEQ ID NO 189
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 189

Ala Leu Glu Arg Arg Ser Leu
1               5

<210> SEQ ID NO 190
<211> LENGTH: 7
<212> TYPE: PRT
<213> ORGANISM: Artificial Sequence
```

```
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 190

Ala Arg Arg Gly Trp Thr Leu
1               5

<210> SEQ ID NO 191
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 191

Ser Met Ser Ile Ala Arg Leu
1               5

<210> SEQ ID NO 192
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 192

Val Ser Phe Leu Glu Tyr Arg
1               5

<210> SEQ ID NO 193
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 193

Arg Gly Arg Trp Leu Ala Leu
1               5

<210> SEQ ID NO 194
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 194

Glu Val Arg Ser Arg Leu Ser
1               5

<210> SEQ ID NO 195
<211> LENGTH: 7
<212> TYPE: PRT
```

```
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 195

Val Arg Ala Arg Leu Met Ser
1               5

<210> SEQ ID NO 196
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 196

Arg Val Gly Leu Val Ala Arg
1               5

<210> SEQ ID NO 197
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 197

Arg Val Arg Leu Val Asn Leu
1               5

<210> SEQ ID NO 198
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(5)

<400> SEQUENCE: 198

Cys Arg Pro Pro Arg
1               5

<210> SEQ ID NO 199
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 199

Cys Gly Arg Lys Ser Lys Thr Val Cys
1               5

<210> SEQ ID NO 200
<211> LENGTH: 6
```

```
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(6)

<400> SEQUENCE: 200

Cys Ala Arg Pro Ala Arg
1               5

<210> SEQ ID NO 201
<211> LENGTH: 6
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(6)

<400> SEQUENCE: 201

Cys Pro Lys Arg Pro Arg
1               5

<210> SEQ ID NO 202
<211> LENGTH: 6
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(6)

<400> SEQUENCE: 202

Cys Lys Arg Ala Val Arg
1               5

<210> SEQ ID NO 203
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 203

Cys Arg Asn Ser Trp Lys Pro Asn Cys
1               5

<210> SEQ ID NO 204
<211> LENGTH: 5
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(5)

<400> SEQUENCE: 204

Arg Gly Ser Ser Ser
1               5

<210> SEQ ID NO 205
```

```
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 205

Cys Arg Ser Thr Arg Ala Asn Pro Cys
1               5

<210> SEQ ID NO 206
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 206

Cys Pro Lys Thr Arg Arg Val Pro Cys
1               5

<210> SEQ ID NO 207
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 207

Cys Ser Gly Met Ala Arg Thr Lys Cys
1               5

<210> SEQ ID NO 208
<211> LENGTH: 7
<212> TYPE: PRT
<213> ORGANISM: Artificial Sequence
<220> FEATURE:
<223> OTHER INFORMATION: synthetic sequence

<400> SEQUENCE: 208

Gly Gly Gly Val Phe Trp Gln
1               5

<210> SEQ ID NO 209
<211> LENGTH: 7
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 209

His Gly Arg Val Arg Pro His
1               5

<210> SEQ ID NO 210
<211> LENGTH: 7
<212> TYPE: PRT
```

```
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(7)

<400> SEQUENCE: 210

Val Val Leu Val Thr Ser Ser
1               5

<210> SEQ ID NO 211
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(8)

<400> SEQUENCE: 211

Cys Leu His Arg Gly Asn Ser Cys
1               5

<210> SEQ ID NO 212
<211> LENGTH: 12
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(12)

<400> SEQUENCE: 212

Cys Arg Ser Trp Asn Lys Ala Asp Asn Arg Ser Cys
1               5                   10

<210> SEQ ID NO 213
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 213

Cys Gly Arg Lys Ser Lys Thr Val Cys
1               5

<210> SEQ ID NO 214
<211> LENGTH: 6
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(6)

<400> SEQUENCE: 214

Cys Lys Arg Ala Val Arg
1               5

<210> SEQ ID NO 215
<211> LENGTH: 9
```

```
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 215

Cys Arg Asn Ser Trp Lys Pro Asn Cys
1               5

<210> SEQ ID NO 216
<211> LENGTH: 9
<212> TYPE: PRT
<213> ORGANISM: Artificial Sequence
<220> FEATURE:
<223> OTHER INFORMATION: synthetic sequence

<400> SEQUENCE: 216

Cys Pro Lys Thr Arg Arg Val Pro Cys
1               5

<210> SEQ ID NO 217
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 217

Cys Ser Gly Met Ala Arg Thr Lys Cys
1               5

<210> SEQ ID NO 218
<211> LENGTH: 6
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(6)

<400> SEQUENCE: 218

Cys Ala Arg Pro Ala Arg
1               5

<210> SEQ ID NO 219
<211> LENGTH: 6
<212> TYPE: PRT
<213> ORGANISM: Artificial Sequence
<220> FEATURE:
<223> OTHER INFORMATION: synthetic sequence

<400> SEQUENCE: 219

Cys Pro Lys Arg Pro Arg
1               5

<210> SEQ ID NO 220
<211> LENGTH: 5
<212> TYPE: PRT
<213> ORGANISM: Artificial Sequence
<220> FEATURE:
<223> OTHER INFORMATION: synthetic sequence
<220> FEATURE:
```

```
<221> NAME/KEY: PEPTIDE
<222> LOCATION: (1)..(5)

<400> SEQUENCE: 220

Cys Asn Gly Arg Cys
1               5

<210> SEQ ID NO 221
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 221

Cys Ser Arg Pro Arg Arg Ser Glu Cys
1               5

<210> SEQ ID NO 222
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 222

Cys Ser Arg Pro Arg Arg Ser Val Cys
1               5

<210> SEQ ID NO 223
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 223

Cys Ser Arg Pro Arg Arg Ser Trp Cys
1               5

<210> SEQ ID NO 224
<211> LENGTH: 31
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(31)

<400> SEQUENCE: 224

Lys Asp Glu Pro Gln Arg Arg Ser Ala Arg Leu Ser Ala Lys Pro Ala
1               5                   10                  15

Pro Pro Lys Pro Glu Pro Lys Pro Lys Lys Ala Pro Ala Lys Lys
            20                  25                  30

<210> SEQ ID NO 225
<211> LENGTH: 10
<212> TYPE: PRT
```

```
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 225

Pro Gln Arg Arg Ser Ala Arg Leu Ser Ala
1               5                   10

<210> SEQ ID NO 226
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(10)

<400> SEQUENCE: 226

Pro Lys Arg Arg Ser Ala Arg Leu Ser Ala
1               5                   10

<210> SEQ ID NO 227
<211> LENGTH: 9
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(9)

<400> SEQUENCE: 227

Cys Asn Arg Arg Thr Lys Ala Gly Cys
1               5

<210> SEQ ID NO 228
<211> LENGTH: 6
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(6)

<400> SEQUENCE: 228

Cys Arg Ser Arg Lys Gly
1               5

<210> SEQ ID NO 229
<211> LENGTH: 4
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(4)

<400> SEQUENCE: 229

Arg Gly Asp Arg
1

<210> SEQ ID NO 230
<211> LENGTH: 14
```

-continued

```
<212> TYPE: PRT
<213> ORGANISM: Human cytomegalovirus
<220> FEATURE:
<221> NAME/KEY: PEPTIDE
<222> LOCATION: (1)..(14)
<223> OTHER INFORMATION: envelope glycoprotein B

<400> SEQUENCE: 230

Leu Asn Ile Thr His Arg Thr Arg Arg Ser Thr Ser Asp Asn
1               5                   10

<210> SEQ ID NO 231
<211> LENGTH: 15
<212> TYPE: PRT
<213> ORGANISM: Measles virus
<220> FEATURE:
<221> NAME/KEY: PEPTIDE
<222> LOCATION: (1)..(15)
<223> OTHER INFORMATION: fusion protein

<400> SEQUENCE: 231

Ser Val Ala Ser Ser Arg Arg His Lys Arg Phe Ala Gly Val Val
1               5                   10                  15

<210> SEQ ID NO 232
<211> LENGTH: 14
<212> TYPE: PRT
<213> ORGANISM: Tick-borne encephalitis virus
<220> FEATURE:
<221> NAME/KEY: PEPTIDE
<222> LOCATION: (1)..(14)
<223> OTHER INFORMATION: PreM protein

<400> SEQUENCE: 232

Lys Gln Glu Gly Ser Arg Thr Arg Arg Ser Val Leu Ile Pro
1               5                   10

<210> SEQ ID NO 233
<211> LENGTH: 14
<212> TYPE: PRT
<213> ORGANISM: respiratory syncytial virus
<220> FEATURE:
<221> NAME/KEY: PEPTIDE
<222> LOCATION: (1)..(14)
<223> OTHER INFORMATION: fusion protein

<400> SEQUENCE: 233

Pro Ala Thr Asn Asn Arg Ala Arg Arg Glu Leu Pro Arg Phe
1               5                   10

<210> SEQ ID NO 234
<211> LENGTH: 15
<212> TYPE: PRT
<213> ORGANISM: Influenza A virus
<220> FEATURE:
<221> NAME/KEY: PEPTIDE
<222> LOCATION: (1)..(15)
<223> OTHER INFORMATION: hemaglutinin

<400> SEQUENCE: 234

Pro Gln Arg Glu Arg Arg Arg Lys Lys Arg Gly Leu Phe Gly Ala
1               5                   10                  15

<210> SEQ ID NO 235
<211> LENGTH: 14
<212> TYPE: PRT
<213> ORGANISM: Human immunodeficiency virus type 1
<220> FEATURE:
<221> NAME/KEY: PEPTIDE
```

```
<222> LOCATION: (1)..(14)
<223> OTHER INFORMATION: envelope precursor gp160

<400> SEQUENCE: 235

Arg Arg Val Val Gln Arg Glu Lys Arg Ala Val Gly Ile Gly
1               5                   10

<210> SEQ ID NO 236
<211> LENGTH: 14
<212> TYPE: PRT
<213> ORGANISM: Ebola virus
<220> FEATURE:
<221> NAME/KEY: PEPTIDE
<222> LOCATION: (1)..(14)
<223> OTHER INFORMATION: virion spike glycoprotein precursor

<400> SEQUENCE: 236

Leu Ile Thr Gly Gly Arg Arg Thr Arg Arg Glu Ala Ile Val
1               5                   10

<210> SEQ ID NO 237
<211> LENGTH: 15
<212> TYPE: PRT
<213> ORGANISM: Mumps virus
<220> FEATURE:
<221> NAME/KEY: PEPTIDE
<222> LOCATION: (1)..(15)
<223> OTHER INFORMATION: fusion protein

<400> SEQUENCE: 237

Pro Ser Ser Gly Ser Arg Arg His Lys Arg Phe Ala Gly Ile Ala
1               5                   10                  15

<210> SEQ ID NO 238
<211> LENGTH: 14
<212> TYPE: PRT
<213> ORGANISM: Artificial Sequence
<220> FEATURE:
<223> OTHER INFORMATION: synthetic sequence
<220> FEATURE:
<221> NAME/KEY: PEPTIDE
<222> LOCATION: (1)..(14)

<400> SEQUENCE: 238

Cys Asp Ser Ala Gly Arg Ser Arg Arg Ser Arg Arg Ala Ile
1               5                   10

<210> SEQ ID NO 239
<211> LENGTH: 13
<212> TYPE: PRT
<213> ORGANISM: Human herpesvirus 4
<220> FEATURE:
<221> NAME/KEY: PEPTIDE
<222> LOCATION: (1)..(13)
<223> OTHER INFORMATION: glycoprotein B

<400> SEQUENCE: 239

Ala Ala Val Leu Arg Arg Arg Arg Arg Asp Ala Gly Asn
1               5                   10

<210> SEQ ID NO 240
<211> LENGTH: 14
<212> TYPE: PRT
<213> ORGANISM: Artificial Sequence
<220> FEATURE:
<223> OTHER INFORMATION: human metapneumo-virus; fusion glycoprotein
      precursor
<220> FEATURE:
<221> NAME/KEY: PEPTIDE
```

<222> LOCATION: (1)..(14)

<400> SEQUENCE: 240

Gln Ile Glu Asn Pro Arg Gln Ser Arg Phe Val Leu Gly Ala
1               5                   10

<210> SEQ ID NO 241
<211> LENGTH: 14
<212> TYPE: PRT
<213> ORGANISM: Human T-cell lymphotropic virus type 2
<220> FEATURE:
<221> NAME/KEY: PEPTIDE
<222> LOCATION: (1)..(14)
<223> OTHER INFORMATION: Env propeptide

<400> SEQUENCE: 241

Pro Pro Pro Ala Thr Arg Arg Arg Arg Ala Val Pro Ile Ala
1               5                   10

<210> SEQ ID NO 242
<211> LENGTH: 14
<212> TYPE: PRT
<213> ORGANISM: Crimean-Congo hemorrhagic fever virus
<220> FEATURE:
<221> NAME/KEY: PEPTIDE
<222> LOCATION: (1)..(14)
<223> OTHER INFORMATION: glycoprotein precursor

<400> SEQUENCE: 242

Pro Ser Pro Thr Asn Arg Ser Lys Arg Asn Leu Lys Met Glu
1               5                   10

<210> SEQ ID NO 243
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 243

Arg Arg Glu Arg
1

<210> SEQ ID NO 244
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 244

Lys Arg Ser Arg
1

<210> SEQ ID NO 245
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 245

Lys Trp Lys Lys
1

<210> SEQ ID NO 246
<211> LENGTH: 4

```
<212> TYPE: PRT
<213> ORGANISM: Artificial Sequence
<220> FEATURE:
<223> OTHER INFORMATION: Synthetic Peptide

<400> SEQUENCE: 246

Arg Arg Leu Lys
1

<210> SEQ ID NO 247
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 247

Lys Leu Arg Lys
1

<210> SEQ ID NO 248
<211> LENGTH: 4
<212> TYPE: PRT
<213> ORGANISM: Artificial Sequence
<220> FEATURE:
<223> OTHER INFORMATION: Synthetic peptide

<400> SEQUENCE: 248

Arg Arg Leu Arg
1

<210> SEQ ID NO 249
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 249

Arg Arg Arg Arg
1

<210> SEQ ID NO 250
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 250

Leu Leu Arg Leu
1

<210> SEQ ID NO 251
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 251

Lys Asp Lys Lys
1

<210> SEQ ID NO 252
<211> LENGTH: 4
<212> TYPE: PRT
```

```
<213> ORGANISM: Artificial Sequence
<220> FEATURE:
<223> OTHER INFORMATION: Synthetic Peptide

<400> SEQUENCE: 252

Lys Phe Lys Lys
1

<210> SEQ ID NO 253
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 253

Lys Lys Lys Lys
1

<210> SEQ ID NO 254
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 254

Lys Lys Pro Arg
1

<210> SEQ ID NO 255
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 255

Lys Pro Pro Arg
1

<210> SEQ ID NO 256
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 256

Lys Gln Arg Arg
1

<210> SEQ ID NO 257
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 257

Lys Arg Ala Arg
1

<210> SEQ ID NO 258
<211> LENGTH: 4
<212> TYPE: PRT
<213> ORGANISM: Artificial Sequence
```

```
<220> FEATURE:
<223> OTHER INFORMATION: Synthetic Peptide

<400> SEQUENCE: 258

Lys Arg Gly Arg
1

<210> SEQ ID NO 259
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 259

Lys Arg Thr Arg
1

<210> SEQ ID NO 260
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 260

Lys Val Ile Arg
1

<210> SEQ ID NO 261
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 261

Lys Val Arg Lys
1

<210> SEQ ID NO 262
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 262

Arg Leu Ala Lys
1

<210> SEQ ID NO 263
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 263

Arg Leu Ile Lys
1

<210> SEQ ID NO 264
<211> LENGTH: 4
<212> TYPE: PRT
<213> ORGANISM: Artificial Sequence
<220> FEATURE:
```

```
<223> OTHER INFORMATION: Synthetic Peptide

<400> SEQUENCE: 264

Arg Arg Pro Lys
1

<210> SEQ ID NO 265
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 265

Arg Arg Thr Lys
1

<210> SEQ ID NO 266
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 266

Arg Ser Phe Lys
1

<210> SEQ ID NO 267
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 267

Arg Val Arg Arg
1
```